(12) United States Patent
Schiemann et al.

(10) Patent No.: US 9,926,319 B2
(45) Date of Patent: *Mar. 27, 2018

(54) PYRIDYL PIPERIDINES

(71) Applicants: MERCK PATENT GMBH, Darmstadt (DE); CANCER RESEARCH TECHNOLOGY LIMITED, London (GB)

(72) Inventors: Kai Schiemann, Seeheim-Jugenheim (DE); Frank Stieber, Einhausen (DE); Michel Calderini, Darmstadt (DE); Julian Blagg, Surrey (GB); Aurelie Mallinger, Affleville (FR); Dennis Waalboer, Ljmuiden (NL); Christian Rink, Bonn (DE); Simon Ross Crumpler, Herfordshire (GB)

(73) Assignees: MERCK PATENT GMBH, Darmstadt (DE); Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/129,338

(22) PCT Filed: Mar. 10, 2015

(86) PCT No.: PCT/EP2015/000528
§ 371 (c)(1),
(2) Date: Sep. 26, 2016

(87) PCT Pub. No.: WO2015/144290
PCT Pub. Date: Oct. 1, 2015

(65) Prior Publication Data
US 2017/0107222 A1 Apr. 20, 2017

(30) Foreign Application Priority Data

Mar. 27, 2014 (EP) .................................... 14001145

(51) Int. Cl.

| | |
|---|---|
| A61P 19/02 | (2006.01) |
| A61P 35/00 | (2006.01) |
| C07D 471/10 | (2006.01) |
| A61K 31/444 | (2006.01) |
| A61P 25/16 | (2006.01) |
| C07D 401/14 | (2006.01) |
| C07D 471/20 | (2006.01) |
| A61K 31/4709 | (2006.01) |
| A61K 31/4725 | (2006.01) |
| A61K 31/499 | (2006.01) |
| A61K 31/5377 | (2006.01) |
| A61K 45/06 | (2006.01) |
| C07D 417/14 | (2006.01) |
| C07D 498/10 | (2006.01) |
| C07D 519/00 | (2006.01) |

(52) U.S. Cl.
CPC .......... *C07D 471/20* (2013.01); *A61K 31/444* (2013.01); *A61K 31/4709* (2013.01); *A61K 31/4725* (2013.01); *A61K 31/499* (2013.01); *A61K 31/5377* (2013.01); *A61K 45/06* (2013.01); *C07D 401/14* (2013.01); *C07D 417/14* (2013.01); *C07D 471/10* (2013.01); *C07D 498/10* (2013.01); *C07D 519/00* (2013.01)

(58) Field of Classification Search
CPC .. C07D 471/20; C07D 401/14; C07D 417/14; C07D 471/10; C07D 498/10; C07D 519/00; A61K 31/444; A61K 31/4709; A61K 31/4725; A61K 31/499; A61K 31/5377; A61K 45/06
USPC ......................................................... 546/208
See application file for complete search history.

(56) References Cited

U.S. PATENT DOCUMENTS

| | | | |
|---|---|---|---|
| 8,778,925 | B2 | 7/2014 | McDonald et al. |
| 2011/0190297 | A1 | 8/2011 | McDonald et al. |
| 2014/0350015 | A1 | 11/2014 | McDonald et al. |
| 2015/0353548 | A1* | 12/2015 | Schiemann .......... C07D 401/14 514/235.5 |

FOREIGN PATENT DOCUMENTS

| | | |
|---|---|---|
| WO | 2010041054 A1 | 4/2010 |
| WO | WO 2014063778 * | 5/2014 |

OTHER PUBLICATIONS

Kahn; Nature Reviews Drug Discovery 2014, 13, 513-532.*

(Continued)

*Primary Examiner* — Daniel R Carcanague
(74) *Attorney, Agent, or Firm* — Millen White Zelano and Branigan, PC

(57) ABSTRACT

The invention provides novel substituted pyridyl piperidine compounds according to Formula (I), their manufacture and use for the treatment of hyperproliferative diseases such as cancer, inflammatory or degenerative diseases.

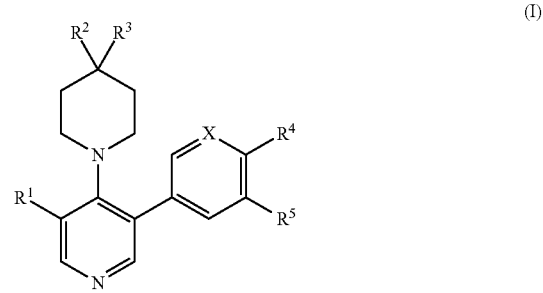

(I)

8 Claims, No Drawings

(56) References Cited

OTHER PUBLICATIONS

Barker; Nat Rev Drug Discov. 2006, 5, 997-1014.*
International Search Report for PCT/EP2015/000528 dated Jul. 13, 2015.
Mallinger, A. et al., "Discovery of Potent, Orally Bioavailable, Small-Molecule Inhibitors of WNT Signaling from a Cell-Based Pathway Screen," Journal of Medical Chemistry, 2015, vol. 58, pp. 1717-1735.

* cited by examiner

PYRIDYL PIPERIDINES

FIELD OF THE INVENTION

The invention relates to a series of novel substituted pyridyl piperidine compounds that are useful in the treatment of hyperproliferative diseases such as cancer, as well as inflammatory or degenerative diseases, in mammals. Also encompassed by the present invention is the use of such compounds in the treatment of hyperproliferative, inflammatory or degenerative diseases in mammals, especially humans, and pharmaceutical compositions containing such compounds.

SUMMARY OF THE RELATED ART

Wnt proteins comprise a large family of cysteine-rich secreted ligands that are highly conserved among species. Currently, three different pathways are believed to be activated by Wnt signaling: the canonical Wnt/β-catenin cascade, the noncanonical planar cell polarity pathway, and the Wnt/Ca$^{2+}$ pathway. Of these three, the canonical pathway is best understood and has the highest cancer relevance. Therefore, this project is focusing on canonical Wnt/β-catenin signaling.

In the canonical pathway, β-catenin is the key mediator of Wnt signaling. In the absence of Wnt ligands, a protein complex, that contains Axin, adenomatous polyposis coli (APC), glycogen synthase kinase 3β (GSK3β) and casein kinase 1 (CK1), functions in phosphorylating β-catenin and thereby marking it for destruction via ubiquitination and degradation by the proteasome. Following Wnt binding to a receptor complex composed of members of the Frizzled (Fz) family of seven transmembrane, serpentine receptors and low density lipoprotein receptor-related proteins 5/6 (LRP5/6), Disheveled (Dsh) and Axin are recruited to the plasma membrane. Subsequently, the Axin-APC-GSK3β complex is inhibited, non-phosphorylated β-catenin accumulates in the cytoplasm and then translocates into the nucleus where it regulates target gene expression in combination with members of the DNA-binding T cell factor/lymphoid enhancer factor (TCF/LEF) family. Many different target genes of canonical Wnt/β-catenin signaling have been described (e.g. c-Myc, Cyclin D1, VEGF, survivin) which are involved in cell growth, migration and survival (Logan & Nusse, Annu Rev Cell Dev Biol. 2004; 20:781-810).

The Wnt/β-catenin signaling cascade is frequently overactivated in different tumor types and several proteins of the pathway act as oncogenes or tumor suppressors (Giles et al., Biochim Biophys Acta. 2003 Jun. 5; 1653(1):1-24, van Es et al., Curr Opin Genet Dev. 2003 Feb. 13(1):28-33).

Most prominently, the tumor suppressor APC is mutated in nearly 60% of all colon cancers. In addition, many colon cancers express mutated β-catenin which cannot be phosphorylated and is therefore stabilized. Furthermore, loss of function mutations of the tumor suppressor Axin have been detected in hepatocellular, lung and colon cancers Thus, interference with Wnt/β-catenin signaling is a conceivable strategy for the treatment of cancer (reviewed in Dihlmann & von Knebel Doeberitz, Int. J. Cancer: 113, 515-524 (2005), Luu et al., Curr Cancer Drug Targets. 2004 Dec. 4(8):653-71).

WO 2010/041054 discloses a series of chemical compounds which act on the Wnt pathway.

However, as a therapeutic directed to this pathway has yet to be commercialized, a significant unmet medical need still exists, so that further promising Wnt pathway inhibitors have to be identified and developed.

For instance, compound "E60" disclosed on page 73 of WO 2010/041054, while exhibiting promising inhibitory activity (see Table A on page 93), at the same time has a high human hepatic microsomal intrinsic clearance (CLint). This is an unfavourable property for a pharmaceutical active ingredient, as it leads to higher and/or more frequent dosing as compared to compounds with a low CLint.

Other Wnt pathway inhibitors are described in PCT/EP2013/002966.

DESCRIPTION OF THE INVENTION

It is, therefore, the object of the present invention to provide novel Wnt pathway inhibitors useful in the treatment of inflammatory or hyperproliferative diseases, such as cancer in mammals, with superior pharmacological properties both with respect to their activities as well as their solubility, metabolic clearance and bioavailability characteristics.

As a result, this invention provides novel substituted pyridyl piperidine compounds or their stereoisomers or tautomers, or pharmaceutically acceptable salts, that are Wnt pathway inhibitors and useful as medicaments, especially in the treatment of the diseases mentioned above and below.

The compounds are defined by Formula (I):

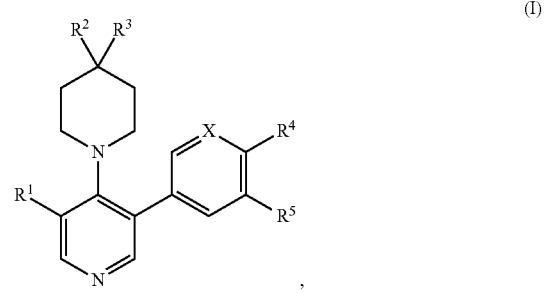

wherein:
X is CH or N,
R$^1$ is LA, Hal, CN,
R$^2$ is H, Hal, NH$_2$, LA, HO(LA)-, NH(LA),
R$^3$ is CN, CONH$_2$, CONH(LA) or
R$^2$, R$^3$ together with the C atom they are attached to, form a 5 or 6 membered non-aromatic heterocycle, having 1-3 heteroatoms, selected from O, S and N, which is substituted by 1 or 2 oxo groups, which heterocycle may further be monosubstituted by LA or OH, and which heterocycle may form a condensed ring system with a phenyl or pyridyl group,
R$^4$ is Cyc, CONH$_2$, COO(LA) or CONH(LA),
R$^5$ is H, or
R$^4$, R$^5$ together with the atoms they are attached to, form a 5 or 6 membered heterocycle, having 1-3 heteroatoms, selected from O, S and N, which is, optionally, independently mono- di- or trisubstituted by oxo, OH, LA, NH$_2$, NH(LA), N(LA)$_2$, NHCOO(LA) or HO(LA)-,
Cyc is a 5 or 6 membered monocyclic, aliphatic or aromatic homo- or heterocycle having 1-3 heteroatoms, selected from O, S and N, which may be mono- or di-substituted by oxo, LA, NH$_2$, NH(LA), N(LA)$_2$, HO(LA)-, or monosubstituted by CA, LA is unbranched or branched alkyl, having 1, 2, 3, 4 or 5 carbon atoms, which may be saturated or partially unsaturated, wherein 1, 2 or 3 H atoms may be replaced by Hal, and/or 1 CH$_3$ group may be replaced by CN, or 1 CH$_2$ group may be replaced by —O—, —NH— or —SO$_2$—, and/or 1 CH group may be replaced by N, CA is cycloalkyl having 3, 4, 5 or 6 carbon atoms, or cycloalkyl alkyl having 3, 4, 5 or 6 ring carbon atoms and 1 or 2 non-ring carbon atoms, in which cycloalkyl or cycloalkyl alkyl one ring atom may be replaced by O, and which cycloalkyl or cycloalkyl alkyl may be monosubstituted by OH, Hal is F, Cl, Br or I.

In general, all residues which occur more than once may be identical or different, i.e. are independent of one another. Above and below, the residues and parameters have the meanings indicated for the Formula (I), unless expressly indicated otherwise.

Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine, and preferably chlorine.

"LA" denotes for example methyl, ethyl, trifluoromethyl, difluoromethyl, 1,1,1-trifluoroethyl, propyl, isopropyl, methoxyethyl, dimethylaminomethyl, butyl, isobutyl, sec-butyl or tert-butyl, isopropenyl, ethenyl, ethynyl or prop-1-ynyl.

"CA" denotes for example cyclopropyl, (cyclopropyl)methyl, cyclobutyl, oxetanyl, hydroxyxyclopentyl or (cyclopentyl)ethyl.

"Cyc" denotes, for example phenyl, oxazolidine-2-, 3-, 4- or 5-yl, isoxazolidine-2-, 3-, 4- or 5-yl, 2,3-dihydro-2-, -3-, -4- or -5-furyl, 2,5-dihydro-2-, -3-, -4- or -5-furyl, tetrahydro-2- or -3-furyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, hexahydro-1-, -3- or -4-pyridazinyl, hexahydro-1-, -2-, -4- or -5-pyrimidinyl, 1-, 2- or 3-piperazinyl, 2- or 3-furyl, 1-, 2- or 3-pyrrolyl, 1-, 2- or 3-pyrrolidinyl, 1-, 2, 4- or 5-imidazolyl, 1-, 3-, 4- or 5-pyrazolyl, 2-, 3- or 4-pyridyl, 2-, 4-, 5- or 6-pyrimidinyl, pyrazin-2- or 3-yl, pyridazin-3- or 4-yl, 1,2,3-triazol-1-, -4- or -5-yl, 1,2,4-triazol-1-, -3- or 5-yl, 1- or 5-tetrazolyl.

In a preferred embodiment the compounds of the invention conform to Subformulae 1 to 15 of Formula (I), wherein in Subformula 1

X is CH,

R$^2$, R$^3$ together with the piperidine ring they are attached to, form 2,8-diaza-spiro[4.5]decan-1-one-yl, 2,8-diaza-spiro[4.5]decane-1,3-dione-yl, 1-oxa-3,8-diaza-spiro[4.5]decan-2-one-yl, 1,3,8-triaza-spiro[4.5]decane-2,4-dione-yl, 1,4,9-triaza-spiro[5.5]undecan-5-one-yl, 1,3,8-triaza-spiro[4.5]decane-4-one-yl, 2-methyl-1,3,8-triaza-spiro[4.5]dec-2-en-4-one-yl, 1,4,9-triaza-spiro[5.5]undecan-2,5-dione-yl, 1-methyl-1,3,8-triaza-spiro[4.5]decane-2,4-dione-yl, 4-hydroxy-2,8-diaza-spiro[4.5]decan-1-one-yl, 1,2,8-triaza-spiro[4.5]decan-3-one-yl, 4-methyl-2,3,8-triaza-spiro[4.5]dec-3-en-1-one-yl, (S)-3-trifluoromethyl-2,8-diaza-spiro[4.5]decan-1-one-yl, (R)-3-trifluoromethyl-2,8-diaza-spiro[4.5]decan-1-one-yl, 4-ethyl-2,3,8-triaza-spiro[4.5]dec-3-en-1-one-yl, 4-trifluoromethyl-2,3,8-triaza-spiro[4.5]dec-3-en-1-one-yl, spiro[1,3-dihydro-pyrrolo[3,2-b]pyridin-3,4'-piperidin]-2-one-yl, spiro[indoline-3,4'-piperidin]-2-one-yl, 4-methyl-1-oxa-3,8-diaza-spiro[4.5]decan-2-one-8-yl, in Subformula 2

X is CH,

R$^2$, R$^3$ together with the C atom they are attached to, form 1,3-Dihydro-indol-2-one-3-yl or 4-aza-1,3-dihydro-indol-2-one-3-yl, in Subformula 3

X is CH,

R$^4$ is pyridinyl, 1H-pyrazolyl, 1H-imidazolyl, each of which may be unsubstituted, or mono- or independently disubstituted by LA, CA, OH, or HO(LA)-, R$^5$ is H, in Subformula 4

R$^4$, R$^5$ together with the phenyl ring they are attached to, form 2H-indazolyl, 1H-indazolyl, 2-oxo-2,3-dihydro-benzooxazolyl, 3H-benzooxazol-2-one-yl, 2-oxo-2,3-dihydro-1H-indolyl, 3,4-dihydro-1H-quinolin-2-one-yl, 2,3-dihydro-1H-indolyl, 2,2-dioxo-2,3-dihydro-1H-benzo[c]isothiazolyl, 1,1-dioxo-2,3-dihydro-1H-benzo[b]thiophenyl, 3,4-dihydro-1H-quinolin-2-one-yl, isoquinolinyl, 3,4-dihydro-1H-[1,8]naphthyridin-2-one-yl, 2-tert-butyl-2,3-dihydro-benzo[d]isothiazole 1,1-dioxide-5-yl, 1,3-dihydro-benzo[c]thiophene 2,2-dioxide-5-yl each of which may be unsubstituted, or substituted by LA, OH, NH$_2$, HO(LA)- or NH(LA)-, NHCOO(LA)

in Subformula 5

X is CH,

R$^1$ is Cl, F or CF$_3$, in Subformula 6

X is CH,

R$^1$ is Cl, in Subformula 7

X is CH,

R$^4$ is 1-methyl-1H-pyrazol-3-yl, 6-amino-pyridin-3-yl, 1-(2-hydroxy-ethyl)-1H-pyrazol-4-yl, (2-hydroxy-2-methyl-propyl)-1H-pyrazol-4-yl, (2-methanesulfonyl-ethyl)-1H-pyrazol-4-yl, 1,2-dimethyl-1H-imidazol-4-yl, 1-Isopropyl-1H-pyrazol-4-yl, 1-cyclopropyl-1H-pyrazol-4-yl, 1-oxetan-3-yl-1H-pyrazol-4-yl, 2-hydroxy-cyclopentyl)-1H-pyrazol-4-yl, (2-cyanoethyl)-1H-pyrazol-4-yl.

R$^5$ is H, in Subformula 8

R$^4$, R$^5$ together with the phenyl ring they are attached to, form 2-ethyl-2H-indazol-5-yl, 1-methyl-1H-indazol-5-yl, 1H-indazol-5-yl, 1H-indazol-6-yl, 1-methyl-1H-indazol-6-yl, 2-methyl-2H-indazol-5-yl, 2-oxo-2,3-dihydro-benzooxazol-5-yl, 2-oxo-2,3-dihydro-1H-indol-6-yl, (3H-benzooxazol-2-one)-5-yl, 1-methyl-2-oxo-2,3-dihydro-1H-indol-5-yl, 1-methyl-2-oxo-2,3-dihydro-1H-indol-6-yl, (3,4-dihydro-1H-quinolin-2-one)-7-yl, 1-methyl-2-oxo-2,3-dihydro-1H-indol-5-yl, 1H-indol-6-yl, 2-oxo-2,3-dihydro-1H-indol-6-yl, 3-amino-1H-indazol-6-yl, 1-methyl-2,2-dioxo-2,3-dihydro-1H-benzo[c]isothiazol-5-yl, 2,2-dioxo-2,3-dihydro-1H-benzo[c]isothiazol-5-yl, 2-isopropyl-2H-indazol-5-yl, 3-hydroxy-1,1-dioxo-2,3-dihydro-1H-benzo[b]thiophen-5-yl, isoquinolin-6-yl, 2-tert-Butyl-1,1-dioxo-2,3-dihydro-1H-benzo[d]isothiazol-5-yl, 3,4-dihydro-1H-[1,8]naphthyridin-2-one-6-yl, 2-oxo-2,3-dihydro-1H-indol-6-yl, (3H-benzooxazol-2-one)-5-yl, (3,4-dihydro-1H-quinolin-2-one)-7-yl, 2,3-dihydro-1H-indol-6-yl, (1H-indazol-3-yl)-carbamic acid methyl ester-5-yl, 1-methyl-1H-indazol-3-ylamine-6-yl, 1-methyl-1,3-dihydro-benzo[c]isothiazole 2,2-dioxide-5-yl, methyl-(1H-indazol-3-yl)-amine-6-yl, in Subformula 9
X is CH,
R² is LA, Hal, NH₂,
R³ is CN, CONH₂,
in Subformula 10
X is CH,
R² is NH₂, methoxy methyl, hydroxy methyl, hydroxy ethyl, F,
R³ is CN, CONH₂,
in Subformula 11
X is CH,
R² is NH₂,
R³ is CONH₂,
in Subformula 12
X is CH,
R², R³ together with the piperidine ring they are attached to, form 1,3,8-triaza-spiro[4.5]decane-4-one-8-yl, 1-oxa-3,8-diaza-spiro[4.5]decan-2-one-8-yl, 2,8-diaza-spiro[4.5]decane-1,3-dione-8-yl, 2-methyl-1,3,8-triaza-spiro[4.5]dec-2-en-4-one-8-yl, 1,3,8-triaza-spiro[4.5]decane-2,4-dione-8-yl, 1,4,9-triaza-spiro[5.5]undecan-5-one-9-yl, 1,4,9-triaza-spiro[5.5]undecan-2,5-dione-9-yl, 2,8-diaza-spiro[4.5]decan-1-one-8-yl, 4-methyl-1-oxa-3,8-diaza-spiro[4.5]decan-2-one-8-yl,
in Subformula 13
X is CH,
R¹ is Cl or CF₃,
R², R³ together with the piperidine ring they are attached to, form 1,3,8-triaza-spiro[4.5]decane-4-one-8-yl, 1-oxa-3,8-diaza-spiro[4.5]decan-2-one-8-yl, 2,8-diaza-spiro[4.5]decane-1,3-dione-8-yl, 2-methyl-1,3,8-triaza-spiro[4.5]dec-2-en-4-one-8-yl, 1,3,8-triaza-spiro[4.5]decane-2,4-dione-8-yl, 1,4,9-triaza-spiro[5.5]undecan-5-one-9-yl, 1,4,9-triaza-spiro[5.5]undecan-2,5-dione-9-yl, 2,8-diaza-spiro[4.5]decan-1-one-8-yl, 4-methyl-1-oxa-3,8-diaza-spiro[4.5]decan-2-one-8-yl,
in Subformula 14
X is CH,
R¹ is Cl or CF₃, $R^1$ is Cl or CF$_3$,
R⁴ is 1-methyl-1H-pyrazol-3-yl, 6-amino-pyridin-3-yl, 1-(2-hydroxy-ethyl)-1H-pyrazol-4-yl, (2-hydroxy-2-methyl-propyl)-1H-pyrazol-4-yl, (2-methanesulfonyl-ethyl)-1H-pyrazol-4-yl, 1,2-dimethyl-1H-imidazol-4-yl, 1-Isopropyl-1H-pyrazol-4-yl, 1-cyclopropyl-1H-pyrazol-4-yl, 1-oxetan-3-yl-1H-pyrazol-4-yl, 2-hydroxy-cyclopentyl)-1H-pyrazol-4-yl, (2-cyanoethyl)-1H-pyrazol-4-yl.
R⁵ is H, or,
R⁴, R⁵ together with the phenyl ring they are attached to, form 1-methyl-2,2-dioxo-2,3-dihydro-1H-benzo[c]isothiazol-5-yl, 1-methyl-1H-indazol-6-yl, 2,2-dioxo-2,3-dihydro-1H-benzo[c]isothiazol-5-yl, 3-Amino-1H-indazol-6-yl, 1-methyl-1H-indazol-5-yl, 1-methyl-2-oxo-2,3-dihydro-1H-indol-5-yl, 2-isopropyl-2H-indazol-5-yl, 2-oxo-2,3-dihydro-benzooxazol-5-yl,
in Subformula 15
X is CH,
R¹ is Cl or CF₃,
R² is NH₂,
R³ is CONH₂, or,
R², R³ together with the piperidine ring they are attached to, form 1,3,8-triaza-spiro[4.5]decane-4-one-8-yl, 1-oxa-3,8-diaza-spiro[4.5]decan-2-one-8-yl, 2,8-diaza-spiro[4.5]decane-1,3-dione-8-yl, 2-methyl-1,3,8-triaza-spiro[4.5]dec-2-en-4-one-8-yl, 1,3,8-triaza-spiro[4.5]decane-2,4-dione-8-yl, 1,4,9-triaza-spiro[5.5]undecan-5-one-9-yl, 1,4,9-

R⁴ is 1-methyl-1H-pyrazol-3-yl, 6-amino-pyridin-3-yl, 1-(2-hydroxy-ethyl)-1H-pyrazol-4-yl, (2-hydroxy-2-methyl-propyl)-1H-pyrazol-4-yl, (2-methanesulfonyl-ethyl)-1H-pyrazol-4-yl, 1,2-dimethyl-1H-imidazol-4-yl, 1-Isopropyl-1H-pyrazol-4-yl, 1-cyclopropyl-1H-pyrazol-4-yl, 1-oxetan-3-yl-1H-pyrazol-4-yl, 2-hydroxy-cyclopentyl)-1H-pyrazol-4-yl, (2-cyanoethyl)-1H-pyrazol-4-yl.
R⁵ is H, or,
R⁴, R⁵ together with the phenyl ring they are attached to, form 1-methyl-2,2-dioxo-2,3-dihydro-1H-benzo[c]isothiazol-5-yl, 1-methyl-1H-indazol-6-yl, 2,2-dioxo-2,3-dihydro-1H-benzo[c]isothiazol-5-yl, 3-Amino-1H-indazol-6-yl, 1-methyl-1H-indazol-5-yl, 1-methyl-2-oxo-2,3-dihydro-1H-indol-5-yl, 2-isopropyl-2H-indazol-5-yl, 2-oxo-2,3-dihydro-benzooxazol-5-yl,
and the remaining residues have the meaning as indicated for Formula (I).

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

It is well known that atoms may have atomic masses or mass numbers which differ from the atomic masses or mass numbers of the atoms which usually occur naturally. Examples of isotopes which are readily commercially available and which can be incorporated into a compound of the present invention by well-known methods include isotopes of hydrogen, carbon, nitrogen, oxygen, phosphorus, fluorine and chlorine, for example ²H, ³H, ¹³C, ¹⁴C, ¹⁵N, ¹⁸O, ¹⁷O, ³¹P, ³²P, ³⁵S, ¹⁸F and ³⁶Cl, respectively. Incorporation of heavier isotopes, especially deuterium (²H), into a compound of the invention has therapeutic advantages owing to the higher metabolic stability of this isotope-labelled compound. Higher metabolic stability translates directly into an increased in vivo half-life or lower dosages. Therefore, these isotopes are included in the definition of atoms H, C, N etc., as used in the chemical compounds of this invention.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
  a) all stereoisomers or tautomers of the compounds, including mixtures thereof in all ratios,
  b) prodrugs of the compounds, or stereoisomers or tautomers of these prodrugs,
  c) pharmaceutically acceptable salts of the compounds and of the items mentioned under (a) and (b),
  d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising a compound of the present invention, or its stereoisomers or tautomers, or pharmaceutically acceptable salts of each of the foregoing, including mixtures thereof in all ratios, as active ingredient, together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or other Wnt pathway inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head & neck, renal, kidney, liver, ovarian, prostate, uterine, oesophageal, testicular, gynecological, thyroid cancer, melanoma, as well as hematologic malignancies such as acute myelogenous leukemia, multiple myeloma, chronic myelogneous leukemia, myeloid cell leukemia, Kaposi's sarcoma, or any other type of solid or liquid tumors. Preferably, the cancer to be treated is chosen from colon, lung, breast and hematological tumor types.

In addition, said compounds and pharmaceutical composition are for the treatment of inflammatory diseases such as multiple sclerosis, rheumatoid arthritis, systemic lupus, inflammatory bowel diseases or degenerative diseases such as osteoarthritis and Alzheimer's disease.

The anti-cancer treatment defined above and below may be applied as a monotherapy or may involve, in addition to the herein disclosed compounds of Formula (I), conventional surgery or radiotherapy or medicinal therapy. Such medicinal therapy, e.g. a chemotherapy or a targeted therapy, may include one or more, but preferably one, of the following anti-tumor agents:

Alkylating agents, such as altretamine, bendamustine, busulfan, carmustine, chlorambucil, chlormethine, cyclophosphamide, dacarbazine, ifosfamide, improsulfan tosilate, lomustine, melphalan, mitobronitol, mitolactol, nimustine, ranimustine, temozolomide, thiotepa, treosulfan, mechloretamine, carboquone, apaziquone, fotemustine, glufosfamide, palifosfamide, pipobroman, trofosfamide, uramustine;

Platinum Compounds, such as carboplatin, cisplatin, eptaplatin, miriplatine hydrate, oxaliplatin, lobaplatin, nedaplatin, picoplatin, satraplatin;

DNA altering agents, such as amrubicin, bisantrene, decitabine, mitoxantrone, procarbazine, trabectedin, clofarabine, amsacrin, brostallicin, pixantrone, laromustine;

Topoisomerase inhibitors, such as etoposide, irinotecan, razoxane, sobuzoxane, teniposide, topotecan, amonafide, belotecan, elliptinium acetate, voreloxin;

Microtubule modifiers, such as cabazitaxel, docetaxel, eribulin, ixabepilone, paclitaxel, vinblastine, vincristine, vinorelbine, vindesine, vinflunine, fosbretabulin, tesetaxel:

Antimetabolites, such as asparaginase, azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur, doxifluridine, elacytarabine, raltitrexed, sapacitabine, tegafur, trimetrexate;

Anticancer antibiotics, such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin, aclarubicin, peplomycin, pirarubicin;

Hormones/Antagonists, such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol, acolbifene, danazol, deslorelin, epitiostanol, orteronel, enzalutamide;

Aromatase inhibitors, such as aminoglutethimide, anastrozole, exemestane, fadrozole, letrozole, testolactone, formestane;

Small molecule kinase inhibitors, such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib, afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib, cabozantinib S-malate, carfilzomib, ibrutinib, icotinib;

Photosensitizers. such as methoxsalen, porfimer sodium, talaporfin, temoporfin;

Antibodies, such as alemtuzumab, besilesomab, brentuximab vedotin, cetuximab, denosumab, ipilimumab, ofatumumab, panitumumab, rituximab, tositumomab, trastuzumab, bevacizumab, catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab, onartuzumab, pertuzumab, racotumomab, tabalumab;

Cytokines, such as aldesleukin, interferon alfa, interferon alfa2a, interferon alfa2b, tasonermin, teceleukin, oprelvekin;

Drug conjugates, such as denileukin diftitox, ibritumomab tiuxetan, iobenguane I123, prednimustine, trastuzumab emtansine, estramustine, gemtuzumab ozogamicin, aflibercept, cintredekin besudotox, edotreotide, inotuzumab ozogamicin, naptumomab estafenatox, oportuzumab monatox, technetium (99mTc) arcitumomab, vintafolide;

Vaccines, such as sipuleucel, vitespen, emepepimut-S, oncoVAX, rindopepimut, troVax, stimuvax;

Miscellaneous agents, such as alitretinoin, bexarotene, bortezomib, everolimus, ibandronic acid, imiquimod, lenalidomide, lentinan, metirosine, mifamurtide, pamidronic acid, pegaspargase, pentostatin, sipuleucel, sizofiran, tamibarotene, temsirolimus, thalidomide, tretinoin, vismodegib, zoledronic acid, thalidomide, vorinostat, celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine, picibanil, reolysin, retaspimycin hydrochloride, trebananib, virulizin.

In particular, this invention relates to a method for inhibiting abnormal cell growth in a mammal or treating a hyperproliferative disorder that comprises administering to the mammal an amount of a compound of the present invention or pharmaceutical composition, in combination with radiotherapy, wherein the amounts of the compound or pharmaceutical composition, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective in sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating inflammatory, degenerative or hyperproliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or its stereoisomers or tautomers, or pharmaceutically acceptable salts of each of the foregoing, including mixtures thereof in all ratios, and
b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

Experimental Section

Some abbreviations that may appear in this application are as follows:

Abbreviations

| Designation | |
|---|---|
| aq. | Aqueous |
| ATP | Adenosine triphosphate |
| b | Broad peak |
| Boc | tert-Butyl carbamate |
| Boc$_2$O | Di-tert-butyl dicarbonate |
| calc | Calculated |
| CDCl$_3$ | Deutero-Chloroforme |
| cHec, CyHex | Cyclohexyl |
| cHex | Cyclohexane |
| d | Doublet |
| dba | Dibenzylidene acetone |
| DCM | Dichloromethane |
| DMAP | 4-(Dimethylamino)-pyridine |
| DME | Ethylene glycol dimethylether |
| DMF | Dimethylformamide |
| DMSO | Dimethyl sulfoxide |
| dppf | Bis(diphenylphosphino)ferrocene |
| EDCl | 1-Ethyl-3-(3-dimethylaminopropyl)carbodiimide |
| Eq. | Equivalents |
| ESI | Electrospray ionisation |
| EtOAc | Ethyl acetate |
| EtOH | Ethanol |
| h, hr | Hour(s) |
| HMDS | Hexamethyldisilazane |
| HPLC | High Pressure Liquid Chromatography |
| HRMS | High resolution mass spectrometry |
| LC/MS | Liquid Chromatography coupled to Mass Spectrometry |
| LiHMDS | Lithium hexamethyldisilazide |
| m | Multiplet |
| m/z | Mass-to-charge ratio |
| min | Minute |
| MS | Mass spectrometry |
| MTBE | Methyl tert.-butyl ether |
| N | Normal (unit of concentration) |
| nd | Not determined |
| NMP | N-Methyl-2-pyrrolidinone |
| NMR, 1H | Nuclear Magnetic Resonance, proton |
| PMB | Para methoxy benzyl |
| q | Quartette (or quartet) |
| Rf | Retention factor |
| RT | Room temperature |
| Rt | Retention time |
| s | Singlet |
| sat. | Saturated |
| t | Triplet |
| TBAF | Tetrybutylammoniumchloride |
| tert | Tertiary |
| TFA | Trifluoro acetic acid |
| THF | Tetrahydrofuran |
| TLC | Thin layer chromatography |
| TMS | Trimethylsilane |
| UV | Ultraviolet |
| Xphos | 2-Dicyclohexylphosphino-2',4',6'-triisopropylbiphenyl |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at RT. Compounds were purified by either silica chromatography or preparative HPLC.

The present invention relates also to a process for the manufacture of compounds of Formula (I), wherein a compound of Formula (V)

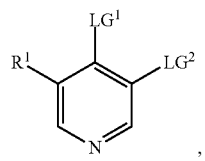

(V)

is reacted with a compound of Formula (IV)

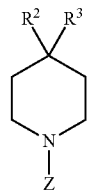

(IV)

to yield a compound of Formula (III)

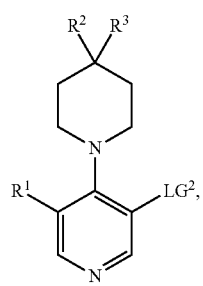

(III)

which is then further reacted with a compound of Formula (II)

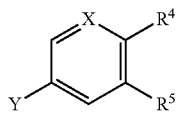

to yield a compound of Formula (I).

LG$^1$ is a leaving group typically used in nucleophilic aromatic substitutions, preferably Hal, such as F, Cl or Br. LG$^2$ is a reactive group capable of reacting in metal-catalyst reactions (e.g. Suzuki reaction), such as Cl, Br or I.

Z is H, or a typical amine protecting group such as BOC, which is cleaved off under the reaction conditions. Y is a boronic acid or a boronic ester.

EXAMPLES

The working examples presented below are intended to illustrate particular embodiments of the invention, and are not intended to limit the scope of the specification or the claims in any way.

Chemical Synthesis

In this section experimental details are provided for a number of Example compounds according to Formula (I), and synthetic intermediates thereof.

General Scheme:

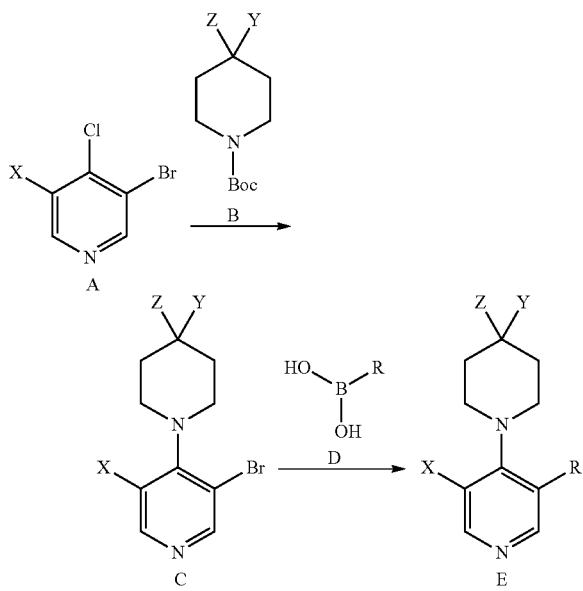

General Procedures:
General Procedure A: Nucleophilic Aromatic Substitution

Pyridine A (1 eq.) and amine-derivative B (1 eq.) were loaded in a microwave vial. The capped vial was evacuated using high vacuum and purged with nitrogen (each three times). Triethylamine (3 eq.) and dry NMP (or dry 1-methoxy-2-propanol) (0.44 mol/L) were added and the mixture was degassed using the high vacuum and purged with nitrogen (each three times). The reaction mixture was heated under microwave irradiation at 220° C. for 1 hr (or until completion) before it was added dropwise into water (10× amount of NMP). The resulting precipitate was filtered off and washed with water to give crude product. If the product did not precipitate, then the mixture was diluted with EtOAc and the organic layer was separated. The aqueous layer was extracted twice with EtOAc. The combined organic layers were washed with water, dried over MgSO$_4$, filtered and the solvent was evaporated under reduced pressure. The resulting oil, or the precipitate obtained from the filtration above, was purified by chromatography on silica gel (biotage, DCM/EtOH) to give the product as a white solid.

When 1-methoxy-2-propanol is used as solvent, the mixture was directly concentrated under vacuum and purified by chromatography on silica gel.

General Procedure B: Suzuki Cross Coupling

Bromopyridine C (1 eq.), boronic acid D (1 eq.) and Pd(dppf)Cl$_2$.CH$_2$Cl$_2$ or Pd(PPh$_3$)$_4$ (0.05 eq.) were loaded in a microwave vial. The capped vial was evacuated using high vacuum and purged with nitrogen (each three times). Degassed acetonitrile (0.15 mol/L) and degassed aqueous sodium carbonate (0.5 M, 1.4 eq.) were added. The mixture was heated under microwave irradiation at 120° C. for 1 hr before being concentrated under reduced pressure. The crude was purified by chromatography on silica gel (biotage, DCM/EtOH) to give the product.

Work Up and Purification Methods A to R:
A—The reaction was diluted with DCM and water. The layers were separated and the aqueous layer was extracted with DCM and the combined organic layers were then dried over MgSO$_4$
B—The reaction was diluted with EtOAc and water. The layers were separated and the aqueous layer was extracted with EtOAc and the combined organic layers were then dried over MgSO$_4$
C—Evaporation of the solvent (rotavapor or biotage V10, azeotropic remove) of water with toluene or drying in high vacuum when necessary)
D—The reaction mixture was poured onto water and the solid was collected by filtration
E—Purification by using an SCX2 cartridge
F—Purification by prep. HPLC (Gilson, acetonitrile/water gradient+0.1% formic acid)
G—Purification by prep. TLC with DCM/EtOH
H—Purification by prep. HPLC (acetonitrile/water gradient)
I—Purification by flash chromatography on silica with DCM/EtOH
J—Purification by flash chromatography on silica with DCM/MeOH
K—Purification by flash chromatography on silica with CyHex/EtOAc
L—Purification by flash chromatography on silica with DCM/EtOAc
M—Purification by trituration with DCM/Et$_2$O
N—Purification by trituration with acetonitrile
O—Purification by trituration with CHCl$_3$/CyHex
P—Purification by trituration with EtOAc
Q—The reaction mixture was diluted with acetonitrile, filtered and the filtrate was evaporated to dryness.
R—The reaction mixture was diluted with EtOAc, filtered and the filtrate was evaporated to dryness.

HPLC Methods A to G:
HPLC Method (A)
   Solvent A: water+0.05% formic acid
   Solvent B: acetonitrile+0.04% formic acid
   Flow: 2.0 mL/min, wave length: 220 nm
   Gradient: 0.0 min 4% B
   2.8 min 100% B
   3.3 min 100% B
   Column: Chromolith Performance RP-18e 100-3

HPLC Method (B)
Solvent A: water+0.1% TFA
Solvent B: acetonitrile+0.1% TFA
Flow: 2.0 mL/min, wave length: 220 nm
Gradient: 0.0 min 1% B
0.2 min 1% B
3.8 min 100% B
4.2 min 100% B
Column: Chromolith Performance RP-18e 100×3 mm HPLC Method (C)
Solvent A: water+0.1% formic acid
Solvent B: acetonitrile+0.08% formic acid
Flow: 0.9 mL/min, wave length: 220 nm
Gradient: 0.0 min 2% B
1.0 min 100% B
1.3 min 100% B
Column: Acquity UPLC® BEH C18 1.7 µM HPLC Method (D)
Solvent A: water+0.1% formic acid
Solvent B: MeOH+0.1% formic acid
Flow: 2.0 mL/min, wave length: 254 nm
Gradient: 0.0 min 10% B
2.5 min 90% B
3.5 min 90% B
3.8 min 10% B
4.0 min 10% B
Column: Chromolith SpeedROD RP-18e 50×4.6 mm (Merck KGaA)

HPLC Method (E)
Solvent A: water+0.1% formic acid
Solvent B: MeOH+0.1% formic acid
Flow: 1.5 mL/min, wave length: 254 nm
Gradient: 0.0 min 10% B
2.5 min 90% B
3.5 min 90% B
3.8 min 10% B
4.0 min 10% B
Column: Purospher STAR RP-18e 30×4 mm (Merck KGaA)

HPLC Method (F)
Solvent A: water+0.1% formic acid
Solvent B: MeOH+0.1% formic acid
Flow: 1.5 mL/min, wave length: 220 nm
Gradient: 0.0 min 10% B
2.5 min 90% B
3.5 min 90% B
3.8 min 10% B
4.0 min 10% B
Column: Purospher STAR RP-18e 30×4 mm (Merck KGaA)

HPLC Method (G)
Solvent A: water+0.1% formic acid
Solvent B: MeOH+0.1% formic acid
Flow: 1.5 mL/min, wave length: 254 nm
Gradient: 0.0 min 10% B
1.0 min 90% B
3.5 min 90% B
3.8 min 10% B
4.0 min 10% B Column: Purospher STAR RP-18e 30×4 mm (Merck KGaA)

Synthesis of 8-[3-chloro-5-[4-(1-methyl-1H-pyrazol-4-yl)-phenyl]-pyridin-4-yl]-2,8-diaza-spiro[4.5]decan-1-one a. 8-(3-Bromo-5-chloropyridin-4-yl)-2,8-diazaspiro[4.5]decan-1-one C1

Synthesised according to general procedure A. From 3-bromo-4,5-dichloropyridine A1 (1.0 g, 4.41 mmol), boc-2,8-diazaspiro[4.5]decan-1-one (1.35 g, 5.29 mmol) and triethylamine (1.8 ml, 13.22 mmol) in 1-methoxy-2-propanol (11 ml), the title product (1.14 g, 75%) was isolated using purification methods C and I.

1H NMR (500 MHz, CDCl$_3$) ppm=8.49 (s, 1H), 8.35 (s, 1H), 6.00 (bs, 1H), 3.41-3.32 (m, 6H), 2.20-2.11 (m, 4H), 1.58-1.52 (m, 2H). LC-MS (ESI, m/z) Rt=2.68 min-346 (M+H)$^+$ (HPLC method E).

b. 8-{3-Chloro-5-[4-(1-methyl-1H-pyrazol-4-yl)-phenyl]-pyridin-4-yl}-2,8-diaza-spiro[4.5]decan-1-one 89

Synthesised according to general procedure B. From 8-(3-bromo-5-chloropyridin-4-yl)-2,8-diazaspiro[4.5]decan-1-one C1 (250 mg, 0.725 mmol), 1-methyl-4-(4-(4,4,5,5-tetramethyl-1,3,2-dioxaborolan-2-yl)phenyl)-1H-pyrazole (268 mg, 0.943 mmol) and Pd(dppf)Cl$_2$·CH$_2$Cl$_2$ (30 mg, 0.036 mmol) in degassed acetonitrile (13 ml) and aqueous sodium carbonate (0.5 M, 2.0 ml, 1.0 mmol), the title product (233 mg, 76%) was isolated using purification methods A and I.

1H NMR (500 MHz, CDCl3) ppm=8.43 (s, 1H), 8.21 (s, 1H), 7.81 (s, 1H), 7.68 (s, 1H), 7.56 (d, J=8.3, 2H), 7.28 (d, J=8.3, 2H), 5.98 (bs, 1H), 3.96 (s, 3H), 3.28 (t, J=6.8, 2H), 3.18-3.13 (m, 2H), 2.78-2.70 (m, 2H), 2.00-1.93 (m, 4H), 1.38-1.32 (m, 2H). HRMS m/z (ESI$^+$) [M+H]$^+$ C$_{23}$H$_{25}$ClN$_5$O, calc 422.1742, found 422.1730, Rt=2.37 min (HPLC method E).

TABLE 1

Intermediates C1 to C15 prepared according to General Procedure A

| No | Structures | Starting material | | Purification method | NMR | MS | RT |
|---|---|---|---|---|---|---|---|
| C1 | (structure) | 3-bromo-4,5-dichloro-pyridine | boc-2,8-diazaspiro[4.5]decan-1-one | C, I | 1H NMR (500 MHz, CDCl$_3$) ppm = 8.49 (s, 1H), 8.35 (s, 1H), 6.00 (bs, 1H), 3.41-3.32 (m, 6H), 2.20-2.11 (m, 4H), 1.58-1.52 (m, 2H) | 344/ 346 | 2.68 (E) |
| C2 | (structure) | 3-bromo-4,5-dichloro-pyridine | 2,8-diazaspiro[4.5]decane-1,3-dione | D | 1H NMR (500 MHz, DMSO-d6) ppm = 11.18 (bs, 1H), 8.57 (s, 1H), 8.47 (s, 1H), 3.30-3.24 (m, 4H), 2.69 (s, 2H), 2.01-1.94 (m, 2H), 1.70-1.64 (m, 2H) | 358/ 360 | 2.50 (E) |
| C3 | (structure) | 3,4,5-trichloro-pyridine | 2,8-diazaspiro[4.5]decane-1,3-dione | E, P | 1H NMR (500 MHz, DMSO-d6) ppm = 8.27 (s, 2H), 8.26 (bs, 1H), 3.56-3.48 (m, 2H), 3.38-3.30 (m, 2H), 2.74 (s, 2H), 2.33-2.25 (m, 2H), 1.75-1.68 (m, 2H) | 314/ 316 | 2.43 (D) |
| C4 | (structure) | 3-bromo-4,5-dichloro-pyridine | spiro[piperidine-4,3'-pyrrolo[2,3-b]pyridin]-2'(1'H)-one dihydrochloride | D, J | 1H NMR (500 MHz, CDCl$_3$) ppm = 8.52 (s, 1H), 8.39 (s, 1H), 8.28 (dd, J = 4.8, 1.5, 1H), 8.09 (s, 1H), 7.19 (dd, J = 7.8, 1.5, 1H), 7.15 (dd, J = 7.8, 4.8, 1H), 3.90-3.70 (m, 4H), 2.10 (m, 4H) | 393/ 395 | 2.91 (E) |

TABLE 1-continued

Intermediates C1 to C15 prepared according to General Procedure A

| No | Structures | Starting material | | Purification method | NMR | MS | RT |
|----|-----------|-------------------|--|---------------------|-----|-----|-----|
| C5 | 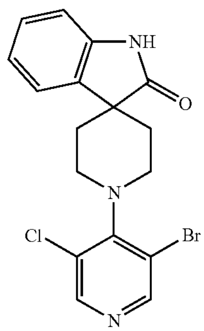 [SMILES: O=C1Nc2ccccc2C12CCN(c1c(Cl)cncc1Br)CC2] | 3-bromo-4,5-dichloro-pyridine | tert-butyl 2-oxospiro[indoline-3,4'-piperidine]-1'-carboxylate | C, J | 1H NMR (500 MHz, CDCl3) ppm = 8.54 (s, 1H), 8.41 (s, 1H), 7.88 (s, 1H), 7.47 (d, J = 7.6, 1H), 7.26 (td, J = 7.8, 1.1, 1H), 7.09 (td, J = 7.6, 1.1, 1H), 6.94 (d, J = 7.8, 1H), 3.89-3.77 (m, 2H), 3.58-3.48 (m, 2H), 2.15-2.06 (m, 2H), 2.04-1.94 (m, 2H) | 394/396 | 3.21 (E) |
| C6 | 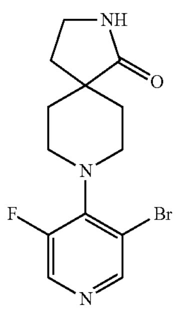 [SMILES: O=C1NCCC12CCN(c1c(F)cncc1Br)CC2] | 3-bromo-4-chloro-5-fluoro-pyridine | boc-2,8-diazaspiro[4.5]decan-1-one | C, I | 1H NMR (500 MHz, CDCl$_3$) ppm = 8.41 (s, 1H), 8.24 (d, J = 3.6, 1H), 6.88 (bs, 1H), 3.52-3.46 (m, 2H), 3.40 (t, J = 6.8, 2H), 3.26-3.19 (m, 2H), 2.17-2.09 (m, 4H), 1.58-1.53 (m, 2H) | 328/330 | 2.55 (E) |
| C7 | 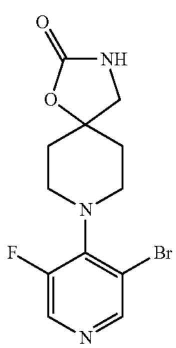 [SMILES: O=C1NCC2(CCN(c3c(F)cncc3Br)CC2)O1] | 3-bromo-4-chloro-5-fluoro-pyridine | 1-oxa-3,8-diazaspiro[4.5]decan-2-one acetate | C, I | 1H NMR (500 MHz, CDCl$_3$) ppm = 8.43 (s, 1H), 8.27 (d, J = 3.3, 1H), 6.22 (bs, 1H), 3.60-3.52 (m, 2H), 3.44 (s, 2H), 3.33-3.26 (m, 2H), 2.14-2.08 (m, 2H), 2.00-1.93 (m, 2H) | 330/332 | 2.32 (E) |
| C8 | 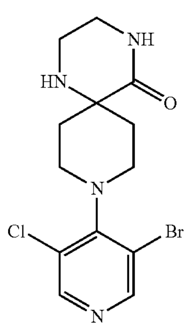 [SMILES: O=C1NCCNC12CCN(c1c(Cl)cncc1Br)CC2] | 3-bromo-4,5-dichloro-pyridine | tert-butyl-5-oxo-1,4,9-triazaspiro[5.5]undecane-9-carboxylate | D, I | 1H NMR (500 MHz, DMSO) ppm = 8.53 (s, 1H), 8.42 (s, 1H), 7.52 (s, 1H), 3.56 (td, J = 11.0 2.2, 2H), 3.15 (td, J = 11.0, 2.2, 2H), 3.06-2.98 (m, 2H), 2.85 (t, J = 4.6, 2H), 2.36 (bs, 1H), 2.12 (td, J = 12.8, 4.6, 2H), 1.68-1.59 (m, 2H). | 359/361 | 1.44 (E) |

TABLE 1-continued

Intermediates C1 to C15 prepared according to General Procedure A

| No | Structures | Starting material | | Purification method | NMR | MS | RT |
|---|---|---|---|---|---|---|---|
| C9 | (structure) | 3-bromo-4,5-dichloro-pyridine | 1-oxa-3,8-diazaspiro[4.5]decan-2-one acetate | D | — | 346/348 | 1.91 (B) |
| C10 | (structure) | 3-bromo-4,5-dichloro-pyridine | 2-methyl-1,3,8-triazaspiro[4.5]dec-1-en-4-one dihydrochloride | A | — | 359/361 | 1.65 (A) |
| C11 | (structure) | 3-bromo-4,5-dichloro-pyridine | 1,2,8-Triazaspiro[4.5]decan-3-one | C, A, J | — | 345/347 | 1.66 (A) |
| C12 | (structure) | 3-bromo-4,5-dichloro-pyridine | 4-Carbamoyl-4-fluoro-piperidine-1-carboxylic acid tert-butyl ester | C, A J | — | 336/338 | 1.93 (A) |

TABLE 1-continued

Intermediates C1 to C15 prepared according to General Procedure A

| No | Structures | Starting material | | Purification method | NMR | MS | RT |
|---|---|---|---|---|---|---|---|
| C13 | (Chiral) structure with CF3, pyrrolidinone spiro piperidine, Cl/Br pyridine | 3-bromo-4,5-dichloro-pyridine | (S)-1-Oxo-3-trifluoro-methyl-2,8-diaza-spiro[4.5]decane-2-carboxylic acid tert-butyl ester | C, B | — | 412/414 | 2.26 (A) |
| C14 | (Chiral) structure with CF3, pyrrolidinone spiro piperidine, Cl/Br pyridine | 3-bromo-4,5-dichloro-pyridine | (R)-1-Oxo-3-trifluoro-methyl-2,8-diaza-spiro[4.5]decane-2-carboxylic acid tert-butyl ester | C, B | — | 412/414 | 2.24 (A) |
| C15 | hydantoin spiro piperidine, Cl/Br pyridine | 3-bromo-4,5-dichloro-pyridine | 1,3,8-Triaza-spiro[4.5]decane-2,4-dione hydrochloride | D | — | 359/361 | 1.75 (A) |
| C16 | 4-methyl oxazolidinone spiro piperidine, Cl/Br pyridine | 3-bromo-4,5-dichloro-pyridine | 4-Methyl-1-oxa-3,8-diaza-spiro[4.5]decan-2-one | D | — | 360/362 | 1.93 (A) |

TABLE 2

Examples E prepared according to General Procedure B.

| No | Structures | Starting material | Purification method | NMR | MS | RT |
|----|-----------|-------------------|---------------------|-----|-----|-----|
| 1 | | C2 | 1-methyl-1H-indazol-5-ylboronic acid | C, H | 1H NMR (500 MHz, DMSO-d6) ppm = 11.06 (s, 1H), 8.55 (s, 1H), 8.28 (s, 1H), 8.15-8.11 (m, 1H), 7.79-7.74 (m, 2H), 7.36 (dd, J = 8.5, 1.6, 1H), 4.10 (s, 3H), 3.14-3.05 (m, 2H), 2.68-2.58 (m, 2H), 2.43 (s, 2H), 1.77 (td, J = 12.3, 4.1, 2H), 1.51-1.42 (m, 2H). | 410 | 1.81 (B) |
| 2 | | C15 | 1-methyl-1H-indazol-5-ylboronic acid | R, H | — | 411 | 1.71 (B) |
| 3 | | C1 | 5-(4,4,5,5-Tetramethyl-1,3,2-dioxaborolan-2-yl)benzo[d]oxazol-2(3H)-one | C, J, H | 1H NMR (500 MHz, DMSO-d6) ppm = 11.78 (s, 1H), 8.55 (s, 1H), 8.25 (s, 1H), 7.51 (s, 1H), 7.40 (d, J = 8.2, 1H), 7.09 (d, J = 1.7, 1H), 7.05 (dd, J = 8.2, 1.8, 1H), 3.15-3.05 (m, 4H), 2.70-2.60 (m, 2H), 1.83 (t, J = 6.8, 2H), 1.75-1.64 (m, 2H), 1.32-1.21 (m, 2H). | 399 | 1.84 (B) |
| 4 | | C9 | 1-methyl-1H-indazol-5-ylboronic acid | R, H | 1H NMR (400 MHz, DMSO-d6) ppm = 8.59 (s, 1H), 8.30 (s, 1H), 8.14 (s, 1H), 7.80-7.76 (m, 2H), 7.43 (s, 1H), 7.36 (dd, J = 8.7, 1.5, 1H), 4.11 (s, 3H), 3.16 (s, 2H), 3.03-2.94 (m, 2H), 2.93-2.83 (m, 2H), 1.77-1.66 (m, 4H). | 398 | 1.76 (B) |

TABLE 2-continued

Examples E prepared according to General Procedure B.

| No | Structures | Starting material | Purification method | NMR | MS | RT |
|---|---|---|---|---|---|---|
| 6 |  | C1 | 1-isopropyl-4-(4-(4,4,5,5-tetramethyl-1,3,2-dioxaborolan-2-yl)phenyl)-1H-pyrazole | Q, J | 1H NMR (500 MHz, DMSO-d6) ppm = 8.45 (s, 1H), 8.31-8.28 (m, 1H), 8.20 (s, 1H), 7.93 (d, J = 0.8, 1H), 7.72-7.67 (m, 2H), 7.48 (s, 1H), 7.35-7.29 (m, 2H), 4.52 (hept, J = 6.7, 1H), 3.11 (t, J = 6.8, 2H), 3.04 (dt, J = 12.7, 3.8, 2H), 2.72-2.62 (m, 2H), 1.83 (t, J = 6.8, 2H), 1.72 (td, J = 12.4, 4.2, 2H), 1.46 (d, J = 6.7, 6H), 1.29-1.22 (m, 2H). | 450 | 2.08 (B) |
| 8 |  | C9 | 5-(4,4,5,5-Tetramethyl-1,3,2-dioxaborolan-2-yl)benzo[d]oxazol-2(3H)-one | R, H | 1H NMR (400 MHz, DMSO-d6) ppm = 11.78 (s, 1H), 8.54 (s, 1H), 8.25 (s, 1H), 7.45 (s, 1H), 7.41 (d, J = 8.2, 1H), 7.10 (d, J = 1.7, 1H), 7.05 (dd, J = 8.2, 1.8, 1H), 3.19 (s, 2H), 2.99-2.86 (m, 4H), 1.79-1.68 (m, 4H). | 401 | 1.62 (B) |
| 9 |  | C9 | 1-methyl-4-(4-(4,4,5,5-tetramethyl-1,3,2-dioxaborolan-2-yl)phenyl)-1H-pyrazole | R, H | 1H NMR (500 MHz, DMSO-d6) ppm = 8.58 (s, 1H), 8.29 (s, 1H), 8.23 (s, 1H), 7.95 (s, 1H), 7.73-7.69 (m, 2H), 7.46 (s, 1H), 7.38-7.33 (m, 2H), 3.88 (s, 3H), 3.19 (s, 2H), 3.04-2.90 (m, 4H), 1.80-1.72 (m, 4H) | 424 | 1.92 (B) |
| 10 |  | C9 | (1-methyl-1H-indazol-6-yl)boronic acid | R, H | 1H NMR (500 MHz, DMSO-d6) ppm = 8.59 (s, 1H), 8.36 (s, 1H), 8.11 (d, J = 0.9, 1H), 7.90-7.86 (m, 1H), 7.71-7.69 (m, 1H), 7.43 (s, 1H), 7.10 (dd, J = 8.3, 1.3, 1H), 4.09 (s, 3H), 3.16 (s, 2H), 3.00-2.88 (m, 4H), 1.76-1.67 (m, 4H). | 398 | 1.89 (B) |

TABLE 2-continued

Examples E prepared according to General Procedure B.

| No | Structures | Starting material | Purification method | NMR | MS | RT |
|---|---|---|---|---|---|---|
| 11 | | C9 | 1-methyl-5-(4,4,5,5-tetramethyl-1,3,2-dioxaborolan-2-yl)indolin-2-one | R, H | 1H NMR (500 MHz, DMSO-d6) ppm = 8.54 (s, 1H), 8.22 (s, 1H), 7.46 (s, 1H), 7.32-7.28 (m, 1H), 7.26-7.23 (m, 1H), 7.12 (d, J = 8.0, 1H), 3.61 (s, 1H), 3.20 (s, 2H), 3.17 (s, 3H), 2.99-2.90 (m, 4H), 1.80-1.69 (m, 4H). | 413 | 1.70 (B) |
| 12 | | C1 | 7-(4,4,5,5-Tetramethyl-[1,3,2]dioxaborolan-2-yl)-3,4-dihydro-1H-quinolin-2-one | R, H | 1H NMR (500 MHz, DMSO-d6) ppm = 8.73-8.70 (m, 1H), 8.34-8.32 (m, 1H), 7.26-7.21 (m, 1H), 6.91-6.86 (m, 1H), 6.85-6.80 (m, 1H), 3.42-3.30 (m, 2H), 3.16-3.11 (m, 2H), 2.96-2.85 (m, 4H), 2.45 (t, J = 7.6, 2H), 1.90 (t, J = 6.8, 2H), 1.82-1.74 (m, 2H), 1.41-1.34 (m, 2H). | 412 | 1.78 (B) |
| 13 | | C15 | 1-methyl-4-(4-(4,4,5,5-tetramethyl-1,3,2-dioxaborolan-2-yl)phenyl)-1H-pyrazole | C, H | 1H NMR (500 MHz, DMSO-d6) ppm = 10.61 (s, 1H), 8.53 (s, 2H), 8.24 (s, 1H), 8.19 (s, 1H), 7.94-7.89 (m, 1H), 7.69-7.64 (m, 2H), 7.38-7.32 (m, 2H), 3.89 (s, 3H), 3.20-3.10 (m, 2H), 3.05-2.94 (m, 2H), 1.90-1.79 (m, 2H), 1.56-1.46 (m, 2H). | 437 | 1.83 (B) |
| 16 | | C9 | 1-methyl-5-(4,4,5,5-tetramethyl-1,3,2-dioxaborolan-2-yl)-1,3-dihydro-benzo[c]isothiazole 2,2-dioxide | Q, J, H | 1H NMR (500 MHz, DMSO-d6) ppm = 8.53 (s, 1H), 8.22 (s, 1H), 7.47 (s, 1H), 7.40-7.37 (m, 1H), 7.36-7.31 (m, 1H), 7.09 (d, J = 8.2, 1H), 4.72 (s, 2H), 3.20 (s, 2H), 3.11 (s, 3H), 3.00-2.87 (m, 4H), 1.80-1.67 (m, 4H). | 449 | 1.75 (B) |

TABLE 2-continued

Examples E prepared according to General Procedure B.

| No | Structures | Starting material | Purification method | NMR | MS | RT |
|----|------------|-------------------|---------------------|-----|-----|-----|
| 18 | 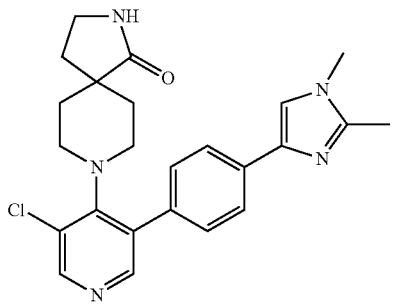 [SMILES: Cc1nc(-c2ccc(-c3cncc(Cl)c3N3CCC4(CCNC4=O)CC3)cc2)cn1C] | C1 | 1,2-dimethyl-4-(4-(4,4,5,5-tetramethyl-1,3,2-dioxaborolan-2-yl)phenyl)-1H-imidazole | Q, H | 1H NMR (500 MHz, DMSO-d6) ppm = 8.52 (s, 1H), 8.25 (s, 1H), 8.13 (s, 1H), 7.87-7.80 (m, 2H), 7.57-7.52 (m, 2H), 7.50 (s, 1H), 3.79 (s, 3H), 3.15-3.01 (m, 4H), 2.76-2.66 (m, 2H), 2.64 (s, 3H), 1.83 (t, J = 6.8, 2H), 1.69 (td, J = 12.7, 4.2, 2H), 1.31-1.20 (m, 2H). | 437 | 1.64 (B) |
| 19 | 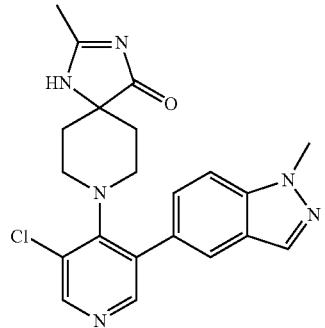 [SMILES: CC1=NC(=O)C2(CCN(c3c(Cl)cncc3-c3ccc4c(cnn4C)c3)CC2)N1] | C10 | 1-methyl-1H-indazol-5-ylboronic acid | R, H | 1H NMR (500 MHz, DMSO-d6) ppm = 8.52 (s, 1H), 8.25 (s, 1H), 8.12-8.11 (m, 1H), 7.80-7.78 (m, 1H), 7.75 (d, J = 8.7, 1H), 7.40 (dd, J = 8.7, 1.6, 1H), 4.10 (s, 3H), 3.21-3.13 (m, 2H), 3.04-2.93 (m, 2H), 2.28 (s, 3H), 1.81-1.72 (m, 2H), 1.66-1.44 (m, 2H). | 409 | 1.53 (A) |
| 20 | 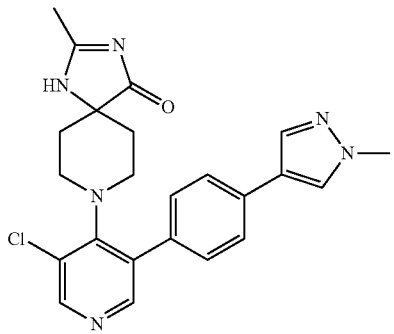 [SMILES: CC1=NC(=O)C2(CCN(c3c(Cl)cncc3-c3ccc(-c4cnn(C)c4)cc3)CC2)N1] | C10 | 1-methyl-4-(4-(4,4,5,5-tetramethyl-1,3,2-dioxaborolan-2-yl)phenyl)-1H-pyrazole | R, H | 1H NMR (500 MHz, DMSO-d6) ppm = 8.51 (s, 1H), 8.23 (s, 1H), 8.20 (s, 1H), 7.95-7.91 (m, 1H), 7.71-7.65 (m, 2H), 7.41-7.34 (m, 2H), 3.89 (s, 3H), 3.22-3.14 (m, 2H), 3.06-2.97 (m, 2H), 2.31 (s, 3H), 1.87-1.77 (M, 2H), 1.70-1.49 (m, 2H). | 435 | 1.63 (A) |
| 22 | 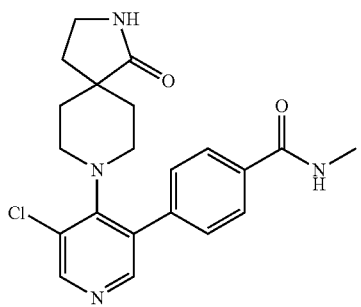 [SMILES: CNC(=O)c1ccc(-c2cncc(Cl)c2N2CCC3(CCNC3=O)CC2)cc1] | C1 | 4-(N-Methylaminocarbonyl)phenylboronic acid | C, H | 1H NMR (400 MHz, DMSO-d6) ppm = 8.52 (q, J = 4.4, 1H), 8.48 (s, 1H), 8.20 (s, 1H), 7.97-7.91 (m, 2H), 7.50 (s, 1H), 7.47-7.40 (m, 2H), 3.11 (t, J = 6.8, 2H), 3.07-2.96 (m, 2H), 2.81 (d, J = 4.5, 3H), 2.62 (t, J = 11.7, 2H), 1.82 (t, J = 6.8, 2H), 1.69 (td, J = 12.3, 4.2, 2H), 1.23 (d, J = 12.9, 2H). | 399 | 1.34 (A) |

TABLE 2-continued

Examples E prepared according to General Procedure B.

| No | Structures | Starting material | Purification method | NMR | MS | RT |
|---|---|---|---|---|---|---|
| 24 | 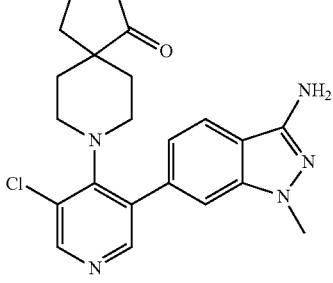 | C1 3-Amino-1-methyl-1H-indazole-6-boronic acid | C, H | 1H NMR (500 MHz, DMSO-d6) ppm = 8.57 (s, 1H), 8.31 (s, 1H), 7.78 (d, J = 8.2, 1H), 7.49 (s, 1H), 7.39 (s, 1H), 6.92-6.86 (m, 1H), 3.79 (s, 3H), 3.17-3.06 (m, 4H), 2.75-2.66 (m, 2H), 1.80 (t, J = 6.8, 2H), 1.70 (td, J = 12.4, 4.1, 2H), 1.29-1.22 (m, 2H). | 412 | 1.64 (B) |
| 25 | 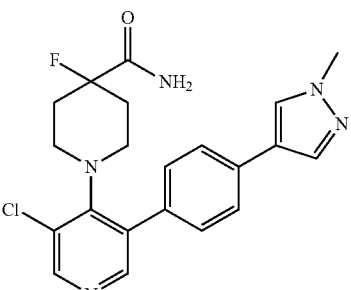 | C12 1-methyl-4-(4-(4,4,5,5-tetramethyl-1,3,2-dioxaborolan-2-yl)phenyl)-1H-pyrazole | C, H | 1H NMR (400 MHz, DMSO-d6) ppm = 8.48 (s, 1H), 8.23 (s, 1H), 8.20 (s, 1H), 7.94-7.92 (m, 1H), 7.70-7.66 (m, 2H), 7.49-7.45 (m, 1H), 7.36-7.31 (m, 3H), 3.88 (s, 3H), 3.05-2.95 (m, 2H), 2.81 (t, J = 12.1, 2H), 2.15-1.93 (m, 2H), 1.65 (t, J = 12.3, 2H). | 414 | 1.61 (A) |
| 26 | 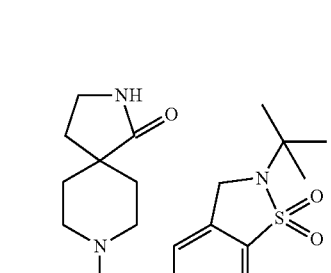 | C1 2-tert-Butyl-1,1-dioxo-2,3-dihydro-1H-benzo[d]isothiazole-5-boronic acid | R, H | 1H NMR (500 MHz, DMSO-d6) ppm = 8.57 (s, 1H), 8.26 (s, 1H), 7.87 (d, J = 8.1, 1H), 7.62 (s, 1H), 7.57-7.54 (m, 1H), 7.53 (s, 1H), 4.63 (s, 2H), 3.16-3.07 (m, 4H), 2.80-2.71 (m, 2H), 1.88 (t, J = 6.8, 2H), 1.72-1.64 (m, 2H), 1.49 (s, 9H), 1.30-1.24 (m, 2H) | 489 | 2.05 (B) |
| 27 | 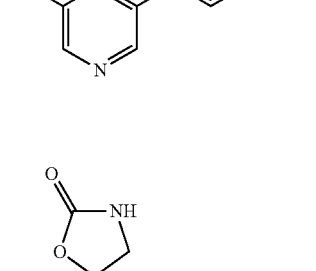 | C9 3-Amino-1-methyl-1H-indazole-6-boronic acid | R, H | 1H NMR (500 MHz, DMSO-d6) ppm = 8.59 (s, 1H), 8.34 (s, 1H), 7.83-7.78 (m, 1H), 7.46-7.42 (m, 2H), 6.90 (dd, J = 8.2, 1.3, 1H), 3.80 (s, 3H), 3.17 (s, 2H), 3.00-2.87 (m, 4H), 1.76-1.69 (m, 4H). | 413 | 1.59 (B) |

TABLE 2-continued

Examples E prepared according to General Procedure B.

| No | Structures | Starting material | Purification method | NMR | MS | RT |
|---|---|---|---|---|---|---|
| 28 | | C2 | 3-Amino-1-methyl-1H-indazole-6-boronic acid | R, H | 1H NMR (500 MHz, DMSO-d6) ppm = 11.07 (s, 1H), 8.58 (s, 1H), 8.33 (s, 1H), 7.80 (d, J = 8.2, 1H), 7.43-7.40 (m, 1H), 6.90 (dd, J = 8.2, 1.3, 1H), 3.81 (s, 3H), 3.18-3.09 (m, 2H), 2.70 (t, J = 11.9, 2H), 2.46 (s, 2H), 1.84-1.74 (m, 2H), 1.53-1.44 (m, 2H) | 425 | 1.61 (B) |
| 29 | | C1 | 3-Hydroxy-1,1-dioxo-2,3-dihydro-1H-benzo[b]thiophene-5-boronic acid | R, H | 1H NMR (500 MHz, DMSO-d6) ppm = 9.06 (s, 1H), 8.81 (s, 1H), 8.43 (d, J = 7.9, 1H), 8.34-8.30 (m, 1H), 8.19 (dd, J = 7.9, 1.5, 1H), 6.69 (s, 1H), 6.07 (t, J = 6.4, 1H), 4.51 (dd, J = 13.4, 6.9, 1H), 4.06-3.99 (m, 1H), 3.95 (dd, J = 13.4, 5.9, 1H), 3.82-3.71 (m, 3H), 3.69-3.61 (m, 1H), 3.49-3.41 (m, 1H), 2.60-2.52 (m, 2H), 2.44-2.35 (m, 1H), 2.05-1.98 (m, 1H), 1.78-1.65 (m, 2H) | 448 | 1.64 (B) |
| 30 | | C11 | 1-methyl-5-(4,4,5,5-tetramethyl-1,3,2-dioxaborolan-2-yl)-1,3-dihydrobenzo[c]isothiazole 2,2-dioxide | C, H | 1H NMR (500 MHz, DMSO-d6) ppm = 9.54-9.12 (m, 1H), 8.52 (s, 1H), 8.21 (s, 1H), 7.37-7.30 (m, 2H), 7.07 (d, J = 8.2, 1H), 4.72 (s, 2H), 3.10 (s, 3H), 3.05-2.94 (m, 2H), 2.86-2.76 (m, 2H), 2.29-2.18 (m, 2H), 1.74-1.60 (m, 4H). | 448 | 1.35 (A) |
| 31 | | C12 | 1-methyl-5-(4,4,5,5-tetramethyl-1,3,2-dioxaborolan-2-yl)-1,3-dihydrobenzo[c]isothiazole 2,2-dioxide | C, H | 1H NMR (500 MHz, DMSO-d6) ppm = 8.47 (s, 1H), 8.19 (s, 1H), 7.51 (s, 1H), 7.46-7.39 (m, 1H), 7.39-7.35 (m, 1H), 7.33 (dd, J = 8.2, 1.8, 1H), 7.06 (d, J = 8.2, 1H), 4.71 (s, 2H), 3.10 (s, 3H), 3.03-2.95 (m, 2H), 2.90-2.81 (m, 2H), 2.09-1.91 (m, 2H), 1.63 (t, J = 12.5, 2H) | 439 | 1.53 (A) |

TABLE 2-continued

Examples E prepared according to General Procedure B.

| No | Structures | Starting material | Purification method | NMR | MS | RT |
|---|---|---|---|---|---|---|
| 32 | | C1 | 2-(2,2-Dioxo-2,3-dihydro-1H-benzo[c]thiophen-5-yl)-4,4,5,5-tetramethyl-[1,3,2]dioxaborolane | Q, H | 1H NMR (500 MHz, DMSO-d6) ppm = 8.55 (s, 1H), 8.25 (s, 1H), 7.55-7.49 (m, 2H), 7.44-7.40 (m, 1H), 7.37 (dd, J = 7.8, 1.7, 1H), 4.57 (s, 4H), 3.16-3.05 (m, 4H), 2.75-2.67 (m, 2H), 1.86 (t, J = 6.8, 2H), 1.75-1.65 (m, 2H), 1.29-1.23 (m, 2H). | 432 | 1.71 (B) |
| 34 | | C1 | [3-(methylamino)-1H-indazol-6-yl]boronic acid | Q, H | 1H NMR (500 MHz, DMSO-d6) ppm = 11.85 (s, 1H), 8.58 (s, 1H), 8.29 (s, 1H), 7.81 (d, J = 8.2, 1H), 7.50 (s, 1H), 7.28 (s, 1H), 6.92-6.89 (m, 1H), 3.17-3.05 (m, 4H), 2.91 (s, 3H), 2.71-2.61 (m, 2H), 1.80 (t, J = 6.8, 2H), 1.75-1.66 (m, 2H), 1.29-1.22 (m, 2H). | 411 | 1.61 (B) |
| 36 | | C9 | 1-isopropyl-4-(4-(4,4,5,5-tetramethyl-1,3,2-dioxaborolan-2-yl)phenyl)-1H-pyrazole | Q, J | 1H NMR (400 MHz, DMSO-d6) ppm = 8.46 (s, 1H), 8.31 (d, J = 0.8, 1H), 8.21 (s, 1H), 7.94 (d, J = 0.8, 1H), 7.72 (d, J = 8.2, 2H), 7.44 (s, 1H), 7.33 (d, J = 8.2, 2H), 4.52 (hept, J = 6.6, 1H), 3.21-3.16 (m, 2H), 2.96-2.85 (m, 4H), 1.80-1.67 (m, 4H), 1.46 (d, J = 6.7, 6H). | 452 | 2.04 (B) |
| 37 | | C15 | 1-methyl-5-(4,4,5,5-tetramethyl-1,3,2-dioxaborolan-2-yl)-1,3-dihydrobenzo[c]isothiazole 2,2-dioxide | C, J, H | 1H NMR (500 MHz, DMSO-d6) ppm = 10.63 (s, 1H), 8.49-8.40 (m, 2H), 8.18 (s, 1H), 7.38-7.30 (m, 2H), 7.03 (d, J = 8.1, 1H), 4.75 (s, 2H), 3.14-3.04 (m, 5H), 2.96-2.83 (m, 2H), 1.88-1.76 (m, 2H), 1.53-1.44 (m, 2H). | 462 | 1.46 (A) |

TABLE 2-continued

Examples E prepared according to General Procedure B.

| No | Structures | | Starting material | Purification method | NMR | MS | RT |
|---|---|---|---|---|---|---|---|
| 39 | | | C9 | 1-(2-methanesulfonyl-ethyl)-4-[4-(4,4,5,5-tetramethyl-[1,3,2]dioxaborolan-2-yl)-phenyl]-1H-pyrazole | Q, H | 1H NMR (400 MHz, DMSO-d6) ppm = 8.47 (s, 1H), 8.36 (s, 1H), 8.21 (s, 1H), 8.04 (s, 1H), 7.74-7.69 (m, 2H), 7.44 (s, 1H), 7.38-7.32 (m, 2H), 4.59 (t, J = 6.9, 2H), 3.75 (t, J = 6.9, 2H), 3.18 (s, 2H), 2.94-2.87 (m, 7H), 1.78-1.70 (m, 4H). | 516 | 1.57 (A) |
| 40 | | | C9 | 3-{4-[4-(4,4,5,5-Tetramethyl-[1,3,2]dioxaborolan-2-yl)-phenyl]-pyrazol-1-yl}-propionitrile | Q, H | 1H NMR (400 MHz, DMSO-d6) ppm = 8.47 (s, 1H), 8.36-8.33 (m, 1H), 8.22 (s, 1H), 8.07-8.04 (m, 1H), 7.74-7.70 (m, 2H), 7.44 (s, 1H), 7.39-7.33 (m, 2H), 4.43 (t, J = 6.4, 2H), 3.18 (s, 2H), 3.12 (t, J = 6.4, 2H), 2.94-2.88 (m, 4H), 1.78-1.70 (m, 4H). | 463 | 1.62 (A) |
| 42 | | Chiral | C13 | 1-methyl-5-(4,4,5,5-tetramethyl-1,3,2-dioxaborolan-2-yl)-1,3-dihydrobenzo[c]isothiazole 2,2-dioxide | Q, H | 1H NMR (500 MHz, DMSO-d6) ppm = 8.52 (s, 1H), 8.44 (s, 1H), 8.18 (s, 1H), 7.38-7.36 (m, 1H), 7.36-7.32 (m, 1H), 7.06 (d, J = 8.1, 1H), 4.77-4.68 (m, 2H), 4.33-4.23 (m, 1H), 3.15-3.11 (m, 1H), 3.10 (s, 3H), 3.00-2.94 (m, 1H), 2.80-2.63 (m, 2H), 2.24 (dd, J = 13.8, 8.9, 1H), 1.85-1.74 (m, 2H), 1.62 (td, J = 12.0, 4.2, 1H), 1.35-1.23 (m, 2H). | 515 | 1.80 (A) |
| 43 | | | C9 | 2-methyl-1-{4-[4-(4,4,5,5-tetramethyl-[1,3,2]dioxaborolan-2-yl)-phenyl]-pyrazol-1-yl}-propan-2-ol | C, H | 1H NMR (500 MHz, DMSO-d6) ppm = 8.46 (s, 1H), 8.21 (s, 1H), 8.19-8.16 (m, 1H), 7.97-7.94 (m, 1H), 7.74-7.68 (m, 2H), 7.44 (s, 1H), 7.37-7.30 (m, 2H), 4.72 (s, 1H), 4.05 (s, 2H), 3.19 (s, 2H), 2.95-2.85 (m, 4H), 1.79-1.69 (m, 4H), 1.10 (s, 6H). | 482 | 1.62 (A) |

TABLE 2-continued

Examples E prepared according to General Procedure B.

| No | Structures | Starting material | Purification method | NMR | MS | RT |
|---|---|---|---|---|---|---|
| 46 | | C10 | 1-methyl-5-(4,4,5,5-tetramethyl-1,3,2-dioxaborolan-2-yl)-1,3-dihydrobenzo[c]isothiazole 2,2-dioxide | Q, H | 1H NMR (500 MHz, DMSO-d6) ppm = 8.52 (s, 1H), 8.23 (s, 1H), 7.45-7.43 (m, 1H), 7.40-7.36 (m, 1H), 7.06 (d, J = 8.2, 1H), 4.72 (s, 2H), 3.21-3.14 (m, 2H), 3.11 (s, 3H), 3.07-2.99 (m, 2H), 2.38 (s, 3H), 1.83-1.74 (m, 2H), 1.70-1.61 (m, 2H). | 460 | 0.74 (C) |
| 47 | | C1 | 2-methyl-1-{4-[4-(4,4,5,5-tetramethyl-[1,3,2]dioxaborolan-2-yl)-phenyl]-pyrazol-1-yl}-propan-2-ol | B, J | 1H NMR (400 MHz, DMSO-d6) ppm = 8.45 (s, 1H), 8.19 (s, 1H), 8.17-8.14 (m, 1H), 7.95-7.93 (m, 1H), 7.71-7.67 (m, 2H), 7.48 (s, 1H), 7.36-7.30 (m, 2H), 4.72 (s, 1H), 4.05 (s, 2H), 3.11 (t, J = 6.8, 2H), 3.07-3.01 (m, 2H), 2.73-2.63 (m, 2H), 1.84 (t, J = 6.8, 2H), 1.72 (td, J = 12.3, 4.2, 2H), 1.30-1.22 (m, 2H), 1.11 (s, 6H). | 480 | 1.91 (B) |
| 48 | | C9 | 2-(2,2-Dioxo-2,3-dihydro-1H-benzo[c]thiophen-5-yl)-4,4,5,5-tetramethyl-[1,3,2]dioxaborolane | Q, H | 1H NMR (400 MHz, DMSO-d6) ppm = 8.49 (s, 1H), 8.19 (s, 1H), 7.52 (d, J = 7.9, 1H), 7.47 (s, 1H), 7.45-7.41 (m, 1H), 7.33 (dd, J = 7.9, 1.7, 1H), 4.58 (s, 2H), 4.55 (s, 2H), 3.19 (s, 2H), 2.98-2.82 (m, 4H), 1.78-1.64 (m, 4H). | 434 | 1.65 (B) |
| 50 | | C9 | Isoquinolin-6-yl-boronic acid | C, H | 1H NMR (500 MHz, DMSO-d6) ppm = 9.39 (s, 1H), 8.57 (d, J = 5.7, 1H), 8.54 (s, 1H), 8.33 (s, 1H), 8.25 (d, J = 8.4, 1H), 8.02-7.98 (m, 1H), 7.90 (d, J = 5.7, 1H), 7.66 (dd, J = 8.4, 1.7, 1H), 7.41 (s, 1H), 3.14 (s, 2H), 2.98-2.85 (m, 4H), 1.74-1.63 (m, 4H). | 395 | 1.31 (A) |

TABLE 2-continued

Examples E prepared according to General Procedure B.

| No | Structures | Starting material | Purification method | NMR | MS | RT |
|---|---|---|---|---|---|---|
| 53 | Chiral | C14 1-methyl-5-(4,4,5,5-tetramethyl-1,3,2-dioxaborolan-2-yl)-1,3-dihydrobenzo[c]isothiazole 2,2-dioxide | B, H | 1H NMR (500 MHz, DMSO-d6) ppm = 8.54 (s, 1H), 8.45 (s, 1H), 8.18 (s, 1H), 7.38-7.33 (m, 2H), 7.06 (d, J = 8.2, 1H), 4.78-4.68 (m, 2H), 4.33-4.25 (m, 1H), 3.14-3.10 (m, 1H), 3.09 (s, 3H), 2.99-2.93 (m, 1H), 2.76-2.62 (m, 2H), 2.24 (dd, J = 13.8, 8.9 1H), 1.82-1.75 (m, 2H), 1.62 (td, J = 12.2, 4.2, 1H), 1.35-1.22 (m, 2H). | 515 | 1.84 (A) |
| 55 | 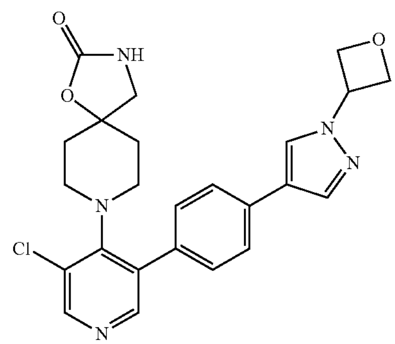 [SMILES: O=C1NCC2(CCN(c3c(Cl)cncc3-c3ccc(-c4cnn(C5COC5)c4)cc3)CC2)O1] | C9 1-(oxetan-3-yl)-4-(4-(4,4,5,5-tetramethyl-1,3,2-dioxaborolan-2-yl)phenyl)-1H-pyrazole | B, H | 1H NMR (500 MHz, DMSO-d6) ppm = 8.49-8.44 (m, 2H), 8.22 (s, 1H), 8.12 (s, 1H), 7.75 (d, J = 8.0, 2H), 7.47 (s, 1H), 7.35 (d, J = 8.0, 2H), 5.60 (p, J = 7.0, 1H), 4.99-4.91 (m, 4H), 3.18 (s, 2H), 2.95-2.83 (m, 4H), 1.76-1.70 (m, 4H). | 466 | 1.64 (A) |
| 56 | 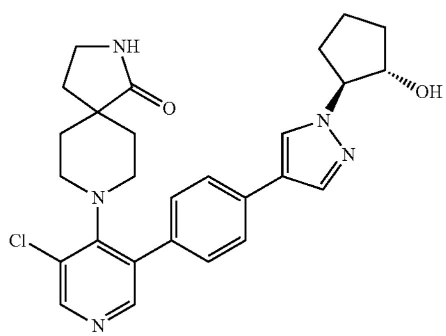 [SMILES: O=C1NCCC12CCN(c1c(Cl)cncc1-c1ccc(-c3cnn([C@H]4CCC[C@@H]4O)c3)cc1)CC2] | C1 (rac)-2-{4-[4-(4,4,5,5-Tetramethyl-[1,3,2]dioxaborolan-2-yl)-phenyl]-pyrazol-1-yl}-cyclopentanol | C, H | 1H NMR (500 MHz, DMSO-d6) ppm = 8.45 (s, 1H), 8.29 (s, 1H), 8.20 (s, 1H), 7.97 (s, 1H), 7.73-7.67 (m, 2H), 7.51 (s, 1H), 7.35-7.29 (m, 2H), 5.13-5.05 (m, 1H), 4.42-4.34 (m, 1H), 4.29-4.21 (m, 1H), 3.10 (t, J = 6.8, 2H), 3.07-2.99 (m, 2H), 2.72-2.61 (m, 2H), 2.24-2.13 (m, 1H), 2.05-1.93 (m, 2H), 1.87-1.66 (m, 6H), 1.63-1.53 (m, 1H), 1.29-1.19 (m, 2H). | 492 | 1.65 (A) |
| 57 | 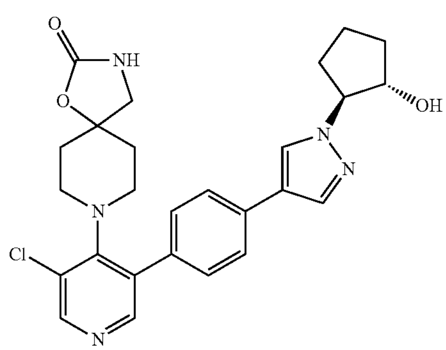 [SMILES: O=C1NCC2(CCN(c3c(Cl)cncc3-c3ccc(-c4cnn([C@H]5CCC[C@@H]5O)c4)cc3)CC2)O1] | C9 (rac)-2-{4-[4-(4,4,5,5-Tetramethyl-[1,3,2]dioxaborolan-2-yl)-phenyl]-pyrazol-1-yl}-cyclopentanol | C, H | 1H NMR (500 MHz, DMSO-d6) ppm = 8.45 (s, 1H), 8.29 (s, 1H), 8.20 (s, 1H), 7.97 (s, 1H), 7.73-7.67 (m, 2H), 7.51 (s, 1H), 7.35-7.29 (m, 2H), 5.13-5.05 (m, 1H), 4.42-4.34 (m, 1H), 4.29-4.21 (m, 1H), 3.10 (t, J = 6.8, 2H), 3.07-2.99 (m, 2H), 2.72-2.61 (m, 2H), 2.24-2.13 (m, 1H), 2.05-1.93 (m, 2H), 1.87-1.66 (m, 6H), 1.63-1.53 (m, 1H), 1.29-1.19 (m, 2H) | 494 | 1.70 (A) |

TABLE 2-continued

Examples E prepared according to General Procedure B.

| No | Structures | Starting material | Purification method | NMR | MS | RT |
|---|---|---|---|---|---|---|
| 60 | | C9 | 1-cyclopropyl-4-(4-(4,4,5,5-tetramethyl-1,3,2-dioxaborolan-2-yl)phenyl)-1H-pyrazole | B, H | 1H NMR (400 MHz, DMSO-d6) ppm = 8.48-8.45 (m, 1H), 8.33-8.30 (m, 1H), 8.21 (s, 1H), 7.94 (d, J = 0.8, 1H), 7.74-7.69 (m, 2H), 7.44 (s, 1H), 7.35-7.30 (m, 2H), 3.78-3.71 (m, 1H), 3.18 (s, 2H), 2.95-2.85 (m, 4H), 1.78-1.68 (m, 4H), 1.12-1.07 (m, 2H), 1.02-0.96 (m, 2H). | 450 | 1.70 (A) |
| 64 | | C1 | 6-(4,4,5,5-tetramethyl-1,3,2-dioxaborolan-2-yl)indolin-2-one | C, I | 1H NMR (500 MHz, DMSO-d6) ppm = 10.49 (s, 1H), 8.46 (s, 1H), 8.18 (s, 1H), 7.55 (bs, 1H), 7.31 (d, J = 7.5, 1H), 6.90 (dd, J = 7.5, 1.4, 1H), 6.77 (d, J = 1.4, 1H), 3.56 (s, 2H), 3.13 (t, J = 6.8, 2H), 3.08-3.00 (m, 2H), 2.68-2.61 (m, 2H), 1.84 (t, J = 6.8, 2H), 1.77-1.69 (m, 2H), 1.30-1.24 (m, 2H) | 397 | 1.98 (E) |
| 65 | | C2 | 1-methyl-5-(4,4,5,5-tetramethyl-1,3,2-dioxaborolan-2-yl)indolin-2-one | C, I | 1H NMR (500 MHz, DMSO-d6) ppm = 11.10 (s, 1H), 8.45 (s, 1H), 8.18 (s, 1H), 7.27 (s, 1H), 7.25 (d, J = 8.0, 1H), 7.09 (d, J = 8.0, 1H), 3.65 (s, 2H), 3.17 (s, 3H), 3.05-2.99 (m, 2H), 2.71-2.62 (m, 2H), 2.50 (s, 2H), 1.82-1.72 (m, 2H), 1.49-1.42 (m, 2H) | 425 | 1.96 (E) |
| 66 | | C2 | (1-methyl-1H-indazol-6-yl)boronic acid | C, I | 1H NMR (500 MHz, DMSO-d6) ppm = 11.07 (bs, 1H), 8.50 (s, 1H), 8.30 (s, 1H), 8.11 (d, J = 0.7, 1H), 7.86 (dd, J = 8.2, 0.7, 1H), 7.69 (s, 1H), 7.09 (dd, J = 8.2, 1.1, 1H), 4.10 (s, 3H), 3.11-3.02 (m, 2H), 2.72-2.61 (m, 2H), 2.43 (s, 2H), 1.80-1.73 (m, 2H), 1.48-1.43 (m, 2H) | 410 | 2.27 (E) |

TABLE 2-continued

Examples E prepared according to General Procedure B.

| No | Structures | Starting material | Purification method | NMR | MS | RT |
|---|---|---|---|---|---|---|
| 67 | 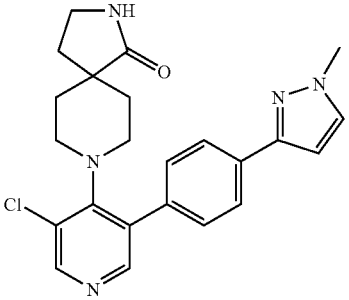 [SMILES: Cn1ccc(-c2ccc(-c3cncc(Cl)c3N3CCC4(CCNC4=O)CC3)cc2)n1] | C1 1-methyl-3-(4-(4,4,5,5-tetramethyl-1,3,2-dioxaborolan-2-yl)phenyl)-1H-pyrazole | C, I | 1H NMR (500 MHz, CDCl3) ppm = 8.45 (s, 1H), 8.24 (s, 1H), 7.90 (d, J = 8.2, 2H), 7.43 (d, J = 2.2, 1H), 7.32 (d, J = 8.2, 2H), 6.61 (d, J = 2.2, 1H), 6.10 (bs, 1H), 3.98 (s, 3H), 3.27 (t, J = 6.9, 2H), 3.19-3.13 (m, 2H), 2.75-2.67 (m, 2H), 2.04-1.95 (m, 2H), 1.97 (t, J = 6.9, 2H), 1.37-1.30 (m, 2H) | 422 | 1.58 (G) |
| 68 | 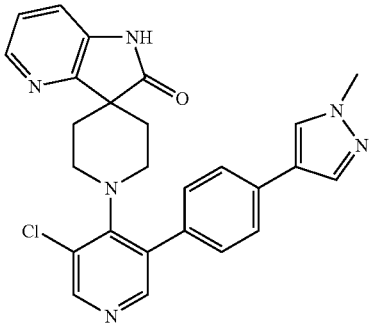 [SMILES: Cn1cc(-c2ccc(-c3cncc(Cl)c3N3CCC4(CC3)C(=O)Nc3cccnc34)cc2)cn1] | C4 1-methyl-4-(4-(4,4,5,5-tetramethyl-1,3,2-dioxaborolan-2-yl)phenyl)-1H-pyrazole | C, I | 1H NMR (500 MHz, CDCl3) ppm = 8.48 (s, 1H), 8.29 (s, 2H), 8.23 (dd, J = 4.6, 1.9, 1H), 7.84 (s, 1H), 7.68 (s, 1H), 7.63 (d, J = 8.1, 2H), 7.41 (d, J = 8.1, 2H), 7.14-7.09 (m, 2H), 3.98 (s, 3H), 3.49-3.30 (m, 4H), 1.99-1.90 (m, 4H) | 471 | 2.61 (E) |
| 69 | 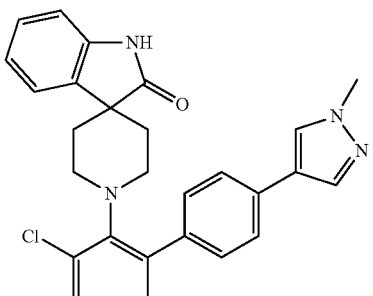 | C5 1-methyl-4-(4-(4,4,5,5-tetramethyl-1,3,2-dioxaborolan-2-yl)phenyl)-1H-pyrazole | C, I, P | 1H NMR (500 MHz, CDCl3) ppm = 8.50 (s, 1H), 8.29 (s, 1H), 7.85 (s, 1H), 7.70 (S, 1H), 7.65 (d, J = 8.2, .72H), 7.40 (d, J = 8.2, 2H), 7.33 (bs, 1H), 7.30 (d, J = 7.4, 1H), 7.22 (td, J = 7.4, 1.2, 1H), 7.04 (td, J = 7.4, 0.9, 1H), 6.86 (d, J = 7.4, 1H), 3.99 (s, 3H), 3.52-3.44 (m, 2H), 3.18-3.10 (m, 2H), 1.94-1.81 (m, 4H) | 470 | 3.01 (E) |
| 71 | 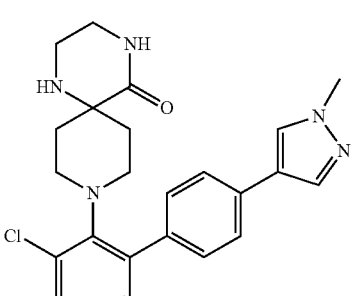 | C8 1-methyl-4-(4-(4,4,5,5-tetramethyl-1,3,2-dioxaborolan-2-yl)phenyl)-1H-pyrazole | C, I, E | 1H NMR (500 MHz, CDCl$_3$) ppm = 8.44 (s, 1H), 8.22 (s, 1H), 7.83 (s, 1H), 7.69 (s, 1H), 7.59 (d, J = 8.2, 2H), 7.32 (d, J = 8.2, 2H), 5.82 (s, 1H), 3.98 (s, 3H), 3.39-3.32 (m, 2H), 3.09-2.99 (m, 6H), 2.33-2.23 (m, 2H), 1.63-1.55 (m, 2H) | 437 | 1.78 (E) |

TABLE 2-continued

Examples E prepared according to General Procedure B.

| No | Structures | Starting material | Purification method | NMR | MS | RT |
|---|---|---|---|---|---|---|
| 72 | | C8 | 5-(4,4,5,5-Tetramethyl-1,3,2-dioxaborolan-2-yl)benzo[d]oxazol-2(3H)-one | C, I, E | 1H NMR (500 MHz, CDCl$_3$) ppm = 8.43 (s, 1H), 8.21 (s, 1H), 7.28 (d, J = 8.0, 1H), 7.25 (s, 1H), 7.05 (dd, J = 8.0, 1.6, 1H), 6.14 (bs, 1H), 3.36 (s, 2H), 3.15 (t, J = 10.5, 2H), 3.09-3.00 (m, 4H), 2.18 (t, J = 10.5, 2H), 1.59-1.50 (m, 2H) | 414 | 1.27 (E) |
| 76 | | C6 | 1-methyl-5-(4,4,5,5-tetramethyl-1,3,2-dioxaborolan-2-yl)-1,3-dihydrobenzo[c]isothiazole 2,2-dioxide | C, I, E | 1H NMR (500 MHz, CDCl3) ppm = 8.27 (d, J = 4.4, 1H), 8.10 (s, 1H), 7.48 (d, J = 8.2, 1H), 7.45 (s, 1H), 6.84 (d, J = 8.2, 1H), 5.95 (s, 1H), 4.48 (s, 2H), 3.33 (t, J = 6.9, 2H), 3.26-3.21 (m, 2H), 3.20 (s, 3H), 3.04-2.97 (m, 2H), 2.05 (t, J = 6.9, 2H), 1.86-1.79 (m, 2H), 1.37-1.31 (m, 2H) | 431 | 1.7 (E) |
| 79 | | C7 | 1-methyl-4-(4-(4,4,5,5-tetramethyl-1,3,2-dioxaborolan-2-yl)phenyl)-1H-pyrazole | C, I | 1H NMR (500 MHz, CDCl3) ppm = 8.28 (d, J = 4.0, 1H), 8.16 (s, 1H), 7.82 (s, 1H), 7.69 (s, 1H), 7.56 (d, J = 8.2, 2H), 7.41 (d, J = 8.2, 2H), 5.81 (s, 1H), 3.98 (s, 3H), 3.28 (s, 2H), 3.31-3.24 (m, 2H), 3.09-3.03 (m, 2H), 1.91-1.85 (m, 2H), 1.74-1.67 (m, 2H) | 408 | 2.07 (E) |
| 80 | | C7 | 1-methyl-5-(4,4,5,5-tetramethyl-1,3,2-dioxaborolan-2-yl)-1,3-dihydrobenzo[c]isothiazole 2,2-dioxide | C, I, E | 1H NMR (500 MHz, CDCl3) ppm = 8.27 (d, J = 4.0, 1H), 8.08 (s, 1H), 7.40 (d, J = 8.2, 1H), 7.32 (s, 1H), 6.82 (d, J = 8.2, 1H), 5.98 (s, 1H), 4.42 (s, 2H), 3.33 (s, 2H), 3.28-3.21 (m, 2H), 3.20 (s, 3H), 3.07-3.01 (m, 2H), 1.91-1.81 (m, 2H), 1.72-1.65 (m, 2H) | 433 | 1.7 (E) |

TABLE 2-continued

Examples E prepared according to General Procedure B.

| No | Structures | Starting material | Purification method | NMR | MS | RT |
|---|---|---|---|---|---|---|
| 84 | | C2 | 5-(4,4,5,5-tetramethyl-1,3,2-dioxaborolan-2-yl)-1,3-dihydrobenzo[c]isothiazole 2,2-dioxide | C, I, E | 1H NMR (500 MHz, DMSO-d6) ppm = 11.10 (bs, 1H), 8.44 (s, 1H), 8.18 (s, 1H), 7.26 (s, 1H), 7.19 (d, J = 8.0, 1H), 6.87 (d, J = 8.0, 1H), 4.54 (s, 2H), 3.05-2.98 (m, 2H), 2.72-2.62 (m, 2H), 2.50 (s, 2H), 1.82-1.73 (m, 2H), 1.51-1.45 (m, 2H) | 447 | 1.83 (E) |
| 86 | | C2 | 1-methyl-4-(4-(4,4,5,5-tetramethyl-1,3,2-dioxaborolan-2-yl)phenyl)-1H-pyrazole | C, I | 1H NMR (500 MHz, DMSO-d6) ppm = 11.12 (bs, 1H), 8.48 (s, 1H), 8.23 (s, 1H), 8.22 (s, 1H), 7.95 (d, J = 0.8, 1H), 7.69 (d, J = 8.2, 1H), 7.34 (d, J = 8.2, 1H), 3.89 (s, 3H), 3.08-3.02 (m, 2H), 2.70-2.62 (m, 2H), 2.48 (s, 2H), 1.85-1.7 (m, 2H), 1.53-1.47 (m, 2H) | 436 | 2.31 (E) |
| 87 | | C2 | 1-methyl-5-(4,4,5,5-tetramethyl-1,3,2-dioxaborolan-2-yl)-1,3-dihydrobenzo[c]isothiazole 2,2-dioxide | C, I, P | 1H NMR (500 MHz, DMSO-d6) δ 11.12 (bs, 1H), 8.46 (s, 1H), 8.19 (s, 1H), 7.34 (s, 1H), 7.34 (d, J = 8.6, 1H), 7.06 (d, J = 8.6, 1H), 4.75 (s, 2H), 3.10 (s, 3H), 3.05-2.99 (m, 2H), 2.71-2.60 (m, 2H), 2.50 (s, 2H), 1.81-1.73 (m, 2H), 1.50-1.44 (m, 2H) | 461 | 2.04 (E) |
| 89 | | C1 | 1-methyl-4-(4-(4,4,5,5-tetramethyl-1,3,2-dioxaborolan-2-yl)phenyl)-1H-pyrazole | A, I | 1H NMR (500 MHz, CDCl3) ppm = 8.43 (s, 1H), 8.21 (s, 1H), 7.81 (s, 1H), 7.68 (s, 1H), 7.56 (d, J = 8.3, 2H), 7.28 (d, J = 8.3, 2H), 5.98 (bs, 1H), 3.96 (s, 3H), 3.28 (t, J = 6.8, 2H), 3.18-3.13 (m, 2H), 2.78-2.70 (m, 2H), 2.00-1.93 (m, 4H), 1.38-1.32 (m, 2H) | 422 | 2.37 (E) |

TABLE 2-continued

Examples E prepared according to General Procedure B.

| No | Structures | Starting material | Purification method | NMR | MS | RT |
|---|---|---|---|---|---|---|
| 90 | 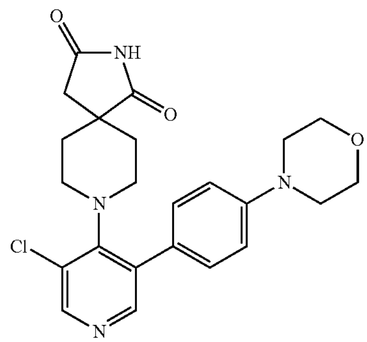 [SMILES: O=C1CC2(CCN(c3c(Cl)cncc3-c3ccc(N4CCOCC4)cc3)CC2)C(=O)N1] | C3 4-(4-(4,4,5,5-tetramethyl-1,3,2-dioxaborolan-2-yl)phenyl)morpholine | C, I, F | 1H NMR (500 MHz, CDCl3) ppm = 8.44 (bs, 1H), 8.23 (bs, 1H), 8.07 (bs, 1H), 7.18 (d, J = 8.7, 2H), 6.99 (d, J = 8.7, 2H), 3.92-3.88 (m, 4H), 3.26-3.23 (m, 4H), 3.25-3.20 (m, 2H), 2.80-2.70 (m, 2H), 2.55 (s, 2H), 2.15-2.06 (m, 2H), 1.51-1.79 (m, 2H) | 441 | 2.20 (D) |
| 91 | 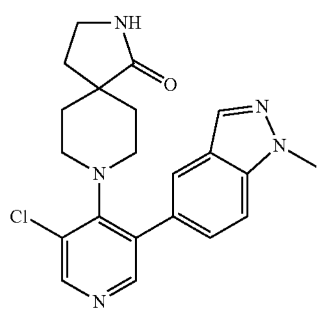 [SMILES: Cn1ncc2cc(-c3cncc(Cl)c3N3CCC4(CCNC4=O)CC3)ccc21] | C1 1-methyl-1H-indazol-5-ylboronic acid | C, I | 1H NMR (500 MHz, CDCl3) ppm = 8.45 (s, 1H), 8.24 (s, 1H), 8.04 (d, J = 0.9, 1H), 7.65 (s, 1H), 7.49 (d, J = 8.6, 1H), 7.32 (dd, J = 8.6, 1.5, 1H), 5.71 (bs, 1H), 4.14 (s, 3H), 3.25 (t, J = 6.9, 2H), 3.18-3.12 (m, 2H), 2.75-2.67 (m, 2H), 1.96-1.89 (m, 4H), 1.35-1.29 (m, 2H) | 396 | 2.11 (E) |
| 92 | 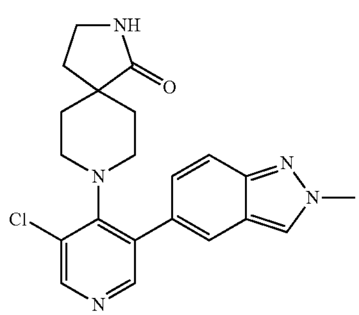 [SMILES: Cn1cc2cc(-c3cncc(Cl)c3N3CCC4(CCNC4=O)CC3)ccc2n1] | C1 2-methyl-5-(4,4,5,5-tetramethyl-1,3,2-dioxaborolan-2-yl)-2H-indazole | C, J, H | 1H NMR (500 MHz, DMSO-d6) ppm = 8.61 (s, 1H), 8.42 (s, 1H), 8.32 (S, 1H), 7.74-7.71 (m, 1H), 7.69 (d, J = 8.9, 1H), 7.49 (s, 1H), 7.18 (dd, J = 8.8, 1.6, 1H), 4.20 (s, 3H), 3.22-3.14 (m, 2H), 3.09 (t, J = 6.8, 2H), 2.79-2.67 (m, 2H), 1.81 (t, J = 6.8, 2H), 1.70 (td, J = 12.4, 4.2, 2H), 1.30-1.22 (m, 2H). | 396 | 1.81 (B) |
| 93 | 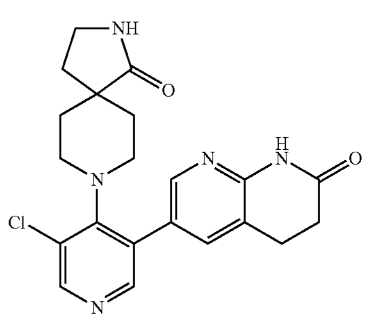 [SMILES: O=C1CCc2cc(-c3cncc(Cl)c3N3CCC4(CCNC4=O)CC3)cnc2N1] | C1 7-oxo-5,6,7,8-tetrahydro-[1,8]naphthyridine-3-boronic acid | Q, F | 1H NMR (500 MHz, DMSO-d6) ppm = 10.60 (s, 1H), 8.55 (s, 1H), 8.28 (s, 1H), 8.11 (d, J = 2.2, 1H), 7.66-7.62 (m, 1H), 7.52 (s, 1H), 3.17 - 3.07 (m, 4H), 2.97 (t, J = 7.6, 2H), 2.84-2.74 (m, 2H), 2.60-2.53 (m, 2H), 1.88 (t, J = 6.8, 2H), 1.72-1.62 (m, 2H), 1.32-1.24 (m, 2H). | 412 | 1.64 (B) |

TABLE 2-continued

Examples E prepared according to General Procedure B.

| No | Structures | Starting material | Purification method | NMR | MS | RT |
|---|---|---|---|---|---|---|
| 94 | | C9 | 2-Isopropyl-5-(4,4,5,5-tetramethyl-[1,3,2]dioxaborolan-2-yl)-2H-indazole | B, H | 1H NMR (400 MHz, DMSO-d6) ppm = 8.50-8.44 (m, 2H), 8.22 (s, 1H), 7.73-7.66 (m, 2H), 7.41 (s, 1H), 7.17 (dd, J = 8.9, 1.7, 1H), 4.86 (hept, J = 6.3, 1H), 3.16 (s, 2H), 2.99-2.85 (m, 4H), 1.77-1.66 (m, 4H), 1.58 (d, J = 6.6, 6H). | 426 | 1.60 (A) |
| 95 | | C9 | 2-ethyl-5-(4,4,5,5-tetramethyl-1,3,2-dioxaborolan-2-yl)-2H-indazole | B, H | 1H NMR (400 MHz, DMSO-d6) ppm = 8.48-8.44 (m, 2H), 8.23 (s, 1H), 7.73-7.66 (m, 2H), 7.41 (s, 1H), 7.17 (dd, J = 8.8, 1.8, 1H), 4.49 (q, J = 7.3, 2H), 3.15 (s, 2H), 2.97-2.85 (m, 4H), 1.75-1.65 (m, 4H), 1.54 (t, J = 7.3, 3H). | 412 | 1.52 (A) |
| 96 | | C16 | 1-methyl-5-(4,4,5,5-tetramethyl-1,3,2-dioxaborolan-2-yl)-1,3-dihydrobenzo[c]isothiazole 2,2-dioxide | Flash chromatography (MeOH/EtOAc) | — | 463 | 1.59 (A) |
| 97 | | C16 | 8-{3-Chloro-1-methyl-4-(4-(4,4,5,5-tetramethyl-1,3,2-dioxaborolan-2-yl)phenyl)-1H-pyrazole | Flash chromatography (MeOH/EtOAc) | — | 438 | 1.70 (A) |

TABLE 2-continued

Examples E prepared according to General Procedure B.

| No | Structures | Starting material | Purification method | NMR | MS | RT |
|----|------------|-------------------|---------------------|-----|-----|-----|
| 98 | 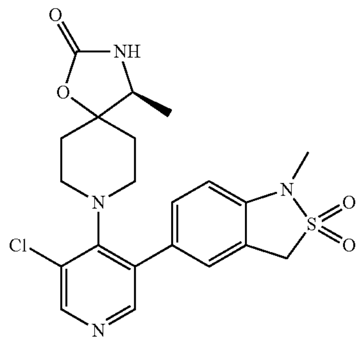 [SMILES: C[C@@H]1NC(=O)OC12CCN(c1c(Cl)cncc1-c1ccc3c(c1)CS(=O)(=O)N3C)CC2] | 96 | Chiral HPLC | 1H NMR (500 MHz, DMSO-d6) ppm = 8.45 (s, 1H), 8.17 (s, 1H), 7.56 (s, 1H), 7.41-7.39 (m, 1H), 7.33-7.30 (m, 1H), 7.09 (d, J = 8.2 Hz, 1H), 4.70 (s, 2H), 3.45 (q, J = 6.5 Hz, 1H), 3.10 (s, 3H), 3.01-2.81 (m, 4H), 1.73-1.53 (m, 4H), 1.00 (d, J = 6.4 Hz, 3H). | 463 | 1.59 (A) |
| 99 | 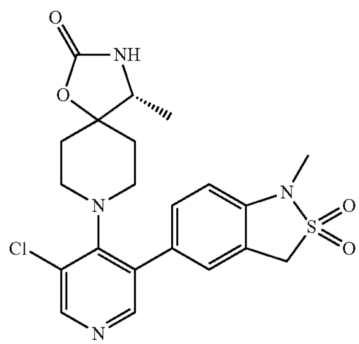 [SMILES: C[C@H]1NC(=O)OC12CCN(c1c(Cl)cncc1-c1ccc3c(c1)CS(=O)(=O)N3C)CC2] | 96 | Chiral HPLC | — | 463 | 1.59 (A) |
| 100 | 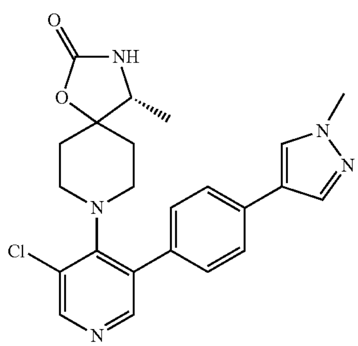 [SMILES: C[C@H]1NC(=O)OC12CCN(c1c(Cl)cncc1-c1ccc(-c3cnn(C)c3)cc1)CC2] | 97 | Chiral HPLC | 1H NMR (400 MHz, DMSO-d6) ppm = 8.46 (s, 1H), 8.22 (s, 1H), 8.21 (s, 1H), 7.94 (s, 1H), 7.73-7.67 (m, 2H), 7.54 (s, 1H), 7.36-7.31 (m, 2H), 3.88 (s, 3H), 3.44 (q, J = 6.4 Hz, 1H), 3.03-2.93 (m, 2H), 2.93-2.79 (m, 2H), 1.71-1.59 (m, 4H), 0.99 (d, J = 6.5 Hz, 3H). | 438 | 1.69 (A) |

Preparation of Compounds that do not Follow the General Scheme

1. Preparation of 8-[3-chloro-5-(1-methyl-1H-indazol-5-yl)-pyridin-4-yl]-4-hydroxy-2,8-diaza-spiro[4.5]decan-1-one 70

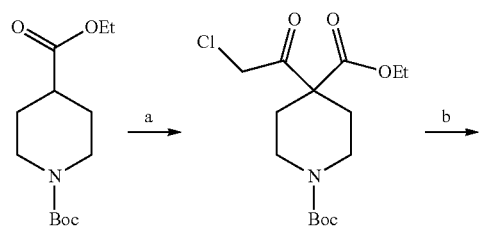

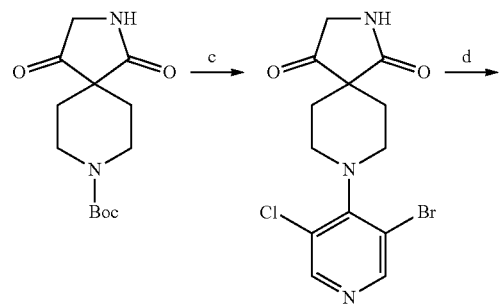

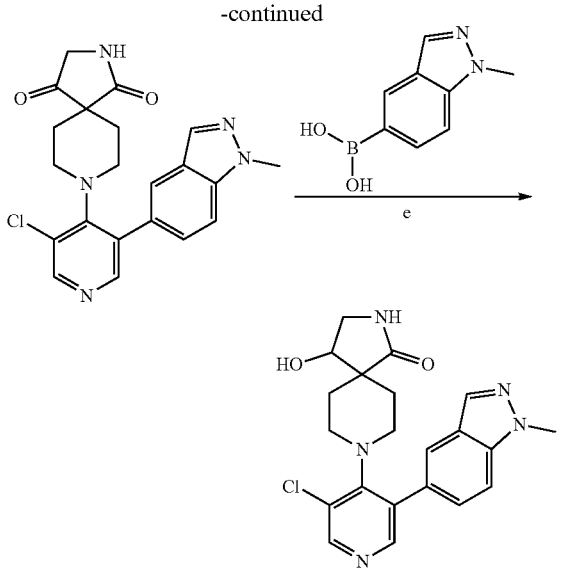

1a. 1-tert-Butyl 4-ethyl 4-(2-chloroacetyl)piperidine-1,4-dicarboxylate

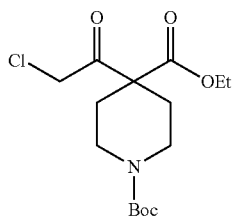 [SMILES: CCOC(=O)C1(C(=O)CCl)CCN(C(=O)OC(C)(C)C)CC1]

To a solution of diisopropylamine (1.318 mL, 9.33 mmol) in THF (50 mL) was added n-butyl lithium (1.6 M in hexane, 5.46 mL, 8.74 mmol) under nitrogen at −78° C. After 10 min a solution of 1-tert-butyl 4-ethyl piperidine-1,4-dicarboxylate (2.0 g, 7.77 mmol) in THF (5 mL) was added dropwise and the reaction mixture was stirred for 30 min and was then transferred by cannula to a solution of chloroacetyl chloride (3.53 mL, 44.3 mmol) in THF (20 mL). The mixture was allowed to warm to RT and the white cloudy suspension was stirred at RT for 20 min before sat. NaHCO$_3$ and EtOAc were added. The layers were separated and the aqueous layer was extracted with EtOAc twice. The combined organic layers were washed with brine, dried over MgSO$_4$ and concentrated in vacuum. The residue was purified by chromatography on silica gel (EtOAc/CyHex, 1:20 to 1:4 with 0.1% of Et$_3$N) to give the product (2.3 g, 89%, impure) as a light brown oil which was used in the next step without further purification

1b. tert-Butyl 1,4-dioxo-2,8-diazaspiro[4.5]decane-8-carboxylate

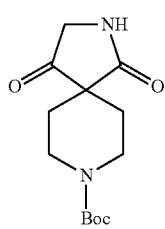

To a solution of 1-tert-butyl 4-ethyl 4-(2-chloroacetyl) piperidine-1,4-dicarboxylate (0.5 g, 1.498 mmol) in DMF (3 mL) was added sodium azide (0.107 g, 1.648 mmol) and the mixture was stirred at RT for 3 hr before it was diluted with water. The aqueous layer was extracted with EtOAc/CyHex (1:1) three times and the combined organic layers were washed with brine, dried over MgSO$_4$, filtrated and concentrated in vacuum. The crude was dissolved in EtOH (50 ml) and Pd/C (10 wt %, 100 mg, 1.498 mmol) was added. The flask was purged with H$_2$ and then reacted for 16 hr under an H$_2$-atmosphere at 40° C. The residue was filtered off and the resulting solution was stirred at reflux for 2 hr before the solvent was evaporated. Purification by chromatography on silica gel (DCM/EtOH, 99:1 to 97:3) gave the product (150 mg, 37%) as a pale yellow solid. 1H NMR (500 MHz, CDCl$_3$) ppm=6.77 (s, 1H), 3.91 (s, 2H), 3.75-3.83 (m, 2H), 3.58 (ddd, J=13.2, 8.2, 3.7, 2H), 1.76-1.86 (m, 2H), 1.66-7.72 (m, 2H), 1.46 (s, 9H). HRMS m/z (ESI$^+$) [M−Boc+H]$^+$ C$_8$H$_{12}$N$_2$O$_2$, calc 169.0972, found 169.0975, Rt=2.44 min (HPLC method E).

1c. 8-(3-Bromo-5-chloropyridin-4-yl)-2,8-diazaspiro[4.5]decane-1,4-dione

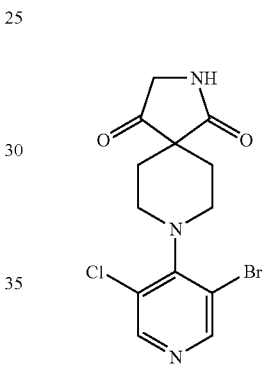

The title compound was prepared by reacting tert-butyl 1,4-dioxo-2,8-diazaspiro[4.5]decane-8-carboxylate and 3-bromo-4,5-dichloropyridine according to the general procedure A and purified by purification methods C and I. 1H NMR (500 MHz, CDCl$_3$) ppm=8.50 (s, 1H), 8.37 (s, 1H), 6.59 (s, 1H), 3.95 (s, 2H), 3.51-3.62 (m, 4H), 2.03-2.11 (m, 2H), 1.90 (td, J=13.5, 4.6, 2H). HRMS m/z (ESI$^+$) [M+H]$^+$ C$_{13}$H$_{14}$BrClN$_3$O$_2$, calc 357.9952, found 357.9944, Rt=2.6 min (HPLC method E).

1d. 8-(3-Chloro-5-(1-methyl-1H-indazol-5-yl)pyridin-4-yl)-2,8-diazaspiro[4.5]decane-1,4-dione

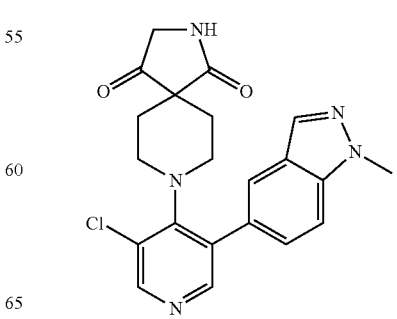

The title compound was prepared by reacting 8-(3-bromo-5-chloropyridin-4-yl)-2,8-diazaspiro[4.5]decane-1,4-dione and 1-methyl-1H-indazole-5-boronic acid according to the general procedure B and purified by purification methods C, J and N. 1H NMR (500 MHz, MeOD/CDCl$_3$, 1:1) ppm=8.36 (s, 1H), 8.17 (s, 1H), 8.06 (d, J=0.9, 1H), 7.71 (dd, J=1.5, 0.9, 1H), 7.62 (td, J=8.8, 0.9, 1H), 7.38 (dd, J=8.8, 1.5, 1H), 4.12 (s, 3H), 3.78 (s, 2H), 3.07-3.19 (m, 4H), 1.81-1.86 (m, 2H), 1.59-1.66 (m, 2H). HRMS m/z (ESI$^+$) [M+H]$^+$ C$_{21}$H$_{21}$ClN$_5$O$_2$, calc 410.1378, found 410.1370, Rt=2.2 min (HPLC method E).

1e. 8-[3-Chloro-5-(1-methyl-1H-indazol-5-yl)-pyridin-4-yl]-4-hydroxy-2,8-diaza-spiro[4.5]decan-1-one 70

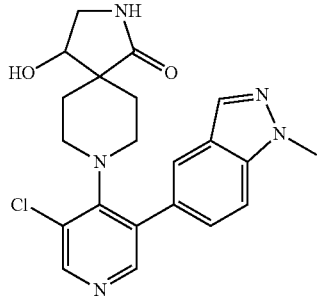 [SMILES: Cn1ncc2cc(-c3cncc(Cl)c3N3CCC4(CC3)C(=O)NCC4O)ccc21]

To a solution of 8-(3-chloro-5-(1-methyl-1H-indazol-5-yl)pyridin-4-yl)-2,8-diazaspiro[4.5]-decane-1,4-dione (10 mg, 0.024 mmol) in MeOH (0.5 mL) and CHCl$_3$ (0.5 mL) was added sodium borohydride (2.7 mg, 0.071 mmol) and the mixture was stirred at RT for 30 min before sat. NH$_4$Cl (0.5 ml) was added and the suspension was concentrated in vacuum. The residue was dissolved with water and CHCl$_3$ and the layers were separated. The aqueous layer was extracted twice with chloroform and the combined organic layers were washed with water, dried over MgSO$_4$ and concentrated in vacuum. The resulting brown oil was purified by prep. TLC (DCM/MeOH) to give the product (9.6 mg, 96%) as a white solid. 1H NMR (500 MHz, MeOD) ppm=8.38 (s, 1H), 8.17 (s, 1H), 8.08 (d, J=0.9, 1H), 7.74 (dd, J=1.5, 0.7, 1H), 7.67 (td, J=8.6, 0.7, 1H), 7.39 (dd, J=8.7, 1.6, 1H), 4.11 (s, 3H), 4.10-4.13 (m, 1H), 3.51 (dd, J=11.0, 5.2, 1H), 3.13-3.24 (m, 2H), 3.08 (dd, J=11.0, 2.3, 1H), 2.85-2.97 (m, 2H), 1.73-1.82 (m, 2H), 1.66 (ddd, J=13.4, 9.4, 4.0, 1H), 1.37-1.44 (m, 1H). HRMS m/z (ESI$^+$) [M+H]$^+$ C$_{21}$H$_{23}$ClN$_5$O$_2$, calc 412.1535, found 412.1527, Rt=1.85 min (HPLC method E).

By analogy to this procedure, compound 51 was also synthesized using 1-methyl-5-(4,4,5,5-tetramethyl-1,3,2-dioxaborolan-2-yl)-1,3-dihydrobenzo[c]iso-thiazole 2,2-dioxide in place of 1-methyl-1H-indazole-5-boronic acid.

8-[3-Chloro-5-(1-methyl-2,2-dioxo-2,3-dihydro-1H-benzo[c]isothiazol-5-yl)-pyridin-4-yl]-4-hydroxy-2,8-diaza-spiro[4.5]decan-1-one 51

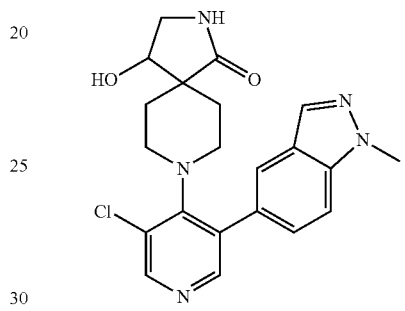

1H NMR (400 MHz, DMSO-d6) ppm=8.53 (s, 1H), 8.23 (s, 1H), 7.49 (s, 1H), 7.38-7.33 (m, 2H), 7.07-7.03 (m, 1H), 4.77-4.66 (m, 2H), 4.05-4.01 (m, 1H), 3.42-3.33 (m, 2H), 3.17-3.07 (m, 5H), 2.95-2.83 (m, 2H), 1.72-1.64 (m, 1H), 1.62-1.45 (m, 2H), 1.39-1.31 (m, 1H). LCMS (Method A): Rt 1.31 min, (M+H) 463.

2. Preparation of (1-(3-chloropyridin-4-yl)piperidin-4-yl)methanol Derivatives 77, 85

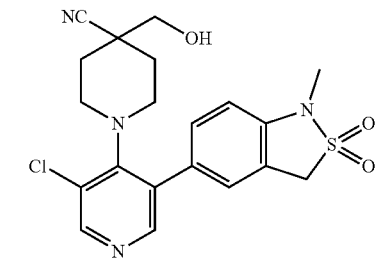

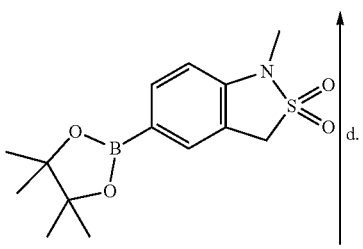

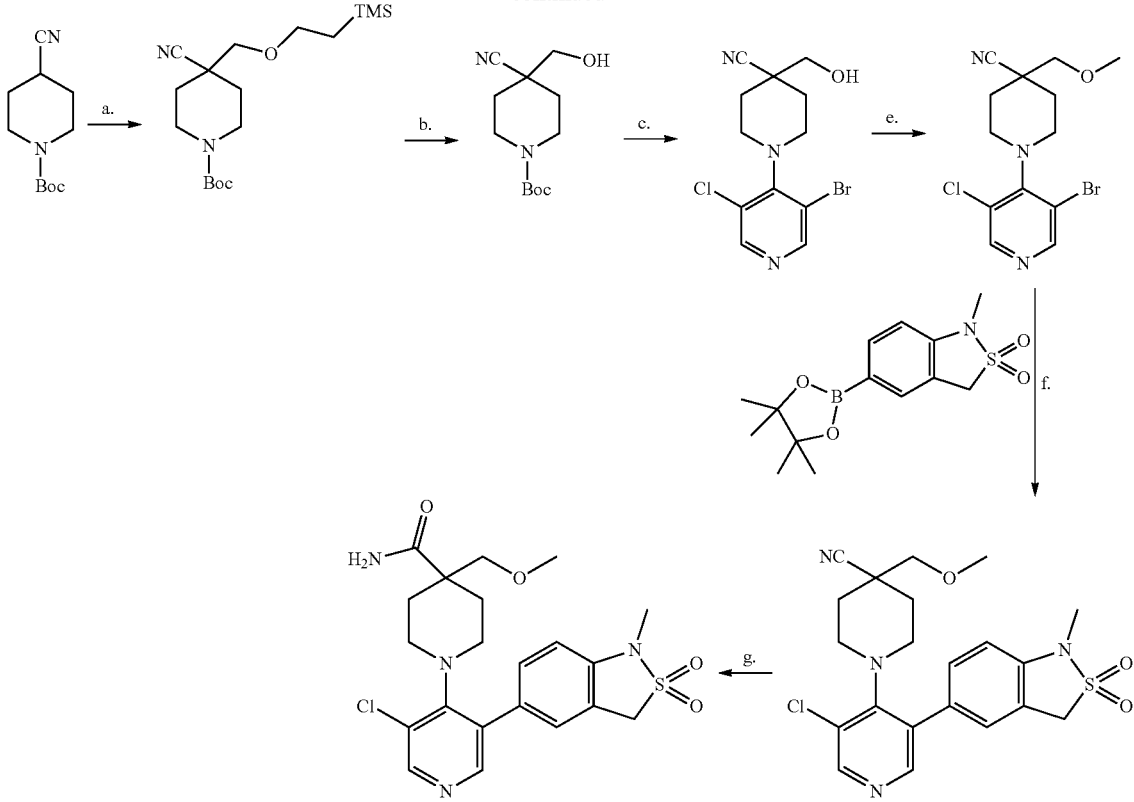

2a. tert-Butyl 4-cyano-4-((2-(trimethylsilyl)ethoxy)methyl)piperidine-1-carboxylate

To a solution of N-boc-4-cyanopiperidine (8.5 g, 40.4 mmol) in THF (130 mL) was added LiHMDS (1M in THF, 60.6 mL, 60.6 mmol) dropwise at 0° C. under nitrogen atmosphere. The reaction mixture was warmed to RT and stirred at RT for 1 hr. 2-(Trimethylsilyl)ethoxymethyl chloride (10.73 mL, 60.6 mmol) was added dropwise and the mixture was stirred at RT overnight before the mixture was diluted with water and EtOAc. The layers were separated and the aqueous layer was extracted with EtOAc three times. The combined organic layers were dried over MgSO$_4$ and concentrated. The resulting oil was purified by chromatography on silica gel (biotage, CyHex/EtOAc, 100:0 to 85:15) to give the product (8.3 g, 60%) as a white solid. 1H NMR (500 MHz, CDCl$_3$) ppm=4.19-4.09 (m, 2H), 3.60 (t, J=9.2, 2H), 3.42 (s, 2H), 3.05 (dd, J=10.8, 10.8, 2H), 1.93 (dd, J=12.8, 4.5, 2H), 1.51 (dd, J=12.8, 4.5, 2H), 1.46 (s, 9H), 0.95 (t, J=9.2, 2H), 0.03 (s, 9H). HRMS m/z (ESI$^+$) [M−Boc+H]$^+$ C$_{12}$H$_{25}$N$_2$OSi, calc 241.1731, found 241.1740, Rt=3.33 min (HPLC method E).

2b. tert-Butyl 4-cyano-4-(hydroxymethyl)piperidine-1-carboxylate

To a solution of tert-butyl 4-cyano-4-((2-(trimethylsilyl)ethoxy)methyl)piperidine-1-carboxylate (1.0 g, 2.94 mmol) in THF (5 mL) was added TBAF (1M in THF, 5.87 mL, 5.87 mmol) and the mixture was heated to 80° C. for 3 hr. Additional TBAF (1M in THF, 5.87 mL, 5.87 mmol) was added to the reaction mixture and the dark yellow solution was stirred at 80° C. for 48 hr before it was diluted with water and EtOAc. The layers were separated and the aqueous layer was extracted with EtOAc three times. The combined organic layers were dried over MgSO$_4$ and concentrated. The resulting oil was purified by chromatography on silica gel (biotage, DCM/EtOH, 100:0 to 96:4) to give the product (530 mg, 75%) as a white solid. 1H NMR (500 MHz, MeOD) ppm=4.14 (dd, J=13.8, 3.5, 2H), 3.59 (s, 2H), 3.12-2.92 (m, 2H), 1.96-1.88 (m, 2H), 1.50 (dd, J=13.8, 3.5, 2H), 1.47 (s, 9H). HRMS m/z (ESI$^+$) [M−Boc+H]$^+$ C₇H₁₃N₂O, calc 141.1022, found 141.1025, Rt=2.43 min (not UV-active) (HPLC method E).

2c. 1-(3-Bromo-5-chloropyridin-4-yl)-4-(hydroxymethyl)piperidine-4-carbonitrile

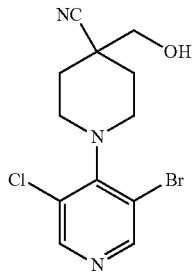 [SMILES: N#CC1(CO)CCN(c2c(Cl)cncc2Br)CC1]

The title compound was prepared by reacting 3-bromo-4,5-dichloropyridine and tert-butyl 4-cyano-4-(hydroxymethyl)piperidine-1-carboxylate according to the general procedure A and purified by purification methods D and K. 1H NMR (500 MHz, DMSO) ppm=8.59 (s, 1H), 8.49 (s, 1H), 5.52 (t, J=5.6, 1H), 3.54 (d, J=5.6, 2H), 3.42 (td, J=13.0, 3.0, 2H), 3.32 (s, 2H), 1.98-1.90 (m, 2H), 1.68 (td, J=13.0, 3.0, 2H). HRMS m/z (ESI⁺) [M+H]⁺ C₁₂H₁₄BrClN₃O, calc 330.0003, found 330.0003, Rt=3.05 min (HPLC method E).

2d. 5'-Chloro-4-hydroxymethyl-3'-(1-methyl-2,2-dioxo-2,3-dihydro-1H-benzo[c]isothiazol-5-yl)-3,4,5,6-tetrahydro-2H-[1,4']bipyridinyl-4-carbonitrile

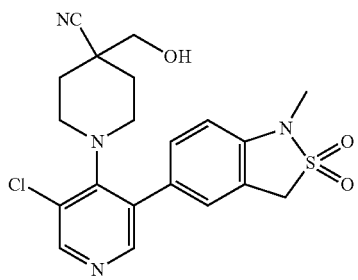 [SMILES: CN1c2ccc(-c3cncc(Cl)c3N3CCC(C#N)(CO)CC3)cc2CS1(=O)=O]

The title compound was prepared by reacting 1-(3-bromo-5-chloropyridin-4-yl)-4-(hydroxymethyl)piperidine-4-carbonitrile and 1-methyl-5-(4,4,5,5-tetramethyl-1,3,2-dioxaborolan-2-yl)-1,3-dihydrobenzo[c]iso-thiazole 2,2-dioxide according to the general procedure B and purified by purification methods C, I and E. 1H NMR (500 MHz, MeOD) ppm=8.43 (s, 1H), 8.21 (s, 1H), 7.42-7.35 (m, 2H), 7.03 (d, J=8.7, 1H), 4.56 (s, 2H), 3.56 (s, 2H), 3.22-3.15 (m, 2H), 3.06-2.91 (m, 2H), 1.87-1.75 (m, 2H), 1.62 (td, J=4.21, 12.9, 2H). HRMS m/z (ESI⁺) [M+H]⁺ C₂₀H₂₁ClN₄O₃S, calc 433.1096, found 433.1098, Rt=2.15 min (HPLC method E).

2e. 1-(3-Bromo-5-chloropyridin-4-yl)-4-(methoxymethyl)piperidine-4-carbonitrile

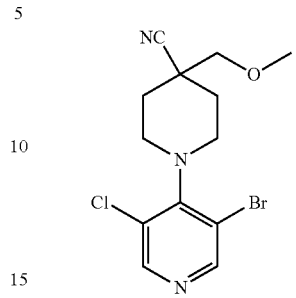

To a solution of 1-(3-bromo-5-chloropyridin-4-yl)-4-(hydroxymethyl)piperidine-4-carbonitrile (100 mg, 0.302 mmol) in dry DMF (1 mL) was added sodium hydride (60% in mineral oil, 14.5 mg, 0.363 mmol) at 0° C. and the mixture was stirred at 0° C. for 20 min before methyl iodide (0.023 mL, 0.363 mmol) was added. The mixture was allowed to warm to RT over 20 min and stirred at RT for 1 hr before the mixture was diluted with water and EtOAc. The layers were separated and the aqueous layer was extracted with EtOAc twice. The combined organic layers were washed with water twice, dried over MgSO₄ and concentrated. The resulting residue was purified by chromatography on silica gel (biotage, CyHex/EtOAc, 95:5 to 70:30) to give the product (91 mg, 87%) as a colourless crystallizing oil. 1H NMR (500 MHz, CDCl₃) ppm=8.48 (s, 1H), 8.35 (s, 1H), 3.62 (dt, J=12.5, 3.1, 2H), 3.46 (s, 2H), 3.43 (s, 3H), 3.32-3.20 (m, 2H), 2.05-1.98 (m, 2H), 1.79 (dt, J=12.5, 3.1, 2H). HRMS m/z (ESI⁺) [M+H]⁺ C₁₃H₁₆BrClN₃O, calc 344.0160, found 344.0147, Rt=2.91 min (HPLC method E).

2f. 1-(3-Chloro-5-(1-methyl-2,2-dioxido-1,3-dihydrobenzo[c]isothiazol-5-yl)pyridin-4-yl)-4-(methoxymethyl)piperidine-4-carbonitrile

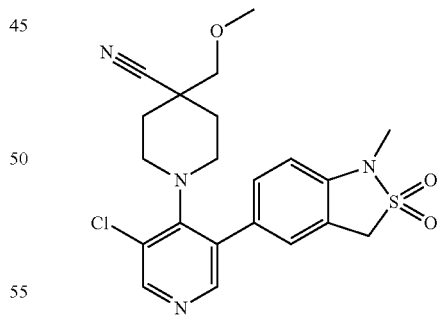

The title compound was prepared by reacting 1-(3-bromo-5-chloropyridin-4-yl)-4-(methoxymethyl)piperidine-4-carbonitrile and 1-methyl-5-(4,4,5,5-tetramethyl-1,3,2-dioxaborolan-2-yl)-1,3-dihydrobenzo[c]iso-thiazole 2,2-dioxide according to the general procedure B and purified by purification methods C and L. 1H NMR (500 MHz, CDCl₃) ppm=8.47 (s, 1H), 8.24 (s, 1H), 7.26 (dd, J=8.2, 1.5, 1H), 7.22 (d, J=1.5, 1H), 6.85 (d, J=8.2, 1H), 4.44 (s, 2H), 3.42 (s, 3H), 3.40 (s, 2H), 3.20 (s, 3H), 3.09 (dt, J=12.9, 3.1, 2H), 2.97 (t, J=12.9, 2H), 1.88-1.82 (m, 2H), 1.64 (td, J=12.7, 4.2, 2H). HRMS m/z (ESI⁺) [M+H]⁺ $C_{21}H_{24}ClN_4O_3S$, calc 447.1252, found 447.1248, Rt=2.58 min (HPLC method E).

2 g. 5'-Chloro-4-methoxymethyl-3'-(1-methyl-2,2-dioxo-2,3-dihydro-1H-benzo[c]isothiazol-5-yl)-3,4,5,6-tetrahydro-2H-[1,4']bipyridinyl-4-carboxylic Acid Amide 77

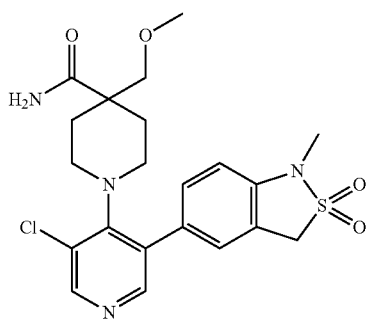 [SMILES: COCC1(C(N)=O)CCN(c2c(Cl)cncc2-c2ccc3c(c2)CS(=O)(=O)N3C)CC1]

To 1-(3-chloro-5-(1-methyl-2,2-dioxido-1,3-dihydrobenzo[c]isothiazol-5-yl)pyridin-4-yl)-4-(methoxymethyl)piperidine-4-carbonitrile (30 mg, 0.067 mmol) was added an ice cold mixture of water (30 μl) and conc. $H_2SO_4$ (717 μl, 13.42 mmol) at 0° C. and the yellow solution was stirred at 50° C. for 3 hr. The mixture was dropped into ice-cooled water and solid NaOH was added (pH 14). To neutralize the mixture sat. $NaHCO_3$ was added (pH 9) and the mixture was diluted with EtOAc. The layers were separated and the aqueous layer was extracted with EtOAc three times. The combined organic layers were washed with water, dried over $MgSO_4$ and concentrated in vacuum. The resulting residue was purified by chromatography on silica gel (biotage, DCM/EtOH, 100:0 to 93:7) and by using an SCX2-cartridge (loading with DCM/MeOH, 9:1, elution with DCM/1N $NH_3$ in MeOH, 9:1) to give the product (14 mg, 45%) as a white solid. 1H NMR (500 MHz, $CDCl_3$) ppm=8.44 (s, 1H), 8.20 (s, 1H), 7.27-7.25 (m, 1H), 7.21 (d, J=1.5, 1H), 6.82 (d, J=8.2, 1H), 6.37 (bs, 1H), 5.51 (bs, 1H), 4.47 (s, 2H), 3.37 (s, 3H), 3.34 (s, 2H), 3.19 (s, 3H), 2.99-2.85 (m, 4H), 1.95 (dt, J=13.6, 4.2, 2H), 1.51 (ddd, J=13.6, 9.3, 4.2, 2H). HRMS m/z (ESI⁺) [M+H]⁺ $C_{21}H_{26}ClN_4O_4S$, calc 465.1358, found 465.1356, Rt=2.04 min (HPLC method E).

3. Preparation of 8-[3-Ethynyl-5-(1-methyl-2,2-dioxo-2,3-dihydro-1H-benzo[c]isothiazol-5-yl)-pyridin-4-yl]-2,8-diaza-spiro[4.5]decan-1-one 81

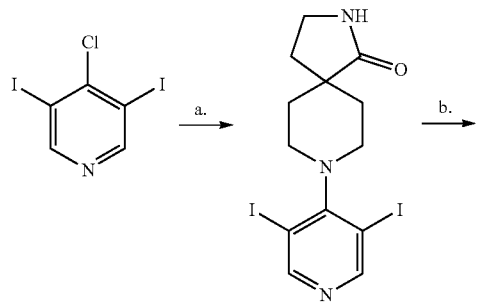

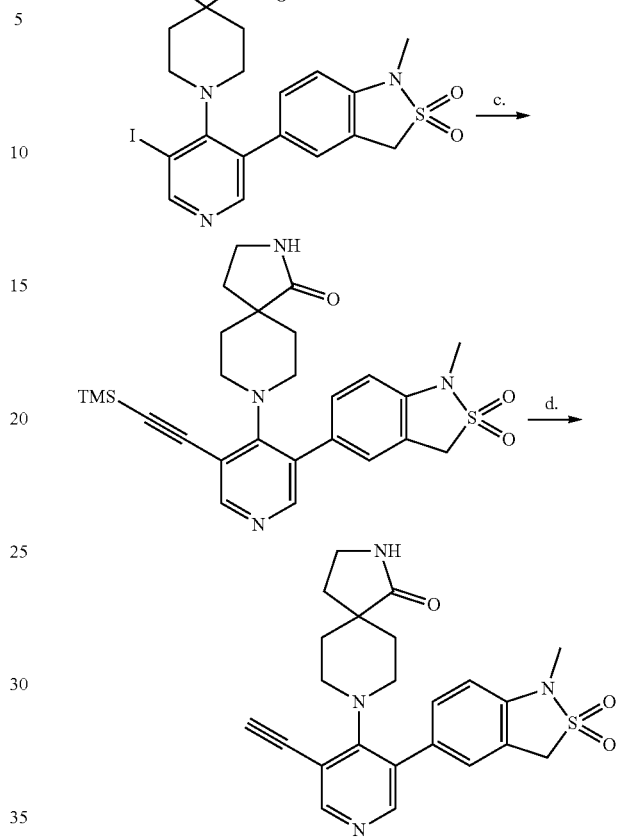

3a. 8-(3,5-Diiodopyridin-4-yl)-2,8-diazaspiro[4.5]decan-1-one

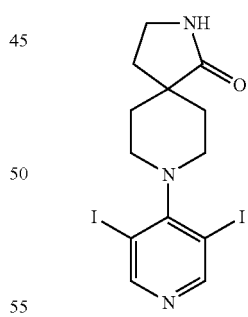

The title compound was prepared by reacting 4-chloro-3,5-diiodopyridine (1.0 g, 2.74 mmol) and 8-boc-2,8-diaza-spiro-[4.5]decan-1-one according to the general procedure A and purified by purification methods D and L. ¹H-NMR (500 MHz, DMSO) ppm=8.78 (bs, 2H), 7.59 (s, 1H), 3.45 (td, J=12.0, 3.1, 2H), 3.21 (t, J=6.7, 2H), 2.95 (dt, J=12.0, 3.1, 2H), 2.03 (t, J=6.7, 2H), 1.98 (td, J=13.0, 3.5, 2H), 1.46 (dt, J=13.0, 3.5, 2H). HRMS m/z (ESI⁺) [M+H]⁺ $C_{13}H_{16}I_2N_3O$, calc 483.9377, found 483.9382, Rt=2.85 min (HPLC method E).

3b. 8-(3-Iodo-5-(1-methyl-2,2-dioxido-1,3-dihydrobenzo[c]isothiazol-5-yl)pyridin-4-yl)-2,8-diazaspiro[4.5]decan-1-one

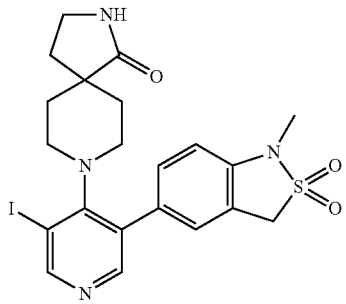 [SMILES: CN1c2ccc(-c3cncc(I)c3N3CCC4(CCNC4=O)CC3)cc2CS1(=O)=O]

The title compound was prepared by reacting 8-(3,5-diiodopyridin-4-yl)-2,8-diazaspiro[4.5]decan-1-one and 1-methyl-5-(4,4,5,5-tetramethyl-1,3,2-dioxaborolan-2-yl)-1,3-dihydrobenzo[c]isothiazole 2,2-dioxide according to the general procedure B and purified by purification methods C and G. $^1$H-NMR (500 MHz, CDCl$_3$) ppm=8.83 (s, 1H), 8.19 (s, 1H), 7.21 (d, J=8.2, 1H), 7.19 (s, 1H), 6.80 (d, J=8.2, 1H), 6.59 (bs, 1H), 4.47 (s, 2H), 3.30 (t, J=6.8, 2H), 3.18 (s, 3H), 3.15-3.06 (m, 2H), 2.76-2.58 (m, 2H), 2.03-1.82 (m, 2H), 1.91 (t, J=6.8, 2H), 1.50-1.40 (m, 2H). HRMS m/z (ESI$^+$) [M+H]$^+$ C$_{21}$H$_{24}$IN$_4$O$_3$S, calc 539.0608, found 539.0618, Rt=2.20 min (HPLC method E).

3c. 8-(3-(1-Methyl-2,2-dioxido-1,3-dihydrobenzo[c]isothiazol-5-yl)-5-((trimethylsilyl)ethynyl)pyridin-4-yl)-2,8-diazaspiro[4.5]decan-1-one

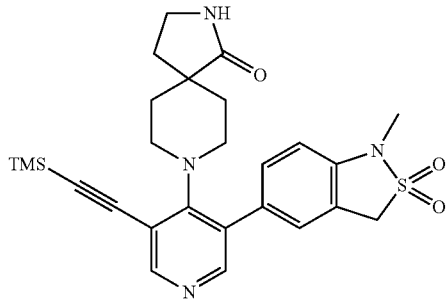 [SMILES: CN1c2ccc(-c3cncc(C#C[Si](C)(C)C)c3N3CCC4(CCNC4=O)CC3)cc2CS1(=O)=O]

A mixture of 8-(3-iodo-5-(1-methyl-2,2-dioxido-1,3-dihydrobenzo[c]isothiazol-5-yl)pyridin-4-yl)-2,8-diazaspiro[4.5]decan-1-one (47 mg, 0.087 mmol), TMS-acetylene (0.015 mL, 0.105 mmol), copper iodide (1.663 mg, 8.73 µmol) and triethylamine (0.017 mL, 0.131 mmol) in dry DMF (1.0 mL) was degassed. Pd(PPh$_3$)$_2$Cl$_2$ (6.13 mg, 8.73 µmol) was added and the mixture was stirred at 50° C. for 1 hr before water and EtOAc were added. The layers were separated and the aqueous layer was extracted with EtOAc three times. The combined organic layers were dried over MgSO$_4$ and concentrated in vacuum. The resulting brown oil was purified by chromatography on silica gel (biotage, DCM/MeOH, 100:0 to 94:6) and by using an SCX2 cartridge (loading with DCM/MeOH, 10:1, elution with DCM/1N NH$_3$ in MeOH, 9:1) and further purified by prep. HPLC (Gilson, acetonitrile/water gradient+0.1% formid acid gradient) to give the product (18 mg, 41%) as crystallizing colourless oil containing aliphatic impurities and small amounts of alkyne-deprotected product. $^1$H-NMR (500 MHz, CDCl$_3$) ppm=8.47 (s, 1H), 8.14 (s, 1H), 7.30 (s, 1H), 7.28 (d, J=7.9, 1H), 6.81 (d, J=7.9, 1H), 6.17 (s, 1H), 4.47 (s, 2H), 3.40-3.28 (m, 4H), 3.18 (s, 3H), 3.05-2.97 (m, 2H), 2.00 (t, J=5.5, 2H), 1.91-1.80 (m, 2H), 1.37 (dt, J=13.8, 5.5, 2H), 0.28 (s, 9H). HRMS m/z (ESI$^+$) [M+H]$^+$ C$_{26}$H$_{33}$N$_4$O$_3$SSi, calc 509.2037, found 509.2060, Rt=2.48 min (HPLC method E).

3d. 8-[3-Ethynyl-5-(1-methyl-2,2-dioxo-2,3-dihydro-1H-benzo[c]isothiazol-5-yl)-pyridin-4-yl]-2,8-diaza-spiro[4.5]decan-1-one 81

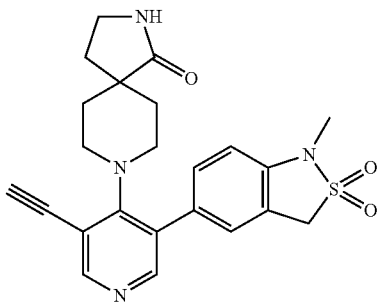 [SMILES: C#Cc1cncc(-c2ccc3c(c2)CS(=O)(=O)N3C)c1N1CCC2(CCNC2=O)CC1]

To a solution of 8-(3-(1-methyl-2,2-dioxido-1,3-dihydrobenzo[c]isothiazol-5-yl)-5-((trimethylsilyl)ethynyl)pyridin-4-yl)-2,8-diazaspiro[4.5]decan-1-one (18.7 mg, 0.037 mmol) in MeOH (0.5 mL) was added potassium carbonate (5.59 mg, 0.040 mmol) and the mixture was stirred at RT for 1 hr before water and DCM were added. The layers were separated and the aqueous layer was extracted with DCM three times. The combined organic layers were dried over MgSO$_4$ and concentrated in vacuum. The resulting brown oil was purified by chromatography on silica gel (biotage, DCM/MeOH, 100:0 to 93:7), by using an SCX2 cartridge (loading with DCM/MeOH, 10:1, eluation with DCM/1N NH$_3$ in MeOH, 9:1) and by prep. TLC (DCM/MeOH, 35:1) to give the product (9 mg, 56%) as crystallizing colourless oil. $^1$H-NMR (500 MHz, CDCl$_3$/MeOD, 1:1) ppm=8.37 (s, 1H), 8.06 (s, 1H), 7.34 (d, J=1.8, 1H), 7.31 (dd, J=8.2, 1.8, 1H), 6.91 (d, J=8.2, 1H), 4.52 (s, 2H), 3.73 (s, 1H), 3.39 (dt, J=13.7, 3.5, 2H), 3.30 (t, J=6.9, 2H), 3.17 (s, 3H), 3.02-2.92 (m, 2H), 2.03 (t, J=6.9, 2H), 1.89-1.79 (m, 2H), 1.35 (dt, J=13.7, 3.5, 2H). HRMS m/z (ESI$^+$) [M+H]$^+$ C$_{23}$H$_{25}$N$_4$O$_3$S, calc 437.1642, found 437.1644, Rt=1.76 min (HPLC method E).

4. Preparation of 8-(3-chloropyridin-4-yl)-1,3,8-triazaspiro[4.5]decan-4-one Derivatives 88

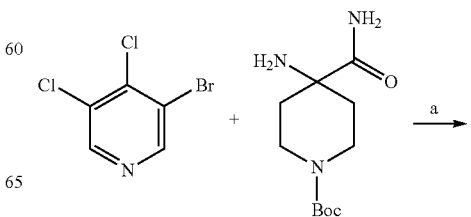

73

-continued

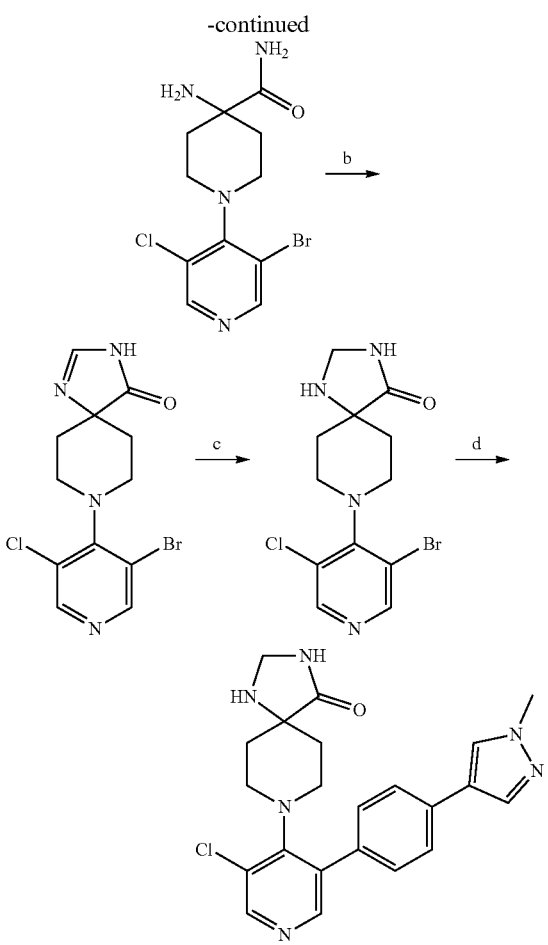

4a. 4-Amino-1-(3-bromo-5-chloropyridin-4-yl)piperidine-4-carboxamide

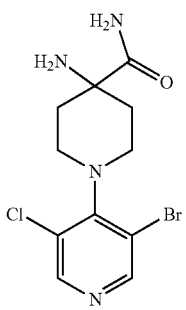 [SMILES: NC(=O)C1(N)CCN(c2c(Cl)cncc2Br)CC1]

The title compound was prepared by reacting 3-bromo-4,5-dichloropyridine and tert-butyl-4-amino-4-carboamoylpiperidine-1-carboxylate according to the general procedure A and purified by purification methods D and I. $^1$H-NMR (500 MHz, DMSO) ppm=8.53 (s, 2H), 8.42 (s, 1H), 7.44 (s, 1H), 6.96 (s, 1H), 3.54 (td, J=12.2, 3.0, 2H), 3.09 (td, J=12.2, 3.0, 2H), 2.08 (td, J=12.9, 4.3, 2H), 1.93 (s, 2H), 1.48-1.41 (m, 1H). HRMS m/z (ESI$^+$) [M+H]$^+$ C$_{11}$H$_{15}$BrClN$_4$O, calc 333.0112, found 333.0110, Rt=1.12 min (HPLC method E).

74

4b. 8-(3-Bromo-5-chloropyridin-4-yl)-1,3,8-triazaspiro[4.5]dec-1-en-4-one

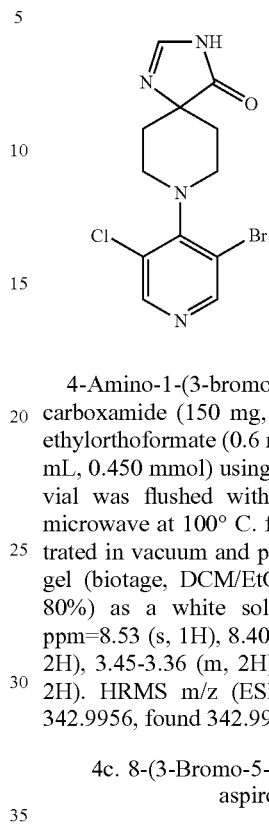

4-Amino-1-(3-bromo-5-chloropyridin-4-yl)piperidine-4-carboxamide (150 mg, 0.450 mmol) was dissolved in triethylorthoformate (0.6 ml, 0.450 mmol) and acetic acid (0.3 mL, 0.450 mmol) using gentle heating with a heat gun. The vial was flushed with argon, sealed and heated in the microwave at 100° C. for 5 min. The mixture was concentrated in vacuum and purified by chromatography on silica gel (biotage, DCM/EtOH) to give the product (124 mg, 80%) as a white solid. $^1$H-NMR (500 MHz, CDCl$_3$) ppm=8.53 (s, 1H), 8.40 (s, 1H), 7.90 (s, 1H), 3.83-3.73 (m, 2H), 3.45-3.36 (m, 2H), 2.28-2.16 (m, 2H), 1.65-1.52 (m, 2H). HRMS m/z (ESI$^+$) [M+H]$^+$ C$_{12}$H$_{13}$BrClN$_4$O, calc 342.9956, found 342.9952, Rt=2.46 min (HPLC method E).

4c. 8-(3-Bromo-5-chloropyridin-4-yl)-1,3,8-triazaspiro[4.5]decan-4-one

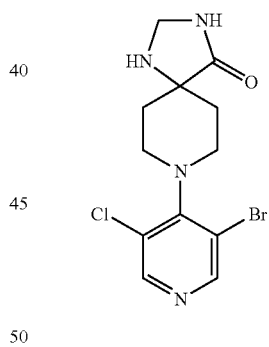

To a solution of 8-(3-bromo-5-chloropyridin-4-yl)-1,3,8-triazaspiro[4.5]dec-1-en-4-one (173 mg, 0.503 mmol) in MeOH (5 mL) and DCM (3 mL) was added sodium borohydride (38.1 mg, 1.007 mmol) under nitrogen atmosphere and the mixture was stirred at RT for 3 hr. The reaction was quenched with 0.5M NaOH and EtOAc was added. The layers were separated and the aqueous layer was extracted with EtOAc three times. The combined organic layers were washed with water, dried over MgSO$_4$ and concentrated in vacuum. The resulting brown oil was purified by chromatography on silica gel (biotage, DCM/EtOH) to give the product (150 mg, 86%) as a white solid. $^1$H-NMR (500 MHz, CDCl$_3$) ppm=8.50 (s, 1H), 8.36 (s, 1H), 7.20 (bs, 1H), 4.43 (s, 2H), 3.57 (td, J=12.7, 3.2, 2H), 3.36-3.25 (m, 2H), 2.19 (td, J=12.7, 3.2, 2H), 1.96 (bs, 1H), 1.68-1.56 (m, 2H). HRMS m/z (ESI$^+$) [M+H]$^+$ C$_{12}$H$_{15}$BrClN$_4$O, calc 345.0112, found 345.0107, Rt=1.78 min (HPLC method E).

4d. 8-{3-Chloro-5-[4-(1-methyl-1H-pyrazol-4-yl)-phenyl]-pyridin-4-yl}-1,3,8-triaza-spiro[4.5]decan-4-one 88

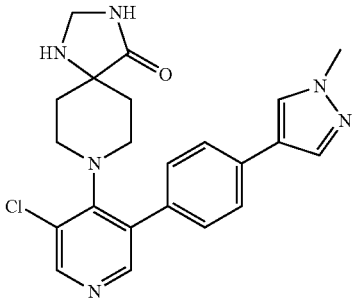 [SMILES: Cn1cc(-c2ccc(-c3cncc(Cl)c3N3CCC4(CC3)NCNC4=O)cc2)cn1]

The title product was prepared by reacting 8-(3-bromo-5-chloropyridin-4-yl)-1,3,8-triazaspiro[4.5]decan-4-one and 1-methyl-4-(4-(4,4,5,5-tetramethyl-1,3,2-dioxaborolan-2-yl)phenyl)-1H-pyrazole according to the general procedure B and purified by purification methods C, I, E and M. $^1$H-NMR (500 MHz, CDCl$_3$) ppm=8.45 (s, 1H), 8.23 (s, 1H), 7.83 (s, 1H), 7.69 (s, 1H), 7.58 (d, J=8.2, 2H), 7.30 (d, J=8.2, 2H), 6.43 (bs, 1H), 4.32 (s, 2H), 3.98 (s, 3H), 3.18-3.08 (m, 2H), 2.96 (t, J=10.5, 2H), 2.07-1.99 (m, 2H), 1.45 (t, J=10.5, 2H). HRMS m/z (ESI$^+$) [M+H]$^+$ C$_{22}$H$_{24}$ClN$_6$O, calc 423.1695, found 423.1691, Rt=1.94 min (HPLC method E).

Using the same procedures, compounds 74, 75, 78, 82 were synthesised using the respective boronic acids: 1-Methyl 6-(4,4,5,5-tetramethyl-1,3,2-dioxaborolan-2-yl) indolin-2-one; 1-methyl-5-(4,4,5,5-tetramethyl-1,3,2-dioxaborolan-2-yl)-1,3-dihydrobenzo[c]isothiazole 2,2-dioxide; 1-isopropyl-4-(4-(4,4,5,5-tetramethyl-1,3,2-dioxaborolan-2-yl)phenyl)-1H-pyrazole or. 1-methyl-1H-indazole-5-boronic acid.

8-[3-Chloro-5-(1-methyl-2-oxo-2,3-dihydro-1H-indol-6-yl)-pyridin-4-yl]-1,3,8-triaza-spiro[4.5]decan-4-one 74

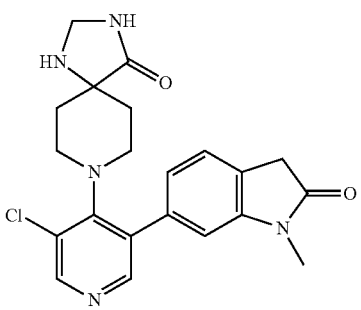 [SMILES: CN1C(=O)Cc2ccc(-c3cncc(Cl)c3N3CCC4(CC3)NCNC4=O)cc21]

1H-NMR (500 MHz, DMSO) ppm=8.45 (s, 1H), 8.21 (s, 1H), 7.99 (bs, 1H), 7.36 (d, J=7.5, 1H), 7.00 (s, 1H), 6.98 (dd, J=7.5, 1.4, 1H), 4.04 (s, 2H), 3.63 (s, 2H), 3.18 (s, 3H), 3.04-2.94 (m, 2H), 2.89 (t, J=12.1, 2H), 1.69 (td, J=12.1, 4.3, 2H), 1.36-1.29 (m, 2H). HRMS m/z (ESI$^+$) [M+H]$^+$ C$_{21}$H$_{23}$ClN$_5$O$_2$, calc 412.1535, found 412.1530, Rt=1.59 min (HPLC method E).

8-[3-Chloro-5-(1-methyl-2,2-dioxo-2,3-dihydro-1H-benzo[c]isothiazol-5-yl)-pyridin-4-yl]-1,3,8-triaza-spiro[4.5]decan-4-one 75

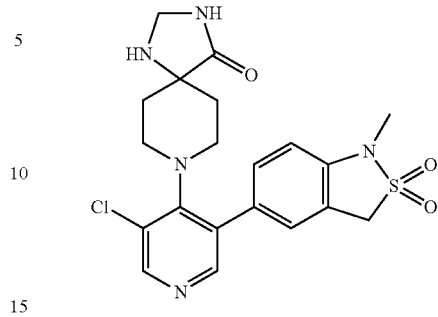

1H-NMR (500 MHz, MeOD) ppm=8.39 (s, 1H), 8.15 (s, 1H), 7.38-7.33 (m, 2H), 7.01 (d, J=8.7, 1H), 4.61 (s, 2H), 4.26 (s, 2H), 3.16 (s, 3H), 3.19-3.12 (m, 2H), 3.05-2.96 (m, 2H), 1.97-1.86 (m, 2H), 1.51-1.45 (m, 2H). HRMS m/z (ESI$^+$) [M+H]$^+$ C$_{20}$H$_{22}$ClN$_5$O$_3$S, calc 448.1205, found 448.1193, Rt=1.58 min (HPLC method E).

8-{3-Chloro-5-[4-(1-isopropyl-1H-pyrazol-4-yl)-phenyl]-pyridin-4-yl}-1,3,8-triaza-spiro[4.5]decan-4-one 78

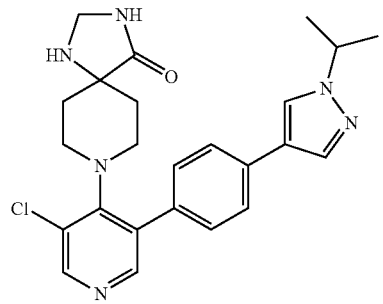 [SMILES: CC(C)n1cc(-c2ccc(-c3cncc(Cl)c3N3CCC4(CC3)NCNC4=O)cc2)cn1]

1H-NMR (500 MHz, CDCl3) ppm=8.45 (s, 1H), 8.23 (s, 1H), 7.85 (d, J=0.8, 1H), 7.76 (d, J=0.8, 1H), 7.60 (d, J=8.2, 2H), 7.30 (d, J=8.2, 2H), 6.47 (bs, 1H), 4.57 (p, J=6.7, 1H), 4.32 (s, 2H), 3.13 (dt, J=12.4, 3.2, 2H), 2.95 (dt, J=12.4, 3.2, 2H), 2.04 (dt, J=12.8, 4.4, 2H), 1.59 (d, J=6.7, 3H), 1.57 (d, J=6.7, 3H), 1.46-1.40 (m, 2H). HRMS m/z (ESI$^+$) [M+H]$^+$ C$_{24}$H$_{28}$ClN$_6$O, calc 451.2008, found 451.1997, Rt=2.33 min (HPLC method E).

8-[3-Chloro-5-(1-methyl-1H-indazol-5-yl)-pyridin-4-yl]-1,3,8-triaza-spiro[4.5]decan-4-one 82

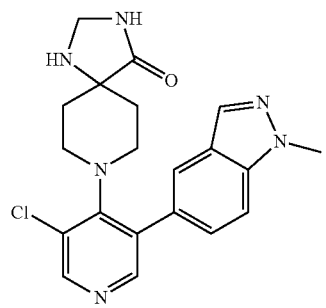 [SMILES: Cn1ncc2cc(-c3cncc(Cl)c3N3CCC4(CC3)NCNC4=O)ccc21]

1H-NMR (500 MHz, CDCl3) ppm=8.47 (s, 1H), 8.26 (s, 1H), 8.06 (d, J=0.6, 1H), 7.67 (d, J=0.6, 1H), 7.51 (d, J=8.6, 1H), 7.34 (dd, J=8.6, 0.6, 1H), 5.73 (bs, 1H), 4.30 (s, 2H), 4.15 (s, 3H), 3.13 (dt, J=13.1, 4.3, 2H), 2.92 (t, J=11.4, 2H), 2.00 (td, J=13.1, 4.3, 2H), 1.45-1.38 (m, 2H). LCMS (Method A): Rt 1.31 min, (M+H) 463. HRMS m/z (ESI+) [M+H]+ C20H21ClN6O, calc 397.1538, found 397.1519, Rt=1.86 min (HPLC method E).

5. Preparation of 4-amino-1-(3-chloropyridin-4-yl)piperidine-4-carboxamide 83

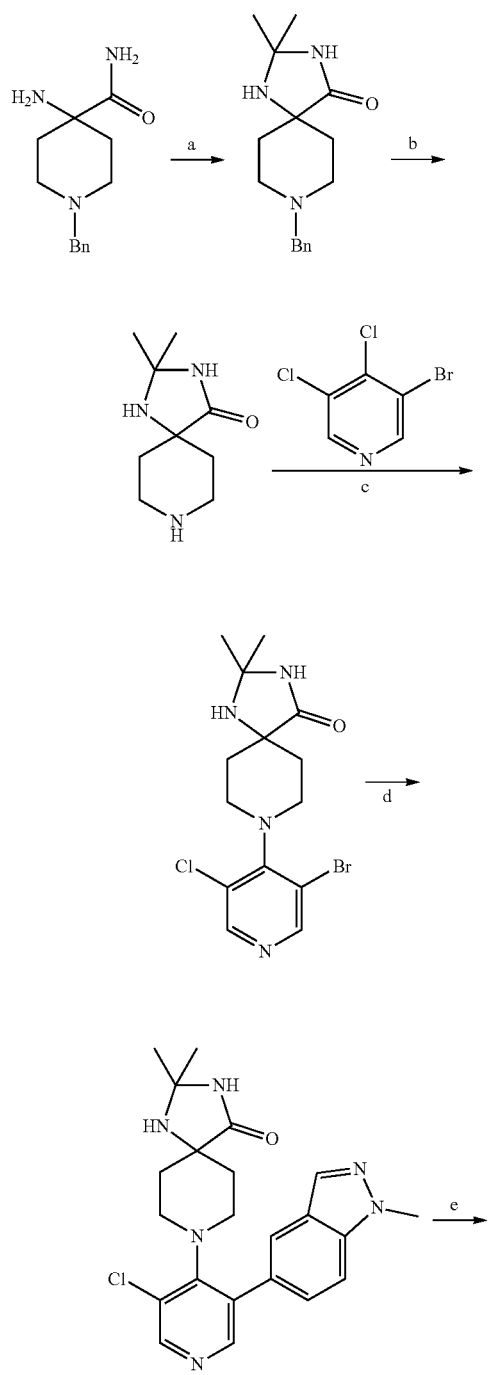

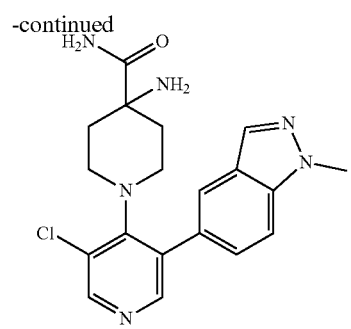

5a. 8-Benzyl-2,2-dimethyl-1,3,8-triazaspiro[4.5]decan-4-one

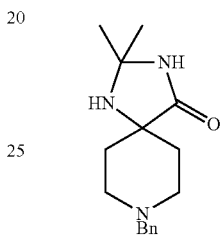

A solution of N-benzyl-4-amino-piperidine-4-carboxamide (1.6 g, 6.86 mmol), 2-dimethoxypropane (26 mL, 6.86 mmol) and acetic acid (13 mL, 6.86 mmol) was heated under microwave irradiation for 25 min at 150° C. The solvent was evaporated by azeotropic removal with toluene and the crude was purified by chromatography on silica gel (biotage, DCM/25% aq. NH4OH in MeOH (1/9)) to give the product (1.6 g, 85%) as a white solid. 1H-NMR (500 MHz, CDCl3) ppm=7.42-7.21 (m, 5H), 6.93 (bs, 1H), 3.63 (s, 2H), 2.90 (dt, J=10.0, 4.0 2H), 2.42 (t, J=10.0, 2H), 2.16-2.08 (m, 2H), 1.65-1.55 (m, 2H), 1.44 (s, 6H). HRMS m/z (ESI+) [M+H]+ C17H23N3O, calc 274.1914, found 274.1924, Rt=0.60 min (HPLC method E).

5b. 2,2-Dimethyl-1,3,8-triazaspiro[4.5]decan-4-one

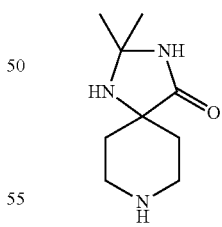

To a solution of 8-benzyl-2,2-dimethyl-1,3,8-triazaspiro[4.5]decan-4-one (1.5 g, 5.49 mmol) in EtOH (25 mL) was added conc. acetic acid (0.941 mL, 16.46 mmol) and palladium hydroxide (20 wt % on carbon, 165 mg, 2.140 mmol) and the suspension was stirred under H2-atmosphere for 8 hr at 40° C. The mixture was filtrated over Celite and the residue was washed with MeOH (250 mL). The filtrate was concentrated in vacuum and the resulting residue was purified using an SCX2 cartridge (loading with DCM/MeOH, 9:1, elution with DCM/1N NH3 in MeOH, 9:1) to give the product (850 mg, 85%) as a white solid. $^1$H-NMR (500 MHz, DMSO) ppm=8.16 (s, 1H), 2.77 (dt, J=12.0, 2.8, 2H), 2.66 (dt, J=12.0, 2.8, 2H), 1.62 (td, J=12.5, 4.4, 2H), 1.31-1.22 (m, 2H), 1.26 (s, 6H). HRMS m/z (ESI$^+$) [M+H]$^+$ $C_9H_{18}N_3O$, calc 184.1444, found 184.1444, Rt=0.22 min (HPLC method E).

5c. 8-(3-Bromo-5-chloropyridin-4-yl)-2,2-dimethyl-1,3,8-triazaspiro[4.5]decan-4-one

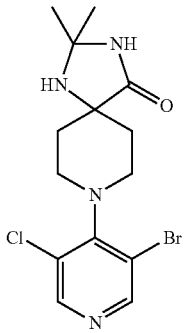 [SMILES: CC1(C)NC(=O)C2(CCN(c3c(Cl)cncc3Br)CC2)N1]

The title compound was prepared by reacting 3-bromo-4,5-dichloropyridine and 2,2-dimethyl-1,3,8-triazaspiro[4.5]decan-4-one according to the general procedure A and purified by purification methods D and I. $^1$H-NMR (500 MHz, DMSO) ppm=8.55 (s, 1H), 8.44 (s, 1H), 8.29 (bs, 1H), 3.46 (td, J=12.3, 2.1, 2H), 3.23-3.14 (m, 2H), 2.87 (bs, 1H), 1.95 (td, J=12.3, 4.3, 2H), 1.55-1.47 (m, 2H), 1.31 (s, 6H). HRMS m/z (ESI$^+$) [M+H]$^+$ $C_{14}H_{18}BrClN_4O$, calc 373.0425, found 373.0420, Rt=1.95 min (HPLC method E).

5d. 8-(3-Chloro-5-(1-methyl-1H-indazol-5-yl)pyridin-4-yl)-2,2-dimethyl-1,3,8-triazaspiro[4.5]decan-4-one

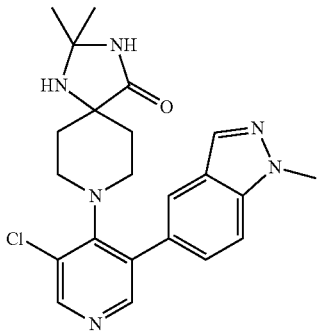 [SMILES: Cn1ncc2cc(-c3cncc(Cl)c3N3CCC4(CC3)NC(C)(C)NC4=O)ccc21]

The title compound was prepared by reacting 8-(3-bromo-5-chloropyridin-4-yl)-2,2-dimethyl-1,3,8-triazaspiro[4.5]decan-4-one and 1-methyl-1H-indazole-5-boronic acid according to the general procedure B and purified by purification methods C, I and E. $^1$H-NMR (500 MHz, DMSO) ppm=8.43 (s, 1H), 8.17 (s, 1H), 8.16 (s, 1H), 8.11 (d, J=1.0, 1H), 7.75 (d, J=8.7, 1H), 7.74 (s, 1H), 7.33 (dd, J=8.7, 1.0, 1H), 4.10 (s, 3H), 3.04-2.96 (m, 2H), 2.82 (t, J=12.0 2H), 2.60 (s, 1H), 1.76 (td, J=12.0, 4.0, 2H), 1.33-1.25 (m, 2H), 1.21 (s, 6H). HRMS m/z (ESI$^+$) [M+H]$^+$ $C_{22}H_{26}ClN_6O$, calc 425.1851, found 425.1846, Rt=1.95 min (HPLC method E).

5e. 4-Amino-5'-chloro-3'-(1-methyl-1H-indazol-5-yl)-3,4,5,6-tetrahydro-2H-[1,4']bipyridinyl-4-carboxylic Acid Amide 83

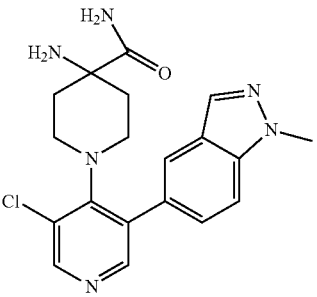 [SMILES: Cn1ncc2cc(-c3cncc(Cl)c3N3CCC(N)(C(N)=O)CC3)ccc21]

To a solution of 8-(3-chloro-5-(1-methyl-1H-indazol-5-yl)pyridin-4-yl)-2,2-dimethyl-1,3,8-triazaspiro[4.5]decan-4-one (16 mg, 0.038 mmol) in MeOH (1.2 mL) was added HCl (1M, 0.075 mL, 0.151 mmol) under nitrogen atmosphere and the mixture was heated under microwave irradiation for 2 hr at 100° C. before the mixture was diluted with sat. NaHCO$_3$ solution and EtOAc. The layers were separated, the aqueous layer was extracted with EtOAc tree times and the combined organic layer were washed with brine, dried over MgSO$_4$, filtrated and concentrated in vacuum. The resulting brown solid was purified by chromatography on silica gel (biotage, DCM/EtOH) to give a light yellow oil which was further purified using an SCX2 cartridge (loading with DCM/MeOH, 9:1, elution with DCM/1N NH$_3$ in MeOH, 5:1) to give the product (5 mg, 35%) as a white solid. $^1$H-NMR (500 MHz, DMSO) ppm=8.44 (s, 1H), 8.18 (s, 1H), 8.10 (d, J=1.1, 1H), 7.74 (s, 1H), 7.73 (d, J=8.8, 1H), 7.34 (dd, J=8.8, 1.1, 1H), 6.98 (bs, 2H), 4.09 (s, 3H), 2.96-2.79 (m, 4H), 1.95-1.85 (m, 2H), 1.33-1.21 (m, 2H). HRMS m/z (ESI$^+$) [M+H]$^+$ $C_{19}H_{22}ClN_6O$, calc 385.1538, found 385.1540, Rt=1.34 min (HPLC method E).

Using the same route, compounds 44 and 73 were synthesised using the respective boronic acids . . . 1-methyl-5-(4,4,5,5-tetramethyl-1,3,2-dioxaborolan-2-yl)-1,3-dihydrobenzo[c]isothiazole 2,2-dioxide or 1-methyl 6-(4,4,5,5-tetramethyl-1,3,2-dioxaborolan-2-yl)indolin-2-one.

4-Amino-5'-chloro-3'-(1-methyl-2,2-dioxo-2,3-dihydro-1H-benzo[c]isothiazol-5-yl)-3,4,5,6-tetrahydro-2H-[1,4']bipyridinyl-4-carboxylic Acid Amide 44

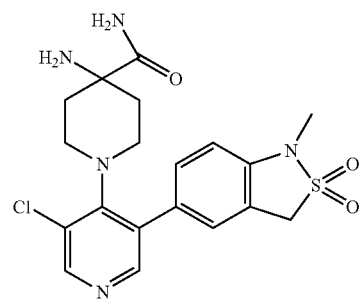 [SMILES: CN1c2ccc(-c3cncc(Cl)c3N3CCC(N)(C(N)=O)CC3)cc2CS1(=O)=O]

1H NMR (400 MHz, DMSO-d6) ppm=8.90 (d, J=1.2, 1H), 8.49 (d, J=1.2, 1H), 7.48-7.41 (m, 2H), 7.09 (d, J=8.2, 1H), 4.73 (s, 2H), 3.36-3.18 (m, 4H), 3.16 (s, 3H), 2.36-2.23 (m, 2H), 1.93-1.82 (m, 2H). LCMS (Method A): Rt 1.12 min, (M+H) 436.

4-Amino-5'-chloro-3'-(1-methyl-2-oxo-2,3-dihydro-1H-indol-6-yl)-3,4,5,6-tetrahydro-2H-[1,4']bipyridinyl-4-carboxylic Acid Amide 73

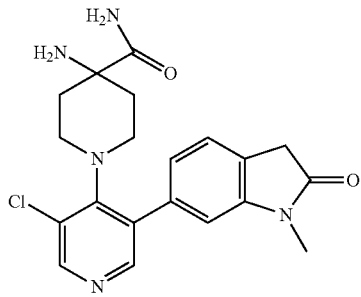 [SMILES: CN1C(=O)Cc2ccc(-c3cncc(Cl)c3N3CCC(N)(C(N)=O)CC3)cc21]

1H-NMR (500 MHz, CDCl3) ppm=8.48 (s, 1H), 8.26 (s, 1H), 7.35 (d, J=7.4, 1H), 7.35 (s, 1H), 6.99 (dd, J=7.4, 1.3, 1H), 6.83 (s, 1H), 5.39 (s, 1H), 3.61 (s, 2H), 3.30 (s, 3H), 3.17-3.10 (m, 2H), 2.97 (t, J=11.4, 2H), 2.26-2.17 (m, 2H), 1.66 (bs, 2H), 1.42-1.35 (m, 2H). LCMS (Method E): Rt 1.27 min, (M+H) 400.

6. Preparation of 8-(3-chloro-5-{4-[1-(2-hydroxy-ethyl)-1H-pyrazol-4-yl]-phenyl}-pyridin-4-yl)-2,8-diaza-spiro[4.5]decan-1-one 5

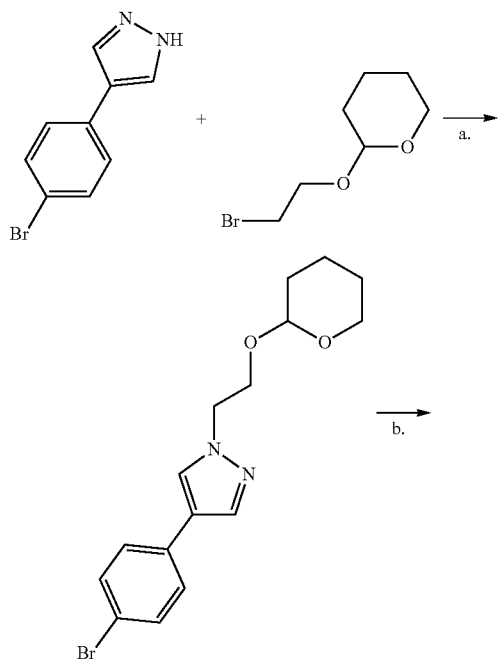

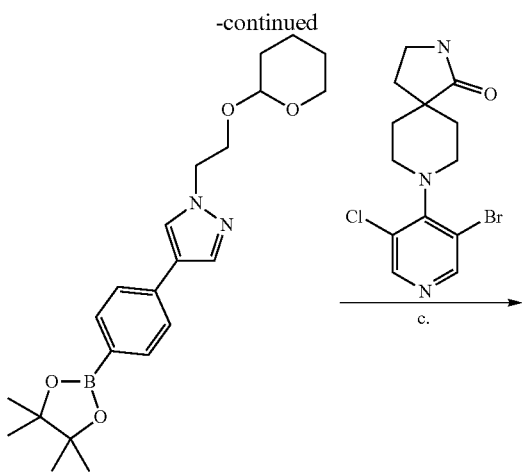

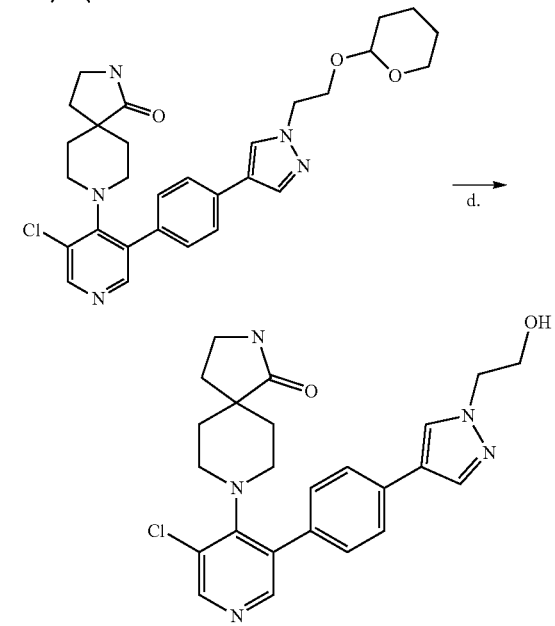

6a. 4-(4-Bromo-phenyl)-1-[2-(tetrahydro-pyran-2-yloxy)-ethyl]-1H-pyrazole

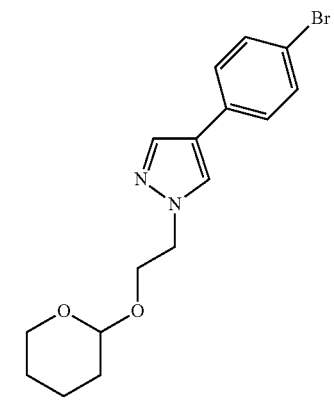 [SMILES: Brc1ccc(-c2cnn(CCOC3CCCCO3)c2)cc1]

4-(4-Bromophenyl)pyrazole (2.00 g, 8.97 mmol) was dissolved in acetonitrile (300 mL). Cesium carbonate (4.38 g, 13.4 mmol mmol) and 2-(2-bromo-ethoxy)-tetrahydropyran (96%, 2.54 g, 11.7 mmol) were added and stirred for 15 hr at RT. Subsequently, the mixture was stirred for 24 hr at 70° C. The pale yellow reaction mixture was filtered over diatomaceous earth and washed with EtOAc. The filtrate was evaporated to dryness and used in the next step without further purification to yield in a yellow oil (94% purity, 3.10 g, 8.31 mmol, 93%). LC/MS (Method B): Rt 2.52 min, (M+H) 353.

6b. 1-[2-(Tetrahydro-pyran-2-yloxy)-ethyl]-4-[4-(4,4,5,5-tetramethyl-[1,3,2]dioxaborolan-2-yl)-phenyl]-1H-pyrazole

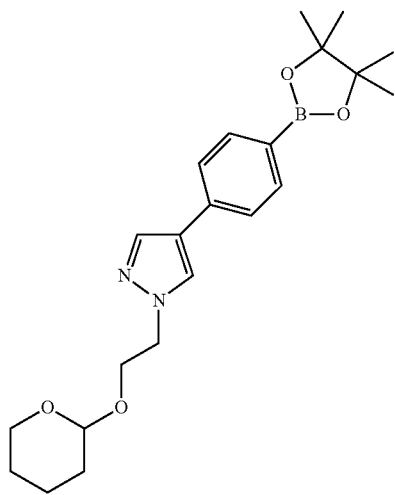 [SMILES: CC1(C)OB(c2ccc(-c3cnn(CCOC4CCCCO4)c3)cc2)OC1(C)C]

4-(4-Bromo-phenyl)-1-[2-(tetrahydro-pyran-2-yloxy)-ethyl]-1H-pyrazole (94%, 3.10 g, 8.31 mmol) was dissolved in THF (100 mL) and bis(pinacolato)diboron (4.22 g, 16.6 mmol), potassium acetate (2.45 g, 24.9 mmol) and Pd(dppf)Cl$_2$.CH$_2$Cl$_2$ (664 mg, 0.83 mmol) were added and the mixture was stirred under nitrogen atmosphere at 70° C. for 15 hr. The reaction mixture was diluted with EtOAc, filtered and evaporated. The dark brown residue was purified by flash chromatography (DCM/MeOH) to yield in 2.35 g (94% purity, 5.55 mmol, 67%) of a yellow, viscous oil. LC/MS (Method B): Rt 3.17 min, (M+H) 399.

6c. 8-[3-Chloro-5-(4-{1-[2-(tetrahydro-pyran-2-yloxy)-ethyl]-1H-pyrazol-4-yl}-phenyl)-pyridin-4-yl]-2,8-diaza-spiro[4.5]decan-1-one

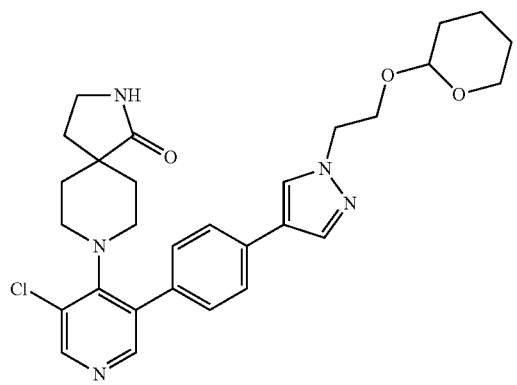 [SMILES: O=C1NCCC12CCN(c1c(Cl)cncc1-c1ccc(-c3cnn(CCOC4CCCCO4)c3)cc1)CC2]

8-(3-bromo-5-chloro-pyridin-4-yl)-2,8-diaza-spiro[4.5]decan-1-one (1.20 g, 3.10 mmol) was suspended in acetonitrile (100 mL). 1-[2-(Tetrahydro-pyran-2-yloxy)-ethyl]-4-[4-(4,4,5,5-tetramethyl-[1,3,2]dioxaborolan-2-yl)-phenyl]-1H-pyrazole (94% purity, 1.97 g, 4.65 mmol), sodium carbonate solution (0.5 M, 12.4 mL, 6.20 mmol) and Pd(dppf)Cl$_2$.CH$_2$Cl$_2$ (127 mg, 0.16 mmol) were added. The reaction mixture was stirred for 15 hr at 70° C. The reaction mixture was treated with EtOAc, filtered under reduced pressure through celite and evaporated to dryness. The brown residue was purified by flash chromatography (DCM/MeOH) to give 1.00 g (60%) of the title compound as honey colored solid. LC/MS (Method B): Rt 2.22 min, (M+H) 536.

6d. 8-(3-Chloro-5-{4-[1-(2-hydroxy-ethyl)-1H-pyrazol-4-yl]-phenyl}-pyridin-4-yl)-2,8-diaza-spiro[4.5]decan-1-one 5

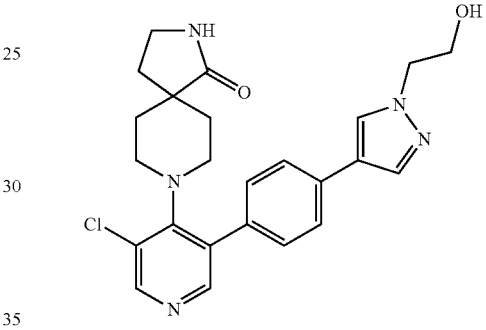

8-[3-chloro-5-(4-{1-[2-(tetrahydro-pyran-2-yloxy)-ethyl]-1H-pyrazol-4-yl}-phenyl)-pyridin-4-yl]-2,8-diaza-spiro[4.5]decan-1-one (1.00 g, 1.87 mmol) was dissolved in DCM SeccoSolv® (40 mL) and treated with HCl in dioxane (4 M, 1.85 mL, 7.39 mmol). A beige precipitate was formed and the suspension was stirred for 15 hr at RT. The resulting solution was filtered and the residue was washed with DCM. The residue was dissolved in water and treated with sodium carbonate. A brown precipitate formed. DCM was added and the mixture was filtered through a phase-separator. The solvent was evaporated to dryness and the residue was purified by flash chromatography (DCM/MeOH). The solid residue was crystallized from diethyl ether/acetonitrile, filtered and washed with diethyl ether to obtain an off-white solid (449 mg, 55%). 1H NMR (500 MHz, DMSO) ppm=8.45 (s, 1H), 8.24-8.17 (m, 2H), 7.95 (d, J=1.0, 1H), 7.72-7.61 (m, 2H), 7.48 (s, 1H), 7.38-7.29 (m, 2H), 4.94-4.83 (m, 1H), 4.21-4.08 (m, 2H), 3.82-3.68 (m, 2H), 3.14-3.00 (m, 4H), 2.71-2.58 (m, 2H), 1.86-1.79 (m, 2H), 1.78-1.64 (m, 2H), 1.25 (d, J=12.8, 2H). LC/MS (Method B): Rt 1.80 min, (M+H) 452.

By analogy to this procedure, compound 15 was also synthesized from intermediate C9.

85
8-(3-Chloro-5-{4-[1-(2-hydroxy-ethyl)-1H-pyrazol-4-yl]-phenyl}-pyridin-4-yl)-1-oxa-3,8-diaza-spiro[4.5]decan-2-one
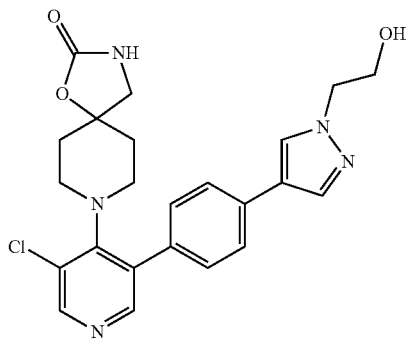 [SMILES: O=C1NCC2(CCN(c3c(Cl)cncc3-c3ccc(-c4cnn(CCO)c4)cc3)CC2)O1]
1H NMR (400 MHz, DMSO-d6) ppm=8.54 (s, 1H), 8.27 (s, 1H), 8.24 (s, 1H), 7.96 (s, 1H), 7.75-7.69 (m, 2H), 7.45 (s, 1H), 7.38-7.31 (m, 2H), 4.17 (t, J=5.6, 2H), 3.78 (t, J=5.6, 2H), 3.19 (s, 2H), 3.03-2.86 (m, 4H), 1.81-1.68 (m, 4H). LCMS (Method B): Rt 1.75 min, (M+H) 454.
7. Preparation of 9-{3-chloro-5-[4-(1-methyl-1H-pyrazol-4-yl)-phenyl]-pyridin-4-yl}-1,4,9-triaza-spiro[5.5]undecane-2,5-dione 17
86
Preparation of 1-(4-methoxy-benzyl)-1,4,9-triaza-spiro[5.5]undecane-2,5-dione Acetate
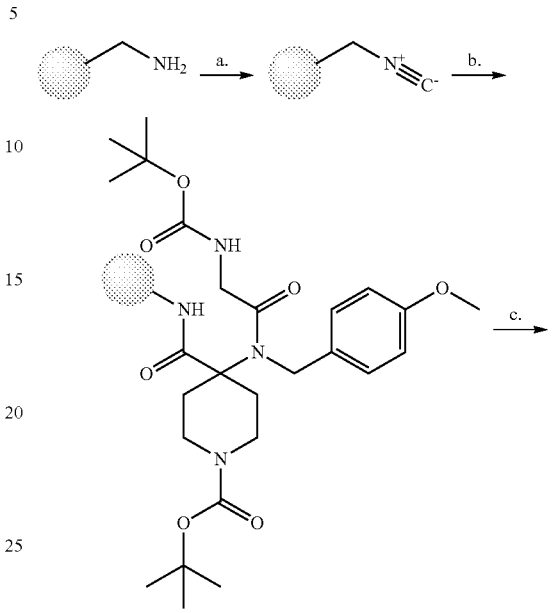
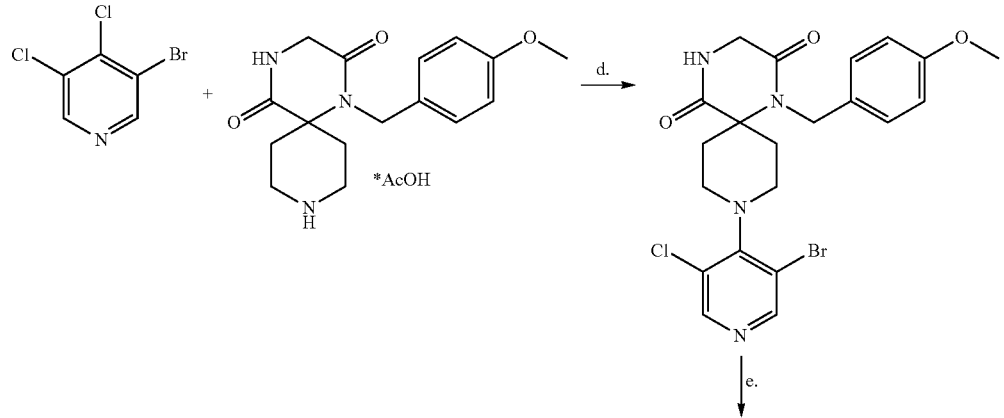
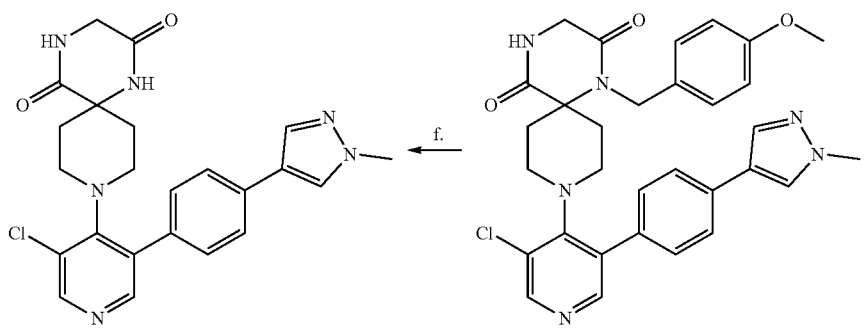

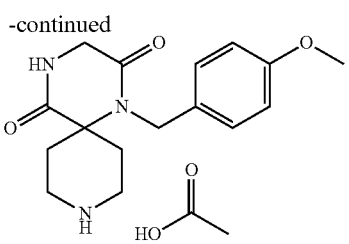

By analogy to the methods reported in Habashita, Hiromu; Kokubo, Masaya; Hamann, Shin-ichi; Hamanaka, Nobuyuki; Toda, Masaaki; Shibayama, Shiro; Tada, Hideaki; Sagawa, Kenji; Fukushima, Daikichi; Maeda, Kenji; Mitsuya, Hiroaki, *J. Med. Chem.* 2006, 4140-4144.

7a. Methylene-Isonitrile Resin

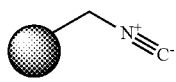

Aminomethyl polystyrene resin (2.00 g, 2.86 mmol) was washed with DMF (20 mL×2) and suspended in a mixture of DMF (20 mL) and ethylformiate (30 mL). The suspension was heated to 70° C. without stirring for 15 h. After cooling to RT, the resin was filtered and washed with DMF (2×25 mL), DCM (4×25 mL), MeOH (4×25 mL) and DCM (4×25 mL). The resin was dried under reduced pressure to give the N-formylated aminomethyl resin. The resin was suspended in DCM (50 mL) and successively treated with triethylamine (2.38 mL, 17.2 mmol), carbon tetrachloride (1.67 mL, 17.2 mmol) and triphenylphosphine (4.50 g, 17.2 mmol). The mixture was heated to 50° C. without stirring for 2 h. After cooling to RT, the resin was filtered and washed with DCM (4×50 mL), MeOH (2×50 mL), and DCM (4×50 mL). The resin was dried under reduced pressure to give the yellow methylene-isonitrile resin (2.70 g, 2.86 mmol).

7b. Polymer bound 4-[(2-tert-butoxycarbonylamino-acetyl)-(4-methoxy-benzyl)-amino]-4-carbamoyl-piperidine-1-carboxylic Acid tert-butyl Ester

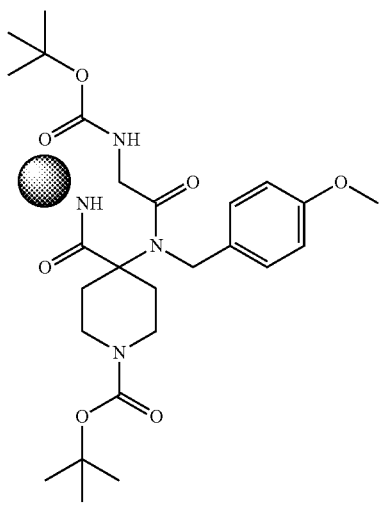 [SMILES: COc1ccc(CN(C(=O)CNC(=O)OC(C)(C)C)C2(C(N)=O)CCN(C(=O)OC(C)(C)C)CC2)cc1]

Methylene-isonitrile resin (2.70 g, 2.86 mmol) was washed with THF/MeOH (1:1, 40 mL) and the resin was suspended in THF/MeOH (1:1, 40 mL). 1-Boc-4-piperidone (2.85 g, 14.3 mmol), 4-methoxybenzylamine (1.96 g, 14.3 mmol) and N-(tert-butoxycarbonyl)-glycine (2.51 g, 14.3 mmol) were added. The mixture was heated at 70° C., without stirring, for 2 days. After cooling to RT, the resin was filtered and washed with MeOH/THF (1:1, 3×50 mL) and DCM (4×50 mL) The resin was dried under reduced pressure to give the title compound (4.0 g, 100%) as a yellow resin.

7c. 1-(4-Methoxy-benzyl)-1,4,9-triaza-spiro[5.5]undecane-2,5-dione Acetate

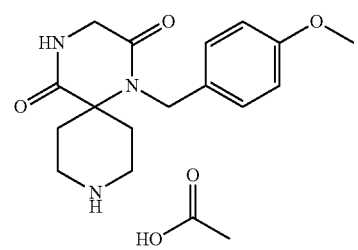

Polymer bound 4-[(2-tert-butoxycarbonylamino-acetyl)-(4-methoxy-benzyl)-amino]-4-carbamoyl-piperidine-1-carboxylic acid tert-butyl ester (3.50 g, 2.50 mmol) was suspended in DCM. At 0° C. trifluoroacetic acid (7 mL) was added, the mixture was allowed to warm up to RT and shaking continued for 4 h. After filtration, the resin was washed with DCM (3×40 mL), toluene (2×40 mL), and 1.25 M acetic acid in toluene (50 mL). The resin was suspended in 1.25 M acetic acid in toluene (50 mL) and heated at reflux for 2 days.

The resin was filtered and washed with DCM/MeOH (1:1, 2×40 mL). The filtrates were collected and evaporated to dryness. The residue was dissolved in MeOH and treated slowly with diethyl ether. The resulting precipitate was filtered under reduced pressure, washed with diethyl ether, and dried under reduced pressure to result in the title compound (560 mg, 54%) as an off-white solid. LC/MS (Method B): Rt 1.69 min, (M+H) 304.

7d. 9-(3-Bromo-5-chloro-pyridin-4-yl)-1-(4-methoxy-benzyl)-1,4,9-triaza-spiro[5.5]undecane-2,5-dione

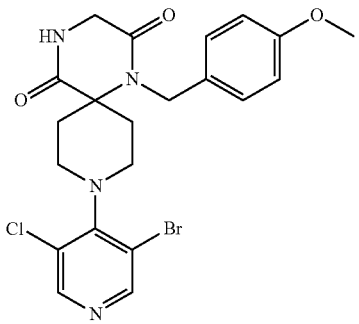 [SMILES: COc1ccc(CN2C(=O)CNC(=O)C23CCN(c2c(Cl)cncc2Br)CC3)cc1]

3-Bromo-4,5-dichloro-pyridine (250 mg, 1.10 mmol) and 1-(4-methoxy-benzyl)-1,4,9-triaza-spiro[5.5]undecane-2,5-dione acetate (400 mg, 1.10 mmol) were dissolved in NMP (8 mL) and triethylamine (0.46 mL, 3.31 mmol) and stirred for 1 hr at 220° C. under microwave irradiation. The mixture was poured into water (80 mL) and extracted with DCM (2×100 mL). The organic layer was dried and evaporated to dryness. The oily residue (containing NMP) was purified by flash chromatography (DCM/MeOH). The solvent was evaporated to dryness. The residue was dissolved in DCM (3 mL) and treated with diethylether (35 mL). The resulting precipitate was filtered and dried under reduced pressure to give the title compound (180 mg, 33%) as an off-white solid. LC/MS (Method B): Rt 2.43 min, (M+H) 495.

7e. 9-{3-Chloro-5-[4-(1-methyl-1H-pyrazol-4-yl)-phenyl]-pyridin-4-yl}-1-(4-methoxy-benzyl)-1,4,9-triaza-spiro[5.5]undecane-2,5-dione

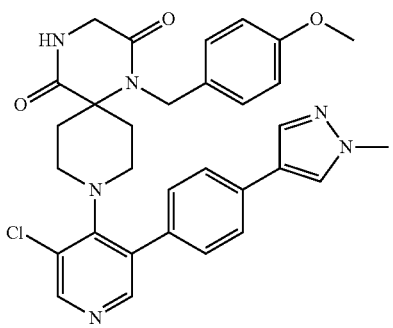 [SMILES: COc1ccc(CN2C(=O)CNC(=O)C23CCN(c2c(Cl)cncc2-c2ccc(-c4cnn(C)c4)cc2)CC3)cc1]

9-(3-Bromo-5-chloro-pyridin-4-yl)-1-(4-methoxy-benzyl)-1,4,9-triaza-spiro[5.5]undecane-2,5-dione (90.0 mg, 0.18 mmol) and 1-methyl-4-[4-(4,4,5,5-tetramethyl-[1,3,2]dioxaborolan-2-yl)-phenyl]-1H-pyrazole (77.7 mg, 0.27 mmol) were dissolved in acetonitrile (4 mL). Sodium carbonate solution (0.5 M, 0.73 mL, 0.36 mmol) and Pd(dppf)Cl$_2$.CH$_2$Cl$_2$ (7.44 mg, 0.01 mmol) were added. The microwave vessel was closed, degassed and flushed with nitrogen and stirred under microwave irradiation for 1 hr at 120° C. The mixture was filtered, evaporated and purified by flash chromatography (DCM/MeOH). The product-containing fractions were combined and evaporated to give the title compound (61.0 mg, 59%) as a white solid. LC/MS (Method B): Rt 2.38 min, (M+H) 685.

7f. 9-{3-Chloro-5-[4-(1-methyl-1H-pyrazol-4-yl)-phenyl]-pyridin-4-yl}-1,4,9-triaza-spiro[5.5]undecane-2,5-dione 17

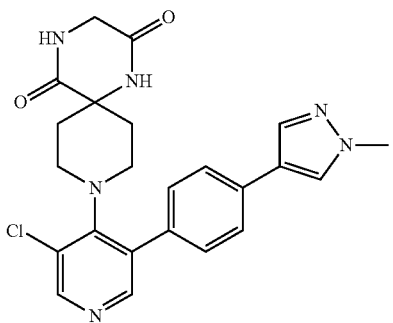 [SMILES: Cn1cc(-c2ccc(-c3cncc(Cl)c3N3CCC4(CC3)NC(=O)CNC4=O)cc2)cn1]

A mixture of 9-{3-chloro-5-[4-(1-methyl-1H-pyrazol-4-yl)-phenyl]-pyridin-4-yl}-1-(4-methoxy-benzyl)-1,4,9-triaza-spiro[5.5]undecane-2,5-dione (61.0 mg, 0.11 mmol) was dissolved in trifluoroacetic acid (4 mL) and stirred at RT for 15 h. The mixture was evaporated and purified by preparative HPLC (MeCN/water). The product containing fractions were combined and lyophilized to give the title compound (32.2 mg, 52%) as white flakes. 1H NMR (400 MHz, DMSO-d6) ppm=8.55 (s, 1H), 8.38 (s, 1H), 8.24 (s, 1H), 8.20 (s, 1H), 7.97-7.94 (m, 1H), 7.93 (d, J=0.8, 1H), 7.71-7.63 (m, 2H), 7.39-7.31 (m, 2H), 3.89 (s, 3H), 3.71 (d, J=2.3, 2H), 3.20-3.04 (m, 4H), 2.05-1.93 (m, 2H), 1.67-1.56 (m, 2H). LC/MS (Method B): Rt 1.73 min, (M+H) 451.

According to this procedure, compound 21 was also synthesized using 1-methyl-5-(4,4,5,5-tetramethyl-1,3,2-dioxaborolan-2-yl)-1,3-dihydrobenzo[c]isothiazole 2,2-dioxide in place of 1-methyl-4-[4-(4,4,5,5-tetramethyl-[1,3,2]dioxaborolan-2-yl)-phenyl]-1H-pyrazole.

9-[3-Chloro-5-(1-methyl-2,2-dioxo-2,3-dihydro-1H-benzo[c]isothiazol-5-yl)-pyridin-4-yl]-1,4,9-triaza-spiro[5.5]undecane-2,5-dione 21

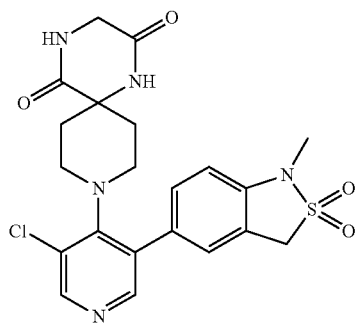 [SMILES: CN1c2ccc(-c3cncc(Cl)c3N3CCC4(CC3)NC(=O)CNC4=O)cc2CS1(=O)=O]

1H NMR (500 MHz, DMSO-d6) ppm=8.52 (s, 1H), 8.34 (s, 1H), 8.22 (s, 1H), 8.00 (s, 1H), 7.40-7.33 (m, 2H), 7.04 (d, J=8.2, 1H), 4.73 (s, 2H), 3.73-3.72 (m, 2H), 3.13-3.05 (m, 7H), 1.99-1.91 (m, 2H), 1.60-1.53 (m, 2H).). LC/MS (Method B): Rt 1.63 min, (M+H) 476.

8. Preparation of {6-[5-chloro-4-(1-oxo-2,8-diaza-spiro[4.5]dec-8-yl)-pyridin-3-yl]-1H-indazol-3-yl}-carbamic Acid Methyl Ester 23

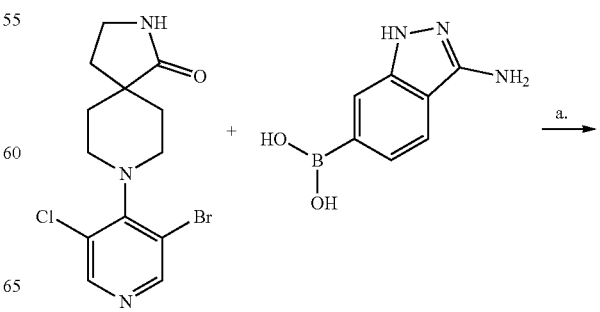

a.

-continued

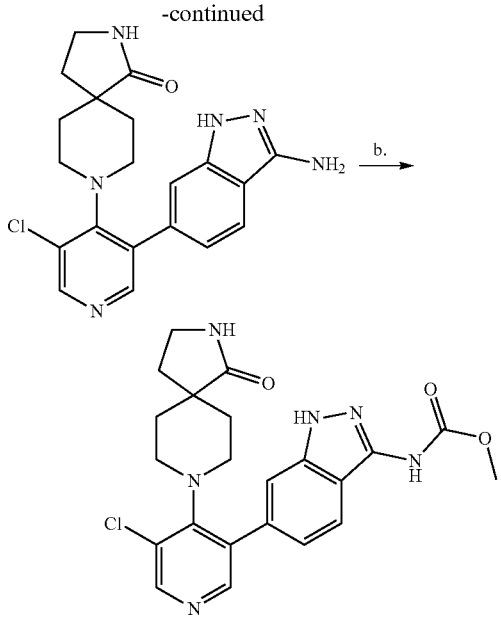

8a. 8-[3-(3-Amino-1H-indazol-6-yl)-5-chloro-pyridin-4-yl]-2,8-diaza-spiro[4.5]decan-1-one 7

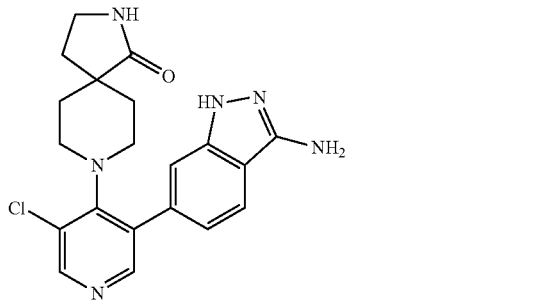 [SMILES: Nc1n[nH]c2cc(-c3cncc(Cl)c3N3CCC4(CCNC4=O)CC3)ccc12]

In a screw-capped vessel 8-(3-bromo-5-chloro-pyridin-4-yl)-2,8-diaza-spiro[4.5]decan-1-one (1.50 g, 4.09 mmol) and (3-amino-1H-indazol-6-yl)boronic acid hydrochloride (1.10 g, 4.91 mmol) were dissolved in acetonitrile (75 mL). Sodium carbonate solution (0.5 M, 24.6 mL, 12.3 mmol) and Pd(dppf)Cl$_2$.CH$_2$Cl$_2$ (167 mg, 0.20 mmol) were added. Nitrogen was flushed through the mixture for 10 min and the mixture was stirred at 80° C. for 2 days. The mixture was diluted with acetonitrile (100 mL), filtered and evaporated to dryness. The residue was purified by flash chromatography (DCM/MeOH). The oily residue was dissolved in DCM/MeOH (3:1, 20 mL) and treated slowly with diethyl ether (100 mL). The resulting beige precipitate was filtered, washed with diethyl ether (20 mL) and dried at 50° C. under reduced pressure for 15 hr to yield in the title compound (346 mg, 21%) as a light brown solid. 1H NMR (500 MHz, DMSO-d6) ppm=11.49 (s, 1H), 8.46 (s, 1H), 8.22 (s, 1H), 7.75 (d, J=8.2, 1H), 7.47 (s, 1H), 7.22-7.16 (m, 1H), 6.82 (dd, J=8.2, 1.3, 1H), 5.39 (s, 2H), 3.09 (t, J=6.8, 2H), 3.06-2.99 (m, 2H), 2.66-2.55 (m, 2H), 1.78 (t, J=6.8, 2H), 1.70 (td, J=12.4, 4.2, 2H), 1.26-1.17 (m, 2H). LC/MS (Method B): Rt 1.59 min, (M+H) 397.

According to this procedure compound 14 was synthesized from intermediate C2.

8-[3-(3-Amino-1H-indazol-6-yl)-5-chloro-pyridin-4-yl]-2,8-diaza-spiro[4.5]decane-1,3-dione

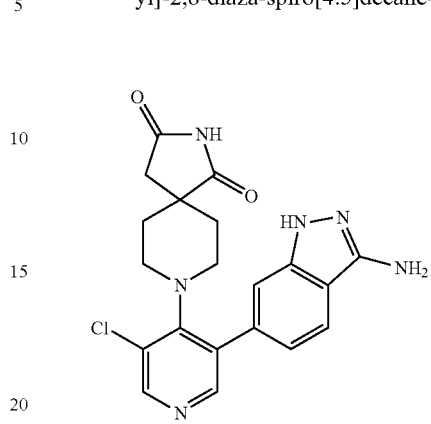

1H NMR (500 MHz, DMSO-d6) ppm=12.71-11.46 (m, 1H), 11.08 (s, 1H), 8.57 (s, 1H), 8.30 (s, 1H), 7.89 (d, J=8.3, 1H), 7.34-7.30 (m, 1H), 6.96 (dd, J=8.3, 1.4, 1H), 3.16-3.07 (m, 2H), 2.70-2.59 (m, 2H), 2.44 (s, 2H), 1.79 (td, J=12.3, 4.1, 2H), 1.52-1.45 (m, 2H). LC/MS (Method B): Rt 1.54 min, (M+H) 411.

8b. {6-[5-Chloro-4-(1-oxo-2,8-diaza-spiro[4.5]dec-8-yl)-pyridin-3-yl]-1H-indazol-3-yl}-carbamic Acid Methyl Ester 23

To a solution of 8-[3-(3-amino-1H-indazol-6-yl)-5-chloro-pyridin-4-yl]-2,8-diaza-spiro[4.5]decan-1-one (30.0 mg, 0.076 mmol) in pyridine (1 mL) in a screw-capped vessel, methyl chloroformate (5.86 µl, 0.076 mmol) was added under ice-cooling. The reaction mixture was stirred under cooling for 3 h. Additional methyl chloroformate (5.90 µl, 0.076 mmol) was added and the reaction mixture was stirred for additional 17 hr at RT. Additional methyl chloroformate (10.0 µl, 0.13 mmol) was added and stirring continued for 4 hr at RT. Additional methyl chloroformate (2.00 mL) was added and stirring continued for 4 days. The red reaction mixture was evaporated to dryness and directly purified by preparative HPLC (MeCN, water) to give the title compound (11 mg, 25%) as an off-white solid. 1H NMR (500 MHz, DMSO-d6) ppm=12.75 (s, 1H), 9.88 (s, 1H), 8.58 (s, 1H), 8.31 (s, 1H), 7.84 (d, J=8.4, 1H), 7.49 (s, 1H), 7.44 (s, 1H), 7.01 (dd, J=8.4, 1.4, 1H), 3.70 (s, 3H), 3.19-3.11 (m, 2H), 3.09 (t, J=6.8, 2H), 2.72-2.61 (m, 2H), 1.80 (t, J=6.8, 2H), 1.75-1.66 (m, 2H), 1.31-1.22 (m, 2H). LC/MS (Method B): Rt 1.82 min, (M+H) 455.

9. Preparation of 5'-chloro-4-(2-hydroxy-ethyl)-3'-(1-methyl-2,2-dioxo-2,3-dihydro-1H-benzo[c]isothiazol-5-yl)-3,4,5,6-tetrahydro-2H-[1,4']bipyridinyl-4-carbonitrile 33

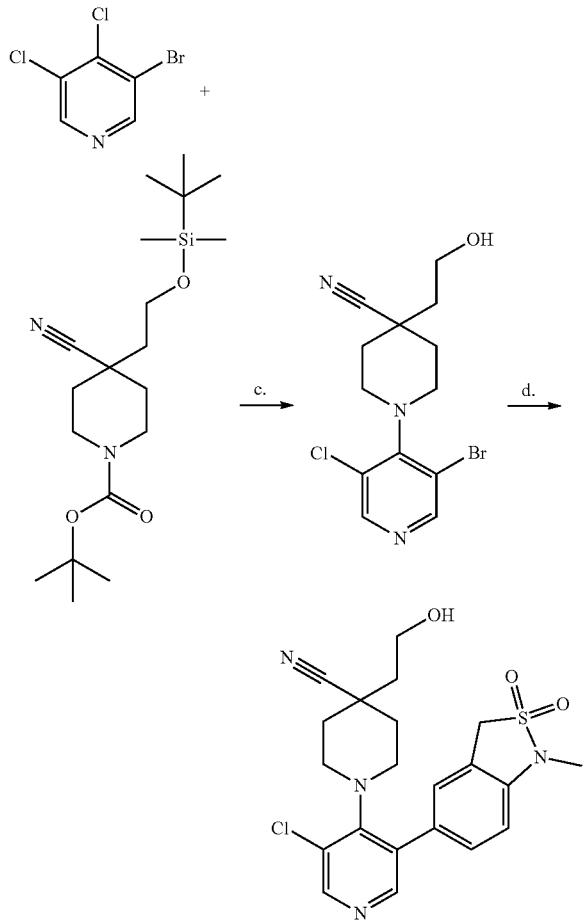

Preparation of 4-[2-(tert-butyl-dimethyl-silanyloxy)-ethyl]-4-cyano-piperidine-1-carboxylic Acid tert-butyl Ester

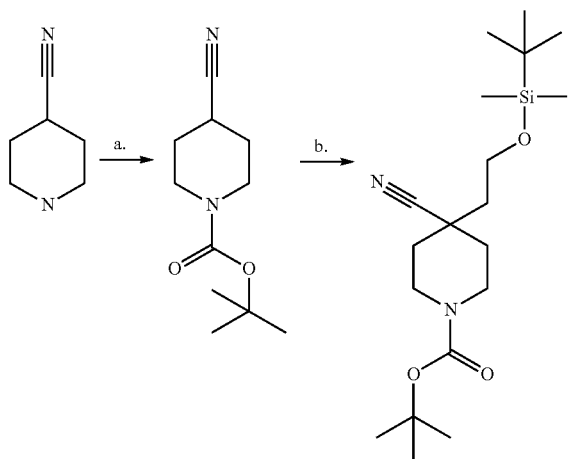 [SMILES: N#CC1CCNCC1 ; CC(C)(C)OC(=O)N1CCC(C#N)CC1 ; CC(C)(C)OC(=O)N1CCC(C#N)(CCO[Si](C)(C)C(C)(C)C)CC1]

9a. 4-Cyano-piperidine-1-carboxylic Acid tert-butyl Ester

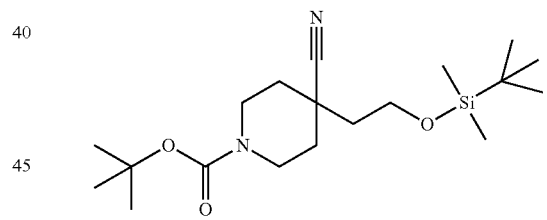

4-Cyanopiperidine (5.00 g, 0.044 mol) was dissolved in 1,4-dioxane (50 mL) and di-tert-butyl dicarbonate (10.4 mL, 0.049 mol) was added dropwise to the reaction mixture at RT. The mixture was stirred overnight at same temperature. The reaction mixture was diluted with DCM, washed with NaHCO₃ solution and NaCl solution, dried over sodium sulfate, filtered and evaporated to dryness to give the title compound (9.00 g, 97%) as a light yellow oil, which was used without further purification. LC/MS (Method B): Rt 2.00 min, (M+Na) 233.

9b. 4-[2-(tert-Butyl-dimethyl-silanyloxy)-ethyl]-4-cyano-piperidine-1-carboxylic Acid tert-butyl Ester 4-Cyano-piperidine-1-carboxylic acid tert-butyl ester (2.00 g, 9.51 mmol) was dissolved in THF SeccoSolv® (40 mL). At −10° C. lithium bis(trimethylsilyl)amide (1.06 M solution in THF/ethylbenzene, 13.5 mL, 14.3 mmol) was added dropwise. To this solution a solution of (2-bromoethoxy)-tert-butyl-dimethyl-silane (3.09 mL, 14.3 mmol) in THF SeccoSolv® (20 mL) was added dropwise at −10° C. The reaction mixture was allowed to warm to RT and was stirred for additional 4 h. The reaction mixture was treated with water and EtOAc and the layers were separated. The organic layer was dried over sodium sulfate, filtered and the solvent was evaporated to dryness. The yellow oil was purified by flash chromatography (heptane/DCM) to obtain the title compound (2.00 g, 41%) as a colorless oil. LC/MS (Method B): Rt 3.62 min, (M+Na)=391.

9c. 3'-Bromo-5'-chloro-4-(2-hydroxy-ethyl)-3,4,5,6-tetrahydro-2H[1,4']bipyridinyl-4-carbonitrile

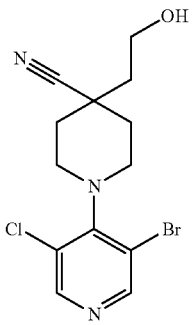 [SMILES: N#CC1(CCO)CCN(c2c(Cl)cncc2Br)CC1]

In a microwave vessel 3-bromo-4,5-dichloro-pyridine (515 mg, 2.27 mmol) was dissolved in NMP (6 mL). 4-[2-(tert-butyl-dimethyl-silanyloxy)-ethyl]-4-cyano-piperidine-1-carboxylic acid tert-butyl ester (1.10 g, 2.27 mmol) and triethylamine (0.94 ml, 6.80 mmol) were added at RT. The mixture was stirred for 2 hr at 220° C. under microwave irradiation. The dark brown reaction mixture was treated with 100 mL of water and EtOAc (100 mL). The organic layer was separated and the aqueous layer was extracted with EtOAc. The combined organic layers were dried, filtered and evaporated to dryness. The oily residue was purified by flash chromatography (DCM/MeOH) to give the title compound (250 mg, 70% purity, 22%) as a white solid. LC/MS (Method B): Rt 2.38 min, (M+H) 344/346.

In addition, silyl-protected derivative 3'-bromo-4-[2-(tert-butyl-dimethyl-silanyloxy)-ethyl]-5'-chloro-3,4,5,6-tetrahydro-2H-[1,4']bipyridinyl-4-carbonitrile was isolated in 34% yield (350 mg). LC/MS (Method B): Rt 3.78 min, (M+H) 458/460.

In a screwcapped glas 3-bromo-4-[2-(tert-butyl-dimethyl-silanyloxy)-ethyl]-5'-chloro-3,4,5,6-tetrahydro-2H-[1,4']bipyridinyl-4-carbonitrile (350 mg, 0.76 mmol) was dissolved in THF SeccoSolv® (10 mL) and tetra-n-butylammonium fluoride trihydrate (397 mg, 1.52 mmol) was added. The reaction mixture was stirred for 15 hr at RT. The reaction mixture was evaporated to dryness and the oily residue was treated with EtOAc and water. The organic layer was washed with water, dried over sodium sulfate and evaporated to dryness. The brown residue was purified by flash chromatography (DCM/MeOH) to yield in the title compound (241 mg, 92%) of as white solid. LC/MS (Method B): Rt 2.39 min, (M+H) 344/346.

9d. 5'-Chloro-4-(2-hydroxy-ethyl)-3'-(1-methyl-2,2-dioxo-2,3-dihydro-1H-benzo[c]isothiazol-5-yl)-3,4,5,6-tetrahydro-2H-[1,4']bipyridinyl-4-carbonitrile 33

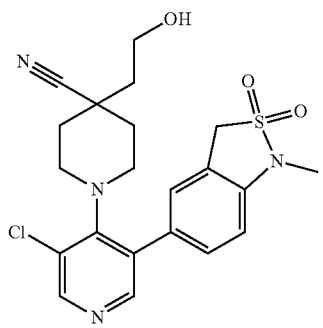 [SMILES: CN1c2ccc(-c3cncc(Cl)c3N3CCC(C#N)(CCO)CC3)cc2CS1(=O)=O]

In a microwave vial 3'-bromo-5'-chloro-4-(2-hydroxy-ethyl)-3,4,5,6-tetrahydro-2H-[1,4']bipyridinyl-4-carbonitrile (70% purity, 125 mg, 0.25 mmol) was dissolved in acetonitrile (3 mL). 1-Methyl-5-(4,4,5,5-tetramethyl-[1,3,2]dioxaborolan-2-yl)-1,3-dihydro-benzo[c]isothiazole 2,2-dioxide (78.5 mg, 0.25 mmol), sodium carbonate solution 0.5 M (1.02 mL, 0.51 mmol) and Pd(dppf)Cl$_2$.CH$_2$Cl$_2$ (10.4 mg, 0.013 mmol) were added. The closed vial was flushed with nitrogen twice and heated at 120° C. under microwave irradiation for 1 hr. The reaction mixture was treated with EtOAc and water. The organic layer was dried over sodium sulfate, filtered and the solvent evaporated under reduced pressure. The brown residue was purified by preparative HPLC (MeCN/water) to give the title compound (27.2 mg, 19%) as a beige solid. 1H NMR (500 MHz, DMSO-d6) ppm=8.53 (s, 1H), 8.25 (s, 1H), 7.40-7.35 (m, 2H), 7.07 (d, J=8.0. 1H), 4.67 (s, 2H), 3.58 (t, J=6.8, 2H), 3.10 (s, 3H), 3.09-3.03 (m, 2H), 2.90-2.78 (m, 2H), 1.87-1.79 (m, 2H), 1.71 (t, J=6.7, 2H), 1.58-1.47 (m, 2H). LC/MS (Method B): Rt 2.51 min, (M+H) 447.

10. Preparation of 8-{3-[4-(1-isopropyl-1H-pyrazol-4-yl)-phenyl]-5-trifluoromethyl-pyridin-4-yl}-1-oxa-3,8-diaza-spiro[4.5]decan-2-one 38

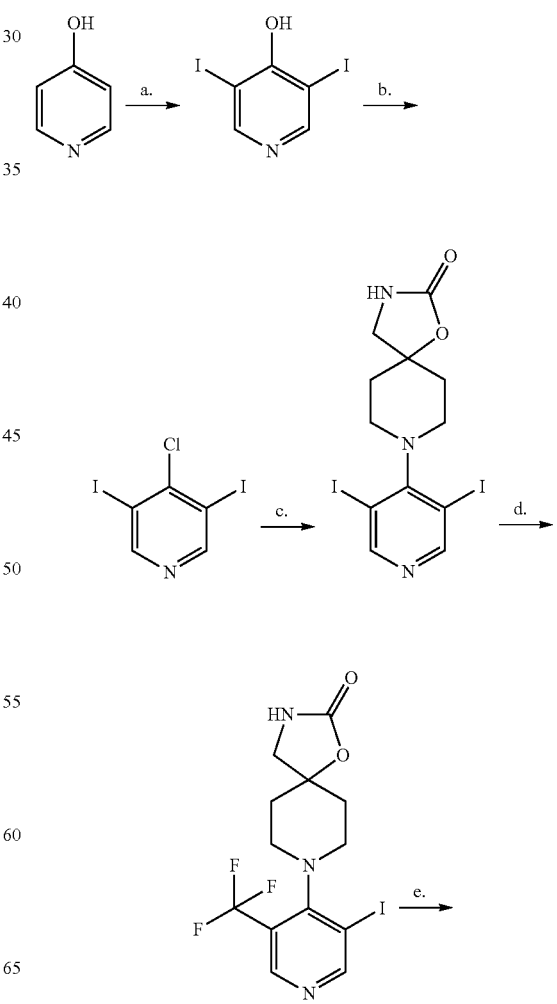

97

-continued

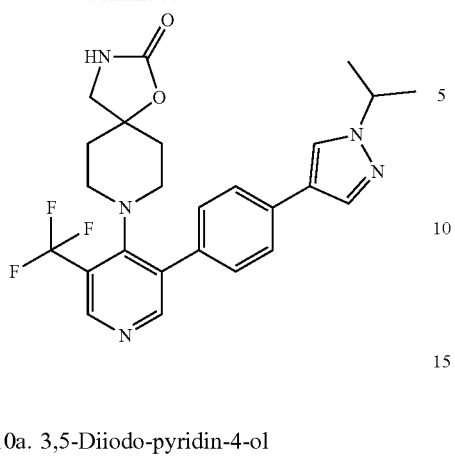

10a. 3,5-Diiodo-pyridin-4-ol

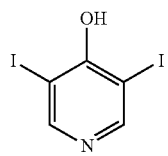

Into a 3 L three necked round bottom flask 1,4-dihydro-pyridin-4-one (50.0 g, 0.50 mol) and N-iodosuccinimide (232 g, 1.00 mmol) were suspended in acetonitrile (1 L). The reaction mixture was refluxed for 3 h. The mixture was cooled down with an ice bath and then filtered and washed with acetonitrile (150 mL). The light yellow solid was dried at 60° C. under reduced pressure for 15 hr to obtain 165 g (95%) of the title compound as a light yellow solid. LC/MS (Method B): Rt 1.34 min, (M+H) 348.

10b. 4-Chloro-3,5-diiodo-pyridine

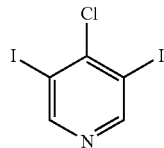

Into a 3 L three necked round bottom flask 3,5-diiodo-pyridin-4-ol (150 g, 432 mmol) was suspended in DMF (1 L). To this mixture was added dropwise at 70° C. phosphoryl chloride (39.7 mL, 432 mmol) (Slightly exothermic reaction). The mixture was further heated to 95° C. for 30 min. The dark brown mixture was cooled down to RT and poured into 6 L of ice water. A beige precipitate was formed. NaHCO₃ was added slowly until no more gas formation was observed. The solid was filtered and washed with water (2 L). The residue was suspended in acetonitrile (800 mL) and filtered again. The residue was washed with acetonitrile (100 mL) and dried at 60° C. under reduced pressure for 15 hr to yield in 142 g (95% purity, 85%) of a yellow solid, which was used without further purification. LC/MS (Method B): Rt 3.06 min, (M+H) 366.

98

10c. 8-(3,5-Diiodo-pyridin-4-yl)-1-oxa-3,8-diaza-spiro[4.5]decan-2-one

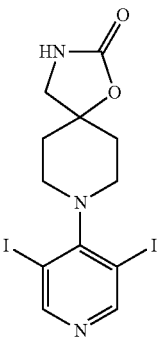 [SMILES: O=C1NCC2(CCN(c3c(I)cncc3I)CC2)O1]

In a microwave vessel 4-chloro-3,5-diiodo-pyridine (95% purity, 1.00 g, 2.63 mmol) and 1-oxa-3,8-diaza-spiro[4.5]decan-2-one acetate (0.68 g, 3.15 mmol) were suspended in NMP (10 mL) and triethylamine (1.10 mL, 7.88 mmol). The mixture was stirred under microwave irradiation 8 times for 2 hr at 220° C. The mixture was poured into water (1 L). The resulting precipitate was filtered and washed with water (100 mL). It was re-dissolved in DCM (80 mL), evaporated to dryness and the residue was purified by flash chromatography (DCM/MeOH). The obtained residue after evaporation was suspended in DCM (15 mL) and diluted with diethyl ether (50 mL). The precipitate was filtered off and washed with diethyl ether (30 mL). It was dried at 60° C. under reduced pressure for 3 hr to yield in the title compound (2.12 g, 20%) as a white solid. LC/MS (Method B): Rt 2.19 min, (M+H) 486.

10d. 8-(3-Iodo-5-trifluoromethyl-pyridin-4-yl)-1-oxa-3,8-diaza-spiro[4.5]decan-2-one

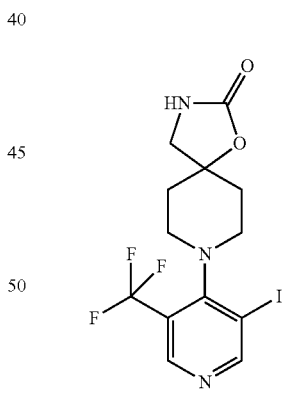

A Schlenck vial containing silver(I) fluoride (281 mg, 2.21 mmol) was evaporated and purged with nitrogen 3 times. DMF (35 mL) and (trifluoromethyl)trimethylsilane (98%, 0.40 mL, 2.65 mmol) were added at RT and the resulting brown suspension was stirred for 15 min at RT. Fine powdered copper (particle size <63 µm, 212 mg, 3.33 mmol) was added and the resulting dark red suspension was stirred for another 3 hr at RT. The reaction mixture turned green and a silver precipitate was formed on the vessel wall. 8-(3,5-Diiodo-pyridin-4-yl)-1-oxa-3,8-diaza-spiro[4.5]decan-2-one (1.00 g, 1.99 mmol) was added and the suspension was stirred at 90° C. for 3 h. The green suspension was diluted with DMF (20 mL), filtered over Celite and washed with DMF (5 mL). The filtrate was evaporated to dryness. The obtained residue was dissolved in DCM (5 mL) and treated with diethyl ether (25 mL). The resulting orange precipitate was filtered and washed with diethyl ether (8 mL). The precipitate was discarded. The filtrate was evaporated to dryness and further purified by flash chromatography (DCM/MeOH) to give the title compound (498 mg, 46%) as orange oily crystals. LC/MS (Method B): Rt 2.58 min, (M+H) 428.

10e. 8-{3-[4-(1-Isopropyl-1H-pyrazol-4-yl)-phenyl]-5-trifluoromethyl-pyridin-4-yl}-1-oxa-3,8-diaza-spiro[4.5]decan-2-one 38

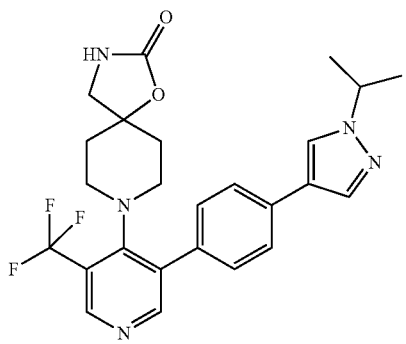 [SMILES: CC(C)n1cc(-c2ccc(-c3cncc(C(F)(F)F)c3N3CCC4(CC3)CNC(=O)O4)cc2)cn1]

In a microwave vessel 1-isopropyl-4-[4-(4,4,5,5-tetramethyl-[1,3,2]dioxaborolan-2-yl)-phenyl]-1H-pyrazole (144 mg, 0.46 mmol), (1,1'-bis(diphenylphosphino)ferrocene)-palladium(II) chloride (8.49 mg, 0.01 mmol) and 8-(3-Iodo-5-trifluoromethyl-pyridin-4-yl)-1-oxa-3,8-diaza-spiro[4.5]decan-2-one (124 mg, 0.23 mmol) were dissolved in acetonitrile (4 mL) and sodium carbonate solution (0.5 M, 1.38 mL, 0.69 mmol) was added. The vial was closed, degassed, flushed with nitrogen and stirred under microwave irradiation for 1 hr at 120° C. The mixture was diluted with acetonitrile (5 mL), filtered and the solvent was evaporated. The residue was purified by flash chromatography (DCM/MeOH). The pure solid was dissolved in 1N HCl (2 mL) and lyophilized to yield the hydrochloride of the title compound (45.4 mg, 38%) as a yellow crystallizing oil. 1H NMR (500 MHz, DMSO-d6) ppm=8.87 (s, 1H), 8.54 (s, 1H), 8.33 (s, 1H), 7.96 (s, 1H), 7.75 (d, J=8.1, 2H), 7.44 (s, 1H), 7.41 (d, J=8.1, 2H), 4.52 (hept, J=6.7, 1H), 3.15 (s, 2H), 2.99-2.94 (m, 4H), 1.70-1.57 (m, 4H), 1.47 (d, J=6.7, 6H). LC/MS (Method C): Rt 1.03 min, (M+H) 486.

According to this procedure compounds 35 and 45 were synthesized using the key intermediates 1-methyl-4-(4-(4,4,5,5-tetramethyl-1,3,2-dioxaborolan-2-yl)phenyl)-1H-pyrazole or boc-2,8-diazaspiro[4.5]decan-1-one and 1-methyl-4-(4-(4,4,5,5-tetramethyl-1,3,2-dioxaborolan-2-yl)phenyl)-1H-pyrazole respectively.

8-{3-[4-(1-Methyl-1H-pyrazol-4-yl)-phenyl]-5-trifluoromethyl-pyridin-4-yl}1-oxa-3,8-diaza-spiro[4.5]decan-2-one 35

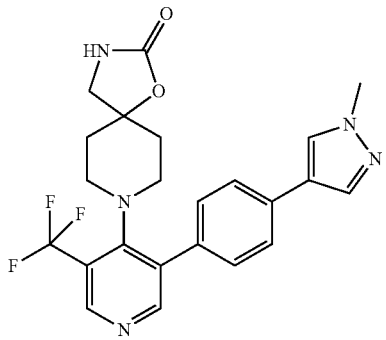 [SMILES: Cn1cc(-c2ccc(-c3cncc(C(F)(F)F)c3N3CCC4(CC3)CNC(=O)O4)cc2)cn1]

1H NMR (500 MHz, DMSO-d6) ppm=8.80 (s, 1H), 8.52 (s, 1H), 8.24-8.20 (m, 1H), 7.96-7.92 (m, 1H), 7.73-7.68 (m, 2H), 7.43-7.36 (m, 3H), 3.88 (s, 3H), 3.12 (s, 2H), 2.96-2.82 (m, 4H), 1.70-1.56 (m, 4H). LC/MS (Method B): Rt 1.98 min, (M+H) 458.

8-{3-[4-(1-Methyl-1H-pyrazol-4-yl)-phenyl]-5-trifluoromethyl-pyridin-4-yl}-2,8-diaza-spiro[4.5]decan-1-one 45

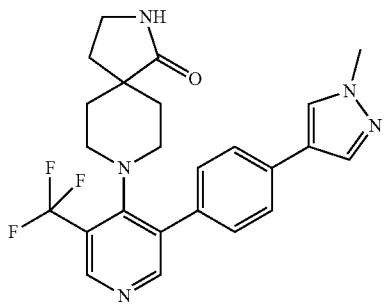 [SMILES: Cn1cc(-c2ccc(-c3cncc(C(F)(F)F)c3N3CCC4(CCNC4=O)CC3)cc2)cn1]

1H NMR (400 MHz, DMSO-d6) ppm=8.82 (s, 1H), 8.52 (s, 1H), 8.22 (s, 1H), 7.94 (d, J=0.8, 1H), 7.72-7.67 (m, 2H), 7.48 (s, 1H), 7.41-7.36 (m, 2H), 3.88 (s, 3H), 3.11-2.98 (m, 4H), 2.73-2.62 (m, 2H), 1.71 (t, J=6.8, 2H), 1.63 (td, J=12.4, 4.1, 2H), 1.21-1.13 (m, 2H). LC/MS (Method C): Rt 0.93 min, (M+H) 456.

11. Preparation of 8-{3-chloro-5-[4-(1-methyl-1H-pyrazol-4-yl)-phenyl]-pyridin-4-yl}-1-methyl-1,3,8-triaza-spiro[4.5]decane-2,4-dione 49

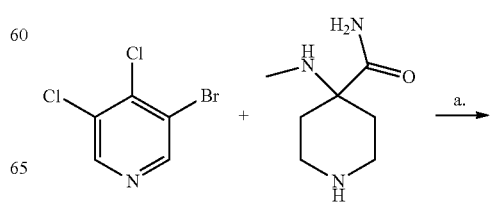

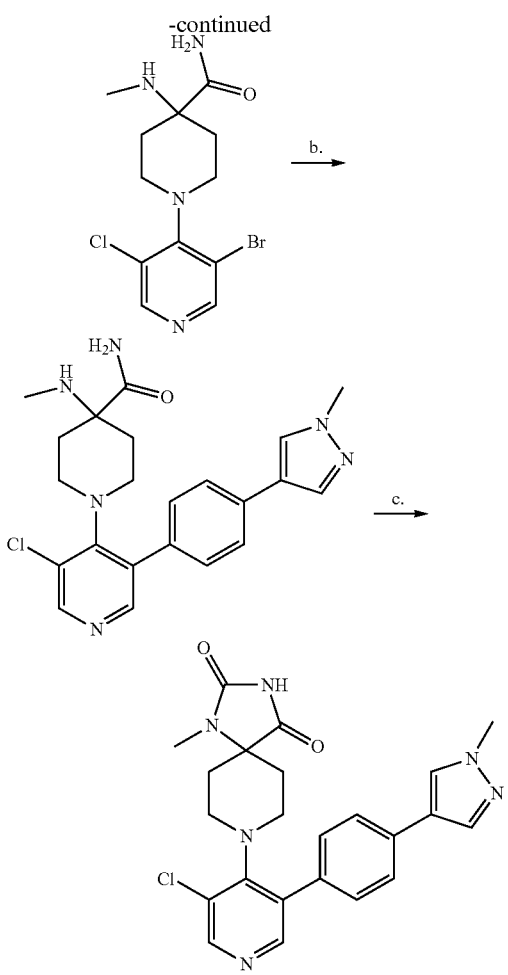

11a. 3'-Bromo-5'-chloro-4-methylamino-3,4,5,6-tetrahydro-2H-[1,4']bipyridinyl-4-carboxylic Acid Amide

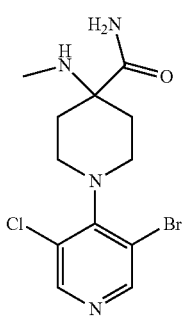 [SMILES: CNC1(C(N)=O)CCN(c2c(Cl)cncc2Br)CC1]

In a microwave vessel 3-bromo-4,5-dichloro-pyridine (400 mg, 1.76 mmol) was dissolved in NMP (5 mL). 4-Methylamino-piperidine-4-carboxylic acid amide (416 mg, 2.64 mmol) and triethylamine (0.73 mL, 5.29 mmol) were added. The closed vial was stirred at 220° C. for 1 hr under microwave irradiation. The brown reaction mixture was treated with water. Since no crystals were formed the mixture was evaporated to dryness and purified by flash chromatography (DCM/MeOH) to give the title compound (467 mg, 72%) of as a pale brown solid. LC/MS (Method B): Rt 1.24 min, (M+H) 347/349.

11b. 5'-Chloro-4-methylamino-3'-[4-(1-methyl-1H-pyrazol-4-yl)-phenyl]-3,4,5,6-tetrahydro-2H-[1,4'] bipyridinyl-4-carboxylic Acid Amide

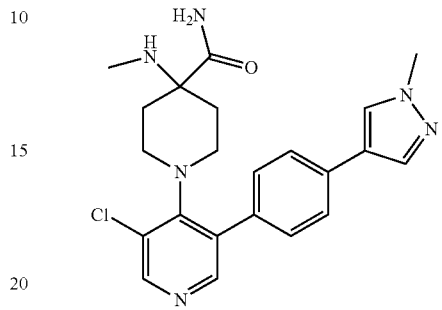

In a microwave vessel 3'-bromo-5'-chloro-4-methylamino-3,4,5,6-tetrahydro-2H-[1,4']bipyridinyl-4-carboxylic acid amide (233 mg, 0.637 mmol) and 1-methyl-4-[4-(4,4,5,5-tetramethyl-[1,3,2]dioxaborolan-2-yl)-phenyl]-1H-pyrazole (300 mg, 0.96 mmol) were dissolved in acetonitrile (5 mL). Sodium carbonate solution (0.5 M, 2.60 mL, 1.27 mmol) and 1,1-bis(diphenylphosphino)ferrocenepalladium (II) dichloride, 99% (47.0 mg, 0.064 mmol) were added. The closed vial was stirred at 120° C. for 1 hr under microwave irradiation. The reaction mixture was evaporated to dryness under reduced pressure. The crude product was purified by flash chromatography (DCM/MeOH) to give the title compound (59.3 mg, 21%) of as a beige solid. LC/MS (Method B): Rt 1.33 min, (M+H) 425.

11c. 8-{3-Chloro-5-[4-(1-methyl-1H-pyrazol-4-yl)-phenyl]-pyridin-4-yl}-1-methyl-1,3,8-triaza-spiro[4.5]decane-2,4-dione 49

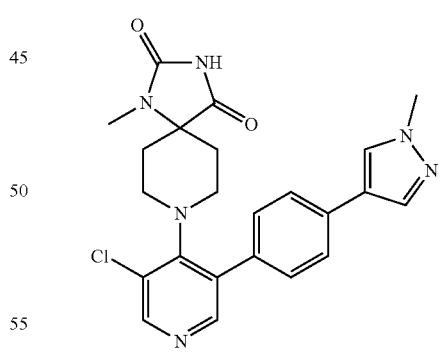

In a screw-capped vessel 5'-chloro-4-methylamino-3'-[4-(1-methyl-1H-pyrazol-4-yl)-phenyl]-3,4,5,6-tetrahydro-2H-[1,4']bipyridinyl-4-carboxylic acid amide (20.0 mg, 0.047 mmol) was dissolved in THF SeccoSolv® (3 mL). N-Ethyldiisopropylamine (16.0 μl, 0.094 mmol) and 1,1'-carbonyldiimidazole (7.63 mg, 0.047 mmol) were added and the reaction mixture was stirred for 15 hr at 60° C. No conversion was observed by LC/MS. To the reaction mixture was added solid sodium hydride (60% suspension in paraffin oil, 4.52 mg, 0.113 mmol) and the reaction mixture was stirred at RT for 3 days. 7% conversion was observed by LC/MS. Additional sodium hydride (60% suspension in paraffin oil, 5.00 mg, 0.125 mmol) and 1,1'-carbonyldiimidazole (4.00 mg, 0.025 mmol) were added and stirring was continued for 15 hr at 70° C. The reaction mixture was evaporated to dryness. Water was added slowly. The mixture was evaporated and then purified by preparative HPLC (MeCN/water) to yield in the title compound (4.04 mg, 16%) as a white fluffy solid. 1H NMR (400 MHz, DMSO-d6) ppm=10.77 (s, 1H), 8.55 (s, 1H), 8.27 (s, 1H), 8.21 (s, 1H), 7.95-7.92 (m, 1H), 7.72-7.67 (m, 2H), 7.41-7.36 (m, 2H), 3.88 (s, 3H), 3.37-3.27 (m, 2H), 3.12-3.04 (m, 2H), 2.66 (s, 3H), 1.90-1.78 (m, 2H), 1.56 (d, J=13.1, 2H). LC/MS (Method B): Rt 1.88 min, (M+H) 451.

12. Preparation of 8-[3-chloro-5-(1-methyl-2,2-dioxo-2,3-dihydro-1H-benzo[c]isothiazol-5-yl)-pyridin-4-yl]-4-ethyl-2,3,8-triaza-spiro[4.5]dec-3-en-1-one 52

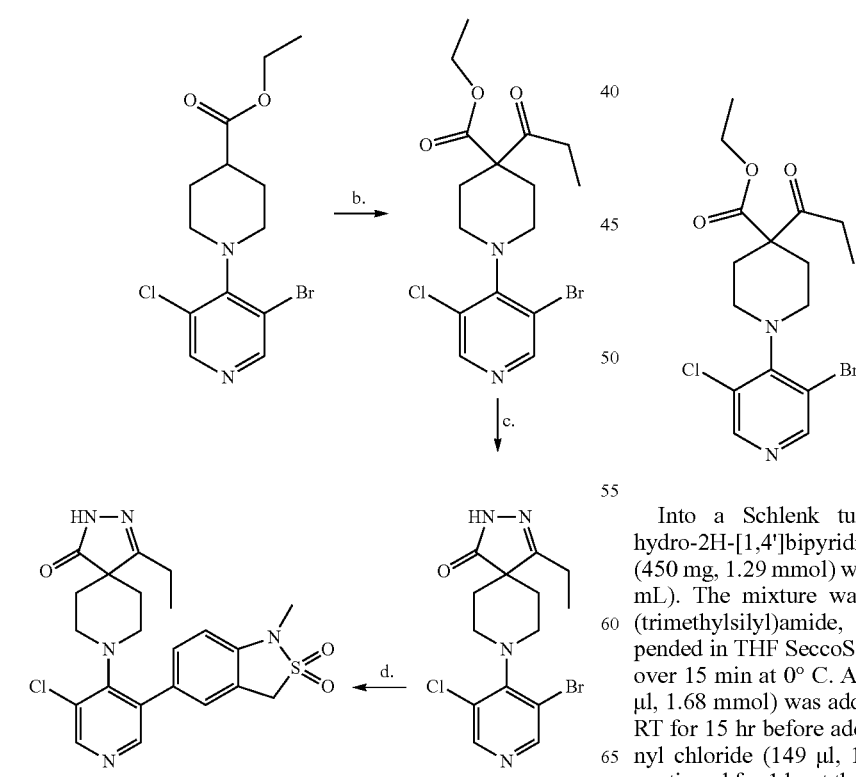

12a. 3'-Bromo-5'-chloro-3,4,5,6-tetrahydro-2H-[1,4']bipyridinyl-4-carboxylic Acid Ethyl Ester

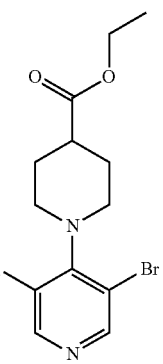

In a microwave vessel 3-bromo-4,5-dichloro-pyridine (1.00 g, 4.41 mmol) and ethyl 1-boc-piperidine-4-carboxylate (99%, 1.68 mL, 6.61 mmol) were dissolved in NMP (10 mL). Triethylamine (1.83 mL, 13.2 mmol) was added and stirred under microwave irradiation for 1 hr at 220° C. While stirring, the mixture was poured into water (200 mL). The product was extracted with EtOAc (2×250 mL). The organic layers were combined, washed with water (2×100 mL), dried over sodium sulfate and evaporated to dryness. The crude residue was further purified by flash chromatography (heptane/EtOAc) to give 450 mg (29%) of the title compound as a colorless oil. LC/MS (Method B): Rt 2.77 min, (M+H) 347.

12b. 3'-Bromo-5'-chloro-4-propionyl-3,4,5,6-tetrahydro-2H-[1,4']bipyridinyl-4-carboxylic Acid Ethyl Ester

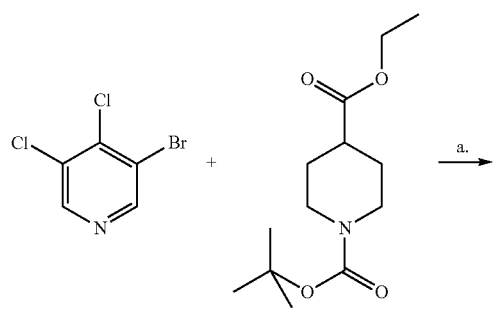

Into a Schlenk tube 3'-bromo-5'-chloro-3,4,5,6-tetrahydro-2H-[1,4']bipyridinyl-4-carboxylic acid ethyl ester (450 mg, 1.29 mmol) was dissolved in THF SeccoSolv® (10 mL). The mixture was cooled to 0° C. and lithium bis (trimethylsilyl)amide, 20% (1.34 mL, 1.20 mmol) suspended in THF SeccoSolv® (10 mL) was added via syringe over 15 min at 0° C. After 20 min, propionyl chloride (149 μl, 1.68 mmol) was added at RT. The mixture was stirred at RT for 15 hr before adding an additional portion of propionyl chloride (149 μl, 1.68 mmol) at RT. The stirring was continued for 1 hr at the same temperature. The mixture was quenched with MeOH (10 mL), evaporated to dryness and purified by flash chromatography (CyHex/EtOAc). The solvent was evaporated to dryness to give the title compound (80% purity, 35.7 mg, 6%) as a colorless oil. LC/MS (Method B): Rt 2.95 min, (M+H) 403.

12c. 8-(3-Bromo-5-chloro-pyridin-4-yl)-4-ethyl-2,3,8-triaza-spiro[4.5]dec-3-en-1-one

Into a microwave vessel 3'-bromo-5'-chloro-4-propionyl-3,4,5,6-tetrahydro-2H-[1,4']bipyridinyl-4-carboxylic acid ethyl ester, 80% (35.7 mg, 0.09 mmol) was dissolved in 1-butanol (2 mL), hydrazinium hydroxide (2.00 mL) was added and the mixture was stirred at 100° C. for 1 hr under microwave irradiation. The mixture was evaporated to dryness. The crude residue was purified by flash chromatography (DCM/MeOH) to yield the title compound (16.0 mg, 49%) as a colorless oil. LC/MS (Method B): Rt 2.27 min, (M+H) 371.

12d. 8-[3-Chloro-5-(1-methyl-2,2-dioxo-2,3-dihydro-1H-benzo[c]isothiazol-5-yl)-pyridin-4-yl]-4-ethyl-2,3,8-triaza-spiro[4.5]dec-3-en-1-one 52

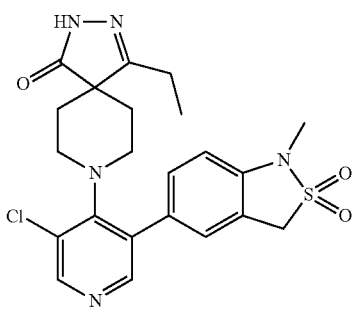 [SMILES: CCC1=NNC(=O)C12CCN(c1c(Cl)cncc1-c1ccc3c(c1)CS(=O)(=O)N3C)CC2]

In a microwave vessel 1-methyl-5-(4,4,5,5-tetramethyl-[1,3,2]dioxaborolan-2-yl)-1,3-dihydro-benzo[c]isothiazole 2,2-dioxide (26.6 mg, 0.09 mmol) and (1,1'-bis(diphenylphosphino)ferrocene)-palladium(II) dichloride (1.59 mg, 0.002 mmol) were suspended in DMF (2 mL). To this suspension 8-(3-bromo-5-chloro-pyridin-4-yl)-4 ethyl-2,3,8-triaza-spiro[4.5]dec-3-en-1-one (16.0 mg, 0.04 mmol) dissolved in DMF (2 mL) and sodium carbonate solution (0.5 M, 0.26 mL, 0.13 mmol) were added. The vial was closed, degassed, flushed with nitrogen and stirred at 120° C. for 1 hr under microwave irradiation. The mixture was diluted with DMF (5 mL), filtered and evaporated to dryness. The crude residue was purified by preparative HPLC (MeCN/water) to give the title compound (10.8 mg, 43%) as a white solid. 1H NMR (500 MHz, DMSO-d6) ppm=11.00 (s, 1H), 8.56 (s, 1H), 8.27 (s, 1H), 7.43-7.38 (m, 2H), 7.08 (d, J=8.0. 1H), 4.71 (s, 2H), 3.39-3.35 (m, 2H), 3.10 (s, 3H), 2.94-2.86 (m, 2H), 2.24 (q, J=7.3, 2H), 1.76-1.65 (m, 2H), 1.49-1.40 (m, 2H), 1.08 (t, J=7.2, 3H). LC/MS (Method B): Rt 1.97 min, (M+H) 474.

According to this procedure compounds 41 and 54 were synthesized using the key intermediates acetyl chloride in place of propionyl chloride and 1-methyl-4-[4-(4,4,5,5-tetramethyl-[1,3,2]dioxaborolan-2-yl)-phenyl]-1H-pyrazole in place of 1-methyl-5-(4,4,5,5-tetramethyl-[1,3,2]dioxaborolan-2-yl)-1,3-dihydro-benzo[c]isothiazole 2,2-dioxide respectively.

8-[3-Chloro-5-(1-methyl-2,2-dioxo-2,3-dihydro-1H-benzo[c]isothiazol-5-yl)-pyridin-4-yl]-4-methyl-2,3,8-triaza-spiro[4.5]dec-3-en-1-one 41

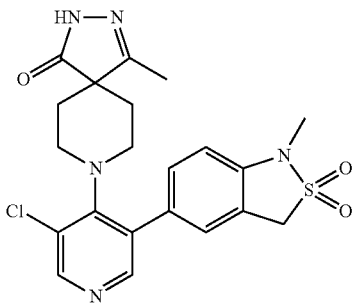 [SMILES: CC1=NNC(=O)C12CCN(c1c(Cl)cncc1-c1ccc3c(c1)CS(=O)(=O)N3C)CC2]

1H NMR (400 MHz, DMSO-d6) ppm=10.93 (s, 1H), 8.47 (s, 1H), 8.23 (s, 1H), 7.41-7.37 (m, 2H), 7.08-7.04 (m, 1H), 4.70 (s, 2H), 3.41-3.32 (m, 2H), 3.10 (s, 3H), 2.90-2.81 (m, 2H), 1.89 (s, 3H), 1.74-1.63 (m, 2H), 1.49-1.39 (m, 2H). LC/MS (Method A): Rt 1.62 min, (M+H) 460.

8-{3-Chloro-5-[4-(1-methyl-1H-pyrazol-4-yl)-phenyl]-pyridin-4-yl}-4-ethyl-2,3,8-triaza-spiro[4.5]dec-3-en-1-one 54

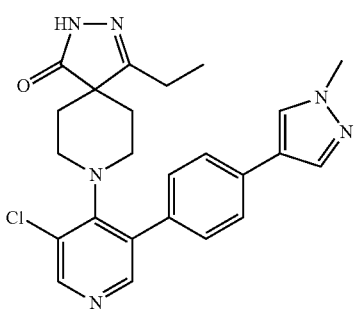 [SMILES: CCC1=NNC(=O)C12CCN(c1c(Cl)cncc1-c1ccc(-c3cnn(C)c3)cc1)CC2]

1H NMR (500 MHz, DMSO-d6) ppm=10.96 (s, 1H), 8.58 (s, 1H), 8.29 (s, 1H), 8.23 (s, 1H), 7.94 (s, 1H), 7.74-7.66 (m, 2H), 7.43-7.36 (m, 2H), 3.88 (s, 3H), 3.49-3.41 (m, 2H), 3.02-2.94 (m, 2H), 2.22 (q, J=7.3, 2H), 1.78-1.67 (m, 2H), 1.47-1.39 (m, 2H), 1.06 (t, J=7.3, 3H). LC/MS (Method B): Rt 2.04 min, (M+H) 449.

13. Preparation of 8-{3-chloro-5-[4-(1-methyl-1H-pyrazol-4-yl)-phenyl]-pyridin-4-yl}-4-trifluoromethyl-2,3,8-triaza-spiro[4.5]dec-3-en-1-one 59

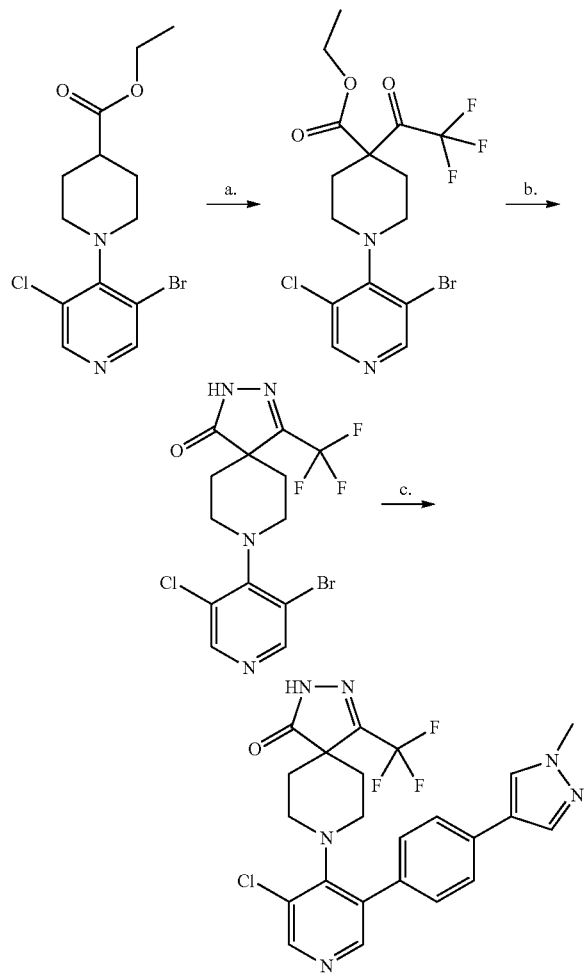

13a. 3'-Bromo-5'-chloro-4-(2,2,2-trifluoro-acetyl)-3,4,5,6-tetrahydro-2H-[1,4']bipyridinyl-4-carboxylic Acid Ethyl Ester

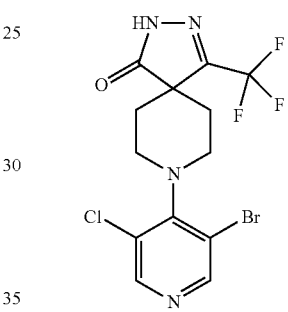

3'-Bromo-5'-chloro-3,4,5,6-tetrahydro-2H-[1,4']bipyridinyl-4-carboxylic acid ethyl ester (1.90 g, 5.47 mmol) was dissolved in THF SeccoSolv® (35 mL). The mixture was cooled to 0° C. and lithium bis(trimethylsilyl)amide (20% purity, 6.67 mL, 7.11 mmol) was added dropwise at 0° C. over 30 min. After 20 min, trifluoroacetic anhydride (1.14 mL, 8.20 mmol) was added. The reaction mixture was stirred for 2 hr at 0° C. and additional 15 hr at RT. The mixture was diluted with MeOH (15 mL), filtered and the solvent was evaporated to dryness. The crude residue was dissolved in EtOAc (150 mL) and washed with saturated sodium hydrogen carbonate solution (100 mL). The organic layer was washed with brine (50 mL), dried over sodium sulfate, filtered and evaporated to dryness. The residue was further purified by flash chromatography (heptane/EtOAc) to give 350 mg (14%) of the title compound as a colorless oil. LC/MS (Method B): Rt 2.69 min, (M+H) 347/349.

13b. 8-(3-Bromo-5-chloro-pyridin-4-yl)-4-trifluoromethyl-2,3,8-triaza-spiro[4.5]dec-3-en-1-one In microwave vessel 3'-bromo-5'-chloro-4-(2,2,2-trifluoro-acetyl)-3,4,5,6-tetrahydro-2H-[1,4']bipyridinyl-4-carboxylic acid ethyl ester (350 mg, 0.47 mmol) was dissolved in 1-butanol (3 mL), hydrazinium hydroxide (2 mL) was added and the reaction mixture was stirred at 100° C. for 1 hr under microwave irradiation. The mixture was evaporated to dryness and the crude residue was purified by flash chromatography (heptane/EtOAc) to give the title compound (180 mg, 92%) as a white solid. LC/MS (Method B): Rt 2.45 min, (M+H) 411/413.

13c. 8-{3-Chloro-5-[4-(1-methyl-1H-pyrazol-4-yl)-phenyl]-pyridin-4-yl}-4-trifluoromethyl-2,3,8-triaza-spiro[4.5]dec-3-en-1-one 59

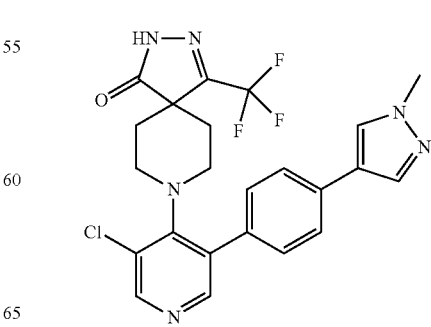

In a microwave vessel 1-methyl-4-[4-(4,4,5,5-tetramethyl-[1,3,2]dioxaborolan-2-yl)-phenyl]-1H-pyrazole (62.1 mg, 0.22 mmol), (1,1-bis(diphenylphosphino)ferrocene)-palladium(II) dichloride (5.38 mg, 0.01 mmol) and 8-(3-bromo-5-chloro-pyridin-4-yl)-4-trifluoromethyl 2,3,8-triaza-spiro[4.5]dec-3-en-1-one (60.0 mg, 0.15 mmol) were dissolved in DMF (4 mL) and sodium carbonate solution (0.5 M, 0.58 mL, 0.29 mmol) were added. The vial was closed, degassed, flushed with nitrogen and stirred at 120° C. for 1 hr under microwave irradiation. The reaction mixture was diluted with acetonitrile (5 mL), filtered and evaporated to dryness. The crude residue was purified by preparative HPLC (MeCN/water) to give 25.0 mg (28%) as the TFA salt of the title compound as a white solid. 1H NMR (400 MHz, DMSO-d6) ppm=12.14 (s, 1H), 8.54 (s, 1H), 8.27 (s, 1H), 8.20 (s, 1H), 7.92 (d, J=0.8, 1H), 7.72-7.65 (m, 2H), 7.42-7.35 (m, 2H), 3.88 (s, 3H), 3.54-3.43 (m, 2H), 3.02-2.92 (m, 2H), 1.99-1.88 (m, 2H), 1.76-1.66 (m, 2H). LC/MS (Method B): Rt 2.26 min, (M+H) 489.

According to this procedure compounds 58 and 61 were synthesized by replacing 1-methyl-4-[4-(4,4,5,5-tetramethyl-[1,3,2]dioxaborolan-2-yl)-phenyl]-1H-pyrazole with 1-methyl-5-(4,4,5,5-tetramethyl-[1,3,2]dioxaborolan-2-yl)-1,3-dihydro-benzo[c]isothiazole 2,2-dioxide or 1-methyl-1H-indazole-5-boronic acid respectively.

8-[3-Chloro-5-(1-methyl-2,2-dioxo-2,3-dihydro-1H-benzo[c]isothiazol-5-yl)-pyridin-4-yl]-4-trifluoromethyl-2,3,8-triaza-spiro[4.5]dec-3-en-1-one 58

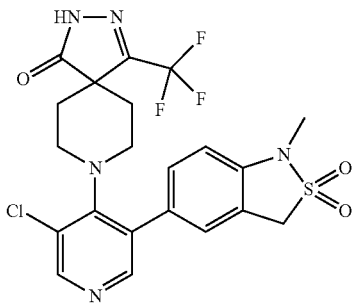 [SMILES: CN1c2ccc(-c3cncc(Cl)c3N3CCC4(CC3)C(=O)NN=C4C(F)(F)F)cc2CS1(=O)=O]

1H NMR (400 MHz, DMSO-d6) ppm=12.19 (s, 1H) 8.27 (s, 1H), 7.44-7.37 (m, 2H), 7.06 (d, J=8.0, 1H), 4.68 (s, 2H), 3.47-3.36 (m, 2H), 3.10 (s, 3H), 2.95-2.85 (m, 2H), 1.99-1.87 (m, 2H), 1.78-1.68 (m, 2H). LC/MS (Method B): Rt 2.22 min, (M+H) 514.

8-[3-Chloro-5-(1-methyl-1H-indazol-5-yl)-pyridin-4-yl]-4-trifluoromethyl-2,3,8-triaza-spiro[4.5]dec-3-en-1-one 61

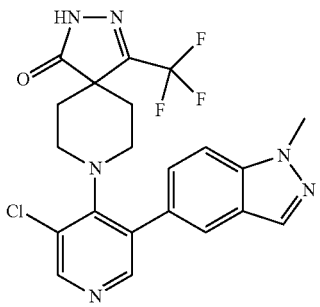 [SMILES: Cn1ncc2cc(-c3cncc(Cl)c3N3CCC4(CC3)C(=O)NN=C4C(F)(F)F)ccc21]

1H NMR (500 MHz, DMSO-d6) ppm=12.13 (s, 1H), 8.58 (s, 1H), 8.31 (s, 1H), 8.11-8.10 (m, 1H), 7.81-7.78 (m, 1H), 7.75 (d, J=8.6, 1H), 7.42 (dd, J=8.6, 1.6, 1H), 4.09 (s, 3H), 3.49-3.37 (m, 2H), 3.01-2.92 (m, 2H), 1.94-1.83 (m, 2H), 1.72-1.62 (m, 2H). LC/MS (Method B): Rt 2.19 min, (M+H) 463.

14. Preparation of 8-(3-chloro-5-{4-[1-((1S,2S)-2-hydroxy-cyclopentyl)-1H-pyrazol-4-yl]-phenyl}-pyridin-4-yl)-1-oxa-3,8-diaza-spiro[4.5]decan-2-one 62 and 8-(3-Chloro-5-{4-[1-((1R,2R)-2-hydroxy-cyclopentyl)-1H-pyrazol-4-yl]-phenyl}-pyridin-4-yl)-1-oxa-3,8-diaza-spiro[4.5]decan-2-one 63

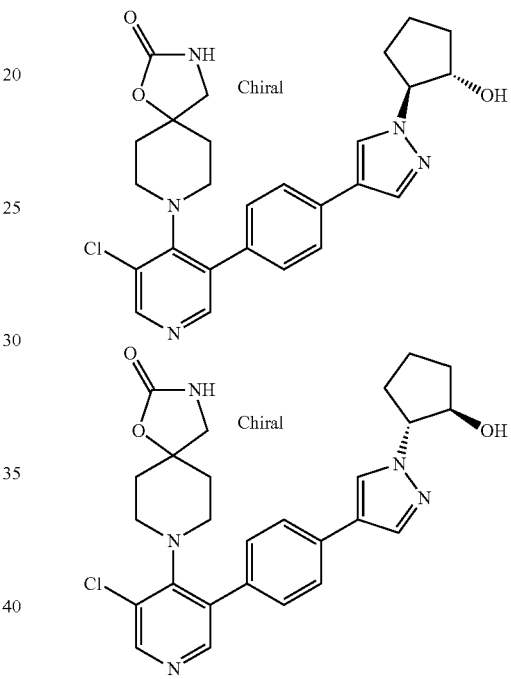

42.6 mg (0.085 mmol) of the racemic mixture dissolved in MeOH (1 mL) were separated into the contained enantiomerically pure materials by chiral HPLC in 40 μL/run portions to yield in combined 14.4 mg (34%) of light yellow crystals as 62 and 14.3 mg (34%) of light yellow crystals as 63. HPLC/MS (chiral): Rt 8.78 min (Method below, 62), Rt 11.21 min (Method below, 63).

Instrument: SFC Berger Minigram; Column: ChiralPak AD-H; Eluent: $CO_2$/MeOH+0.5% diethylamine 60:40, isocratic; Flow: 5 mL/min; detection: 220 nm.

62: 1H NMR (500 MHz, DMSO-d6) ppm=8.46 (s, 1H), 8.30 (s, 1H), 8.22 (s, 1H), 7.98 (s, 1H), 7.74-7.70 (m, 2H), 7.47 (s, 1H), 7.34-7.31 (m, 2H), 5.09 (d, J=5.0, 1H), 4.40-4.34 (m, 1H), 4.28-4.22 (m, 1H), 3.18 (s, 2H), 2.94-2.84 (m, 4H), 2.22-2.14 (m, 1H), 2.05-1.93 (m, 2H), 1.83-1.75 (m, 2H), 1.75-1.69 (m, 4H), 1.62-1.53 (m, 1H). LC/MS: Rt 1.80 min, (M+H) 494. 63: 1H NMR (500 MHz, DMSO-d6) ppm=8.47 (s, 1H), 8.31 (s, 1H), 8.22 (s, 1H), 7.98 (s, 1H), 7.74-7.70 (m, 2H), 7.47 (s, 1H), 7.35-7.31 (m, 2H), 5.10 (d, J=4.9, 1H), 4.41-4.34 (m, 1H), 4.29-4.22 (m, 1H), 3.18 (s, 2H), 2.94-2.85 (m, 4H), 2.22-2.14 (m, 1H), 2.05-1.93 (m, 2H), 1.82-1.70 (m, 6H), 1.61-1.53 (m, 1H).

Preparation of Compounds A

3-Bromo-4,5-dichloropyridine A1

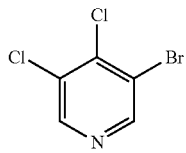

nButyllithium (1.6 M in hex, 7.15 mL, 11.43 mmol) was added to a solution of diisopropylamine (1.689 mL, 11.95 mmol) in THF (30 mL) at −78° C. The reaction was stirred for 30 min and then 3-bromo-5-chloropyridine (2 g, 10.39 mmol) in THF (10 mL) was added dropwise over 7 min. The reaction was stirred for 45 min resulting in a yellow/brown suspension. Hexachloroethane (4.92 g, 20.79 mmol) in THF (7 mL) was added at −78° C. and the dark brown reaction mixture was stirred at −78° C. for 75 min. The cooling bath was removed and the brown suspension was allowed to warm to RT (about 30 min) The clear brown solution was then quenched with sat. aq. NH$_4$Cl (100 mL) and the water layer was extracted with ether (3×70 ml). The combined organic layers were washed with water (2×100 ml) and brine (70 mL), dried over MgSO$_4$, filtered and the solvent evaporated in vacuo. The crude was purified by flash chromatography (DCM/CyHex 1:4 to 1:3, crude soluble in eluent) to give the product (2.05 g, 87%) as a white solid. $^1$H-NMR (500 MHz, CDCl$_3$) δ8.64 (s, 1H), 8.54 (s, 1H). LCMS (Method E): Rt 3.01 min, (M+H) 225/227.

Preparation of Substituted Piperidines (B)

1. Preparation of tert-butyl 2-oxospiro[indoline-3,4'-piperidine]-1-carboxylate

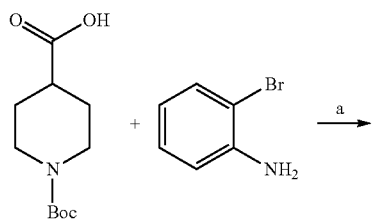

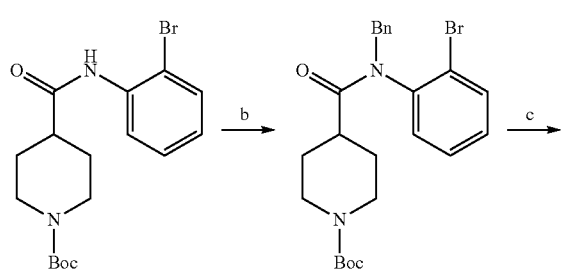

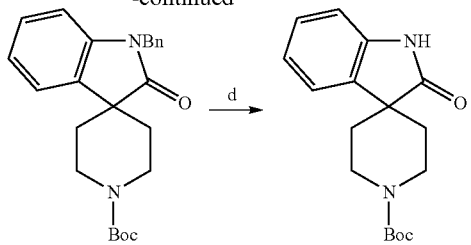

1a. tert-Butyl 4-((2-bromophenyl)carbamoyl)piperidine-1-carboxylate

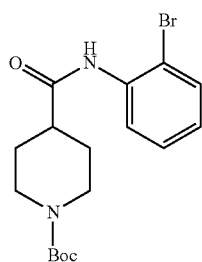 [SMILES: CC(C)(C)OC(=O)N1CCC(C(=O)Nc2ccccc2Br)CC1]

EDCl (1.568 g, 8.18 mmol) was added to a solution of 1-(tert-butoxycarbonyl)piperidine-4-carboxylic acid (1.25 g, 5.45 mmol), 2-bromoaniline (0.938 g, 5.45 mmol) and DMAP (0.133 g, 1.090 mmol) in DCM (20 mL). The reaction was stirred for 24 hr at RT. More 1-(tert butoxycarbonyl)piperidine-4-carboxylic acid was added (300 mg) and the reaction stirred at RT for another 24 h. After a total of 48 hr, the reaction mixture was diluted with DCM (150 mL) and washed with aqueous HCl (0.5 M, 75 mL), water (75 mL), NaHCO$_3$ (75 mL) and brine (75 mL). The organic layer was dried over MgSO$_4$, filtered and the solvent evaporated. The crude product was dissolved in a small amount of chloroform and diluted with an equal volume of CyHex. The product was charged on a silica gel column and eluted with EtOAc/CyHex (1:10 to 1:5)+1% Et$_3$N to afford the title compound as a white solid (1.5 g, 72%). 1H NMR (500 MHz, CDCl$_3$) ppm=8.35 (d, J=8.1, 1H), 7.70 (bs, 1H), 7.54 (dd, J=8.1, 1.4, 1H), 7.33-7.30 (m, 1H), 6.98 (ddd, J=8.1, 7.5, 1.6, 1H), 4.20 (bs, 2H), 2.90-2.75 (m, 2H), 2.47 (tt, J=11.6, 3.8, 11.6, 1H), 1.97 (bd, J=12.1, 2H), 1.75 (dq, J=4.3, 12.1 Hz, 2H), 1.47 (s, 9H).

1b. tert-Butyl 4-(benzyl(2-bromophenyl)carbamoyl)piperidine-1-carboxylate

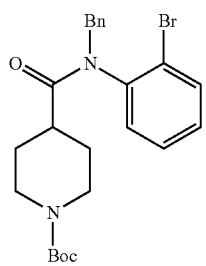 [SMILES: CC(C)(C)OC(=O)N1CCC(C(=O)N(Cc2ccccc2)c2ccccc2Br)CC1]

To a stirred, cooled suspension of sodium hydride (0.188 g, 4.70 mmol) in DMF (10 mL) was added tert-butyl 4-((2-bromophenyl)carbamoyl)piperidine-1-carboxylate (1.5 g, 3.91 mmol) dissolved in DMF (10 mL). The reaction mixture was stirred at 0° C. for 15 min and 30 min at RT. At this time effervescence had ceased and the reaction mixture was cooled to 0° C. Benzyl bromide (0.562 mL, 4.70 mmol) was added and the solution was allowed to slowly warm to RT. After 2 hr the reaction was complete. Water was carefully added to the reaction mixture resulting in a white slurry. The slurry was poured into water (250 mL) and extracted with ether (3×100 mL). The combined organic layers were washed with brine (100 mL), dried over $MgSO_4$, filtered and the solvent evaporated. The crude product was purified by flash chromatography (EtOAc/CyHex 1:10 to 1:5 to give the title compound as a white solid (1.63 g, 88%). $^1$H-NMR (500 MHz, $CDCl_3$) ppm=7.71 (dd, J=7.7, 1.7, 1H), 7.27-7.15 (m, 7H), 6.76 (dd, J=7.5, 1.7, 1H), 5.63 (d, J=14.3, 1H), 4.04 (bs, 2H), 3.98 (d, J=14.3, 1H), 2.51 (bs, 1H), 2.37 (bs, 1H), 2.07 (tt, J=11.3, 3.9, 1H), 1.86 (ddd, J=15.8, 12.8, 4.4, 1H), 1.74-1.63 (m, 2H), 1.51 (d, J=12.9, 1H), 1.43 (s, 9H). No LCMS found 1c. tert-Butyl 1-benzyl-2-oxospiro[indoline-3,4'-piperidine]-1'-carboxylate

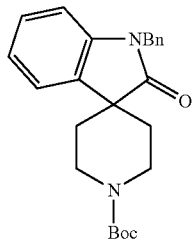 [SMILES: CC(C)(C)OC(=O)N1CCC2(CC1)C(=O)N(Cc1ccccc1)c1ccccc12]

Sodium tert-butoxide (0.469 g, 4.88 mmol), palladium acetate (0.037 g, 0.163 mmol) and tricyclohexylphosphine (0.046 g, 0.163 mmol) were loaded in a round bottom flask and air was removed by three vacuum/nitrogen cycles. Dioxane (23 mL) was added and after stirring for 5 min a solution of tert-butyl 4-(benzyl(2-bromophenyl)carbamoyl)piperidine-1-carboxylate (1.54 g, 3.25 mmol) in dioxane (10 mL) was added. The reaction was heated to 60° C. for 3 hr and subsequently cooled to RT. The reaction was poured into saturated aqueous ammonia and extracted with ether (3×60 mL). The combined organic layers were washed with brine (60 mL), dried over $MgSO_4$, filtered and the solvent was evaporated. Purification by flash chromatography (silica gel, EtOAc/CyHex 1:40 to 1:3) afforded the title compound as cream white solid (674 mg, 53%). 1H NMR (500 MHz, $CDCl_3$) ppm=7.33-7.29 (m, 3H), 7.27-7.24 (m, 3H), 7.17 (dt, J=7.7, 1.2, 1H), 7.03 (dt, J=7.6, 1.0, 7.6, 1H), 6.74 (d, J=7.8, 1H), 4.91 (s, 2H), 3.90 (ddd, J=13.0, 9.0, 3.8, 2H), 3.82 (bs, 2H), 1.91-1.88 (m, 2H), 1.85-1.77 (m, 2H), 1.51 (s, 9H). LC-MS (ESI, m/z) Rt=3.30 min-293 (M−Boc+H)$^+$ (HPLC method E).

1d. tert-Butyl 2-oxospiro[indoline-3,4'-piperidine]-1-carboxylate

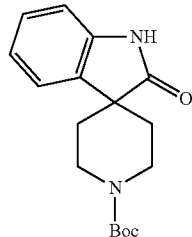 [SMILES: CC(C)(C)OC(=O)N1CCC2(CC1)C(=O)Nc1ccccc12]

Ammonia (17 mL) was condensed in a 100 mL three neck flask at −78° C. under a nitrogen atmosphere. Sodium (173 mg, 7.53 mmol) metal was added and the mixture was stirred at −78° C. for 5 minutes. A solution of tert-butyl-1-benzyl-2-oxospiro[indoline-3,4'-piperidine]-1'-carboxylate (633 mg, 1.613 mmol) in THF (3.5 mL) was added to the mixture and the resulting solution was stirred for 1 h. The reaction was quenched with 5.5 mL of MeOH and excess $NH_3$ was evaporated at RT overnight open to air. The solvent was evaporated and the crude sample was purified by flash chromatography (silica gel, EtOAc/CyHex 1:3 to 1:1) to give the title compound as a white solid (397 mg, 81%). 1H NMR (500 MHz, $CDCl_3$) ppm=8.10 (s, 1H), 7.28 (d, J=7.3, 1H), 7.23 (dt, J=7.7, 1.2, 1H), 7.04 (dt, J=7.6, 1.0, 1H), 6.91 (d, J=7.7, 1H), 3.86 (ddd, J=12.9, 8.8, 3.8, 2H), 3.82-3.72 (bs, 2H), 1.88 (td, J=13.3, 4.7, 2H), 1.83-1.73 (m, 2H), 1.50 (s, 9H). LC-MS (ESI, m/z) Rt=2.96 min-203 (M−Boc+H)$^+$ (HPLC method E).

2. Preparation of 2,8-diazaspiro[4.5]decane-1,3-dione

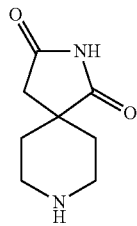 [SMILES: O=C1CC2(CCNCC2)C(=O)N1]

To a suspension of 8-benzyl-2,8-diazaspiro[4.5]decane-1,3-dione (1.2 g, 4.65 mmol) and conc. acetic acid (0.266 mL, 4.65 mmol) in ethanol (20 mL) was added palladium hydroxide (20 wt % on carbon, wet, 360 mg, 4.65 mmol) and the mixture was stirred under $H_2$-atmosphere for 24 hr at RT. The mixture was filtered over Celite, washed with EtOH and 1M $NH_3$ in MeOH. The filtrate was concentrated purified on an SCX2 cartridge (loading with DCM, by-product elution with DCM/MeOH 9/1, elution of product with DCM/MeOH/$NH_3$ 9/1/0.01) to give the product (754 g, 97%) as a white solid. $^1$H-NMR (500 MHz, DMSO) ppm=2.86 (dt, J=12.5, 3.9, 2H), 2.56 (s, 2H), 2.53-2.44 (m, 2H), 1.65 (td, J=12.5, 3.9, 2H), 1.41 (dd, J=12.5, 1.4, 2H). HRMS m/z (ESI$^+$) [M+H$^+$] $C_8H_{12}N_2O_2$, calc. 169.0972, found 169.0971, Rt=0.17 (HPLC method E).

3. Preparation of 1,2,8-triaza-spiro[4.5]decan-3-one

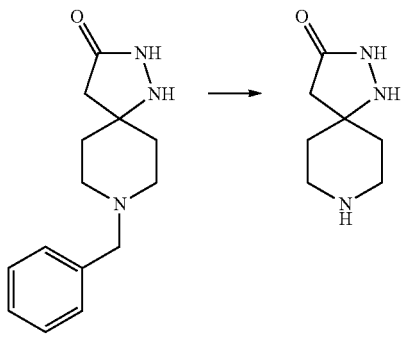 [SMILES: O=C1CC2(CCN(Cc3ccccc3)CC2)NN1 ; O=C1CC2(CCNCC2)NN1]

1.00 g (3.87 mmol) 8-benzyl-1,2,8-triazaspiro[4.5]decan-3-one (95%) was dissolved in MeOH (10 mL), 0.50 g of Pd/C (5%, E101 R) was then added and the reaction mixture was stirred under hydrogen for 15 hr at RT. The mixture was filtered and the solvent evaporated to give 668 mg (100%) of a light brown oil, which was used for the next step without further purification. LC/MS (Method A): Rt=0.43 min, (M+H) 156.

4. Preparation of 4-carbamoyl-4-fluoro-piperidine-1-carboxylic Acid tert-butyl Ester

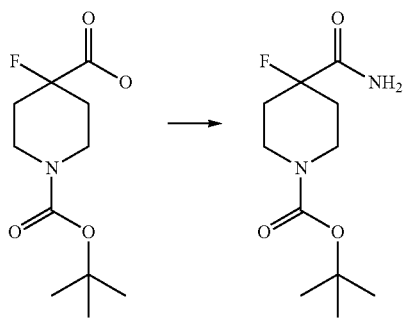 [SMILES: CC(C)(C)OC(=O)N1CCC(F)(C(=O)O)CC1 ; CC(C)(C)OC(=O)N1CCC(F)(C(N)=O)CC1]

A solution of 1-boc-4-fluoro-4-piperidinecarboxylic acid (300 mg, 1.15 mmol) in ethylene glycol dimethyl ether (15 mL) was treated with 4-methylmorpholine (0.13 mL, 1.15 mmol) and isopropyl chloroformate (1 M solution in toluene, 1.38 mL, 1.38 mmol) at −15° C. After stirring for 10 min, ammonia solution (0.5 M in dioxane, 3.50 mL, 1.75 mmol) was added. The reaction mixture was stirred at RT for 18 h. The solvents were evaporated under reduced pressure, the crude product was dissolved in EtOAc, washed with 1N NaOH solution, water and brine and the organic layers were dried over sodium sulfate, filtered and evaporated to dryness to get 185 mg (65%) of a white powder. The product was used for the next step without further purification. LC/MS (Method A): Rt=1.79 min, (M+H) 173.

5. Preparation of (S)-1-Oxo-3-trifluoromethyl-2,8-diaza-spiro[4.5]decane-2-carboxylic Acid tert-butyl Ester

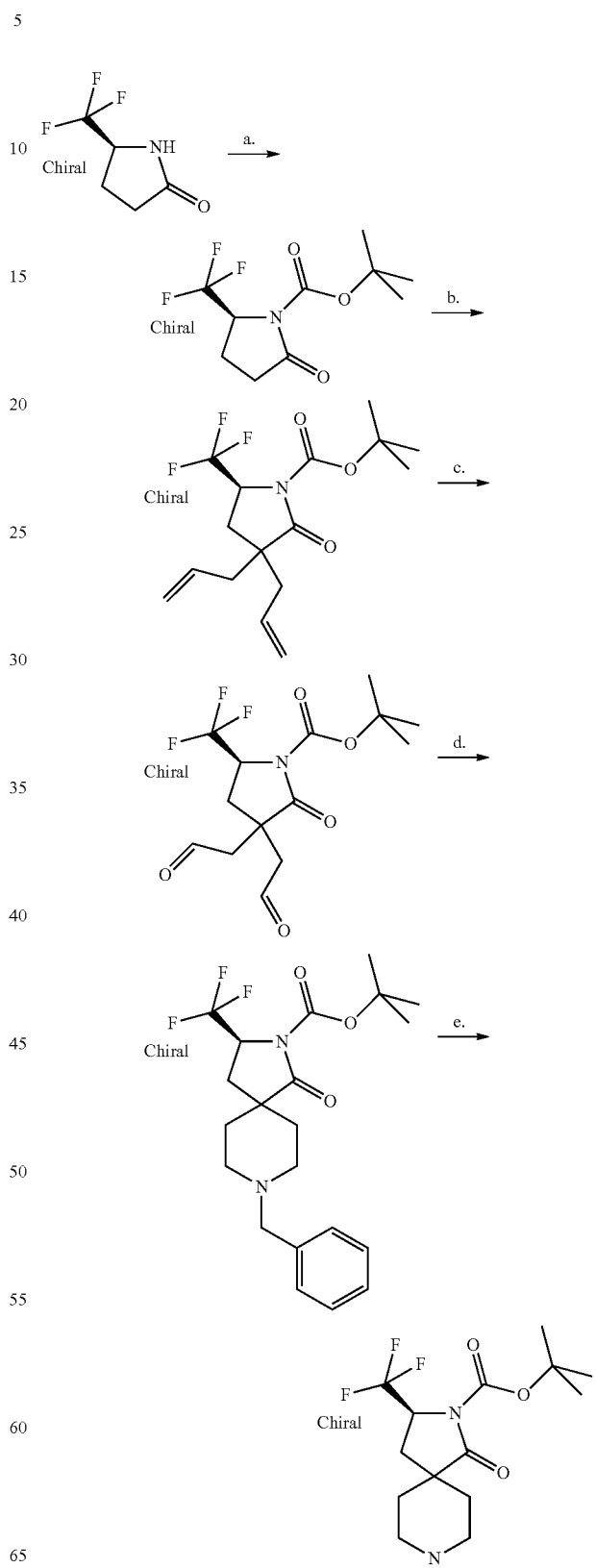

5a. (S)-2-Oxo-5-trifluoromethyl-pyrrolidine-1-carboxylic Acid tert-butyl Ester

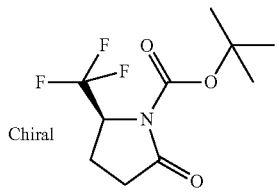 [SMILES: CC(C)(C)OC(=O)N1C(=O)CC[C@H]1C(F)(F)F]

(S)-5-Trifluoromethyl-pyrrolidine-2-one (4.02 g, 26.3 mmol) and triethylamine (4.37 mL, 31.5 mmol) were dissolved in DCM (15 mL). To this mixture a solution of di-tertbutyldicarbonate (6.88 g, 31.5 mmol) in DCM (20 mL) was added dropwise at RT within 20 min. The mixture was stirred for additional 24 hr at RT. The reaction mixture was diluted in DCM and washed three times with water then with brine. The organic layers were dried over sodium sulfate, filtered and evaporated. The oily product crystallized when cooled down to RT to give 6.50 g (98%) of the title compound as a white solid. LC/MS (Method A): Rt 2.13 min, (M+H-56) 198.

5b. (S)-3,3-Diallyl-2-oxo-5-trifluoromethyl-pyrrolidine-1-carboxylic Acid tert-butyl Ester

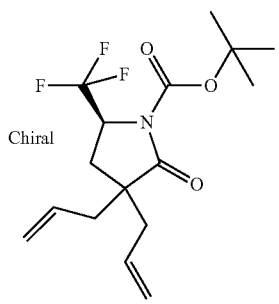 [SMILES: C=CCC1(CC=C)C[C@@H](C(F)(F)F)N(C(=O)OC(C)(C)C)C1=O]

To a solution of (S)-2-oxo-5-trifluoromethyl-pyrrolidine-1-carboxylic acid tert-butyl ester (3.00 g, 11.7 mmol) in THF SeccoSolv® (100 mL) stirred at −65° C. under nitrogen was added lithium bis(trimethylsilyl)amide (1M solution in THF, 29.3 mL, 29.3 mmol). After 15 min stirring 1,3-dimethyl 3,4,5,6-tetrahydro-2(1H)-pyrimidinone (9.02 g, 70.4 mmol) and then 3-bromo-1-propene (7.09 g, 58.6 mmol) were added via syringe. After stirring for 30 min at −60° C. the temperature was slowly raised to −30° C. and the reaction mixture was stirred for additional 90 min. The mixture was quenched with saturated $NH_4Cl$ solution and extracted with DCM. The organic phase was washed twice with water, then with brine, dried over sodium sulfate, filtered and evaporated to dryness. The yellow crude product was purified by flash chromatography (heptane/EtOAc) to get 2.58 g (65%) of the title compound as a colorless oil. LC/MS (Method A): Rt 2.72 min, (M+H−56) 278.

5c-d. (S)-2-Oxo-3,3-bis-(2-oxo-ethyl)-5-trifluoromethyl-pyrrolidine-1-carboxylic Acid tert-butyl Ester/ (S)-8-Benzyl-1-oxo-3-trifluoromethyl-2,8-diazaspiro[4.5]decane-2-carboxylic Acid tert-butyl Ester

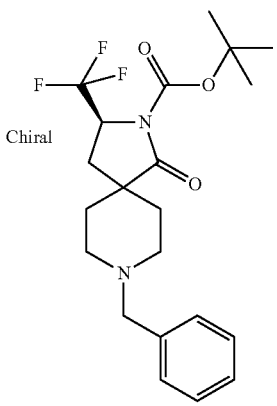 [SMILES: CC(C)(C)OC(=O)N1C(=O)C2(CCN(Cc3ccccc3)CC2)C[C@H]1C(F)(F)F]

(S)-3,3-Diallyl-2-oxo-5-trifluoromethyl-pyrrolidine-1-carboxylic acid tert-butyl ester (2.58 g, 7.74 mmol) was dissolved in DCM (60 mL). The clear colorless solution was cooled to −70° C. (dry-ice/iPrOH). Oxygen (75 L/h) was passed through the solution and the ozone generator (Fischer M503) was started (pale blue solution after 15 min). After 15 min the ozone flow was replaced by nitrogen resulting in a clear colorless solution and triphenylphosphine polymer bound (200-400 mesh, ~3 mmol/g, 5.20 g, 15.6 mmol) was added. The dry-ice/iPrOH-bath was removed and the solution was left stirring at RT for 1 h. The polymer was filtered off and the filtrate was directly used in the next step without further purification. LC/MS (Method A): Rt 1.61 min, (M+H) 337.

To a solution of crude material of (S)-2-oxo-3,3-bis-(2-oxo-ethyl)-5-trifluoromethyl-pyrrolidine-1-carboxylic acid tert-butyl ester in DCM (100 mL) was added benzyl amine (900 mg, 8.40 mmol), N-ethyldiisopropylamine (1.38 mL, 8.09 mmol) and molecular sieves (0.4 nm beads, 1.50 g) and the solution was stirred for 5 min. Sodium triacetoxyborohydride (4.90 g, 23.1 mmol) was added and the mixture was stirred for 16 hr at RT. The mixture was diluted with DCM and washed with water and brine. The organic layers were dried over sodium sulfate and the solvent was evaporated. The residue was suspended in diethyl ether and sonicated to form a white precipitation, which was filtered off and dried to give 980 mg (31%, 2 steps) of the title compound as a white solid. LC/MS (Method A): Rt 1.75 min, (M+H) 413.

5e. (S)-1-Oxo-3-trifluoromethyl-2,8-diaza-spiro[4.5]decane-2-carboxylic Acid tert-butyl Ester

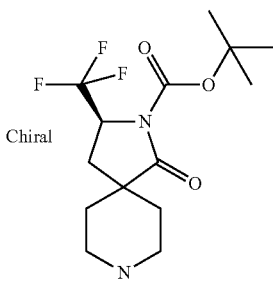 [SMILES: CC(C)(C)OC(=O)N1C(=O)C2(CCNCC2)C[C@H]1C(F)(F)F]

(S)-8-Benzyl-1-oxo-3-trifluoromethyl-2,8-diaza-spiro[4.5]decane-2-carboxylic acid tert-butyl ester (980 mg, 2.38 mmol) was dissolved in MeOH (10 mL) and acetic acid (1 mL). 0.50 g of Pd/C (5%) was added and the reaction mixture was stirred under hydrogen for 15 hr at RT. Additional 0.50 g Pd/C (5%) was added and stirring under hydrogen continued for 15 hr. The reaction mixture was filtered and the solvent evaporated under reduced pressure. The residue was suspended in EtOAc, washed with saturated sodium carbonate solution and the mixture was extracted twice with EtOAc to give the free base. The organic layer was dried over sodium sulfate, filtered and evaporated to give the title compound (512 mg, 67%) of as a light yellow oil. LC/MS (Method A): Rt 1.44 min, (M+H) 323.

The corresponding enantiomer was synthesised using the same route starting with (R)-5-trifluoromethyl-pyrrolidin-2-one.

Preparation of Boronic Ester Intermediates (D)

1. Preparation of 6-(4,4,5,5-tetramethyl-1,3,2-dioxaborolan-2-yl)indolin-2-one

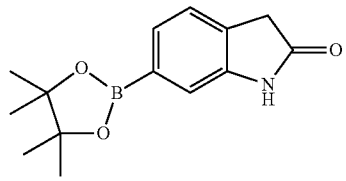 [SMILES: CC1(C)OB(c2ccc3c(c2)NC(=O)C3)OC1(C)C]

Four microwave vials were loaded as follows: 6-bromoindolin-2-one (500 mg, 2.36 mmol), bis(pinacolato)diboron (898 mg, 3.54 mmol), potassium acetate (694 mg, 7.07 mmol) and Pd(dppf)Cl$_2$.CH$_2$Cl$_2$ (96.0 mg, 0.118 mmol) were dissolved in DME (17 mL). The reaction was heated at 80° C. overnight. The content of the four vials was then combined, concentrated and purified by column chromatography (CyHex/EtOAc) to afford the title compound as a white solid (2.27 g, 75%, purity 80%). 1H NMR (500 MHz, CDCl$_3$) ppm=8.57 (bs, 1H), 7.48 (d, J=7.3, 1H), 7.31 (s, 1H), 7.23 (d, J=7.3, 1H), 3.55 (s, 2H), 1.33 (s, 12H); LC-MS (ESI, m/z) Rt=2.75 min-260 (M+H)$^+$ (HPLC method E).

2. Preparation of 1-methyl-3-(4-(4,4,5,5-tetramethyl-1,3,2-dioxaborolan-2-yl)phenyl)-1H-pyrazole

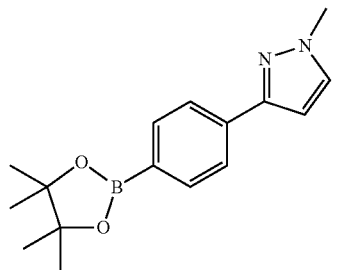 [SMILES: Cn1ccc(-c2ccc(B3OC(C)(C)C(C)(C)O3)cc2)n1]

3-(4-Bromophenyl)-1-methyl-1H-pyrazole (500 mg, 2.11 mmol), bis(pinacolato)diboron (876 mg, 3.45 mmol), potassium acetate (621 mg, 6.33 mmol) and Pd(dppf)Cl$_2$.CH$_2$Cl$_2$ (86 mg, 0.105 mmol) were loaded in a microwave vial and then DME (15 mL) was added. The reaction mixture was stirred in an oil bath at 80° C. overnight and then concentrated. The residue was purified by column chromatography (CyHex/EtOAc) to afford the title compound as a white solid (551 mg, 92%). $^1$H NMR (500 MHz, CDCl$_3$) ppm=7.83 (d, J=8.3, 2H), 7.80 (d, J=8.3, 2H), 7.37 (d, J=2.2, 1H), 6.57 (d, J=2.2, 1H), 3.95 (s, 3H), 1.35 (s, 12H); LC-MS (ESI, m/z) Rt=3.06 min-285 (M+H)$^+$ (HPLC method E).

3. Preparation of 1-methyl-4-(4-(4,4,5,5-tetramethyl-1,3,2-dioxaborolan-2-yl)phenyl)-1H-pyrazole

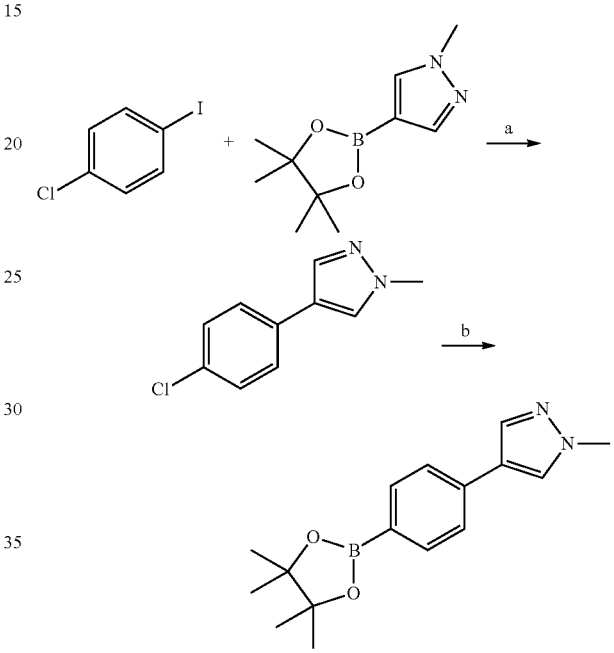

3a. 4-(4-Chlorophenyl)-1-methyl-1H-pyrazole

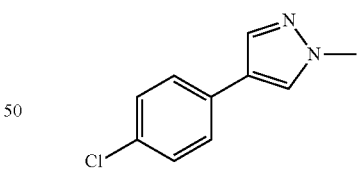

1-Chloro-4-iodobenzene (6.39 g, 26.8 mmol), 1-methyl-4-(4,4,5,5-tetramethyl-1,3,2-dioxaborolan-2-yl)-1H-pyrazole (5.58 g, 26.8 mmol), sodium carbonate (6.25 g, 59.0 mmol) and Pd(dppf)Cl$_2$.CH$_2$Cl$_2$ (2.20 g, 2.68 mmol) were loaded in a flask and then a mixture of THF/H$_2$O 3/1 (117 mL) was added. The reaction mixture was heated in an oil bath at 80° C. overnight. It was then concentrated under vacuum and the residue purified by column chromatography (CyHex/EtOAc) to afford the title compound as a white solid (3.80 g, 74%). $^1$H NMR (500 MHz, CDCl$_3$) ppm=7.72 (s, 1H), 7.57 (s, 1H), 7.38 (d, J=8.7, 2H), 7.31 (d, J=8.7, 2H), 3.93 (s, 3H); LC-MS (ESI, m/z) Rt=2.88 min-193 (M+H)$^+$ (HPLC method E).

3b. 1-Methyl-4-(4-(4,4,5,5-tetramethyl-1,3,2-dioxaborolan-2-yl)phenyl)-1H-pyrazole

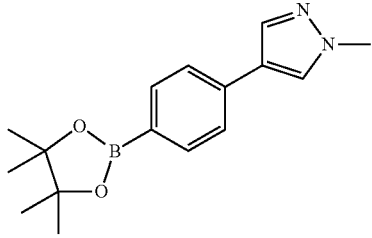

4-(4-Chlorophenyl)-1-methyl-1H-pyrazole (3.30 g, 17.1 mmol), bis(pinacolato)diboron (5.20 g, 20.6 mmol), potassium acetate (5.00 g, 51.4 mmol), Xphos (650 mg, 1.37 mmol) and Pd$_2$dba$_3$ (310 mg, 0.343 mmol) were loaded in a flask and then dioxane (34.3 mL) was added. The reaction mixture was stirred in an oil bath at 85° C. overnight. The solvent was evaporated and the crude product purified by column chromatography (CyHex/EtOAc) to afford the title compound as a white solid (3.9 g contaminated by 10% of 1-methyl-4-phenyl-1H-pyrazole, corrected yield 75%). 1H NMR (500 MHz, CDCl$_3$) ppm=7.79 (d, J=8.3, 2H), 7.79 (s, 1H), 7.64 (s, 1H), 7.47 (d, J=8.3, 2H), 3.93 (s, 3H), 1.35 (s, 12H); LC-MS (ESI, m/z) Rt=3.06 min-285 (M+H)$^+$ (HPLC method E).

4. Preparation of 1-methyl-5-(4,4,5,5-tetramethyl-1,3,2-dioxaborolan-2-yl)-1,3-dihydrobenzo[c]isothiazole 2,2-dioxide and 5-(4,4,5,5-tetramethyl-1,3,2-dioxaborolan-2-yl)-1,3-dihydrobenzo[c]isothiazole 2,2-dioxide

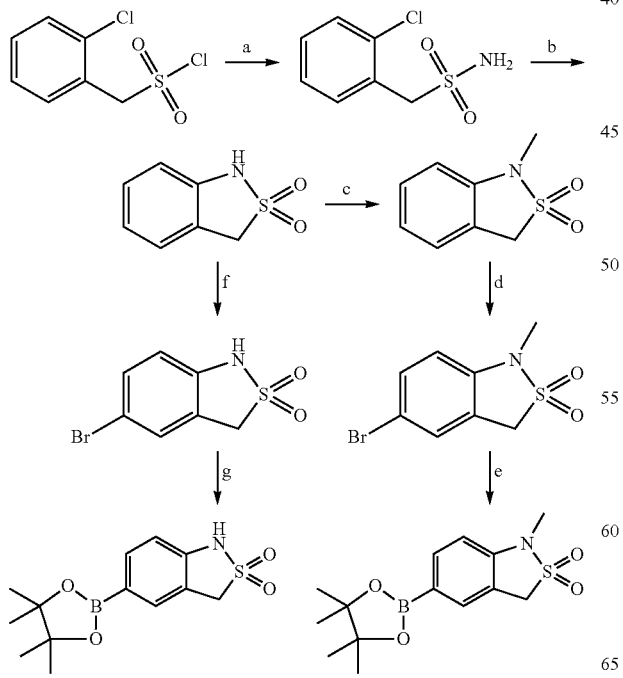

4a. (2-Chlorophenyl)methanesulfonamide

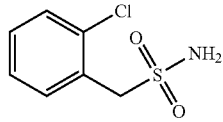 [SMILES: NS(=O)(=O)Cc1ccccc1Cl]

2-Chlorobenzylsulfonyl chloride (1.86 g, 8.26 mmol) was dissolved in acetone (27 mL) and then ammonium hydroxide (18.0 mL, 158 mmol) was added. The reaction was stirred for 2.5 hr at RT and the solvent was evaporated. The reaction mixture was diluted with EtOAc and water was added. The two layers were separated and the aqueous layer was extracted with EtOAc. The combined organic layers were dried over magnesium sulphate and concentrated under vacuum. The crude product was purified by column chromatography (DCM/EtOH) to afford the title compound as a white solid (1.50 g, 88%). $^1$H NMR (500 MHz, CDCl$_3$) ppm=7.56-7.53 (m, 1H), 7.47-7.44 (m, 1H), 7.36-7.30 (m, 2H), 4.66 (bs, 2H), 4.57 (s, 2H); Rt=1.77 min (HPLC method F).

4b. 1,3-Dihydrobenzo[c]isothiazole 2,2-dioxide

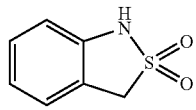

(2-Chlorophenyl)methanesulfonamide (450 mg, 2.19 mmol), tris(dibenzylideneacetone) dipalladium (100 mg, 0.109 mmol), 2-di-tert butylphosphino-2',4',6'-tri-isopropylbiphenyl (186 mg, 0.438 mmol) and potassium carbonate (605 mg, 4.38 mmol) were loaded in a microwave vial and THF (8.8 mL) was added. The reaction mixture was stirred at 80° C. for 13 hr before being quenched with a sat. NH$_4$Cl solution. The solvent was then evaporated and the residue was purified by column chromatography (CyHex/acetone) to afford the title compound as a white solid (296 mg, 80%). $^1$H NMR (500 MHz, CDCl$_3$) ppm=7.31-7.26 (m, 1H), 7.26-7.23 (m, 1H), 7.07 (td, J=7.6, 0.9, 1H), 6.90 (d, J=8.0, 1H), 6.48 (bs, 1H), 4.39 (s, 2H); Rt=1.69 min (HPLC method F).

4c. 1-Methyl-1,3-dihydrobenzo[c]isothiazole-2,2-dioxide

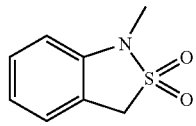

To a suspension of 1,3-dihydrobenzo[c]isothiazole-2,2-dioxide (280 mg, 1.655 mmol) and potassium carbonate (229 mg, 1.66 mmol) in DMF (5 mL) was added iodomethane (414 µL, 6.62 mmol). The reaction was stirred for 6 hr at RT and was then quenched with a sat. NH$_4$Cl solution. The reaction mixture was concentrated and purified by column chromatography (CyHex/acetone) to afford the title compound as a white solid (270 mg, 89%). $^1$H NMR (500 MHz, CDCl$_3$) ppm=7.37-7.32 (m, 1H), 7.27-7.24 (m, 1H), 7.02 (td, J=7.6, 1.0, 1H), 6.73 (d, J=8.0, 1H), 4.34 (s, 2H), 3.14 (s, 3H); Rt=2.07 min (HPLC method F).

4d. 5-Bromo-1-methyl-1,3-dihydrobenzo[c]isothiazole-2,2-dioxide

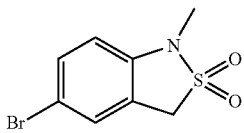

1-Methyl-1,3-dihydrobenzo[c]isothiazole-2,2-dioxide (272 mg, 1.49 mmol) was dissolved in DMF (1.5 mL) and then N-bromosuccinimide (264 mg, 1.49 mmol) was added. The reaction mixture was stirred at RT for 4 h. After addition of water, the reaction mixture was concentrated. The residue was purified by column chromatography (CyHex/acetone) to afford the title compound as a white solid (330 mg, 85%). $^1$H NMR (500 MHz, CDCl$_3$) ppm=7.45-7.41 (m, 1H), 7.37-7.35 (m, 1H), 6.59 (d, J=8.5, 1H), 4.30 (s, 2H), 3.09 (s, 3H); Rt=2.46 min (HPLC method E).

4e. 1-Methyl-5-(4,4,5,5-tetramethyl-1,3,2-dioxaborolan-2-yl)-1,3-dihydrobenzo[c]isothiazole 2,2-dioxide

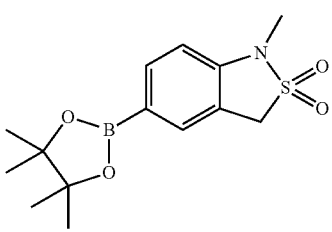 [SMILES: CN1c2ccc(B3OC(C)(C)C(C)(C)O3)cc2CS1(=O)=O]

5-Bromo-1-methyl-1,3-dihydrobenzo[c]isothiazole-2,2-dioxide (267 mg, 1.02 mmol), bis(pinacolato)diboron (388 mg, 1.53 mmol), potassium acetate (300 mg, 3.06 mmol) and Pd(dppf)Cl$_2$.CH$_2$Cl$_2$ (42.0 mg, 0.051 mmol) were loaded in a microwave vial and DME (7.4 mL) was added. The reaction was stirred in an oil bath at 80° C. overnight. The reaction was concentrated and purified by column chromatography (CyHex/acetone) to afford the title compound as a white solid (290 mg, 92%). $^1$H NMR (500 MHz, CDCl$_3$) ppm=7.80-7.77 (m, 1H), 7.69-7.67 (m, 1H), 6.71 (d, J=8.0, 1H), 4.32 (s, 2H), 3.15 (s, 3H), 1.33 (s, 12H); LC-MS (ESI, m/z) Rt=2.82 min-310 (M+H)$^+$ (HPLC method E).

4f. 5-bromo-1,3-dihydrobenzo[c]isothiazole 2,2-dioxide

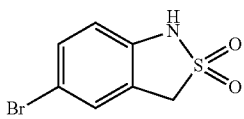 [SMILES: O=S1(=O)Cc2cc(Br)ccc2N1]

1,3-Dihydro-benzo[c]isothiazole 2,2-dioxide (0.50 g, 3.14 mmol, 1.00 eq.) was solubilized in acetic acid (5 mL) at RT under nitrogen atmosphere. Bromine (0.45 g, 3.14 mmol, 1.00 eq.) in acetic acid (5 mL) was added dropwise over 5 minutes and the reaction mixture was stirred for 0.5 h. Potassium, acetate (0.28 g, 3.14 mmol, 1.00 eq.) was added and the reaction mixture was concentrated to dryness. The residue was taken in 2% NaHCO$_3$ solution and stirred for 10 minutes. This solution was acidified to pH 2 using conc. HCl (2.5 mL) and extracted with MTBE (50 mL). The MTBE layer was washed with water (50 mL), brine solution (25 mL), dried over Na$_2$SO$_4$ and concentrated to get the crude product as brown solid. The crude product was triturated with petroleum ether (10 mL), filtered to a light brown solid (HPLC purity app. 86%) which was further purified by column chromatography using 60-120 mesh silica gel, 15% ethyl acetate in petroleum ether as eluent to get a yellow solid (HPLC purity app. 90%). The resulting product was then triturated with ethanol (5 mL), filtered and dried to get the title compounds as light yellow solid (0.35 g, 47.7%, 94% purity).

4g. 5-(4,4,5,5-tetramethyl-1,3,2-dioxaborolan-2-yl)-1,3-dihydrobenzo[c]isothiazole 2,2-dioxide

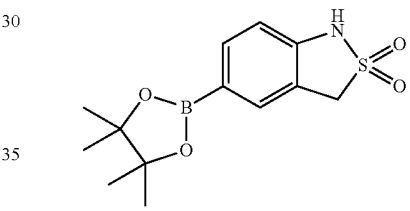

5-Bromo-1,3-dihydrobenzo[c]isothiazole 2,2-dioxide (500 mg, 2.02 mmol), bis(pinacolato)diboron (768 mg, 3.02 mmol), potassium acetate (593 mg, 6.05 mmol) and Pd(dppf)Cl$_2$.CH$_2$Cl$_2$ (82 mg, 0.10 mmol) were loaded in a microwave vial and DME (14.6 mL) was added. The reaction mixture was heated at 80° C. overnight. The solvent was evaporated and the crude was purified by column chromatography on silica gel (CyHex/acetone) to give the title compound (580 mg contaminated by 23% of pinacol, corrected yield 75%). as a white solid. 1H NMR (500 MHz, CDCl$_3$) ppm=7.72 (d, J=7.9, 1H), 7.68 (s, 1H), 7.85 (d, J=7.9, 1H), 6.79 (s, 1H), 4.37 (s, 2H), 1.33 (s, 12H). LC-MS (ESI, m/z) Rt=2.67 min-232 (M-SO2+H)$^+$ (HPLC method E).

5. Preparation of 1-isopropyl-4-(4-(4,4,5,5-tetramethyl-1,3,2-dioxaborolan-2-yl)phenyl)-1H-pyrazole

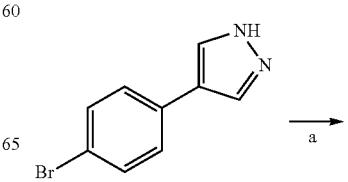

-continued

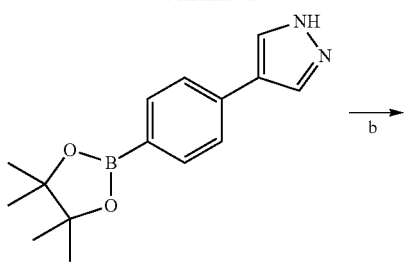

5a. 4-(4-(4,4,5,5-Tetramethyl-1,3,2-dioxaborolan-2-yl)phenyl)-1H-pyrazole

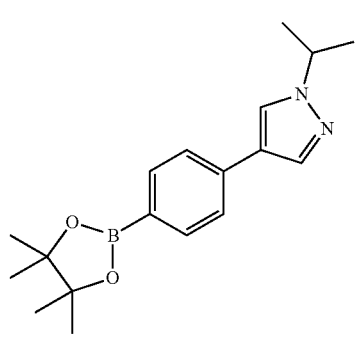 [SMILES: CC(C)n1cc(-c2ccc(B3OC(C)(C)C(C)(C)O3)cc2)cn1]

4-(4-Bromophenyl)-1H-pyrazole (1.00 g, 4.48 mmol), bis(pinacolate)diborane (1.70 g, 6.72 mmol), potassium acetate (1.32 g, 13.45 mmol) and Pd(dppf)Cl$_2$.CH$_2$Cl$_2$ (183 mg, 0.224 mmol) were loaded in a flask and DME (32.5 mL) was added. The reaction was heated at 80° C. overnight. Another 170 mg of Pd(dppf)Cl$_2$.CH$_2$Cl$_2$ were added and the reaction mixture was heated for 30 h. After addition of water and DCM, the aqueous layer was extracted with DCM. The organic layers were dried over MgSO$_4$, filtered and the solvent was evaporated under reduced pressure. The crude was purified by chromatography on silica gel (CyHex/EtOAc) to give the title compound (820 mg, 68%) as a white solid. $^1$H NMR (500 MHz, CDCl$_3$) ppm=7.94 (s, 2H), 7.84 (d, J=8.2, 2H), 7.54 (d, J=8.2, 2H), 1.38 (s, 12H). LC-MS (ESI, m/z) Rt=2.94 min-271 (M+H)$^+$ (HPLC method E).

5b. 1-Isopropyl-4-(4-(4,4,5,5-tetramethyl-1,3,2-dioxaborolan-2-yl)phenyl)-1H-pyrazole

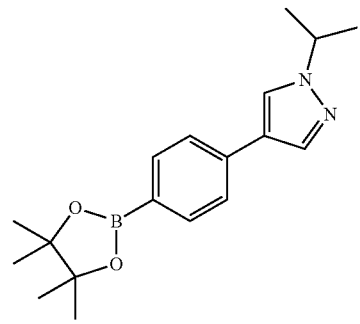

To a solution of 4-(4-(4,4,5,5-tetramethyl-1,3,2-dioxaborolan-2-yl)phenyl)-1H-pyrazole (390 mg, 1.43 mmol) in DMF (7.1 mL) was added potassium carbonate (515 mg, 3.72 mmol) and 2-iodopropane (180 μL, 1.80 mmol). The reaction was stirred at RT overnight. Another 180 μL of 2-iodopropane were added and the reaction mixture was stirred at RT for one day. The conversion was not complete at this stage therefore an additional 360 μL of 2-iodopropane was added and the reaction mixture was stirred at RT for 2 days. It was then filtered and concentrated under reduced pressure. The crude was purified by chromatography on silica gel (CyHex/EtOAc) to give the title compound (150 mg, 34%) as a white solid. 1H NMR (500 MHz, CDCl$_3$) ppm=7.83 (s, 1H), 7.81 (d, J=8.2, 2H), 7.73 (s, 1H), 7.51 (d, J=8.2, 2H), 4.54 (septuplet, J=6.7, 1H), 1.56 (d, J=6.7, 6H), 1.37 (s, 12H). LC-MS (ESI, m/z) Rt=3.20 min-313 (M+H)$^+$ (HPLC method E).

6. Preparation of dihydroxyboryl-2-ethyl-2,3-dihydro-benzo[d]isothiazole 1,1-dioxide

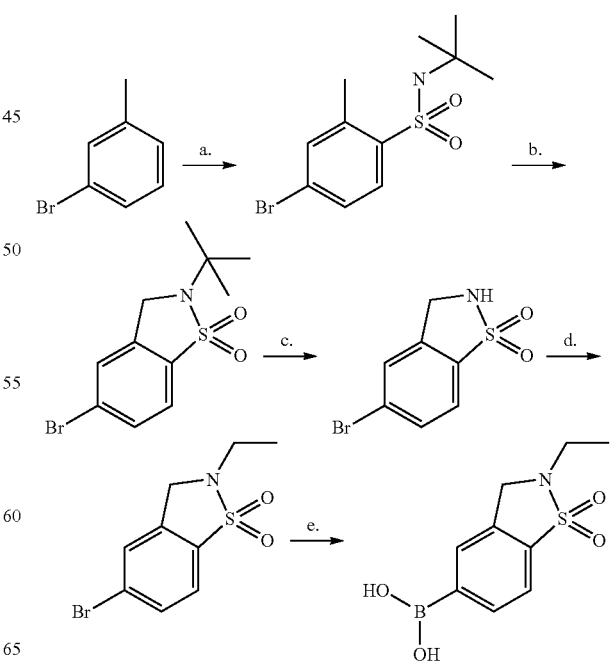

6a. 4-Bromo-N-(tert-butyl)-2-methylbenzenesulfonamide

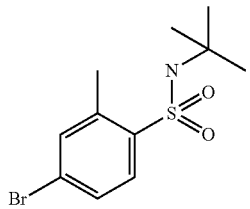 [SMILES: Cc1cc(Br)ccc1S(=O)(=O)NC(C)(C)C]

In a 100 mL three necked flask under N$_2$ containing 3-bromotoluene (3.55 mL, 29.2 mmol) dissolved in anhydrous DCM (50 mL) at −20° C. (dry ice bath with CH$_3$CN) was added chlorosulfonic acid (13.7 mL, 205 mmol) dropwise over 15 min. The reaction mixture was stirred under N$_2$ atmosphere for 2 hr at 0° C. and 4 hr at RT. The reaction mixture was poured cautiously on ice and the resulting suspension was extracted with DCM (3×80 mL). The combined organic phases were washed with cold saturated brine, dried over MgSO$_4$, filtered and concentrated until 50 mL was reached. To a 100 mL three necked flask under N$_2$ containing triethylamine (4.27 mL, 30.7 mmol) and tert-butylamine (3.23 mL, 30.7 mmol) dissolved in anhydrous DCM (30 mL) at RT, was added the solution of sulfonyl chloride prepared above. Addition was done over 20 minutes keeping the temperature below 20° C. The reaction mixture was stirred for 15 hr at RT until completion. The mixture was washed with HCl (0.1 N, 100 mL), a saturated solution of NaHCO$_3$, and brine. Then the organic layers were dried over MgSO$_4$, filtered and concentrated to give the title compound (8.09 g, 90%) as yellowish solid.

6b. 5-Bromo-2-tert-butyl-2,3-dihydro-1,2-benzisothiazole 1,1-dioxide

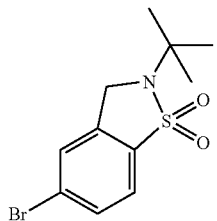 [SMILES: CC(C)(C)N1Cc2cc(Br)ccc2S1(=O)=O]

In a 150 mL flask containing 4-bromo-N-(tert-butyl)-2-methylbenzenesulfonamide (8.09 g, 26.4 mmol) in CHCl$_3$ (40 mL) at RT, N-bromosuccinimide (4.70 g, 26.4 mmol) was added in one portion followed by α,α'-azoisobutyronitrile (86.8 mg, 0.53 mmol). The reaction mixture was stirred for 16 hr at reflux. After concentration and dilution in MeOH (40 mL), sodium hydroxide (2.11 g, 52.8 mmol) was added and the reaction mixture was stirred for 3 hr at RT under vigorous agitation. The mixture was poured into water and the resulting suspension was filtered to give a white solid, which was washed with diethyl ether and dried over MgSO$_4$ to give the title compound (1.72 g, 21.4%) as white solid.

6c. 5-Bromo-2,3-dihydro-benzo[d]isothiazole 1,1-dioxide

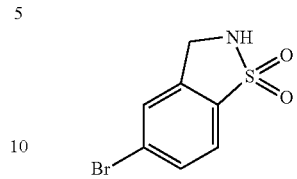

In a screw-capped-vial 5-bromo-2-tert-butyl-2,3-dihydrobenzo[d]isothiazole 1,1-dioxide (388 mg, 1.28 mmol) was dissolved in trifluoroacetic acid (6 mL) and the mixture was stirred at 50° C. for 16 h. The mixture was evaporated to dryness and the pale beige residue was purified by flash-chromatography (n-heptane/DCM) to yield an off-white solid (316 mg, 1.28 mmol, 100%). Rt=2.063 min (HPLC method B)

6d. 5-Bromo-2-ethyl-2,3-dihydro-benzo[d]isothiazole 1,1-dioxide

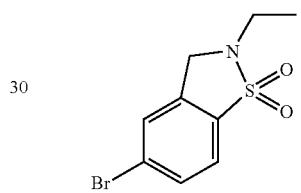

In a 12 mL screw-capped vessel 5-bromo-2,3-dihydrobenzo[d]isothiazole 1,1-dioxide (316 mg, 1.28 mmol) was dissolved in DMF (8 mL), potassium carbonate (0.44 g, 3.20 mmol) and iodoethane (399 mg, 2.56 mmol) were added and the reaction mixture was stirred at RT for 2 days. The mixture was treated with 50 mL water. The white precipitate formed was filtered under vacuum and washed with water. The solid was dissolved in DCM, filtered through a phase-separator and evaporated to dryness to give 246 mg (60%) of the title compound as an off-white solid. Rt=2.477 min (HPLC method B).

6e. 5-Dihydroxyboryl-2-ethyl-2,3-dihydro-benzo[d]isothiazole 1,1-dioxide

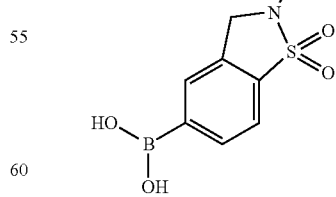

In a 50 mL screw-capped vessel 5-bromo-2-ethyl-2,3-dihydro-benzo[d]isothiazole 1,1-dioxide (246 mg, 0.89 mmol) was dissolved in tetrahydrofuran (15 mL). Bis(pinacolato)diboron (339 mg, 1.34 mmol), potassium acetate (262 mg, 2.67 mmol) and Pd(dppf)Cl$_2$.CH$_2$Cl$_2$ (72.7 mg, 0.089 mmol) were added. The red reaction mixture was stirred at 70° C. for 16 h. The dark brown reaction mixture was treated with EtOAc, filtered and evaporated. The crude residue was purified by flash-chromatography (n-heptane/DCM) to give 107 mg (45%) of the title compound as a white solid. Rt=1.82 min (HPLC method B).

7. Preparation of 1-(2-methanesulfonyl-ethyl)-4-[4-(4,4,5,5-tetramethyl-[1,3,2]dioxaborolan-2-yl)-phenyl]-1H-pyrazole

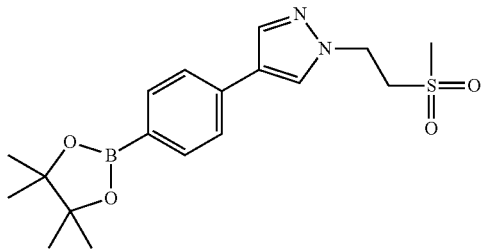 [SMILES: CC1(C)OB(c2ccc(-c3cnn(CCS(C)(=O)=O)c3)cc2)OC1(C)C]

A screw-capped vessel was charged with 4-bromo-1-(2-methanesulfonyl-ethyl)-1H-pyrazole (200 mg, 0.75 mmol), 1-methyl-4-[4-(4,4,5,5-tetramethyl-[1,3,2]dioxaborolan-2-yl)-phenyl]-1H-pyrazole (506 mg, 1.50 mmol), potassium carbonate (207 mg, 1.50 mmol), Pd(dppf)Cl$_2$.CH$_2$Cl$_2$ (30.7 mg, 0.038 mmol), acetonitrile (10 mL) and water (2 mL). The reaction mixture was stirred for 1 hr at 90° C. under microwave irradiation. The solvents were evaporated, the residue was sonificated with acetonitrile and non-soluble parts were filtered off. The filtrate was evaporated to dryness and purified by flash chromatography (DCM/heptane) to give 108 mg (27%) of an off-white product with an estimated purity of about 70%. LC/MS (Method A): Rt=2.30 min, (M+H) 377.

8. Preparation of 3-{4-[4-(4,4,5,5-tetramethyl-[1,3,2]dioxaborolan-2-yl)-phenyl]-pyrazol-1-yl}-propionitrile

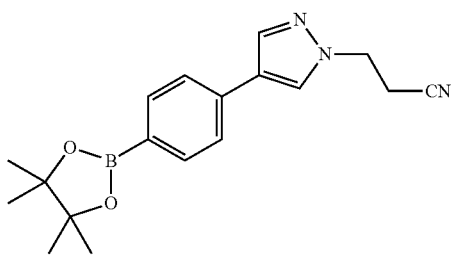 [SMILES: CC1(C)OB(c2ccc(-c3cnn(CCC#N)c3)cc2)OC1(C)C]

A 10 mL screw cap vessel was charged with 3-(4-bromo-pyrazol-1-yl)-propionitrile (250 mg, 1.25 mmol), 1-methyl-4-[4-(4,4,5,5-tetramethyl-[1,3,2]dioxaborolan-2-yl)-phenyl]-1H-pyrazole (842 mg, 2.50 mmol), potassium carbonate (345 mg, 2.50 mmol), Pd(dppf)Cl$_2$.CH$_2$Cl$_2$ (51.03 mg; 0.062 mmol; 5.00 mol %) and then acetonitrile (10 mL) and water (2 mL) were added. The mixture was heated for 1 hr at 120° C. in the microwave oven. The solvents were evaporated, the residue sonificated in acetonitrile and non-soluble parts were filtered off. The filtrate was evaporated and the crude product was purified by flash chromatography (n-heptane/DCM) to give 117 mg (29%) of a colorless oil.

9. Preparation of 2-methyl-1-{4-[4-(4,4,5,5-tetramethyl-[1,3,2]dioxaborolan-2-yl)-phenyl]-pyrazol-1-yl}-propan-2-ol

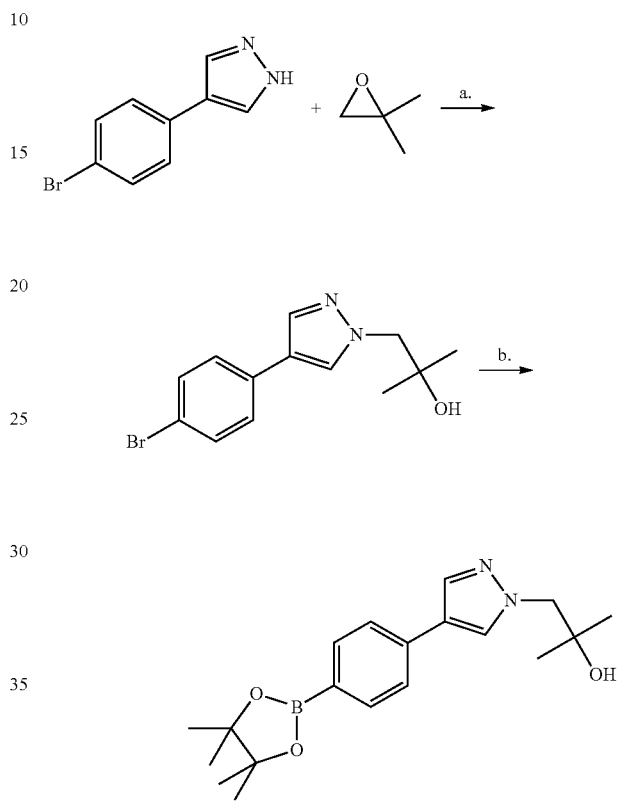

9a. 1-[4-(4-Bromo-phenyl)-pyrazol-1-yl]-2-methyl-propan-2-ol

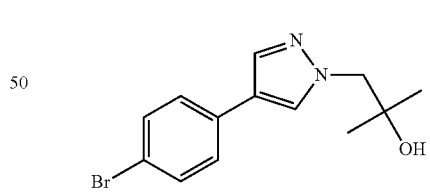

4-(4-Bromo-phenyl)-1H-pyrazole (500 mg, 2.24 mmol) was dissolved in DMF (5 mL) in a heavy walled reaction tube. Potassium carbonate (435 mg, 3.14 mmol) and 2,2-dimethyl-oxirane (0.40 mL, 4.48 mmol) were added and the tube was sealed with a teflon screw cap and heated to 100° C. for 15 h. After cooling to RT, the reaction mixture was diluted with water and extracted with EtOAc twice. The combined organic layers were dried over sodium sulfate, filtered and the solvent was evaporated to dryness to obtain 639 mg (96%) of the title compound as a white solid. LC/MS (Method B): Rt 2.17 min, (M+H) 295/297.

9b. 2-Methyl-1-{4-[4-(4,4,5,5-tetramethyl-[1,3,2]dioxaborolan-2-yl)-phenyl]-pyrazol-1-yl}-propan-2-ol

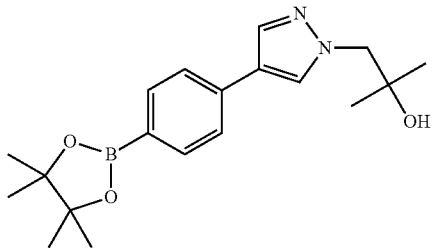 [SMILES: CC(C)(O)Cn1cc(-c2ccc(B3OC(C)(C)C(C)(C)O3)cc2)cn1]

In a screw-capped glass 1-[4-(4-bromo-phenyl)pyrazol-1-yl]-2-methyl-propan-2-ol (639 mg, 2.16 mmol), bis(pinacolato)diboron (1.10 g, 4.33 mmol), potassium acetate (636 mg, 6.48 mmol) and 1,1 bis(diphenylphosphino)ferrocenepalladium(II) dichloride (99%, 158 mg, 0.22 mmol) were suspended in acetonitrile (30 mL). The mixture was stirred for 15 hr at 70° C. The reaction mixture was filtered and the solvent evaporated to dryness. The residue was purified by flash chromatography (heptane/EtOAc) to give the title compound (280 mg, 73% purity, 25%) as a yellow solid. LC/MS (Method B): Rt=2.37 min, (M+H) 243.

10. Preparation of 5-(4,4,5,5-tetramethyl-1,3,2-dioxaborolan-2-yl)benzo[d]oxazol-2(3H)-one

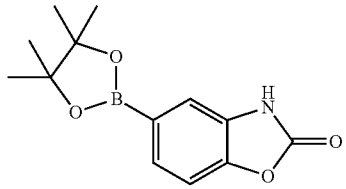 [SMILES: CC1(C)OB(c2ccc3oc(=O)[nH]c3c2)OC1(C)C]

5-Bromo-2-benzoxazolinone (200 mg, 0.935 mmol), bis(pinacole)diborane (309 mg, 1.215 mmol), potassium acetate (275 mg, 2.80 mmol) and Pd(dppf)Cl$_2$CH$_2$Cl$_2$ (153 mg, 0.187 mmol) were loaded in a microwave vial. The capped vial was evacuated using high vacuum and purged with nitrogen (each three times). Dry THF (4 mL) was added and the mixture was degassed again by using the high vacuum and purged with nitrogen again (each three times). The mixture was heated conventional at 80° C. for 3 days before it was filtered over Celite and the residue was washed with CHCl$_3$/MeOH. The filtrate was concentrated in vacuum and the resulting brown oil was purified by chromatography on silica gel (biotage, DCM/EtOH) to give the product (40 mg, 16%, purity 76%) as a light yellow sticky solid containing bis(pinacole)diborane. $^1$H-NMR (500 MHz, CDCl$_3$) ppm=7.99 (bs, 1H). 7.62 (dd, J=8.0, 1.0, 1H), 7.50 (s, 1H), 7.22 (d, J=8.0, 1H), 1.36 (s, 12H). HRMS m/z (ESI$^+$) [M+H]$^+$ C$_{13}$H$_{16}$BNO$_4$, calc 261.1281, found 261.1284, Rt=2.89 min (HPLC method E).

11. Preparation of 1-methyl-5-(4,4,5,5-tetramethyl-1,3,2-dioxaborolan-2-yl)indolin-2-one

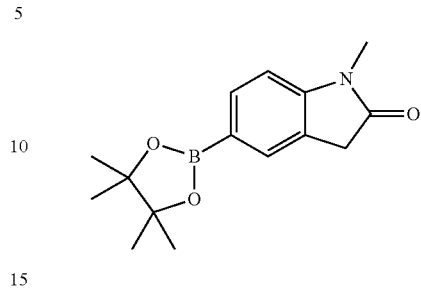

5-Bromo-1-methylindolin-2-one (537 mg, 2.375 mmol), bis(pinacolate)diborane (987 mg, 3.89 mmol), potassium acetate (636 mg, 6.48 mmol) and Pd(dppf)Cl$_2$.CH$_2$Cl$_2$ (88 mg, 0.108 mmol) were loaded in a microwave vial and DME (15.6 ml) was added. The reaction mixture was heated at 80° C. overnight and was then concentrated. The crude was purified by chromatography on silica gel (biotage, CyHex/EtOAc) to give the product (500 mg, 85%). $^1$H-NMR (500 MHz, CDCl$_3$) ppm=7.78 (d, J=7.7, 1H), 7.69 (s, 1H), 6.84 (d, J=7.7, 1H), 3.52 (s, 2H), 3.24 (s, 3H), 1.36 (s, 12H). LC-MS (ESI, m/z) Rt=2.90 min-274 (M+H)$^+$ (HPLC method E).

12. Preparation of 1-isopropyl-4-[4-(4,4,5,5-tetramethyl-[1,3,2]dioxaborolan-2-yl)-phenyl]-1H-pyrazole

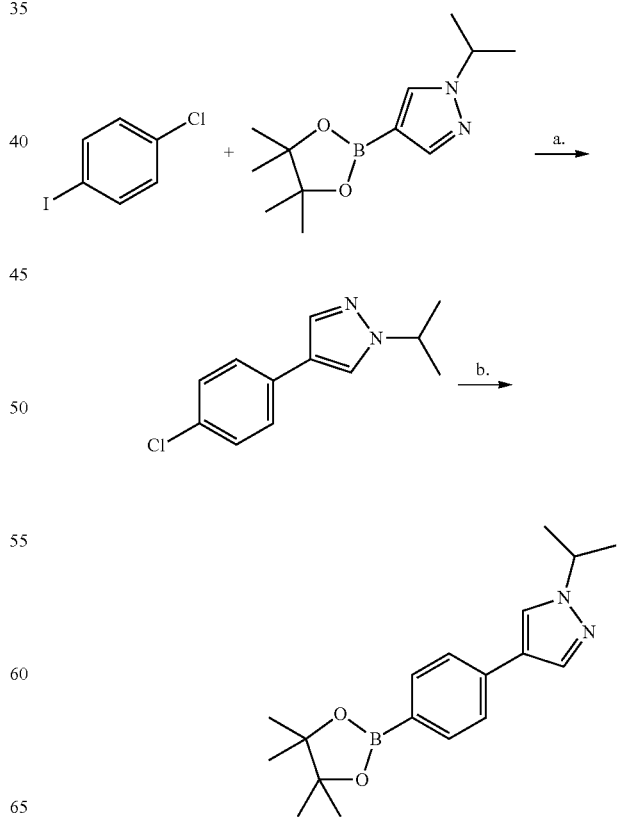

12a. 4-(4-Chloro-phenyl)-1-isopropyl-1H-pyrazole

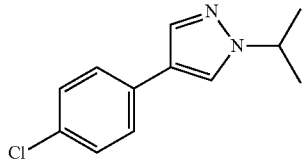

Into a 50 mL screw cap jar 1-chloro-4-iodo-benzene (500 mg, 2.08 mmol) and 1-isopropyl-4-(4,4,5,5-tetramethyl-[1,3,2]dioxaborolan-2-yl)-1H-pyrazole (500 mg, 2.12 mmol) were dissolved in acetonitrile (20 mL). Sodium carbonate solution (0.5 M, 8.30 mL, 4.15 mmol) and 1,1'-bis(diphenylphosphino)ferrocene)-palladium(II) chloride DCM complex (0.17 g, 0.21 mmol) were added. The reaction mixture was stirred at 90° C. for 1 hr and then diluted with acetonitrile (30 mL), filtered and the filtrate was evaporated to dryness. The crude residue was purified by flash chromatography (heptane/DCM). The solvent was evaporated to dryness to obtain 379 mg (83%) of a light brown solid. LC/MS (Method B): Rt 3.04 min, (M+H) 221.

12b. 1-Isopropyl-4-[4-(4,4,5,5-tetramethyl-[1,3,2]dioxaborolan-2-yl)-phenyl]-1H-pyrazole

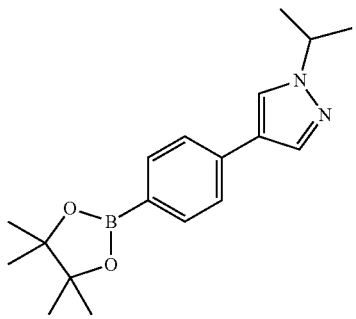 [SMILES: CC(C)n1cc(-c2ccc(B3OC(C)(C)C(C)(C)O3)cc2)cn1]

4-(4-Chloro-phenyl)-1-isopropyl-1H-pyrazole (379 mg, 1.72 mmol), bis(pinacolato)diboron (872 mg, 3.43 mmol), 2-dicyclohexylphosphino-2',4',6'-triisopropylbiphenyl (98%, 65.5 mg, 0.14 mmol), tris(dibenzylideneacetone)dipalladium(0) (47.2 mg, 0.05 mmol) and potassium acetate (506 mg, 5.15 mmol) were suspended in acetonitrile (12 mL). The vessel was closed, degassed and flushed with nitrogen. The reaction mixture was stirred at 90° C. for 15 h. Bis(pinacolato)diboron (872 mg, 3.43 mmol), 2-dicyclohexylphosphino-2',4',6'-triisopropylbiphenyl (98%, 65.5 mg, 0.14 mmol) and tris(dibenzylideneacetone)dipalladium (0) (47.2 mg, 0.05 mmol) were added. The reaction mixture was further stirred at 90° C. for 2 days. The mixture was then diluted with acetonitrile (15 mL) filtered and evaporated to dryness. The crude residue was purified by flash chromatography (heptane/DCM) to obtain 250 mg (47%) of a colorless oil. LC/MS (Method B): Rt 3.29 min, (M+H) 313.

1,2-Dimethyl-4-(4-(4,4,5,5-tetramethyl-1,3,2-dioxaborolan-2-yl)phenyl)-1H-imidazole, 1-(oxetan-3-yl)-4-(4-(4,4,5,5-tetramethyl-1,3,2-dioxaborolan-2-yl)phenyl)-1H-pyrazole and 1-cyclopropyl-4-(4-(4,4,5,5-tetramethyl-1,3,2-dioxaborolan-2-yl)phenyl)-1H-pyrazole were synthesised using the same procedures.

13. Preparation of 2-tert-butyl-1,1-dioxo-2,3-dihydro-1H-benzo[d]isothiazole-5-boronic Acid

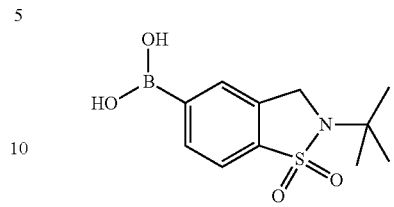

In a screw-capped vessel 5-bromo-2-tert-butyl-2,3-dihydro-benzo[d]isothiazole 1,1-dioxide (500 mg, 1.64 mmol) was dissolved in THF SeccoSolv® (25 mL). Bis(pinacolato)diboron (835 mg, 3.29 mmol), potassium acetate (484 mg, 4.93 mmol) and Pd(dppf)Cl$_2$.CH$_2$Cl$_2$ (134 mg, 0.16 mmol) were added and the red reaction mixture was stirred for 15 hr at 70° C. The black reaction mixture was treated with EtOAc, filtered and evaporated to dryness at reduced pressure. The dark brown residue was purified by flash chromatography (heptane/DCM) to give the title compound (442 mg, 100%) as an off-white solid. LC/MS (Method B): Rt=2.04 min, (M+Na) 292.

14. Preparation of 3-amino-1-methyl-1H-indazole-6-boronic Acid

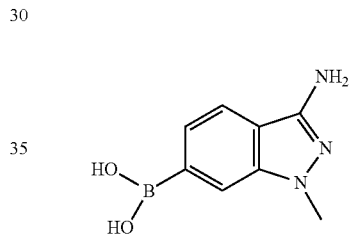

In a screw-capped vessel 3-amino-6-bromo-1-methyl-1H-indazole (100 mg, 0.44 mmol) was dissolved in tetrahydrofuran SeccoSolv® (4 mL). Bis(pinacolato)diboron (225 mg, 0.89 mmol), potassium acetate (130 mg, 1.33 mmol) and Pd(dppf)Cl$_2$.CH$_2$Cl$_2$ (36.1 mg, 0.044 mmol) were added and the red reaction mixture were stirred at 70° C. for 3 days. The dark reaction mixture was treated with EtOAc, filtered and the filtrate was evaporated to dryness at reduced pressure. The dark brown residue was purified by flash chromatography (DCM/MeOH) to give the title compound (113 mg, 55% purity, 74%) as a pale yellow solid. LC/MS (Method B): Rt=1.38 min, (M+H) 192.

15. Preparation of 3-hydroxy-1,1-dioxo-2,3-dihydro-1H-benzo[b]thiophene-5-boronic Acid

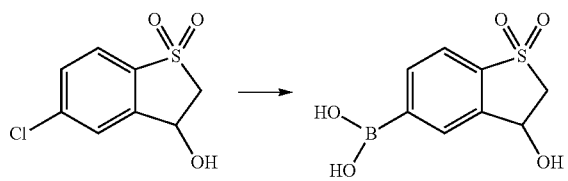 [SMILES: O=S1(=O)CC(O)c2cc(Cl)ccc21 ; O=S1(=O)CC(O)c2cc(B(O)O)ccc21]

In a screw-capped vessel 5-chloro-3-hydroxy-2,3-dihydro-1{6}-benzothiophene-1,1-dione (300 mg, 1.37 mmol)

was dissolved in 1,4-dioxane (5 mL). Bis(pinacolato)diboron (523 mg, 2.06 mmol), potassium acetate (404 mg, 4.12 mmol), 2-dicyclohexylphosphino-2',4',6'-triisopropylbiphenyl, 98% (52.3 mg, 0.11 mmol) and tris(dibenzylideneacetone)dipalladium(0), 99% (25.1 mg, 0.027 mmol) were added and the red reaction mixture was stirred at 85° C. for 2 days. The dark brown residue was purified by flash chromatography (DCM/MeOH) to give 312 mg (100%) of the title compound as a yellow solid. LC/MS (Method B): Rt 1.00 min, M+H−18=211.

16. Preparation of 2-(2,2-dioxo-2,3-dihydro-1H-benzo[c]thiophen-5-yl)-4,4,5,5-tetramethyl-[1,3,2]dioxaborolane

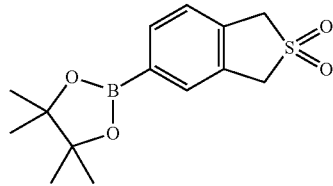 [SMILES: CC1(C)OB(c2ccc3c(c2)CS(=O)(=O)C3)OC1(C)C]

In a screw-capped vessel 5-bromo-1,3-dihydro-benzo[c]thiophene 2,2-dioxide (100 mg, 0.40 mmol), bis(pinacolato)diboron (206 mg, 0.81 mmol), potassium acetate (119 mg, 1.21 mmol) and Pd(dppf)Cl$_2$·CH$_2$Cl$_2$ (33.1 mg, 0.04 mmol) were suspended in THF SeccoSolv® (5 mL). Nitrogen was bubbled through the mixture for 5 min. The reaction mixture was stirred at 70° C. for 15 h. The mixture was diluted with THF (7 mL), filtered and the filtrate was evaporated to dryness. The crude residue was purified by flash chromatography (heptane/DCM) to yield in 89.0 mg (75%) of the title compound as an off-white solid. LC/MS (Method B): Rt=2.53 min, (M+Na) 317.

17. Preparation of [3-(methylamino)-1H-indazol-6-yl]boronic Acid

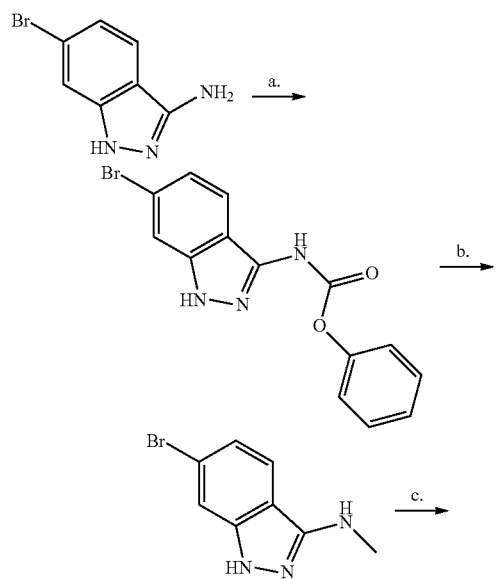

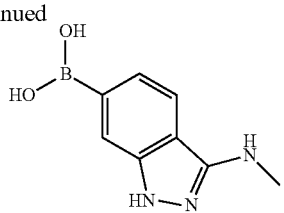

17a. (6-Bromo-1H-indazol-3-yl)-carbamic Acid Phenyl Ester

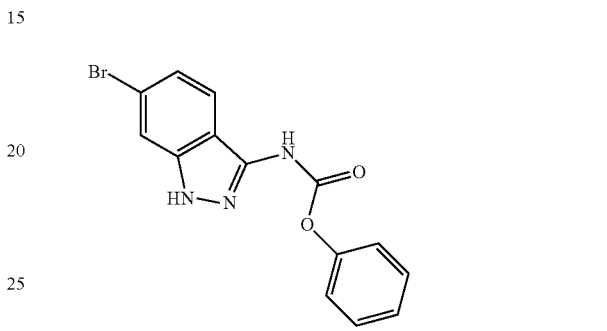

In a screw-capped vessel, 6-bromo-1H-indazol-3-amine (95%, 1.00 g, 4.48 mmol) was dissolved in pyridine SeccoSolv® (20). At 0° C. phenyl chloroformate, 99% (0.62 mL, 4.93 mmol) was added dropwise. The mixture was stirred at 0° C. for 4 hr before the mixture was diluted with DCM (50 mL) and water (50 mL). The organic layer was separated, washed with brine, dried over sodium sulfate, filtered and the solvent was evaporated to dryness. The residue was purified by flash chromatography (heptane/DCM) to yield in of the title compound (54 mg, 3%) as a white solid. LC/MS (Method B): Rt=2.62 min, (M+H) 332/334.

In addition 346 mg (17%) of 3-amino-6-bromo-indazole-1-carboxylic acid phenyl ester was isolated as a white solid.

17b. (6-Bromo-1H-indazol-3-yl)-methyl-amine

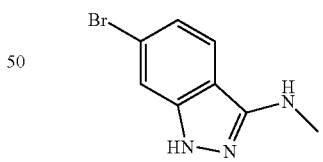

In a screw-capped vessel (6-bromo-1H-indazol-3-yl)-carbamic acid phenyl ester (54.0 mg, 0.16 mmol) was dissolved in THF SeccoSolv® (3 mL). Lithium aluminium hydride solution (1.0 M in THF, 325 µl, 0.33 mmol) was added dropwise to the solution at RT (exothermic reaction!) under N$_2$ atmosphere. The solution turned from colorless to yellow. The mixture was stirred at RT for 2 hr and was then treated with water (2 mL) and diluted with THF (8 mL). The suspension was filtered over Celite. The filtrate was evaporated to dryness to give 41.1 mg (99%) of the title compound as a yellow solid, which was used without further purification. LC/MS (Method B): Rt 1.95 min, (M+H) 226.

137

17c. [3-(Methylamino)-1H-indazol-6-yl]boronic Acid

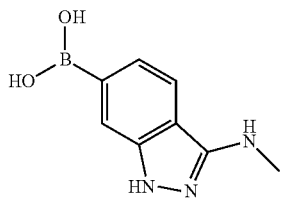

In a microwave vessel (6-bromo-1H-indazol-3-yl)-methyl-amine (41.0 mg, 0.16 mmol), bis(pinacolato)diboron (82.0 mg, 0.32 mmol), potassium acetate (47.5 mg, 0.48 mmol) and Pd(dppf)Cl$_2$.CH$_2$Cl$_2$ (13.2 mg, 0.02 mmol) were suspended in acetonitrile (4 mL). The vial was closed, degassed, flushed with nitrogen and stirred in the microwave for 1 hr at 120° C. The mixture was diluted with acetonitrile (10 mL), filtered and the filtrate was evaporated to dryness. The crude residue (230 mg, 13% purity, 100%) was used without further purification. LC/MS (Method B): Rt=1.83 min, (M+H) 192.

18. Preparation of (rac)-2-{4-[4-(4,4,5,5-tetramethyl-[1,3,2]dioxaborolan-2-yl)-phenyl]-pyrazol-1-yl}-cyclopentanol

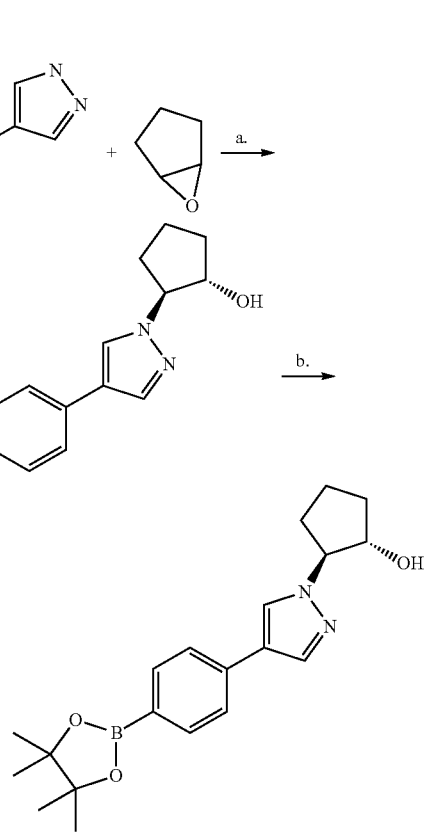

138

18a. (rac)-2-[4-(4-Bromo-phenyl)-pyrazol-1-yl]-cyclopentanol

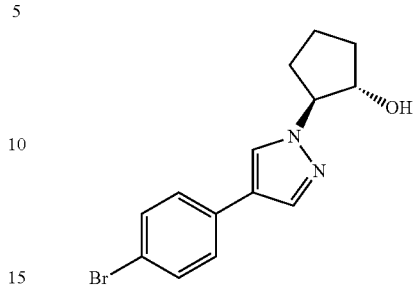

4-(4-Bromo-phenyl)-1H-pyrazole (500 mg, 2.24 mmol) was dissolved in DMF (5 mL) in a heavy walled reaction tube. Potassium carbonate (465 mg, 3.36 mmol) and 1,2-epoxycyclopentane (390 mg, 4.48 mmol) were added and the tube was sealed with a teflon screw cap and stirred at 140° C. for 3 days. After cooling to RT, the reaction was diluted with water and the resulting precipitate was filtered and dried in vacuo to give 606 mg (87%) of the title compound as white crystals. LC/MS (Method A): Rt 2.27 min, (M+H) 307/309.

18b. (rac)-2-{4-[4-(4,4,5,5-Tetramethyl-[1,3,2]dioxaborolan-2-yl)-phenyl]-pyrazol-1-yl}-cyclopentanol

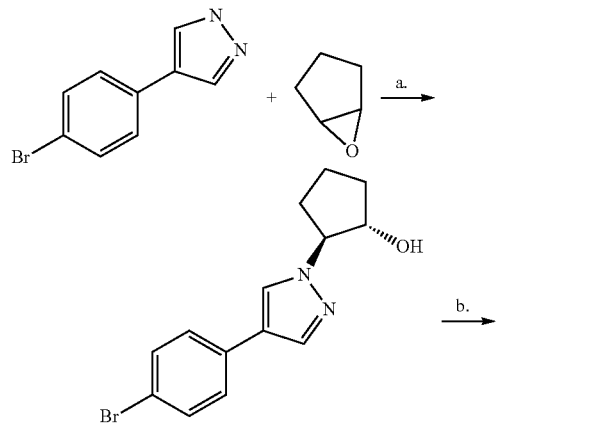

In a microwave vessel (rac)-2-[4-(4-bromo-phenyl)-pyrazol-1-yl]-cyclopentanol (255 mg, 0.82 mmol), bis(pinacolato)diboron (415 mg, 1.63 mmol), potassium acetate (240 mg, 2.45 mmol) and 1,1-bis(diphenylphosphino)ferrocenepalladium (II) dichloride, (99%, 60.0 mg, 0.082 mmol) were suspended in acetonitrile (10 mL). The closed vial was stirred 4 times at 70° C. for 1 hr under microwave irradiation. Then the reaction mixture was stirred again at 80° C. for 15 hr. The reaction mixture was filtered and evaporated. The crude residue was purified by flash chromatography to give the title compound (93% purity, 168 mg, 54%) of as a light yellow oil. LC/MS (Method A): Rt=2.43 min, (M+H) 355.

19. Preparation of 2-isopropyl-5-(4,4,5,5-tetramethyl-[1,3,2]dioxaborolan-2-yl)-2H-indazole

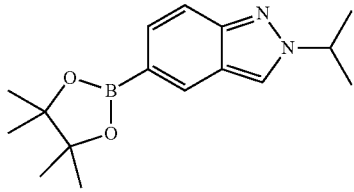 [SMILES: CC(C)n1cc2cc(B3OC(C)(C)C(C)(C)O3)ccc2n1]

A microwave vessel was charged with 5-bromo-2-isopropyl-2H-indazole (97%, 159 mg, 0.67 mmol), potassium acetate (196 mg, 2.00 mmol) and 1,1-bis(diphenylphosphino)ferrocenepalladium(II) dichloride DCM complex (27.2 mg, 0.033 mmol) and acetonitrile (80 mL) was added. The mixture was stirred at 100° C. for 90 min under microwave irradiation. The mixture was diluted with EtOAc, washed twice with water and once with brine. The organic layer was dried over sodium sulfate, filtered and the solvent was evaporated. The dark red residue was purified by preparative chromatography to give of the title compound (90% purity, 25.3 mg, 12%) as a colorless oil. LC/MS (Method A): Rt=2.36, (M+H) 287.

2-Methyl-5-(4,4,5,5-tetramethyl-1,3,2-dioxaborolan-2-yl)-2H-indazole and 2-ethyl-5-(4,4,5,5-tetramethyl-1,3,2-dioxaborolan-2-yl)-2H-indazole were synthesised using the same procedure.

20. Preparation of 7-(4,4,5,5-tetramethyl-[1,3,2]dioxaborolan-2-yl)-3,4-dihydro-1H-quinolin-2-one

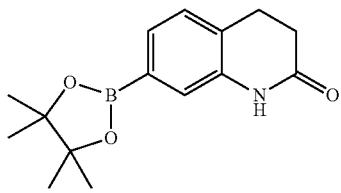 [SMILES: CC1(C)OB(c2ccc3c(c2)NC(=O)CC3)OC1(C)C]

In a screw-capped vessel 7-bromo-3,4-dihydro-1H-quinolin-2-one (100 mg, 0.44 mmol) was dissolved in THF SeccoSolv® (3 mL). bis(pinacolato)diboron (225 mg, 0.89 mmol), potassium acetate (130 mg, 1.33 mmol) and 1,1-bis(diphenylphosphino)ferrocenepalladium(II) dichloride DCM complex (18.1 mg, 0.022 mmol) were added and the red reaction mixture was stirred overnight at 70° C. The dark reaction mixture was treated with water (30 mL). The brown precipitate was filtered and washed with water to yield in 92.0 mg (86% purity, 65%) of a brownish solid identified as the title compound. LC/MS (Method B): Rt 2.70 min, (M+H) 274.

21. Preparation of (3-amino-1H-indazol-6-yl)boronic Acid

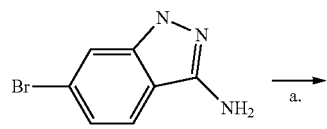

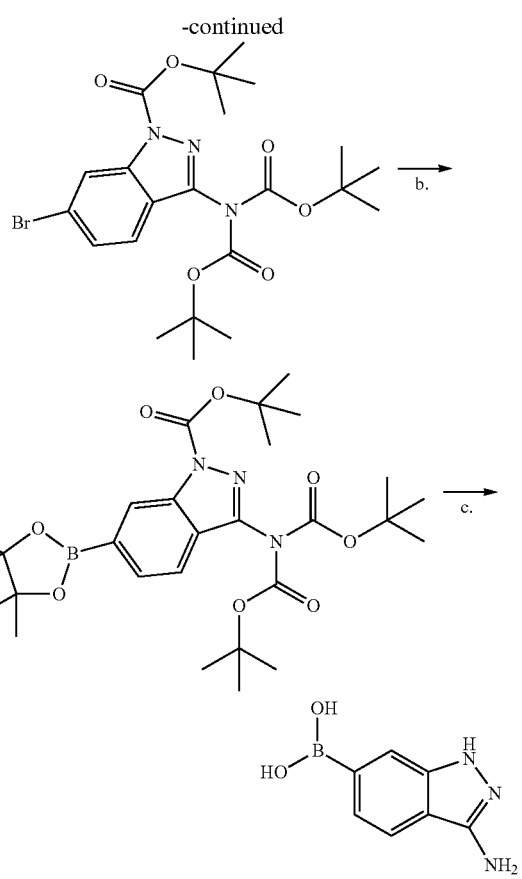

21a. tert-Butyl 3-[bis(tert-butoxycarbonyl)amino]-6-bromo-indazole-1-carboxylate

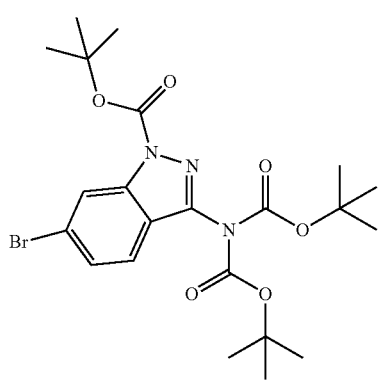 [SMILES: CC(C)(C)OC(=O)N(C(=O)OC(C)(C)C)c1nn(C(=O)OC(C)(C)C)c2cc(Br)ccc12]

In a screw-tapped vessel 6-bromo-1H-indazol-3-amine (95% purity, 500 mg, 2.36 mmol) and 4-(dimethylamino)-pyridine (57.6 mg, 0.47 mmol) were dissolved in THF SeccoSolv® (10 mL). Di-tert-butyldicarbonate (2.52 mL, 11.8 mmol) and triethylamine (3.27 mL, 23.6 mmol) were added and the reaction solution was stirred 3 days at RT. The reaction mixture was treated with 100 mL of water. The oily residue did not crystallize. The mixture was taken up in EtOAc and washed with water, dried, filtered and evaporated to dryness to give the title compound (1.01 g, 73% purity, 86%) as a colorless oil, which was used without further purification. LC/MS (Method B): Rt 3.87 min, (M+Na) 534/536.

21b. tert-Butyl 3-[bis(tert-butoxycarbonyl)amino]-6-(4,4,5,5-tetramethyl-1,3,2-dioxaborolan-2-yl)indazole-1-carboxylate

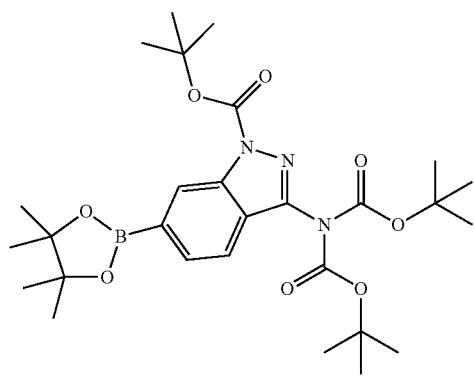 [SMILES: CC(C)(C)OC(=O)N(C(=O)OC(C)(C)C)c1nn(C(=O)OC(C)(C)C)c2cc(B3OC(C)(C)C(C)(C)O3)ccc12]

In a screw-capped vessel tert-butyl 3-[bis(tert-butoxycarbonyl)amino]-6-bromo-indazole-1-carboxylate (73% purity, 980 mg, 1.91) was dissolved in THF SeccoSolv® (16 mL). Bis(pinacolato)diboron (486 mg, 1.91 mmol), potassium acetate (375 mg, 3.83 mmol) and Pd(dppf)Cl$_2$.CH$_2$Cl$_2$ (78.1 mg, 0.096 mmol) were added and the red reaction mixture was stirred for 15 hr at 70° C. Bis(pinacolato)diboron (486 mg, 1.91 mmol), potassium acetate (130 mg, 1.33 mmol) and Pd(dppf)Cl$_2$.CH$_2$Cl$_2$ (78.1 mg, 0.096 mmol) were added and stirring was continued at 70° C. for additional 4 h. The black reaction mixture was treated with EtOAc, filtered and evaporated to dryness under reduced pressure. The dark brown residue was purified by flash chromatography (heptane/DCM) to give the title compound (1.00 g, 90% purity, 84%) as a yellow solid. LC/MS (Method B): Rt 3.82 min, (M+H) 560.

21c. (3-Amino-1H-indazol-6-yl)boronic Acid Hydrochloride

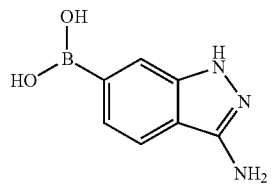 [SMILES: Nc1n[nH]c2cc(B(O)O)ccc12]

tert-Butyl 3-[bis(tert-butoxycarbonyl)amino]-6-(4,4,5,5-tetramethyl-1,3,2-dioxaborolan-2-yl)indazole-1-carboxylate (90% purity, 1.00 g, 1.79 mmol) was treated with HCl in dioxane (25 mL). The pale yellow solution was stirred at RT for 15 hr. The solution was evaporated to dryness and the residue was treated with diethyl ether to obtain a beige solid. The mixture was filtered and the residue was washed with diethyl ether. 390 mg (97%) of the title compound were obtained as a beige solid. LC/MS (Method B): Rt 1.32 min, (M+H) 178.

22. 7-Oxo-5,6,7,8-tetrahydro-[1,8]naphthyridine-3-boronic Acid

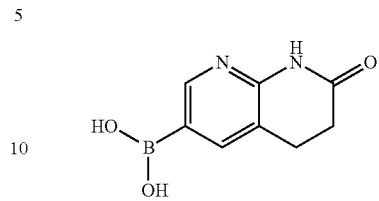

In a screw-tapped vessel 6-bromo-3,4-dihydro-1H-[1,8]naphthyridin-2-one (100 mg, 0.44 mmol) was dissolved in tetrahydrofurane SeccoSolv® (3 mL). Bis(pinacolato)diboron (145 mg, 0.57 mmol), potassium acetate (130 mg, 1.32 mmol) and 1,1 bis(diphenylphosphino)ferrocenepalladium (II) dichloride DCM complex (18.0 mg, 0.022 mmol) were added and the red reaction mixture was stirred overnight at 80° C. The crude mixture was filtered, the solvent evaporated to dryness and the dark residue was purified by chromatography (DCM/MeOH) to give 100 mg (84% purity, 99% yield) of an off-white solid identified as the title compound. LC/MS (Method B): Rt 1.29 min, (M+H) 193.

23. Preparation of 8-{3-Chloro-5-[4-(1-methyl-1H-pyrazol-4-yl)-phenyl]-pyridin-4-yl}-4-methyl-1-oxa-3,8-diaza-spiro[4.5]decan-2-one 97

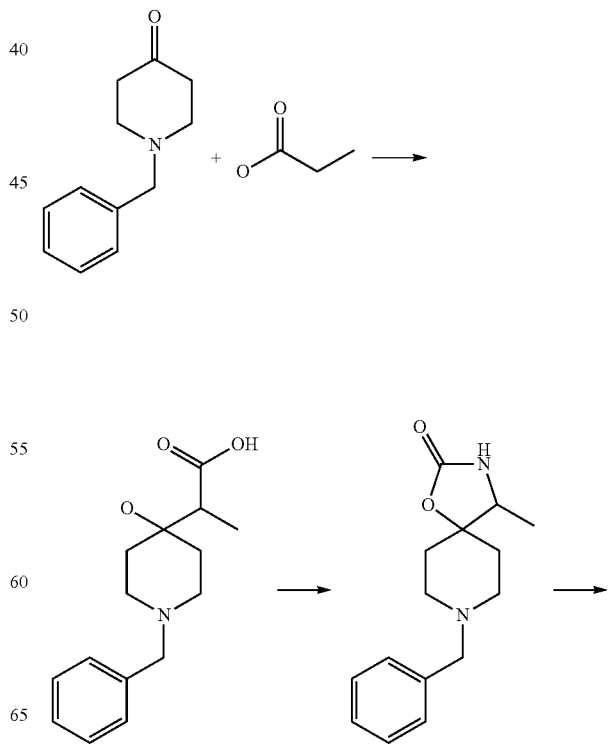

23a. 8-Benzyl-4-methyl-1-oxa-3,8-diaza-spiro[4.5]decan-2-one

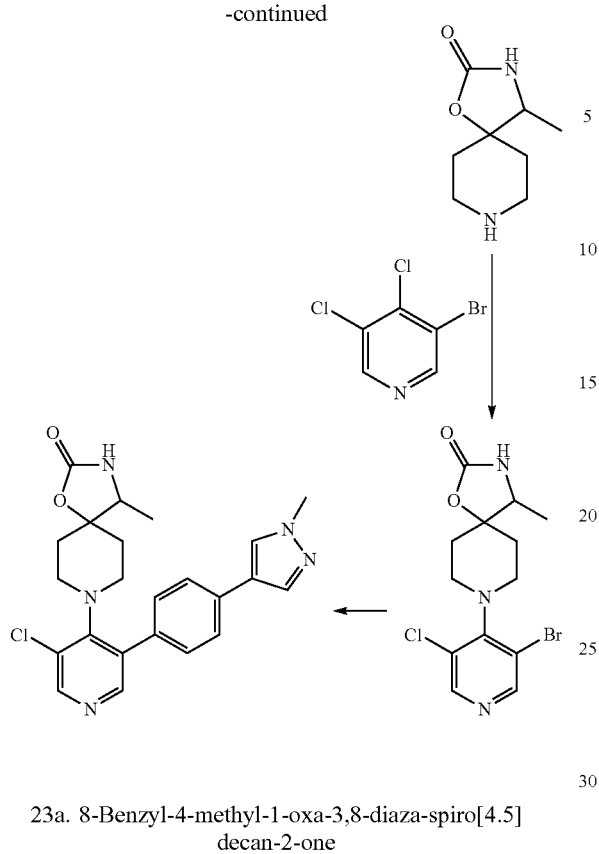

To a 100 ml flask maintained under argon are added diisopropyl amine (3.20 mL, 22.8 mmol) and tetrahydrofuran (30 mL). The contents of the flask are cooled to 0° C. and are maintained at that temperature. A solution of N-butyllithium solution (14.3 mL, 22.8 mmol) was added, the temperature rose to 20° C., followed by stirring at this temperature for 5 minutes. Propionic acid (0.76 mL, 10.1 mmol) was added and the mixture was stirred for 15 minutes at 20° C. The mixture was cooled to −70° C. and a solution of 1-benzyl-piperidin-4-one (2.40 g, 12.7 mmol) in tetrahydrofuran (10 mL) was added at such a rate that the temperature remained below −50° C. The mixture was allowed to warm to room temperature and was poured into diethyl ether and water. The organic layer was discarded. The water phase was evaporated, triturated with methanol, filtered and the filtrate was evaporated was evaporated to dryness to yield in 2.48 g (74%) of the title compound as light yellow crystals.

23b. 2,2-Dimethyl-1,3,8-triazaspiro[4.5]decan-4-one

A mixture of 2-(1-benzyl-4-hydroxy-piperidin-4-yl)-propionic acid (2.48 g, 9.42 mmol), diphenylphosphoryl azide (1.70 mL, 7.53 mmol), triethylamine (1.00 mL, 7.53 mmol) and toluene (80 mL) was heated at reflux for 18 h. Evaporation of the solvent gave a residue which was taken up in dichlormethane and washed with 1 N hydrochloric acid and sodium bicarbonate solution. The organic phase was evaporated to dryness followed by trituration with diethyl ether to yield in 834 mg (34%) of the title compound as a light yellow solid.

23c. 4-Methyl-1-oxa-3,8-diaza-spiro[4.5]decan-2-one

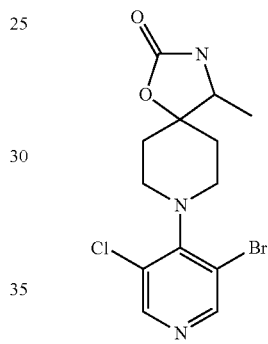

2,2-Dimethyl-1,3,8-triazaspiro[4.5]decan-4-one (834 mg, 3.20 mmol) was dissolved in methanol (10 mL). 1.00 g of Pd/C (5%) was added and the reaction mixture was stirred under hydrogen for 15 h at RT. The reaction mixture was filtered and the solvent evaporated under reduced pressure. The residue was suspended in ethyl acetate, washed with saturated sodium carbonate solution and the aqueous phase was extracted twice with ethyl acetate. The combined organic layer was dried over sodium sulfate, filtered and evaporated to give the title compound (486 mg, 89%) of as a colorless solid.

23d. 8-(3-Bromo-5-chloro-pyridin-4-yl)-4-methyl-1-oxa-3,8-diaza-spiro[4.5]decan-2-one In a microwave vessel 3-bromo-4,5-dichloro-pyridine (430 mg, 1.90 mmol) was dissolved in 1-methyl-2-pyrrolidon (5 mL). 4-Methyl-1-oxa-3,8-diaza-spiro[4.5]decan-2-one (484 mg, 2.84 mmol) and triethyl amine (0.79 mL, 5.69 mmol) were added. The closed vial was stirred at 220° C. for 1 h under microwave irradiation. The brown reaction mixture were treated with water. The beige precipitate was filtered off, washed with water and dried in vacuo to yield in 293 mg (43%) of the title compound as a brownish solid.

23e. 8-{3-Chloro-5-[4-(1-methyl-1H-pyrazol-4-yl)-phenyl]-pyridin-4-yl}-4-methyl-1-oxa-3,8 diaza-spiro[4.5]decan-2-one 97

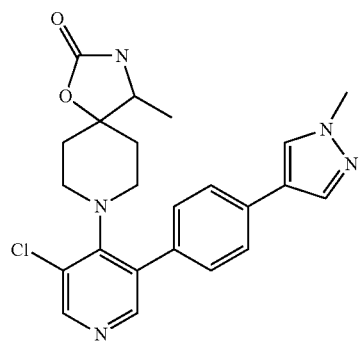 [SMILES: CC1NC(=O)OC12CCN(c1c(Cl)cncc1-c1ccc(-c3cnn(C)c3)cc1)CC2]

In a microwave vessel 8-(3-bromo-5-chloro-pyridin-4-yl)-4-methyl-1-oxa-3,8-diaza-spiro[4.5]decan-2-one (145 mg, 0.40 mmol) and 1-methyl-4-[4-(4,4,5,5-tetramethyl-[1,3,2]dioxaborolan-2-yl)-phenyl]-1H-pyrazole (280 mg, 0.80 mmol) were dissolved in acetonitrile (5 mL). Sodium carbonate solution, 0.5 M (1.60 mL, 0.80 mmol) and 1,1 bis(diphenylphosphino)ferrocenedichloropalladium(II) (30.0 mg, 0.04 mmol) were added. The closed vial was stirred at 120° C. for 1 h under microwave irradiation. The reaction mixture was evaporated to dryness. The crude product was purified by flash chromatography (ethyl acetate/methanol) to yield in 113 mg (64%) of the title compound as white solid. Rt=1.70 min (HPLC method A).

The racemic mixture was separated into the enantiomers by chiral HPLC to result in example 100. Using the same route, compound 96 was synthesized using the respective boronic acid 1-methyl-5-(4,4,5,5-tetramethyl-[1,3,2]dioxaborolan-2-yl)-1,3-dihydro-benzo[c]isothiazole 2,2-dioxide and separated into its enantiomers 98 and 99.

Biological Activity

1. Cellular Assay for Wnt Pathway Activity

Compounds were tested for their Wnt pathway inhibitory activities using a luciferase reporter cell based assay. A HEK293 luciferase reporter cell line was used which contained an Estrogen Receptor-Disheveled (ER-DSH) construct and a T-Cell Factor (TCF) dependent gene promoter luciferase construct.

Compounds, in concentrations from 30 µM down to 1 nM, were incubated for 24 hours on the cells, which were induced for TCF-dependent transcription by the addition of estrogen (1 µM). Luciferase activities were determined using the ONE GLO Luciferase Assay System (Promega) and the ENVISION microplate reader (Perkin Elmer).

For analysis, the obtained data were normalized against the untreated vehicle control and fitted for determination of the $IC_{50}$ values using the Assay Explorer software (Accelrys).

An additional test was run to confirm the specificity of the compounds on the Wnt pathway: Compounds were tested in HEK293 cells, containing the TCF-dependent gene promoter, for inhibition of cellular viabilities using an ATP quantification readout. The compounds of the present invention were inactive in this test, pointing to Wnt pathway specific activity.

To assess the inhibitory potential of the compounds on the Wnt pathway, $IC_{50}$-values were determined, as shown in Table 3 below.

2. CLint (Intrinsic Clearance) Assay

Instrumentation

A Tecan Genesis workstation (RWS ASY 150/8) was used to perform the microsomal incubations. Analysis was carried out using a Waters ACQUITY UPLC system coupled to an ABSciex API3000 mass spectrometer. Data analysis was performed using Assay Explorer (Symyx).

UPLC Conditions

Column: Acquity UPLC BEH C18, 2.1×50 mm, 1.7 um (Waters)

Mobile phases: A=0.1% formic acid in water
B=acetonitrile

| | Time | % A | % B |
|---|---|---|---|
| Gradient: | initial | 90 | 10 |
| | 0.47 | 5 | 95 |
| | 0.65 | 5 | 95 |
| | 0.66 | 90 | 10 |

Flow rate: 0.750 mL/min
Detection: ESI, MRM
Injection: 10 uL
Column temperature: 50° C.

Chemicals 0.1 M potassium phosphate buffer pH 7.4 containing 1 mM $MgCl_2$ 15 mM NADPH in phosphate buffer 5.0 mg protein/mL liver microsomes in phosphate buffer acetonitrile 20% DMSO in water Microsomal Incubation Each experiment consists of 12 test and 2 reference compounds. The reference compounds are incubated as a cocktail.

Dilution of test compounds was done in 2 steps from a 10 mM DMSO stock solution. First 4 µL stock solution was added to 196 µL of 20% DMSO in potassium phosphate buffer pH 7.4. In a second step 10 µL of the first dilution were added to 1890 µL potassium phosphate buffer and 100 µL internal standard solution to a final concentration of 0.8 µM. 100 µL of the final compound dilution were aliquoted into a 96 deep well plate. 12.5 µL liver microsomes were added to each well (0.5 mg/mL final protein concentration) and the samples preincubated for 5 min at 37° C. and 800 rpm agitation.

After the preincubation, 250 µL cold acetonitrile were added to the 0 min samples to prevent a reaction. Following this, 12.5 µL NADPH solution were added to all wells to start the incubation, with the exception of the 0 min and 30 min controls without cofactor, where the NADPH was substituted for phosphate buffer.

The incubations were stopped after 5, 10, 20 and 30 min by adding 250 µL cold acetonitrile to the individual wells.

The quenched samples were then centrifuged at 4000 g for 1 h at 4° C. 100 µL of the supernatant were transferred into 96 well plates for analysis.

Data Analysis

The metabolic stability of each compound was determined by measurement of the change in LC-MS/MS peak area over time. Assay Explorer software was used to automatically calculate the slope k of the decline. The intrinsic clearance (CLint) of each compound was then calculated according to the formula:

$$CLint(\mu L/min/mg\ protein) = k1000/\text{protein concentration}.$$

CLint is shown for each compound in Table 3 below.

TABLE 3

Potency and Stability of compounds 1 to 100

| Example Number | Chemical Name | 7df3 IC50 (uM) | Human Clint [µL/min/mg] |
|---|---|---|---|
| 1 | 8-[3-Chloro-5-(1-methyl-1H-indazol-5-yl)-pyridin-4-yl]-2,8-diaza-spiro[4.5]decane-1,3-dione | 0.0034 | 11 |

TABLE 3-continued

Potency and Stability of compounds 1 to 100

| Example Number | Chemical Name | 7df3 IC50 (uM) | Human Clint [µL/min/mg] |
|---|---|---|---|
| 2 | 8-[3-Chloro-5-(1-methyl-1H-indazol-5-yl)-pyridin-4-yl]-1,3,8-triaza-spiro[4.5]decane-2,4-dione | 0.046 | 15 |
| 3 | 5-[5-Chloro-4-(1-oxo-2,8-diaza-spiro[4.5]dec-8-yl)-pyridin-3-yl]-3H-benzooxazol-2-one | 0.0044 | 35 |
| 4 | 8-[3-Chloro-5-(1-methyl-1H-indazol-5-yl)-pyridin-4-yl]-1-oxa-3,8-diaza-spiro[4.5]decan-2-one | 0.01 | 23 |
| 5 | 8-(3-Chloro-5-{4-[1-(2-hydroxy-ethyl)-1H-pyrazol-4-yl]-phenyl}-pyridin-4-yl)-2,8-diaza-spiro[4.5]decan-1-one | 0.0046 | 40 |
| 6 | 8-{3-Chloro-5-[4-(1-isopropyl-1H-pyrazol-4-yl)-phenyl]-pyridin-4-yl}-2,8-diaza-spiro[4.5]decan-1-one | 0.0062 | 90 |
| 7 | 8-[3-(3-Amino-1H-indazol-6-yl)-5-chloro-pyridin-4-yl]-2,8-diaza-spiro[4.5]decan-1-one | 0.014 | 27 |
| 8 | 8-[3-Chloro-5-(2-oxo-2,3-dihydro-benzooxazol-5-yl)-pyridin-4-yl]-1-oxa-3,8-diaza-spiro[4.5]decan-2-one | 0.0097 | 16 |
| 9 | 8-{3-Chloro-5-[4-(1-methyl-1H-pyrazol-4-yl)-phenyl]-pyridin-4-yl}-1-oxa-3,8-diaza-spiro[4.5]decan-2-one | 0.015 | 40 |
| 10 | 8-[3-Chloro-5-(1-methyl-1H-indazol-6-yl)-pyridin-4-yl]-1-oxa-3,8-diaza-spiro[4.5]decan-2-one | 0.028 | 13 |
| 11 | 8-[3-Chloro-5-(1-methyl-2-oxo-2,3-dihydro-1H-indol-5-yl)-pyridin-4-yl]-1-oxa-3,8-diaza-spiro[4.5]decan-2-one | 0.033 | <10 |
| 12 | 7-[5-Chloro-4-(1-oxo-2,8-diaza-spiro[4.5]dec-8-yl)-pyridin-3-yl]-3,4-dihydro-1H-quinolin-2-one | 0.043 | 27 |
| 13 | 8-{3-Chloro-5-[4-(1-methyl-1H-pyrazol-4-yl)-phenyl]-pyridin-4-yl}-1,3,8-triaza-spiro[4.5]decane-2,4-dione | 0.023 | <10 |
| 14 | 8-[3-(3-Amino-1H-indazol-6-yl)-5-chloro-pyridin-4-yl]-2,8-diaza-spiro[4.5]decane-1,3-dione | 0.018 | <10 |
| 15 | 8-(3-Chloro-5-{4-[1-(2-hydroxy-ethyl)-1H-pyrazol-4-yl]-phenyl}-pyridin-4-yl)-1-oxa-3,8-diaza-spiro[4.5]decan-2-one | 0.017 | <10 |
| 16 | 8-[3-Chloro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one | 0.0014 | 18 |
| 17 | 9-{3-Chloro-5-[4-(1-methyl-1H-pyrazol-4-yl)-phenyl]-pyridin-4-yl}-1,4,9-triaza-spiro[5.5]undecane-2,5-dione | 0.011 | 11 |
| 18 | 8-{3-Chloro-5-[4-(1,2-dimethyl-1H-imidazol-4-yl)-phenyl]-pyridin-4-yl}-2,8-diaza-spiro[4.5]decan-1-one | 0.019 | 13 |
| 19 | 8-[3-Chloro-5-(1-methyl-1H-indazol-5-yl)-pyridin-4-yl]-2-methyl-1,3,8-triaza-spiro[4.5]dec-2-en-4-one | 0.021 | <10 |
| 20 | 8-{3-Chloro-5-[4-(1-methyl-1H-pyrazol-4-yl)-phenyl]-pyridin-4-yl}-2-methyl-1,3,8-triaza-spiro[4.5]dec-2-en-4-one | 0.022 | 24 |
| 21 | 9-[3-Chloro-5-(1-methyl-2,2-dioxo-2,3-dihydro-1H-2l6-benzo[c]isothiazol-5-yl)-pyridin-4-yl]-1,4,9-triaza-spiro[5.5]undecane-2,5-dione | 0.031 | <10 |
| 22 | 4-[5-Chloro-4-(1-oxo-2,8-diaza-spiro[4.5]dec-8-yl)-pyridin-3-yl]-N-methyl-benzamide | 0.046 | 27 |
| 23 | {6-[5-Chloro-4-(1-oxo-2,8-diaza-spiro[4.5]dec-8-yl)-pyridin-3-yl]-1H-indazol-3-yl}-carbamic acid methyl ester | 0.039 | 49 |
| 24 | 8-[3-(3-Amino-1-methyl-1H-indazol-6-yl)-5-chloro-pyridin-4-yl]-2,8-diaza-spiro[4.5]decan-1-one | 0.0018 | 78 |
| 25 | 5'-Chloro-4-fluoro-3'-[4-(1-methyl-1H-pyrazol-4-yl)-phenyl]-3,4,5,6-tetrahydro-2H-[1,4']bipyridinyl-4-carboxylic acid amide | 0.007 | 23 |
| 26 | 8-[3-(2-tert-Butyl-1,1-dioxo-2,3-dihydro-1H-1l6-benzo[d]isothiazol-5-yl)-5-chloro-pyridin-4-yl]-2,8-diaza-spiro[4.5]decan-1-one | 0.02 | 30 |
| 27 | 8-[3-(3-Amino-1-methyl-1H-indazol-6-yl)-5-chloro-pyridin-4-yl]-1-oxa-3,8-diaza-spiro[4.5]decan-2-one | 0.002 | 58 |
| 28 | 8-[3-(3-Amino-1-methyl-1H-indazol-6-yl)-5-chloro-pyridin-4-yl]-2,8-diaza-spiro[4.5]decane-1,3-dione | 0.0013 | 60 |
| 29 | 8-[3-Chloro-5-(3-hydroxy-1,1-dioxo-2,3-dihydro-1H-1l6-benzo[b]thiophen-5-yl)-pyridin-4-yl]-2,8-diaza-spiro[4.5]decan-1-one | 0.016 | 12 |
| 30 | 8-[3-Chloro-5-(1-methyl-2,2-dioxo-2,3-dihydro-1H-2l6-benzo[c]isothiazol-5-yl)-pyridin-4-yl]-1,2,8-triaza-spiro[4.5]decan-3-one | 0.013 | 27 |

TABLE 3-continued

Potency and Stability of compounds 1 to 100

| Example Number | Chemical Name | 7df3 IC50 (uM) | Human Clint [μL/min/mg] |
|---|---|---|---|
| 31 | 5'-Chloro-4-fluoro-3'-(1-methyl-2,2-dioxo-2,3-dihydro-1H-2l6-benzo[c]isothiazol-5-yl)-3,4,5,6-tetrahydro-2H-[1,4']bipyridinyl-4-carboxylic acid amide | 0.0028 | 51 |
| 32 | 8-[3-Chloro-5-(2,2-dioxo-2,3-dihydro-1H-2l6-benzo[c]thiophen-5-yl)-pyridin-4-yl]-2,8-diaza-spiro[4.5]decan-1-one | 0.0047 | 70 |
| 33 | 5'-Chloro-4-(2-hydroxy-ethyl)-3'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile | 0.0006 | 88 |
| 34 | 8-[3-Chloro-5-(3-methylamino-1H-indazol-6-yl)-pyridin-4-yl]-2,8-diaza-spiro[4.5]decan-1-one | 0.0029 | 52 |
| 35 | 8-{3-[4-(1-Methyl-1H-pyrazol-4-yl)-phenyl]-5-trifluoromethyl-pyridin-4-yl}-1-oxa-3,8-diaza-spiro[4.5]decan-2-one | 0.024 | <10 |
| 36 | 8-{3-Chloro-5-[4-(1-isopropyl-1H-pyrazol-4-yl)-phenyl]-pyridin-4-yl}-1-oxa-3,8-diaza-spiro[4.5]decan-2-one | 0.022 | 40 |
| 37 | 8-[3-Chloro-5-(1-methyl-2,2-dioxo-2,3-dihydro-1H-2l6-benzo[c]isothiazol-5-yl)-pyridin-4-yl]-1,3,8-triaza-spiro[4.5]decane-2,4-dione | 0.036 | 11 |
| 38 | 8-{3-[4-(1-Isopropyl-1H-pyrazol-4-yl)-phenyl]-5-trifluoromethyl-pyridin-4-yl}-1-oxa-3,8-diaza-spiro[4.5]decan-2-one | 0.033 | 16 |
| 39 | 8-(3-Chloro-5-{4-[1-(2-methanesulfonyl-ethyl)-1H-pyrazol-4-yl]-phenyl}-pyridin-4-yl)-1-oxa-3,8-diaza-spiro[4.5]decan-2-one | 0.014 | 12 |
| 40 | 3-(4-{4-[5-Chloro-4-(2-oxo-1-oxa-3,8-diaza-spiro[4.5]dec-8-yl)-pyridin-3-yl]-phenyl}-pyrazol-1-yl)-propionitrile | 0.0039 | 61 |
| 41 | 8-[3-Chloro-5-(1-methyl-2,2-dioxo-2,3-dihydro-1H-2l6-benzo[c]isothiazol-5-yl)-pyridin-4-yl]-4-methyl-2,3,8-triaza-spiro[4.5]dec-3-en-1-one | 0.000075 | 85 |
| 42 | (S)-8-[3-Chloro-5-(1-methyl-2,2-dioxo-2,3-dihydro-1H-2l6-benzo[c]isothiazol-5-yl)-pyridin-4-yl]-3-trifluoromethyl-2,8-diaza-spiro[4.5]decan-1-one | 0.0024 | 57 |
| 43 | 8-(3-Chloro-5-{4-[1-(2-hydroxy-2-methyl-propyl)-1H-pyrazol-4-yl]-phenyl}-pyridin-4-yl)-1-oxa-3,8-diaza-spiro[4.5]decan-2-one | 0.05 | 11 |
| 44 | 4-Amino-5'-chloro-3'-(1-methyl-2,2-dioxo-2,3-dihydro-1H-2l6-benzo[c]isothiazol-5-yl)-3,4,5,6-tetrahydro-2H-[1,4']bipyridinyl-4-carboxylic acid amide | 0.0051 | <10 |
| 45 | 8-{3-[4-(1-Methyl-1H-pyrazol-4-yl)-phenyl]-5-trifluoromethyl-pyridin-4-yl}-2,8-diaza-spiro[4.5]decan-1-one | 0.0035 | 81 |
| 46 | 8-[3-Chloro-5-(1-methyl-2,2-dioxo-2,3-dihydro-1H-2l6-benzo[c]isothiazol-5-yl)-pyridin-4-yl]-2-methyl-1,3,8-triaza-spiro[4.5]dec-1-en-4-one | 0.034 | 16 |
| 47 | 8-(3-Chloro-5-{4-[1-(2-hydroxy-2-methyl-propyl)-1H-pyrazol-4-yl]-phenyl}-pyridin-4-yl)-2,8-diaza-spiro[4.5]decan-1-one | 0.013 | 23 |
| 48 | 8-[3-Chloro-5-(2,2-dioxo-2,3-dihydro-1H-2l6-benzo[c]thiophen-5-yl)-pyridin-4-yl]-1-oxa-3,8-diaza-spiro[4.5]decan-2-one | 0.042 | 23 |
| 49 | 8-{3-Chloro-5-[4-(1-methyl-1H-pyrazol-4-yl)-phenyl]-pyridin-4-yl}-1-methyl-1,3,8-triaza-spiro[4.5]decane-2,4-dione | 0.00069 | 20 |
| 50 | 8-(3-Chloro-5-isoquinolin-6-yl-pyridin-4-yl)-1-oxa-3,8-diaza-spiro[4.5]decan-2-one | 0.023 | 28 |
| 51 | 8-[3-Chloro-5-(1-methyl-2,2-dioxo-2,3-dihydro-1H-2l6-benzo[c]isothiazol-5-yl)-pyridin-4-yl]-4-hydroxy-2,8-diaza-spiro[4.5]decan-1-one | 0.0024 | 38 |
| 52 | 8-[3-Chloro-5-(1-methyl-2,2-dioxo-2,3-dihydro-1H-2l6-benzo[c]isothiazol-5-yl)-pyridin-4-yl]-4-ethyl-2,3,8-triaza-spiro[4.5]dec-3-en-1-one | 0.00002 | 70 |
| 53 | (R)-8-[3-Chloro-5-(1-methyl-2,2-dioxo-2,3-dihydro-1H-2l6-benzo[c]isothiazol-5-yl)-pyridin-4-yl]-3-trifluoromethyl-2,8-diaza-spiro[4.5]decan-1-one | 0.015 | 42 |
| 54 | 8-{3-Chloro-5-[4-(1-methyl-1H-pyrazol-4-yl)-phenyl]-pyridin-4-yl}-4-ethyl-2,3,8-triaza-spiro[4.5]dec-3-en-1-one | 0.00092 | 82 |

TABLE 3-continued

Potency and Stability of compounds 1 to 100

| Example Number | Chemical Name | 7df3 IC50 (uM) | Human Clint [µL/min/mg] |
|---|---|---|---|
| 55 | 8-{3-Chloro-5-[4-(1-oxetan-3-yl-1H-pyrazol-4-yl)-phenyl]-pyridin-4-yl}-1-oxa-3,8-diaza-spiro[4.5]decan-2-one | 0.02 | 23 |
| 56 | 8-(3-Chloro-5-{4-[1-((1S,2S)-2-hydroxy-cyclopentyl)-1H-pyrazol-4-yl]-phenyl}-pyridin-4-yl)-2,8-diaza-spiro[4.5]decan-1-one | 0.0076 | 44 |
| 57 | 8-(3-Chloro-5-{4-[1-((1S,2S)-2-hydroxy-cyclopentyl)-1H-pyrazol-4-yl]-phenyl}-pyridin-4-yl)-1-oxa-3,8-diaza-spiro[4.5]decan-2-one | 0.018 | 32 |
| 58 | 8-[3-Chloro-5-(1-methyl-2,2-dioxo-2,3-dihydro-1H-2l6-benzo[c]isothiazol-5-yl)-pyridin-4-yl]-4-trifluoromethyl-2,3,8-triaza-spiro[4.5]dec-3-en-1-one | 0.0033 | 89 |
| 59 | 8-{3-Chloro-5-[4-(1-methyl-1H-pyrazol-4-yl)-phenyl]-pyridin-4-yl}-4-trifluoromethyl-2,3,8-triaza-spiro[4.5]dec-3-en-1-one | 0.017 | 43 |
| 60 | 8-{3-Chloro-5-[4-(1-cyclopropyl-1H-pyrazol-4-yl)-phenyl]-pyridin-4-yl}-1-oxa-3,8-diaza-spiro[4.5]decan-2-one | 0.0061 | 23 |
| 61 | 8-[3-Chloro-5-(1-methyl-1H-indazol-5-yl)-pyridin-4-yl]-4-trifluoromethyl-2,3,8-triaza-spiro[4.5]dec-3-en-1-one | 0.017 | 38 |
| 62 | 8-(3-Chloro-5-{4-[1-((1S,2S)-2-hydroxy-cyclopentyl)-1H-pyrazol-4-yl]-phenyl}-pyridin-4-yl)-1-oxa-3,8-diaza-spiro[4.5]decan-2-one | 0.034 | 37 |
| 63 | 8-(3-Chloro-5-{4-[1-((1R,2R)-2-hydroxy-cyclopentyl)-1H-pyrazol-4-yl]-phenyl}-pyridin-4-yl)-1-oxa-3,8-diaza-spiro[4.5]decan-2-one | 0.03 | 29 |
| 64 | 8-[3-Chloro-5-(2-oxo-2,3-dihydro-1H-indol-6-yl)-pyridin-4-yl]-2,8-diaza-spiro[4.5]decan-1-one | 0.019 | 49 |
| 65 | 8-[3-Chloro-5-(1-methyl-2-oxo-2,3-dihydro-1H-indol-5-yl)-pyridin-4-yl]-2,8-diaza-spiro[4.5]decane-1,3-dione | 0.021 | <10 |
| 66 | 8-[3-Chloro-5-(1-methyl-1H-indazol-6-yl)-pyridin-4-yl]-2,8-diaza-spiro[4.5]decane-1,3-dione | 0.015 | <10 |
| 67 | 8-{3-Chloro-5-[4-(1-methyl-1H-pyrazol-3-yl)-phenyl]-pyridin-4-yl}-2,8-diaza-spiro[4.5]decan-1-one | 0.041 | 30 |
| 68 | | 0.0014 | 65 |
| 69 | | 0.0011 | 89 |
| 70 | 8-[3-Chloro-5-(1-methyl-1H-indazol-5-yl)-pyridin-4-yl]-4-hydroxy-2,8-diaza-spiro[4.5]decan-1-one | 0.02 | 24 |
| 71 | 9-{3-Chloro-5-[4-(1-methyl-1H-pyrazol-4-yl)-phenyl]-pyridin-4-yl}-1,4,9-triaza-spiro[5.5]undecan-5-one | 0.012 | 49 |
| 72 | 9-[3-Chloro-5-(2-oxo-2,3-dihydro-benzooxazol-5-yl)-pyridin-4-yl]-1,4,9-triaza-spiro[5.5]undecan-5-one | 0.035 | <10 |
| 73 | 4-Amino-5'-chloro-3'-(1-methyl-2-oxo-2,3-dihydro-1H-indol-6-yl)-3,4,5,6-tetrahydro-2H-[1,4']bipyridinyl-4-carboxylic acid amide | 0.012 | 17 |
| 74 | 8-[3-Chloro-5-(1-methyl-2-oxo-2,3-dihydro-1H-indol-6-yl)-pyridin-4-yl]-1,3,8-triaza-spiro[4.5]decan-4-one | 0.02 | 20 |
| 75 | 8-[3-Chloro-5-(1-methyl-2,2-dioxo-2,3-dihydro-1H-2l6-benzo[c]isothiazol-5-yl)-pyridin-4-yl]-1,3,8-triaza-spiro[4.5]decan-4-one | 0.0047 | 20 |
| 76 | 8-[3-Fluoro-5-(1-methyl-2,2-dioxo-2,3-dihydro-1H-2l6-benzo[c]isothiazol-5-yl)-pyridin-4-yl]-2,8-diaza-spiro[4.5]decan-1-one | 0.0091 | 36 |
| 77 | 5'-Chloro-4-methoxymethyl-3'-(1-methyl-2,2-dioxo-2,3-dihydro-1H-2l6-benzo[c]isothiazol-5-yl)-3,4,5,6-tetrahydro-2H-[1,4']bipyridinyl-4-carboxylic acid amide | 0.00043 | 75 |
| 78 | 8-{3-Chloro-5-[4-(1-isopropyl-1H-pyrazol-4-yl)-phenyl]-pyridin-4-yl}-1,3,8-triaza-spiro[4.5]decan-4-one | 0.0038 | 30 |
| 79 | 8-{3-Fluoro-5-[4-(1-methyl-1H-pyrazol-4-yl)-phenyl]-pyridin-4-yl}-1-oxa-3,8-diaza-spiro[4.5]decan-2-one | 0.043 | 24 |
| 80 | 8-[3-Fluoro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one | 0.012 | 18 |
| 81 | 8-[3-Ethynyl-5-(1-methyl-2,2-dioxo-2,3-dihydro-1H-2l6-benzo[c]isothiazol-5-yl)-pyridin-4-yl]-2,8-diaza-spiro[4.5]decan-1-one | 0.00066 | 66 |
| 82 | 8-[3-Chloro-5-(1-methyl-1H-indazol-5-yl)-pyridin-4-yl]-1,3,8-triaza-spiro[4.5]decan-4-one | 0.0073 | 47 |

TABLE 3-continued

Potency and Stability of compounds 1 to 100

| Example Number | Chemical Name | 7df3 IC50 (uM) | Human Clint [μL/min/mg] |
|---|---|---|---|
| 83 | 4-Amino-5'-chloro-3'-(1-methyl-1H-indazol-5-yl)-3,4,5,6-tetrahydro-2H-[1,4']bipyridinyl-4-carboxylic acid amide | 0.0071 | 37 |
| 84 | 8-[3-Chloro-5-(2,2-dioxo-2,3-dihydro-1H-2l6-benzo[c]isothiazol-5-yl)-pyridin-4-yl]-2,8-diaza-spiro[4.5]decane-1,3-dione | 0.015 | <10 |
| 85 | 5'-Chloro-4-hydroxymethyl-3'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile | 0.0007 | 51 |
| 86 | 8-{3-Chloro-5-[4-(1-methyl-1H-pyrazol-4-yl)-phenyl]-pyridin-4-yl}-2,8-diaza-spiro[4.5]decane-1,3-dione | 0.0022 | 21 |
| 87 | 8-[3-Chloro-5-(1-methyl-2,2-dioxo-2,3-dihydro-1H-2l6-benzo[c]isothiazol-5-yl)-pyridin-4-yl]-2,8-diaza-spiro[4.5]decane-1,3-dione | 0.00016 | 13 |
| 88 | 8-{3-Chloro-5-[4-(1-methyl-1H-pyrazol-4-yl)-phenyl]-pyridin-4-yl}-1,3,8-triaza-spiro[4.5]decan-4-one | 0.0032 | <10 |
| 89 | 8-{3-Chloro-5-[4-(1-methyl-1H-pyrazol-4-yl)-phenyl]-pyridin-4-yl}-2,8-diaza-spiro[4.5]decan-1-one | 0.0062 | 83 |
| 90 | 8-[3-Chloro-5-(4-morpholin-4-yl-phenyl)-pyridin-4-yl]-2,8-diaza-spiro[4.5]decane-1,3-dione | 0.0088 | 66 |
| 91 | 8-[3-Chloro-5-(1-methyl-1H-indazol-5-yl)-pyridin-4-yl]-2,8-diaza-spiro[4.5]decan-1-one | 0.0082 | 79 |
| 92 | 8-[3-Chloro-5-(2-methyl-2H-indazol-5-yl)-pyridin-4-yl]-2,8-diaza-spiro[4.5]decan-1-one | 0.014 | 33 |
| 93 | 6-[5-Chloro-4-(1-oxo-2,8-diaza-spiro[4.5]dec-8-yl)-pyridin-3-yl]-3,4-dihydro-1H-[1,8]naphthyridin-2-one | 0.034 | 48 |
| 94 | 8-[3-Chloro-5-(2-isopropyl-2H-indazol-5-yl)-pyridin-4-yl]-1-oxa-3,8-diaza-spiro[4.5]decan-2-one | 0.028 | <10 |
| 95 | 8-[3-Chloro-5-(2-ethyl-2H-indazol-5-yl)-pyridin-4-yl]-1-oxa-3,8-diaza-spiro[4.5]decan-2-one | 0.0045 | <10 |
| 96 | 8-[3-Chloro-5-(1-methyl-2,2-dioxo-2,3-dihydro-1H-2l6-benzo[c]isothiazol-5-yl)-pyridin-4-yl]-4-methyl-1-oxa-3,8-diaza-spiro[4.5]decan-2-one | 0.0042 | 39 |
| 97 | 8-{3-Chloro-5-[4-(1-methyl-1H-pyrazol-4-yl)-phenyl]-pyridin-4-yl}-4-methyl-1-oxa-3,8-diaza-spiro[4.5]decan-2-one | 0.042 | 26 |
| 98 | (S)-8-[3-Chloro-5-(1-methyl-2,2-dioxo-2,3-dihydro-1H-2l6-benzo[c]isothiazol-5-yl)-pyridin-4-yl]-4-methyl-1-oxa-3,8-diaza-spiro[4.5]decan-2-one | 0.0043 | 35 |
| 99 | (R)-8-[3-Chloro-5-(1-methyl-2,2-dioxo-2,3-dihydro-1H-2l6-benzo[c]isothiazol-5-yl)-pyridin-4-yl]-4-methyl-1-oxa-3,8-diaza-spiro[4.5]decan-2-one | 0.0052 | 39 |
| 100 | (R)-8-{3-Chloro-5-[4-(1-methyl-1H-pyrazol-4-yl)-phenyl]-pyridin-4-yl}-4-methyl-1-oxa-3,8-diaza-spiro[4.5]decan-2-one | 0.037 | 31 |

The invention claimed is:

1. A compound of Formula (I)

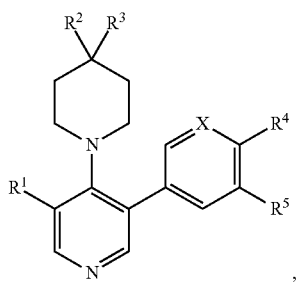

or its stereoisomers or tautomers, or pharmaceutically acceptable salts of each of the foregoing, including mixtures thereof in all ratios, wherein:
X is CH or N,
$R^1$ is LA, Hal or CN,
$R^2$, $R^3$ together with the C atom they are attached to, form a 5 or 6 membered non-aromatic heterocycle, having 1-3 heteroatoms, selected from O, S and N, which is substituted by 1 or 2 oxo groups, which heterocycle is optionally further monosubstituted by LA or OH, and which heterocycle optionally forms a condensed ring system with a phenyl or pyridyl group,
$R^4$ is Cyc, $CONH_2$, COO(LA) or CONH(LA),
$R^5$ is H, or
$R^4$, $R^5$ together with the atoms they are attached to, form a 5 or 6 membered heterocycle, having 1-3 heteroatoms, selected from O, S and N, which is, optionally, independently mono- di- or trisubstituted by oxo, OH, LA, $NH_2$, NH(LA), $N(LA)_2$, NHCOO(LA) or HO(LA)-,
Cyc is a 5 or 6 membered monocyclic, aliphatic or aromatic homo- or heterocycle having 1-3 heteroatoms, selected from O, S and N, which is optionally mono- or di-substituted by oxo, LA, $NH_2$, NH(LA), $N(LA)_2$, HO(LA) or monosubstituted by CA, LA is unbranched or branched alkyl, having 1, 2, 3, 4 or 5 carbon atoms, which is optionally saturated or partially unsaturated, wherein 1, 2 or 3 H atoms is optionally replaced by Hal, and/or 1 $CH_3$ group is optionally replaced by CN, or 1 $CH_2$ group is optionally replaced by —O—, —NH— or —$SO_2$—, and/or 1 CH group is optionally replaced by N, CA is cycloalkyl having 3, 4, 5 or 6 carbon atoms, or cycloalkyl alkyl having 3, 4, 5 or 6 ring carbon atoms and 1 or 2 non-ring carbon atoms, in which cycloalkyl or cycloalkyl alkyl one ring atom is optionally replaced by O, and which cycloalkyl or cycloalkyl alkyl is optionally monosubstituted by OH, Hal is F, Cl, Br or I.

2. The compound according to claim 1, or its stereoisomers or tautomers, or pharmaceutically acceptable salts of each of the foregoing, wherein the compound is selected from the following subformulae and wherein, for each subformula, any residue not designated below is as defined in claim 1:

Subformula 1
X is CH,
$R^2$, $R^3$ together with the piperidine ring they are attached to, form 2,8-diaza-spiro[4.5]decan-1-one-yl, 2,8-diaza-spiro[4.5]decane-1,3-dione-yl, 1-oxa-3,8-diaza-spiro[4.5]decan-2-one-yl, 1,3,8-triaza-spiro[4.5]decane-2,4-dione-yl, 1,4,9-triaza-spiro[5.5]undecan-5-one-yl, 1,3,8-triaza-spiro[4.5]decane-4-one-yl, 2-methyl-1,3,8-triaza-spiro[4.5]dec-2-en-4-one-yl, 1,4,9-triaza-spiro[5.5]undecan-2,5-dione-yl, 1-methyl-1,3,8-triaza-spiro[4.5]decane-2,4-dione-yl, 4-hydroxy-2,8-diaza-spiro[4.5]decan-1-one-yl, 1,2,8-triaza-spiro[4.5]decan-3-one-yl, 4-methyl-2,3,8-triaza-spiro[4.5]dec-3-en-1-one-yl, (S)-3-trifluoromethyl-2,8-diaza-spiro[4.5]decan-1-one-yl, (R)-3-trifluoromethyl-2, 8-diaza-spiro[4.5]decan-1-one-yl, 4-ethyl-2,3,8-triaza-spiro[4.5]dec-3-en-1-one-yl, 4-trifluoromethyl-2,3,8-triaza-spiro[4.5]dec-3-en-1-one-yl, spiro[1,3-dihydro-pyrrolo[3,2-b]pyridin-3,4'-piperidin]-2-one-yl or spiro[indoline-3,4'-piperidin]-2-one-yl, or Subformula 2
X is CH,
$R^2$, $R^3$ together with the C atom they are attached to, form 1,3-Dihydro-indol-2-one-3-yl or 4-aza-1,3-dihydro-indol-2-one-3-yl, or Subformula 3
X is CH,
$R^4$ is pyridinyl, 1H-pyrazolyl or 1H-imidazolyl, each of which is unsubstituted, or mono- or independently disubstituted by LA, OH, or HO(LA)-, or optionally monosubstituted by CA,
$R^5$ is H, or Subformula 4
$R^4$, $R^5$ together with the ring they are attached to, form 2H-indazolyl, 1H-indazolyl, 2-oxo-2,3-dihydro-benzooxazolyl, 3H-benzooxazol-2-one-yl, 2-oxo-2,3-dihydro-1H-indolyl, 3,4-dihydro-1H-quinolin-2-one-yl, 2,3-dihydro-1H-indolyl, 2,2-dioxo-2,3-dihydro-1H-benzo[c]isothiazolyl, 1,1-dioxo-2,3-dihydro-1H-benzo[b]thiophenyl, 3,4-dihydro-1H-quinolin-2-one-yl, isoquinolinyl, 3,4-dihydro-1H-[1,8]naphthyridin-2-one-yl, 2-tert-butyl-2,3-dihydro-benzo[d]isothiazole 1,1-dioxide-5-yl or 1,3-dihydro-benzo[c]thiophene 2,2-dioxide-5-yl each of which is unsubstituted, or substituted by LA, OH, $NH_2$, HO(LA)- or NH (LA) or NHCOO(LA) or Subformula 5
X is CH,
$R^1$ is Cl, F or $CF_3$, or Subformula 6
X is CH,
$R^1$ is Cl, or Subformula 7
X is CH,
$R^4$ is 1-methyl-1H-pyrazol-3-yl, 6-amino-pyridin-3-yl, 1-(2-hydroxy-ethyl)-1H-pyrazol-4-yl, (2-hydroxy-2-methyl-propyl)-1H-pyrazol-4-yl, (2-methanesulfonyl-ethyl)-1H-pyrazol-4-yl, 1,2-dimethyl-1H-imidazol-4-yl, 1-Isopropyl-1H-pyrazol-4-yl, 1-cyclopropyl-1H-pyrazol-4-yl, 1-oxetan-3-yl-1H-pyrazol-4-yl, 1-(2-hydroxy-cyclopentyl)-1H-pyrazol-4-yl or (2-cyanoethyl)-1H-pyrazol-4-yl,
$R^5$ is H, or Subformula 8
$R^4$, $R^5$ together with the ring they are attached to, form 2-ethyl-2H-indazol-5-yl, 1-methyl-1H-indazol-5-yl, 1H-indazol-5-yl, 1H-indazol-6-yl, 1-methyl-1H-indazol-6-yl, 2-methyl-2H-indazol-5-yl, 2-oxo-2,3-dihydro-benzooxazol-5-yl, 2-oxo-2,3-dihydro-1H-indol-6-yl, (3H-benzooxazol-2-one)-5-yl, 1-methyl-2-oxo-2,3-dihydro-1H-indol-5-yl, 1-methyl-2-oxo-2,3-dihydro-1H-indol-6-yl, (3,4-dihydro-1H-quinolin-2-one)-7-yl, 1-methyl-2-oxo-2,3-dihydro-1H-indol-5-yl, 1H-indol-6-yl, 2-oxo-2,3-dihydro-1H-indol-6-yl, 3-amino-1H-indazol-6-yl, 1-methyl-2,2-dioxo-2,3-dihydro-1H-benzo[c]isothiazol-5-yl, 2,2-dioxo-2,3-dihydro-1H-benzo[c]isothiazol-5-yl, 2-isopropyl-2H-indazol-5-yl, 3-hydroxy-1,1-dioxo-2,3-dihydro-1H-benzo[b]thiophen-5-yl, isoquinolin-6-yl, 2-tert-Butyl-1,1-dioxo-2,3-dihydro-1H-benzo[d]isothiazol-5-yl, 3,4-dihydro-1H-[1,8]naphthyridin-2-one-6-yl, 2-oxo-2,3-dihydro-1H-indol-6-yl, (3H-benzooxazol-2-one)-5-yl, (3,4-dihydro-1H-quinolin-2-one)-7-yl, 2,3-dihydro-1H-indol-6-yl, (1H-indazol-3-yl)-carbamic acid methyl ester-5-yl, 1-methyl-1H-indazol-3-ylamine-6-yl, 1-methyl-1,3-dihydro-benzo[c]isothiazole 2,2-dioxide-5-yl or methyl-(1H-indazol-3-yl)-amine-6-yl, or Subformula 12
X is CH,
$R^2$, $R^3$ together with the piperidine ring they are attached to, form 1,3,8-triaza-spiro[4.5]decane-4-one-8-yl, 1-oxa-3,8-diaza-spiro[4.5]decan-2-one-8-yl, 2,8-diaza-spiro[4.5]decane-1,3-dione-8-yl, 2-methyl-1,3,8-triaza-spiro[4.5]dec-2-en-4-one-8-yl, 1,3,8-triaza-spiro[4.5]decane-2,4-dione-8-yl, 1,4,9-triaza-spiro[5.5]undecan-5-one-9-yl, 1,4,9-triaza-spiro[5.5]undecan-2,5-dione-9-yl or 2,8-diaza-spiro[4.5]decan-1-one-8-yl, or Subformula 13
X is CH,
$R^1$ is Cl or $CF_3$,
$R^2$, $R^3$ together with the piperidine ring they are attached to, form 1,3,8-triaza-spiro[4.5]decane-4-one-8-yl, 1-oxa-3,8-diaza-spiro[4.5]decan-2-one-8-yl, 2,8-diaza-spiro[4.5]decane-1,3-dione-8-yl, 2-methyl-1,3,8-triaza-spiro[4.5]dec-2-en-4-one-8-yl, 1,3,8-triaza-spiro[4.5]decane-2,4-dione-8-yl, 1,4,9-triaza-spiro[5.5]undecan-5-one-9-yl, 1,4,9-triaza-spiro[5.5]undecan-2,5-dione-9-yl or 2,8-diaza-spiro[4.5]decan-1-one-8-yl, or Subformula 14
X is CH,
$R^1$ is Cl or $CF_3$,
$R^4$ is 1-methyl-1H-pyrazol-3-yl, 6-amino-pyridin-3-yl, 1-(2-hydroxy-ethyl)-1H-pyrazol-4-yl, (2-hydroxy-2-methyl-propyl)-1H-pyrazol-4-yl, (2-methanesulfonyl-ethyl)-1H-pyrazol-4-yl, 1,2-dimethyl-1H-imidazol-4-yl, 1-Isopropyl-1H-pyrazol-4-yl, 1-cyclopropyl-1H-pyrazol-4-yl, 1-oxetan-3-yl-1H-pyrazol-4-yl, 1-(2-hydroxy-cyclopentyl)-1H-pyrazol-4-yl or (2-cyanoethyl)-1H-pyrazol-4-yl,
$R^5$ is H, or,
$R^4$, $R^5$ together with the phenyl ring they are attached to, form 1-methyl-2,2-dioxo-2,3-dihydro-1H-benzo[c]isothiazol-5-yl, 1-methyl-1H-indazol-6-yl, 2,2-dioxo-2,3-dihydro-1H-benzo[c]isothiazol-5-yl, 3-Amino-1H-indazol-6-yl, 1-methyl-1H-indazol-5-yl, 1-methyl-2-oxo-2,3-dihydro-1H-indol-5-yl or 2-isopropyl-2H-indazol-5-yl, 2-oxo-2,3-dihydro-benzooxazol-5-yl, or Subformula 15
X is CH,
$R^1$ is Cl or $CF_3$,
$R^2$, $R^3$ together with the piperidine ring they are attached to, form 1,3,8-triaza-spiro[4.5]decane-4-one-8-yl, 1-oxa-3,8-diaza-spiro[4.5]decan-2-one-8-yl, 2,8-diaza-spiro[4.5]decane-1,3-dione-8-yl, 2-methyl-1,3,8-triaza-spiro[4.5]dec-2-en-4-one-8-yl, 1,3,8-triaza-spiro[4.5]decane-2,4-dione-8-yl, 1,4,9-triaza-spiro[5.5]undecan-5-one-9-yl, 1,4,9-triaza-spiro[5.5]undecan-2,5-dione-9-yl or 2,8-diaza-spiro[4.5]decan-1-one-8-yl,
$R^4$ is 1-methyl-1H-pyrazol-3-yl, 6-amino-pyridin-3-yl, 1-(2-hydroxy-ethyl)-1H-pyrazol-4-yl, (2-hydroxy-2-methyl-propyl)-1H-pyrazol-4-yl, (2-methanesulfonyl-ethyl)-1H-pyrazol-4-yl, 1,2-dimethyl-1H-imidazol-4-yl, 1-Isopropyl-1H-pyrazol-4-yl, 1-cyclopropyl-1H-pyrazol-4-yl, 1-oxetan-3-yl-1H-pyrazol-4-yl, 1-(2-hydroxy-cyclopentyl)-1H-pyrazol-4-yl or (2-cyanoethyl)-1H-pyrazol-4-yl,
$R^5$ is H, or,
$R^4$, $R^5$ together with the phenyl ring they are attached to, form 1-methyl-2,2-dioxo-2,3-dihydro-1H-benzo[c]isothiazol-5-yl, 1-methyl-1H-indazol-6-yl, 2,2-dioxo-2,3-dihydro-1H-benzo[c]isothiazol-5-yl, 3-Amino-1H-indazol-6-yl, 1-methyl-1H-indazol-5-yl, 1-methyl-2-oxo-2,3-dihydro-1H-indol-5-yl, 2-isopropyl-2H-indazol-5-yl or 2-oxo-2,3-dihydro-benzooxazol-5-yl.

3. The compound according to claim 1, wherein the compound is selected from the group consisting of:
8-{3-Chloro-5-[4-(1-methyl-1H-pyrazol-4-yl)-phenyl]-pyridin-4-yl}-1,3,8-triaza-spiro[4.5]decan-4-one,
8-(3-Chloro-5-{4-[1-(2-hydroxy-2-methyl-propyl)-1H-pyrazol-4-yl]-phenyl}-pyridin-4-yl)-1-oxa-3,8-diaza-spiro[4.5]decan-2-one,
8-(3-Chloro-5-{4-[1-(2-hydroxy-ethyl)-1H-pyrazol-4-yl]-phenyl}-pyridin-4-yl)-1-oxa-3,8-diaza-spiro[4.5]decan-2-one,
8-(3-Chloro-5-{4-[1-(2-methanesulfonyl-ethyl)-1H-pyrazol-4-yl]-phenyl}-pyridin-4-yl)-1-oxa-3,8-diaza-spiro[4.5]decan-2-one,
8-[3-(3-Amino-1H-indazol-6-yl)-5-chloro-pyridin-4-yl]-2,8-diaza-spiro[4.5]decane-1,3-dione,
8-[3-Chloro-5-(1-methyl-1H-indazol-5-yl)-pyridin-4-yl]-1,3,8-triaza-spiro[4.5]decane-2,4-dione,
8-[3-Chloro-5-(1-methyl-1H-indazol-5-yl)-pyridin-4-yl]-2,8-diaza-spiro[4.5]decane-1,3-dione,
8-[3-Chloro-5-(1-methyl-1H-indazol-5-yl)-pyridin-4-yl]-2-methyl-1,3,8-triaza-spiro[4.5]dec-2-en-4-one,
8-[3-Chloro-5-(1-methyl-1H-indazol-6-yl)-pyridin-4-yl]-1-oxa-3,8-diaza-spiro[4.5]decan-2-one,
8-[3-Chloro-5-(1-methyl-1H-indazol-6-yl)-pyridin-4-yl]-2,8-diaza-spiro[4.5]decane-1,3-dione,
8-[3-Chloro-5-(1-methyl-2,2-dioxo-2,3-dihydro-1H-benzo[c]isothiazol-5-yl)-pyridin-4-yl]-1,3,8-triaza-spiro[4.5]decane-2,4-dione,
8-[3-Chloro-5-(1-methyl-2,2-dioxo-2,3-dihydro-1H-benzo[c]isothiazol-5-yl)-pyridin-4-yl]-1-oxa-3,8-diaza-spiro[4.5]decan-2-one,
8-[3-Chloro-5-(1-methyl-2,2-dioxo-2,3-dihydro-1H-benzo[c]isothiazol-5-yl)-pyridin-4-yl]-2,8-diaza-spiro[4.5]decane-1,3-dione,
8-[3-Chloro-5-(1-methyl-2,2-dioxo-2,3-dihydro-1H-benzo[c]isothiazol-5-yl)-pyridin-4-yl]-2-methyl-1,3,8-triaza-spiro[4.5]dec-1-en-4-one,
8-[3-Chloro-5-(1-methyl-2-oxo-2,3-dihydro-1H-indol-5-yl)-pyridin-4-yl]-1-oxa-3,8-diaza-spiro[4.5]decan-2-one,
8-[3-Chloro-5-(1-methyl-2-oxo-2,3-dihydro-1H-indol-5-yl)-pyridin-4-yl]-2,8-diaza-spiro[4.5]decane-1,3-dione,
8-[3-Chloro-5-(2,2-dioxo-2,3-dihydro-1H-benzo[c]isothiazol-5-yl)-pyridin-4-yl]-2,8-diaza-spiro[4.5]decane-1,3-dione,
8-[3-Chloro-5-(2-ethyl-2H-indazol-5-yl)-pyridin-4-yl]-1-oxa-3,8-diaza-spiro[4.5]decan-2-one,
8-[3-Chloro-5-(2-isopropyl-2H-indazol-5-yl)-pyridin-4-yl]-1-oxa-3,8-diaza-spiro[4.5]decan-2-one,
8-[3-Chloro-5-(2-oxo-2,3-dihydro-benzooxazol-5-yl)-pyridin-4-yl]-1-oxa-3,8-diaza-spiro[4.5]decan-2-one,
8-[3-Chloro-5-(3-hydroxy-1,1-dioxo-2,3-dihydro-1H-benzo[b]thiophen-5-yl)-pyridin-4-yl]-2,8-diaza-spiro[4.5]decan-1-one,
8-{3-[4-(1-Isopropyl-1H-pyrazol-4-yl)-phenyl]-5-trifluoromethyl-pyridin-4-yl}-1-oxa-3,8-diaza-spiro[4.5]decan-2-one,
8-{3-[4-(1-Methyl-1H-pyrazol-4-yl)-phenyl]-5-trifluoromethyl-pyridin-4-yl}-1-oxa-3,8-diaza-spiro[4.5]decan-2-one,
8-{3-Chloro-5-[4-(1,2-dimethyl-1H-imidazol-4-yl)-phenyl]-pyridin-4-yl}-2,8-diaza-spiro[4.5]decan-1-one,
8-{3-Chloro-5-[4-(1-methyl-1H-pyrazol-4-yl)-phenyl]-pyridin-4-yl}-1,3,8-triaza-spiro[4.5]decane-2,4-dione,
9-[3-Chloro-5-(1-methyl-2,2-dioxo-2,3-dihydro-1H-benzo[c]isothiazol-5-yl)-pyridin-4-yl]-1,4,9-triaza-spiro[5.5]undecane-2,5-dione,
9-[3-Chloro-5-(2-oxo-2,3-dihydro-benzooxazol-5-yl)-pyridin-4-yl]-1,4,9-triaza-spiro[5.5]undecan-5-one, and
9-{3-Chloro-5-[4-(1-methyl-1H-pyrazol-4-yl)-phenyl]-pyridin-4-yl}-1,4,9-triaza-spiro[5.5]undecane-2,5-dione or its stereoisomers or tautomers, or pharmaceutically acceptable salts of each of the foregoing, including mixtures thereof in all ratios.

4. A pharmaceutical composition comprising a compound according to claim 1, or its stereoisomers or tautomers, or pharmaceutically acceptable salts of each of the foregoing, including mixtures thereof in all ratios, as active ingredient, together with a pharmaceutically acceptable carrier.

5. A method for the treatment of a hyperproliferative, inflammatory or degenerative disease, which disease is selected from the group consisting of: brain cancer, lung cancer, colon cancer, epidermoid cancer, squamous cell cancer, bladder cancer, gastric cancer, pancreatic cancer, breast cancer, head & neck cancer, renal cancer, kidney cancer, liver cancer, ovarian cancer, prostate cancer, uterine cancer, oesophageal cancer, testicular cancer, gynecological cancer, thyroid cancer, melanoma, acute myelogenous leukemia, multiple myeloma, chronic myelogneous leukemia, myeloid cell leukemia and Kaposi's sarcoma; comprising administering a compound according to claim 1, or its stereoisomers or tautomers, or pharmaceutically acceptable salts of each of the foregoing, including mixtures thereof in all ratios.

6. A method for the preparation of a medicament for the treatment of a hyperproliferative, inflammatory or degenerative disease, which disease is selected from the group consisting of: brain cancer, lung cancer, colon cancer, epidermoid cancer, squamous cell cancer, bladder cancer, gastric cancer, pancreatic cancer, breast cancer, head & neck cancer, renal cancer, kidney cancer, liver cancer, ovarian cancer, prostate cancer, uterine cancer, oesophageal cancer, testicular cancer, gynecological cancer, thyroid cancer, melanoma, acute myelogenous leukemia, multiple myeloma, chronic myelogneous leukemia, myeloid cell leukemia and Kaposi's sarcoma; which comprises incorporating into a medicament a compound of claim 1, or its stereoisomers or tautomers, or pharmaceutically acceptable salts of each of the foregoing, including mixtures thereof in all ratios.

7. A kit consisting of separate packs of
  a) an effective amount of a compound according to claim 1, or its stereoisomers or tautomers, or pharmaceutically acceptable salts of each of the foregoing, including mixtures thereof in all ratios, and
  b) an effective amount of a further medicament active ingredient.

8. Process for the manufacture of compounds of Formula (I) of claim 1, wherein a compound of Formula (V)

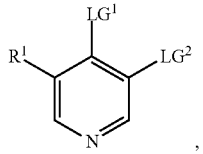

(V)

is reacted with a compound of Formula (IV)

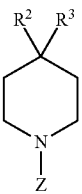

(IV)

to yield a compound of Formula (III)

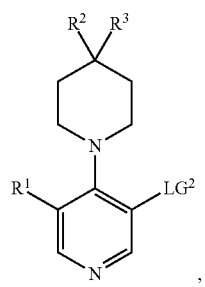

(III)

which is then further reacted with a compound of Formula (II)

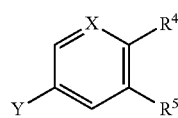

wherein
  $LG^1$, $LG^2$ are independently Hal,
  Z is H or an amine protecting group,
  Y is boronic acid or a boronic ester,
to yield a compound of Formula (I).

* * * * *